(12) United States Patent
Iwaki et al.

(10) Patent No.: US 8,822,534 B2
(45) Date of Patent: *Sep. 2, 2014

(54) SUBSTITUTED AMINOPROPIONIC DERIVATIVES AS NEPRILYSIN INHIBITORS

(71) Applicant: Novartis AG, Basel (CH)

(72) Inventors: Yuki Iwaki, Tokyo (JP); Rajeshri Ganesh Karki, Somerville, MA (US); Gary Michael Ksander, Amherst, NH (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,630

(22) Filed: Nov. 29, 2012

(65) Prior Publication Data
US 2013/0096127 A1 Apr. 18, 2013

Related U.S. Application Data

(63) Continuation of application No. 12/788,766, filed on May 27, 2010, now Pat. No. 8,394,853.

(60) Provisional application No. 61/324,943, filed on Apr. 16, 2010, provisional application No. 61/263,145, filed on Nov. 20, 2009, provisional application No. 61/181,756, filed on May 28, 2009.

(51) Int. Cl.
A61K 31/235 (2006.01)
C07C 229/34 (2006.01)

(52) U.S. Cl.
USPC .............. 514/533; 514/563; 546/335; 560/41

(58) Field of Classification Search
None
See application file for complete search history.

(56) References Cited

U.S. PATENT DOCUMENTS

| | | | |
|---|---|---|---|
| 4,281,180 A | 7/1981 | Umezawa et al. | |
| 4,610,816 A | 9/1986 | Berger | |
| 4,719,231 A | 1/1988 | Umezawa et al. | |
| 4,721,726 A | 1/1988 | Berger | |
| 4,738,803 A | 4/1988 | Roques et al. | |
| 4,918,105 A | 4/1990 | Cartwright et al. | |
| 5,200,426 A | 4/1993 | Hersh et al. | |
| 5,217,996 A * | 6/1993 | Ksander .................. | 514/533 |
| 5,250,522 A | 10/1993 | De Lombaert | |
| 5,273,990 A | 12/1993 | De Lombaert | |
| 5,294,632 A | 3/1994 | Erion et al. | |
| 5,354,892 A * | 10/1994 | Ksander .................. | 562/444 |
| 5,414,017 A | 5/1995 | Delaney et al. | |
| 5,449,662 A | 9/1995 | Scarborough | |
| 5,517,996 A | 5/1996 | Okada et al. | |
| 5,550,119 A | 8/1996 | De Lombaert et al. | |
| 5,710,171 A | 1/1998 | Dinsmore et al. | |
| 5,891,912 A | 4/1999 | Kawashima et al. | |
| 5,968,980 A | 10/1999 | Kawashima et al. | |
| 6,169,103 B1 | 1/2001 | Purchase, Jr. et al. | |
| 2002/0193562 A1 | 12/2002 | Robl | |
| 2004/0063761 A1 | 4/2004 | Kuduk et al. | |
| 2008/0119557 A1 | 5/2008 | Webb et al. | |
| 2008/0188533 A1 | 8/2008 | Choi et al. | |
| 2008/0269305 A1 | 10/2008 | Allegretti et al. | |
| 2010/0305131 A1 | 12/2010 | Coppola et al. | |
| 2010/0305145 A1 | 12/2010 | Coppola et al. | |
| 2011/0124695 A1 | 5/2011 | Iwaki et al. | |

FOREIGN PATENT DOCUMENTS

| | | | |
|---|---|---|---|
| EP | 0214639 A2 | 3/1987 | |
| WO | 97/43249 A1 | 11/1997 | |

OTHER PUBLICATIONS

Ksander et al., Dicarboxylic Acid Dipeptide Neutral Endopeptidase Inhibitors, J. Med. Chem., 1995, 38, 1689-1700.*
Lombaert et al., Chemical and Plasma Hydrolyses of a diphenyl a-aminomethyl phosphonate prodrug inhibitor of neutral endopeptidase 24.11, Bioorganic and Medicinal Chemistry Letters, vol. 4, No. 7, pp. 899-902, 1994.*
Patani et al., Bioisosterism: A Rational Approach in Drug Design, Chem. Rev. 1996, 96, 3147-3176.*
Patent Publication No. 2012-0122977, published May 17, 2012, U.S. Appl. No. 13/294,262, filed Nov. 11, 2011—Office Action dated Aug. 8, 2013 and response to same, dated Sep. 16, 2013.

* cited by examiner

Primary Examiner — Svetlana M Ivanova
(74) Attorney, Agent, or Firm — Sophie Binet Cross

(57) ABSTRACT

The present invention provides a compound of formula I';

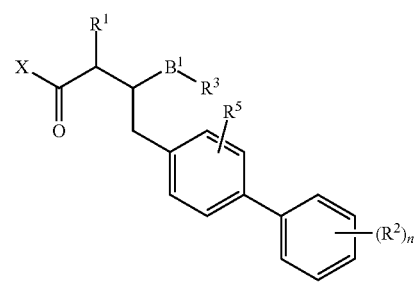

Formula I' or a pharmaceutically acceptable salt thereof, wherein $R^1$, $R^2$, $R^3$, $R^5$, $B^1$, X and n are defined herein. The invention also relates a method for manufacturing the compounds of the invention, and its therapeutic uses. The present invention further provides a combination of pharmacologically active agents and a pharmaceutical composition.

2 Claims, No Drawings

SUBSTITUTED AMINOPROPIONIC DERIVATIVES AS NEPRILYSIN INHIBITORS

This application is a continuation of U.S. application Ser. No. 12/788,766, filed on May 27, 2010, which claims benefit under 35 U.S.C. §119(e) of U.S. Provisional Application No. 61/181,756, filed May 28, 2009; U.S. Provisional Application No. 61/263,145, filed on Nov. 20, 2009 and U.S. Provisional Application No. 61/324,943 filed on Apr. 16, 2010; the contents of which are incorporated herein by reference in their entirety.

BACKGROUND OF THE INVENTION

Endogenous atrial natriuretic peptides (ANP), also called atrial natriuretic factors (ANF) have diuretic, natriuretic and vasorelaxant functions in mammals. The natural ANF peptides is metabolically inactivated, in particular by a degrading enzyme which has been recognized to correspond to the enzyme neutral endopeptidase (NEP) EC 3.4.24.11, also responsible for e.g. the metabolic inactivation of enkephalins.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEPi) should increase plasma levels of ANF and, hence, are expected to induce natriuretic and diuretic effects.

This enzyme is involved in the breakdown of several bioactive oligopeptides, cleaving peptide bonds on the amino side of hydrophobic amino acid residues. The peptides metabolised include atrial natriuretic peptides (ANP), bombesin, bradykinin, calcitonin gene-related peptide, endothelins, enkephalins, neurotensin, substance P and vasoactive intestinal peptide. Some of these peptides have potent vasodilatory and neurohormone functions, diuretic and natriuretic activity or mediate behaviour effects.

SUMMARY OF THE INVENTION

The aim of the present invention is to provide novel compounds which are useful as neutral endopeptidase inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of this invention are thus particularly useful for the treatment of conditions and disorders responsive to the inhibition of neutral endopeptidase (NEP) EC 3.4.24.11.

Thus, the compounds of the invention, by inhibiting the neutral endopeptidase EC.3.4.24.11, can potentiate the biological effects of bioactive peptides. Thus, in particular the compounds have utility in the treatment of a number of disorders, including hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), pulmonary arterial hypertension, renal failure (including edema and salt retension), cyclical oedema, Menieres disease, hyperaldosteroneism (primary and secondary) and hypercalciuria, ascites. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of menstrual disorders, preterm labour, pre-eclampsia, endometriosis, and reproductive disorders (especially male and female infertility, polycystic ovarian syndrome, implantation failure). Also the compounds of the invention should treat asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and athereosclerosis, male and female sexual dysfunction. In a preferred embodiment the compounds of the invention are useful in the treatment of cardiovascular disorders.

The invention pertains to the compounds, methods for using them, and uses thereof as described herein. Examples of compounds of the invention include the compounds according to anyone of Formulae I' and I to VIIC, or a pharmaceutically acceptable salt thereof, and the compounds of the examples.

The invention therefore provides a compound of the formula (I'):

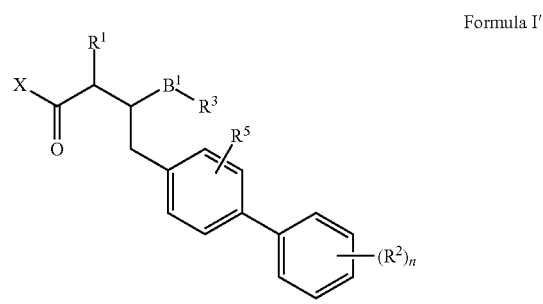

Formula I' or a pharmaceutically acceptable salt thereof, wherein:
$R^1$ is H, $C_{1-7}$alkyl, hydroxy, $C_{1-7}$alkoxy, halogen, —SH, —S—$C_{1-7}$alkyl or $NR^aR^b$;

$R^2$ for each occurrence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^aR^b$, $C_{6-10}$aryl, heteroaryl or heterocyclyl;

wherein $R^a$ and $R^b$ for each occurrence are independently H or $C_{1-7}$alkyl;

$R^3$ is $A^1$-C(O)$X^1$ or $A^2$-$R^4$;

$R^4$ is $C_{6-10}$aryl or a heteroaryl, which can be monocyclic or bicyclic, and which can be optionally substituted with one or more substituents independently selected from the group consisting of hydroxy, hydroxy$C_{1-7}$alkyl, nitro, —$NR^aR^b$, —C(O)$C_{1-7}$alkyl, C(O)—O—$C_{1-7}$alkyl, $C_{1-7}$alkoxy, halo, $C_{1-7}$alkyl, halo-$C_{1-7}$alkoxy, $C_{1-7}$alkenyl, $C_{6-10}$aryl, heteroaryl, —NHSO$_2$—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, —$NR^aR^b$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of $C_{6-10}$aryl, heteroaryl, heterocyclyl, C(O)NH$_2$, C(O)NH—$C_{1-6}$alkyl, and C(O)N($C_{1-6}$alkyl)$_2$;

$B^1$ is —C(O)NH— or —NHC(O)—;

$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a linear or branched $C_{1-7}$alkenylene; or $A^1$ is a linear $C_{1-4}$ alkylene wherein one or more carbon atom(s) is/are replaced with an heteroatom selected from O, $NR^c$; and $A^1$ is optionally substituted with one or more substituents independently selected from the group consisting of halo and $C_{1-7}$alkyl; in which $R^c$ for each occurrence, is independently H, $C_{1-7}$alkyl, —C(O)—O—$C_{1-7}$alkyl or —CH$_2$C(O)OH; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^aR^b$, —OCH$_2$CO$_2$H, and —OCH$_2$C(O)NH$_2$; or $A^1$ is a $C_{3-7}$cycloalkyl;

$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

The invention therefore provides a compound of the formula (I):

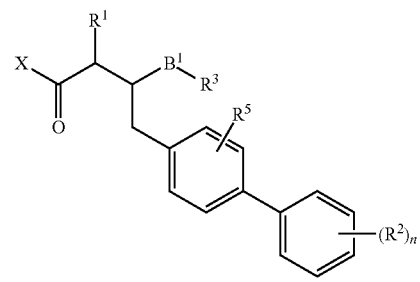

Formula I or a pharmaceutically acceptable salt thereof, wherein:

$R^1$ is H or $C_{1-7}$alkyl;

$R^2$ for each occurrence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^aR^b$, $C_{6-10}$aryl, heteroaryl or heterocyclyl;

wherein $R^a$ and $R^b$ for each occurrence are independently H or $C_{1-7}$alkyl;

$R^3$ is $A^1$-C(O)$X^1$ or $A^2$-$R^4$;

$R^4$ is $C_{6-10}$aryl or a heteroaryl, which can be monocyclic or bicyclic, and which can be optionally substituted with one or more substituents independently selected from the group consisting of hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, $NR^aR^b$, or —O—$C_{6-10}$aryl; wherein alkyl is optionally substituted with one or more substituents independently selected from the group consisting of $C_{6-10}$aryl, heteroaryl, heterocyclyl, C(O)NH$_2$, C(O)NH—$C_{1-6}$alkyl, and C(O)N($C_{1-6}$alkyl)$_2$;

$B^1$ is —C(O)NH— or —NHC(O)—;

$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^aR^b$, —OCH$_2$CO$_2$H, and —OCH$_2$C(O)NH$_2$; or $A^1$ is a $C_{3-7}$cycloalkyl;

$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

In another embodiment, the invention pertains to a method for treating a disorders or diseases responsive to the inhibition of neutral endopeptidase EC 3.4.24.11 (NEP), in a subject, by administering to the subject a therapeutically effective amount of a compound according to anyone of Formulae I' and I to VIIC, or a pharmaceutically acceptable salt thereof, such that the disorder or disease responsive to the inhibition of neutral endopeptidase EC 3.4.24.11 (NEP) in the subject is treated.

In yet another embodiment, the invention pertains to a method for treating hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathey, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), pulmonary arterial hypertension, renal failure (including edema and salt retension), cyclical oedema, Menieres disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction; comprising administering to the subject a therapeutically effective amount of a compound according to anyone of Formulae I' and I to VIIC, or a pharmaceutically acceptable salt thereof, such that the subject is treated.

In yet another embodiment, the invention pertains to pharmaceutical compositions, comprising of a compound according to anyone of Formulae I' and I to VIIC, or a pharmaceutically acceptable salt thereof, and one or more pharmaceutically acceptable carriers.

In still another embodiment, the invention pertains to combinations including a compound according to anyone of Formulae I' and I-VIC, or a pharmaceutically acceptable salt thereof, and pharmaceutical combinations of one or more therapeutically active agents.

In another embodiment, the invention pertains to a method for inhibiting neutral endopeptidase EC 3.4.24.11 in a subject by administering to the subject a therapeutically effective amount of a compound according to anyone of Formulae I' and I to VIIC, or a pharmaceutically acceptable salt thereof, such that neutral endopeptidase EC 3.4.24.11 is inhibited.

DETAILED DESCRIPTION OF THE INVENTION

Compounds of the Invention

References hereinafter to compounds of Formula I or I' apply equally to compounds according to anyone of Formulae IA to VIIC.

References hereinafter to embodiments of the invention apply equally to compounds of Formula I or I' and compounds according to anyone of Formulae IA to VIIC, insofar as the embodiments are present.

Various embodiments of the invention are described herein. It will be recognized that features specified in each embodiment may be combined with other specified features to provide further embodiments.

In one embodiment the invention provides a compound of the Formula I or I', or a pharmaceutically acceptable salt thereof, wherein:

$R^1$ is H or $C_{1-7}$alkyl;

$R^2$ for each occurrence, is independently $C_{1-7}$alkyl, halo, $C_{3-7}$cycloalkyl, hydroxy, $C_{1-7}$alkoxy, halo$C_{1-7}$alkyl, —$NR^aR^b$, $C_{6-10}$aryl, heteroaryl or heterocyclyl; wherein $R^a$ and $R^b$ for each occurrence are independently H or $C_{1-7}$alkyl;

$R^3$ is $A^1$-C(O)$X^1$ or $A^2$-$R^4$;

$R^4$ is $C_{6-10}$aryl or a heteroaryl, which can be monocyclic or bicyclic and which can be optionally substituted with one or more substituents independently selected from the group consisting of hydroxy, $C_{1-7}$alkoxy, halo, $C_{1-7}$alkyl, halo-$C_{1-7}$alkyl $C_{6-10}$aryl, heteroaryl, —$NHSO_2$—$C_{1-7}$alkyl and benzyl;

$R^5$ is H; and

X and $X^1$ are independently OH, —O—$C_{1-7}$alkyl or $NR^aR^b$;

$B^1$ is —C(O)NH— or —NHC(O)—;

$A^1$ is a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^aR^b$, —$OCH_2CO_2H$, and —$OCH_2C(O)NH_2$; and $A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl; and n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

Certain compounds of Formula I or I' include compounds of Formula IA wherein the stereochemistry at the carbon bearing the biphenyl group is (R):

Formula IA

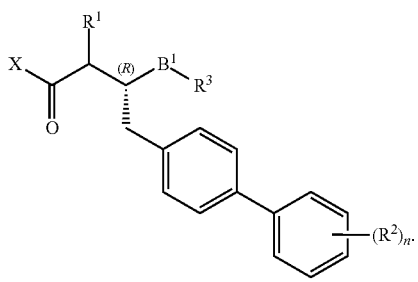

or a pharmaceutically acceptable salt thereof, wherein X, $R^1$, $R^2$, $B^1$, $R^3$ and n have the definitions of Formula I or I', supra.

In one embodiment, the invention pertains to compounds of Formula I or I' or a pharmaceutically acceptable salt thereof, wherein n is 1, 2, 3, 4 or 5; $R^2$ is halo and is attached to the meta position and the other optional $R^2$ groups are independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl. This embodiment is illustrated by compounds of Formulae IB and IC:

Formula IB

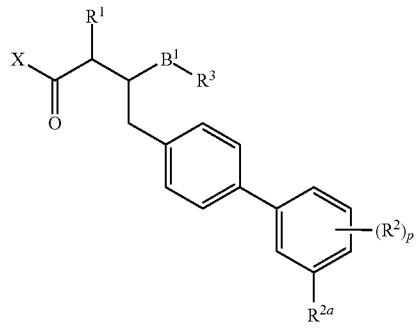

Formula IC

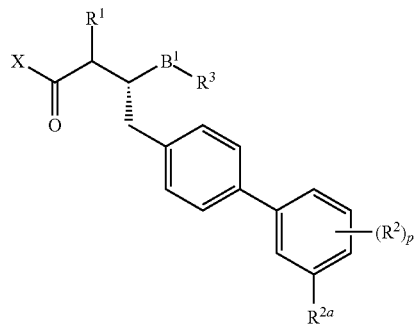

or a pharmaceutically acceptable salt thereof, wherein X, $R^1$, $R^2$, $B^1$, $R^3$ have the definitions of Formula I or I', supra; p is 0, 1, 2, 3 or 4 and $R^{2a}$ is halo.

Certain compounds of Formula I or I' include compounds of Formula II:

Formula II

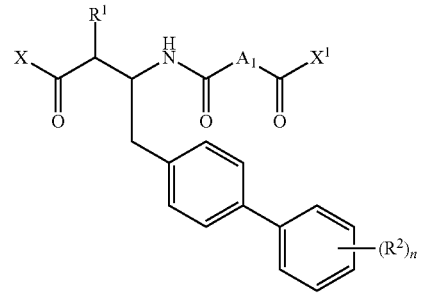

or a pharmaceutically acceptable salt thereof, wherein X, $X^1$, $A^1$, $R^1$, $R^1$, $R^2$ and n have the definitions of Formula I or I', supra.

In a further embodiment, the invention pertains to compounds of Formula II wherein the stereochemistry of the carbon bearing the biphenyl groups is (R). This embodiment is illustrated by compounds of Formula IIA:

Formula IIA

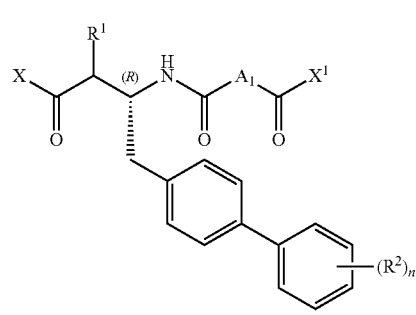

or a pharmaceutically acceptable salt thereof, wherein X, $X^1$, $A^1$, $R^1$, $R^2$ and n have the definitions of Formula I or I', supra.

Certain compounds of Formula I, I' or II include compounds of Formula IIB or IIC:

Formula IIB

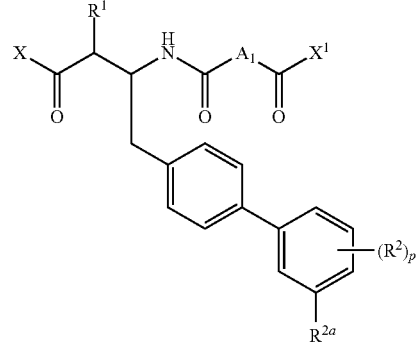

Formula IIC

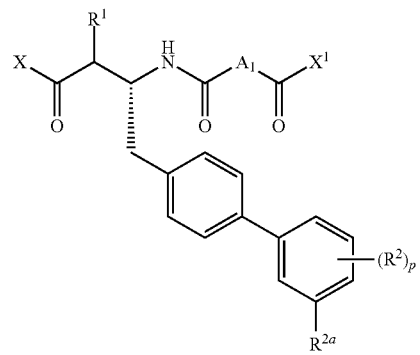

or a pharmaceutically acceptable salt thereof, wherein X, $X^1$, $A^1$, $R^1$, $R^2$ have the definitions of Formula I or I', supra; p is 0, 1, 2, 3 or 4 and $R^{2a}$ is halo.

Certain compounds of Formula I or I' include compounds of Formula III:

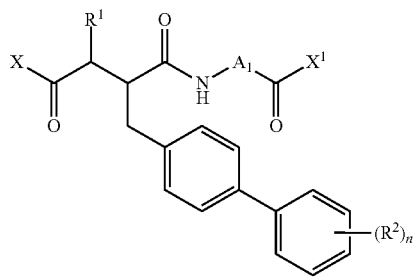

Formula III or a pharmaceutically acceptable salt thereof, wherein X, X$^1$, A$^1$, R$^1$, R$^2$ and n have the definitions of Formula I or I', supra.

In a further embodiment, the invention pertains to compounds of Formula III wherein the stereochemistry of the carbon bearing the biphenyl groups is (R). This embodiment is illustrated by compounds of Formula IIIA:

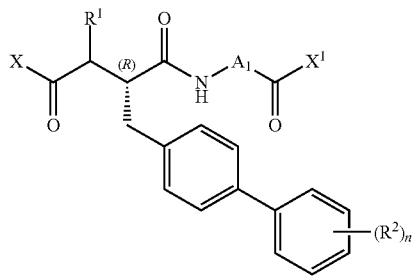

Formula IIIA or a pharmaceutically acceptable salt thereof, wherein X, X$^1$, A$^1$, R$^1$, R$^2$ and n have the definitions of Formula I or I', supra.

Certain compounds of Formula III include compounds of Formula IIIB or IIIC:

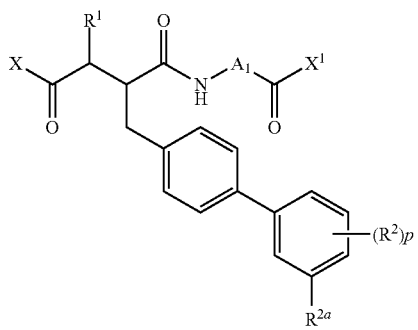

Formula IIIB

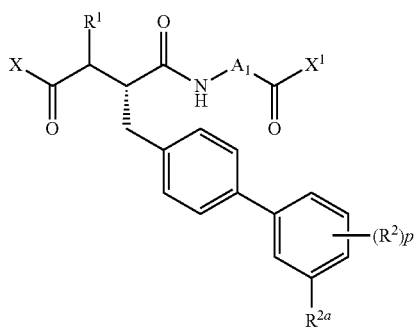

Formula IIIC or a pharmaceutically acceptable salt thereof, wherein X, X$^1$, A$^1$, R$^1$, R$^2$ have the definitions of Formula I or I', supra; p is 0, 1, 2, 3 or 4 and R$^{2a}$ is halo.

In another embodiment the invention provides a compound according to anyone of formulae I', I to IC, II to IIC and III to IIIC or of any classes and subclasses described herein, or a pharmaceutically acceptable salt or solvate thereof, wherein A$^1$ is a linear C$_{1-7}$alkylene, which is optionally substituted with one or more substituents independently selected from the group consisting of halo, C$_{1-7}$alkoxy, hydroxy, O-acetate and C$_{3-7}$cycloalkyl; in which two geminal alkyl can optionally combine to form a C$_{3-7}$cycloalkyl.

A further embodiment include compounds according to anyone of Formulae I', I to IC, II to IIC and III to IIIC or of any classes and subclasses described herein, or a pharmaceutically acceptable salt thereof, wherein A$^1$ is —CH$_2$—, —CH$_2$CH$_2$—, —CH$_2$CH$_2$CH$_2$— or A$^1$ has the following formulae:

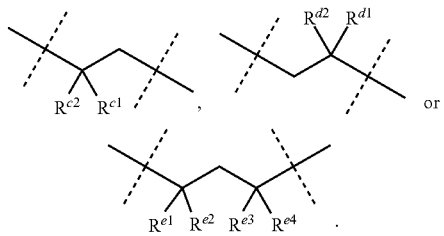

in which R$^{c1}$, R$^{c2}$, R$^{d1}$, R$^{d2}$, R$^{e1}$, R$^{e2}$, R$^{e3}$ and R$^{e4}$ are independently H, halo, C$_{3-7}$cycloalkyl, or C$_{1-7}$alkyl; and alternatively R$^{c1}$ and R$^{c2}$ or R$^{d1}$ and R$^{d2}$ can form together with the atoms to which they are attached a C$_{3-7}$cycloalkyl. In one aspect of this embodiment, A$^1$ is one of the following:

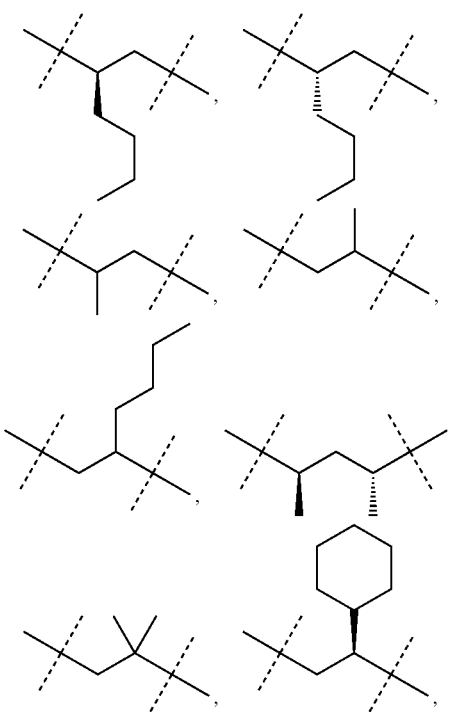

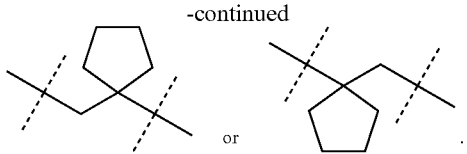

Yet another further embodiment includes compounds according to anyone of Formulae I', I to IC, II to IIC and III to IIIC or of any classes and subclasses described herein, or a pharmaceutically acceptable salt thereof, wherein $A^1$ has the following formulae:

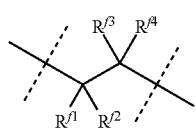

in which $R^{f1}$, $R^{f2}$, $R^{f3}$ and $R^{f4}$ are independently H, halo, O-acetate or $C_{1-7}$alkyl. In a further embodiment, $A^1$ is one of the following:

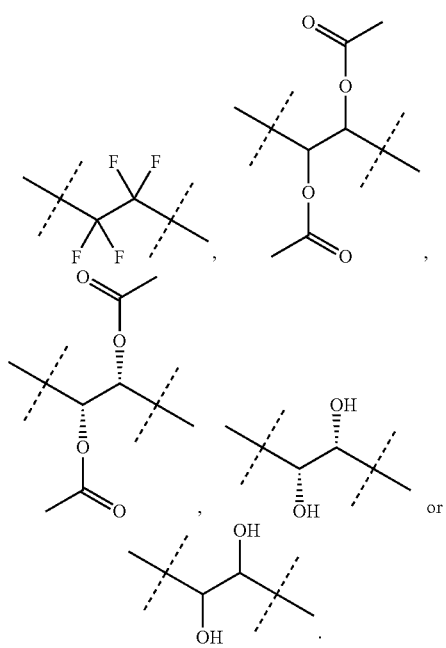

In yet another embodiment, the invention provides a compound according to anyone of Formulae I', I to IC, II to IIC and III to IIIC or of any classes and subclasses described herein, or a pharmaceutically acceptable salt or solvate thereof, wherein $A^1$ is a $C_{3-7}$cycloalkyl. Examples of this embodiment are compounds of anyone of Formulae I', I to IC, II to IIC and III to IIIC, wherein A1 is selected from the following:

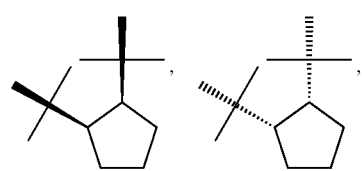

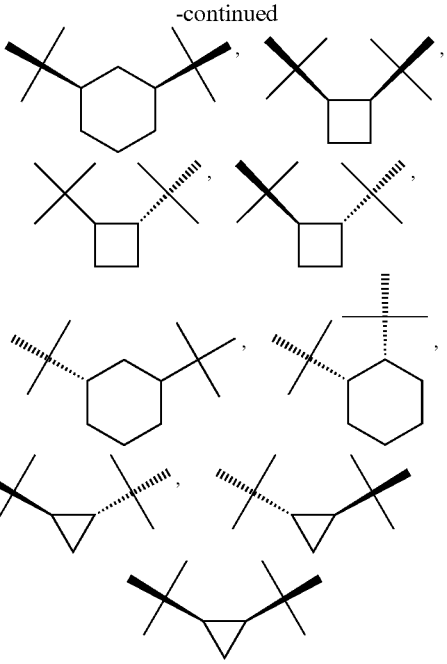

In yet another embodiment, the invention provides a compound according to anyone of Formulae I', I to IC, II to IIC and III to IIIC or of any classes and subclasses described herein, or a pharmaceutically acceptable salt or solvate thereof, wherein $A^1$ is a linear or branched $C_{2-7}$alkenylene. An example of $C_{2-7}$alkenylene is trans CH=CH.

In yet another embodiment, the invention provides a compound according to anyone of Formulae I', I to IC, II to IIC and III to IIIC or of any classes and subclasses described herein, or a pharmaceutically acceptable salt or solvate thereof, wherein $A^1$ is a linear $C_{1-4}$ alkylene wherein one or more carbon atom(s) is/are replaced with an heteroatom selected from O, $NR^c$; and $A^1$ is optionally substituted with one or more substituents independently selected from the group consisting of halo and $C_{1-7}$alkyl; in which $R^c$ for each occurrence is independently H, $C_{1-7}$alkyl, —C(O)O $C_{1-7}$alkyl or $CH_2C(O)OH$. One further embodiment includes compounds of Formulae I', I to IC, II to IIC and III to IIIC wherein $A^1$ is one of the following:

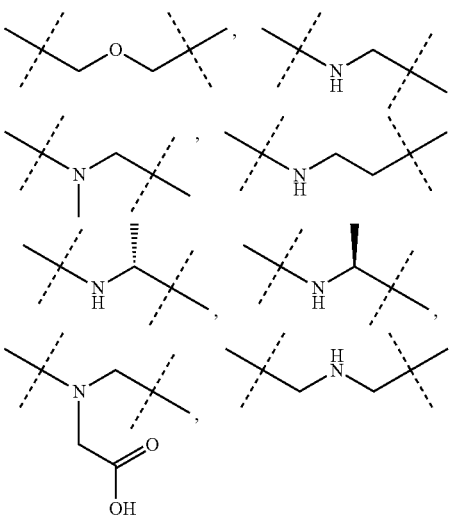

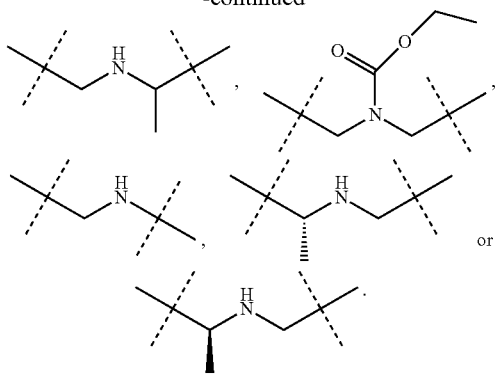

In yet another embodiment, the invention provides a compound according to anyone of Formulae I', I to IC, II to IIC and III to IIIC or of any classes and subclasses described herein, or a pharmaceutically acceptable salt or solvate thereof, wherein $A^1$ is optionally substituted phenyl or heteroaryl, wherein optional substituents are defined as in Formula I or I'.

Certain compounds of the above embodiment include compounds according to anyone of Formula I', I to IC, II to IIC and III to IIIC or a pharmaceutically acceptable salt thereof, wherein $A^1$ is a 5-membered ring heteroaryl. This embodiment is illustrated by compounds of Formula IV:

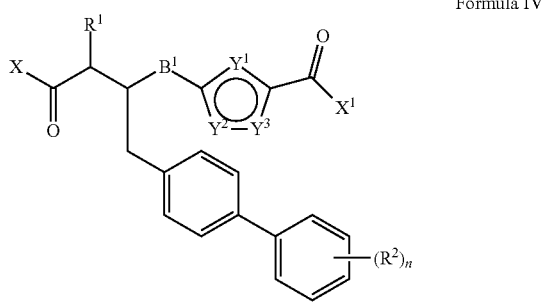

Formula IV or a pharmaceutically acceptable salt thereof, wherein X, $X^1$, $B^1$, $R^1$, $R^2$ and n have the definitions of Formula I or I', supra and $Y^1$, $Y^2$ and $Y^3$ are independently N, NH, S, O or CH and form together with the ring atoms to which they are attached a 5-membered heteroaryl ring.

In one aspect of this embodiment, the invention pertains to compounds of Formula IVA:

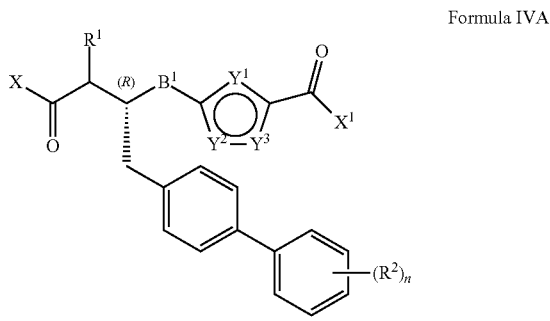

Formula IVA or a pharmaceutically acceptable salt thereof, wherein X, $X^1$, $B^1$, $R^1$, $R^2$, $Y^1$, $Y^2$, $Y^3$ and n have the definitions of Formulae I, I' or IV, supra.

In one aspect of this embodiment, $Y^1$, $Y^2$ and $Y^3$ form together with the ring atoms to which they are attached a 5-membered heteroaryl ring selected from furan, thiophene, pyrrole, pyrazole, oxazole, thiazole, oxadiazole, thiadiazole, and triazole. One further embodiment includes compounds of Formula IV or VIA, or a pharmaceutically acceptable salt thereof, wherein the 5-membered heteroaryl is one of the following:

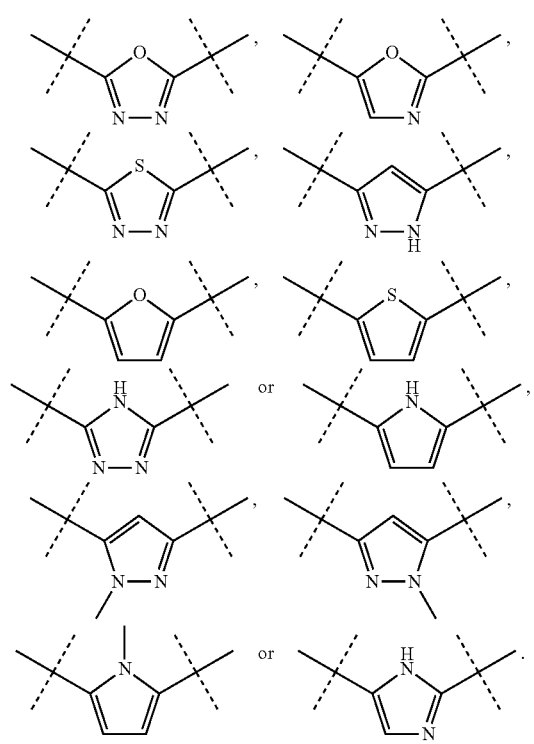

In a further embodiment, the invention pertains to compounds of Formula IV or IVA wherein n is 1, 2, 3, 4 or 5; $R^2$ is halo in the meta position and the other optional $R^2$ groups are independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl.

In yet another aspect of the above embodiment, the invention pertains to compounds of Formula I', I to IC, II to IIC or III to IIIC, or a pharmaceutically acceptable salt thereof, wherein $A^1$ is a 5-membered ring heteroaryl attached to the amide $B^1$ at a nitrogen atom. This embodiment is illustrated by compounds of Formulae V or VA:

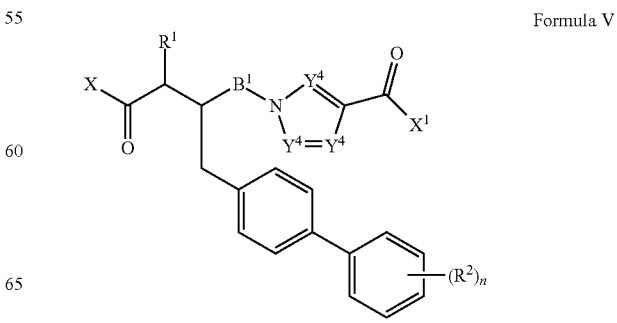

Formula V

15
-continued

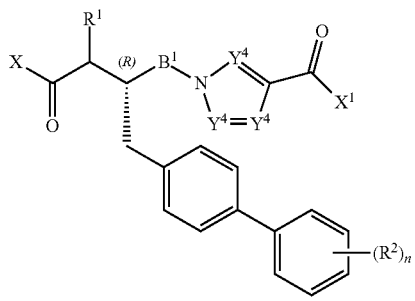

Formula VA or a pharmaceutically acceptable salt thereof, wherein X, X$^1$, B$^1$, R$^1$, R$^2$ and n have the definitions of Formula I or I', supra and each Y$^4$ are independently N, S, O or CH. In a further embodiment, the invention pertains to compounds of Formula V or VA wherein n is 1, 2, 3, 4 or 5; R$^2$ is halo in the meta position and the other optional R$^2$ groups are independently C$_{1-7}$alkyl, NO$_2$, CN, halo, C$_{3-7}$cycloalkyl, hydroxy, C$_{1-7}$alkoxy, halo-C$_{1-7}$alkyl, NR$^b$R$^c$, C$_{6-10}$aryl, heteroaryl or heterocyclyl.

In yet another aspect of the above embodiment the invention provides a compound according to anyone of Formulae I', I to IC, II to IIC and III to IIIC or of any classes and subclasses described herein, or a pharmaceutically acceptable salt or solvate thereof, wherein A$^1$ is a phenyl or a 6-membered ring heteroaryl in which phenyl and heteroaryl are optionally substituted with C$_{1-7}$alkyl, C$_{3-7}$cycloalkyl, halo-C$_{1-7}$alkyl, hydroxy, C$_{1-7}$alkoxy, halo, NR$^a$R$^b$, —OCH$_2$CO$_2$H, or —OCH$_2$C(O)NH$_2$. One aspect of this embodiment include compounds according to anyone of Formulae I', I to IC, II to IIC and III to IIIC, or pharmaceutically acceptable salt thereof, wherein A$^1$ is connected to the amide B$^1$ and to the C(O)X$^1$ moieties in a para arrangement. Another aspect of this embodiment include compounds according to anyone of Formula I', I to IC, II to IIC and III to IIIC wherein A$^1$ is connected to the amide B$^1$ and to the C(O)X$^1$ moieties in a meta arrangement. Compounds of this embodiment include compounds of Formula VI:

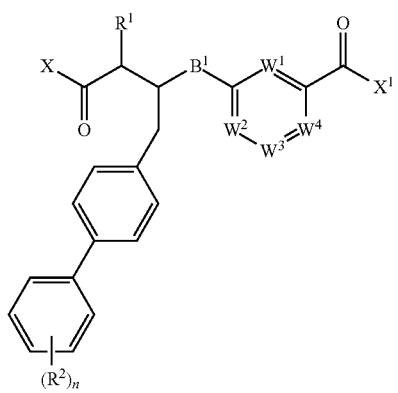

Formula VI or a pharmaceutically acceptable salt thereof, wherein X, X$^1$, B$^1$, R$^1$, R$^2$ and n have the definitions of Formula I or I', supra and W$^1$, W$^2$, W$^3$ and W$^4$ are independently N or CR$^e$, in which each R$^e$ is independently H, C$_{1-7}$alkyl, C$_{3-7}$cycloalkyl, halo-C$_{1-7}$alkyl, hydroxy, C$_{1-7}$alkoxy, halo, —NR$^a$Rb, —OCH$_2$CO$_2$H or —OCH$_2$C(O)NH$_2$. In one aspect of this embodiment A$^1$ is phenyl, pyridine or pyrimidine.

16

In a further embodiment, the invention pertains to compounds of Formula VIA:

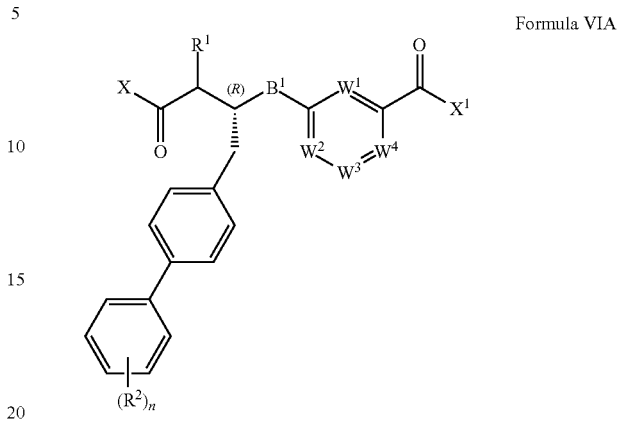

Formula VIA or a pharmaceutically acceptable salt thereof, wherein X, X$^1$, B$^1$, R$^1$, R$^2$, W$^1$, W$^2$, W$^3$ and W$^4$ and n have the definitions of Formulae I, I' or VI, supra.

One further embodiment includes compounds of Formula VI or VIA, or a pharmaceutically acceptable salt thereof, wherein A$^1$ is one of the following:

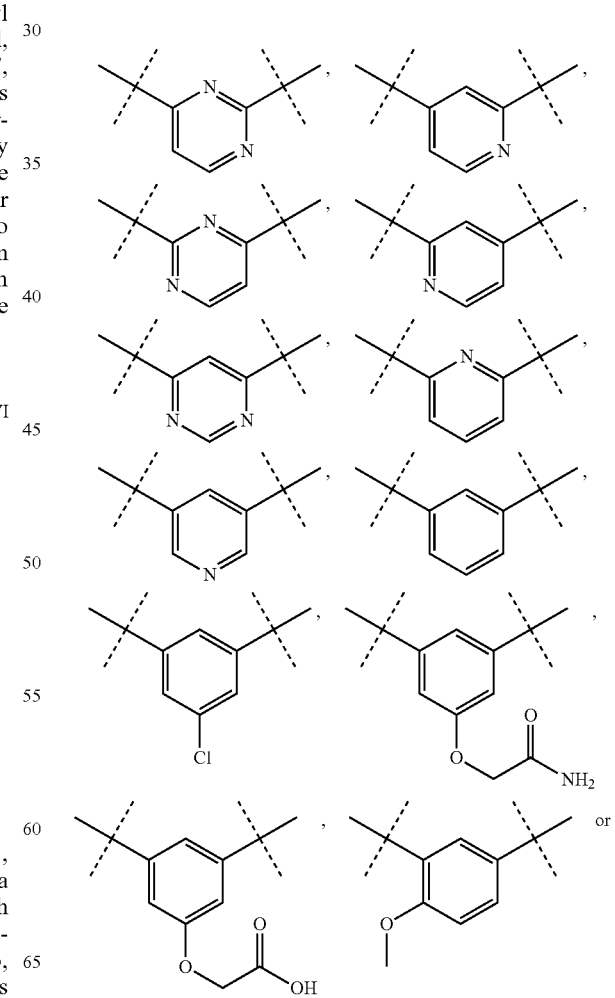

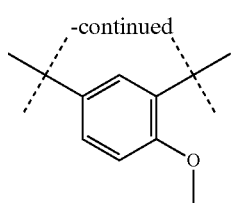

In a further embodiment, the invention pertains to compounds of Formula VI or VIA, or a pharmaceutically acceptable salt thereof, wherein n is 1, 2, 3, 4 or 5; $R^2$ is halo in the meta position and the other optional $R^2$ groups are independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl.

In one aspect of the previous embodiment, the invention pertains to compounds according to anyone of Formulae I', I to IC, IV to IVC, V to VC and VI to VIC, or pharmaceutically acceptable salt thereof, wherein $B^1$ is —C(O)NH—. In another embodiment, $B^1$ is —NHC(O)—.

Certain compounds of the above embodiment include compounds according to anyone of Formulae I', I to IC, II to IIC and III to IIIC, or a pharmaceutically acceptable salt thereof, wherein $A^1$ is —$C_{1-4}$alkylene-$C_{6-10}$-aryl-, —$C_{1-4}$alkylene-heteroaryl- or —$C_{1-4}$alkylene-heterocyclyl-, —$C_{6-10}$aryl-$C_{1-4}$-alkylene-, -heteroaryl-$C_{1-4}$alkylene or -heterocyclyl-$C_{1-4}$alkylene-. In one aspect of this embodiment, $A^1$ is —$C_{1-4}$alkylene-$C_{6-10}$-aryl-, —$C_{1-4}$alkylene-heteroaryl- or —$C_{1-4}$alkylene-heterocyclyl-, wherein the alkylene portion is attached to $B^1$ amide group and the aryl, heteroaryl or heterocyclyl moities are attached to $C(O)X^1$. In another aspect of this embodiment, $A^1$ is —$CH_2$-phenyl- or -phenyl-$CH_2$—. In another aspect of this embodiment, $A^1$ is —$CH_2$-heteroaryl or -heteroaryl-$CH_2$—. In a further embodiment, $A^1$ is —$CH_2$-heterocyclyl or -heterocyclyl-$CH_2$—. Representative examples of $A^1$ are the following:

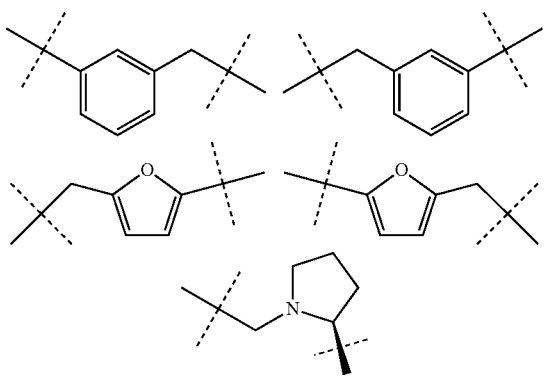

Certain compounds of Formula I or I' include compounds of Formula VII:

Formula VII

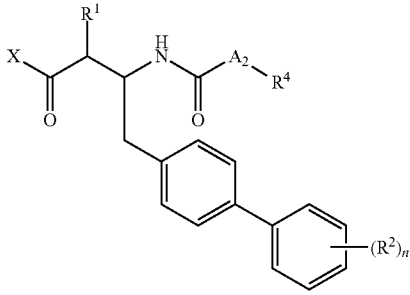

or a pharmaceutically acceptable salt thereof, wherein X, $A^2$, $R^1$, $R^2$, $R^4$ and n have the definitions of Formula I or I', supra. A further embodiment includes compounds of Formula VIIA:

Formula VIIA

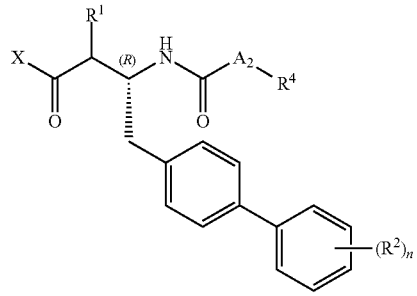

or a pharmaceutically acceptable salt thereof, wherein X, $A^2$, $R^1$, $R^2$, $R^4$ and n have the definitions of Formula I or I', supra.

Certain compounds of Formula VII or VIIA have the formula VIIB or VIIC:

Formula VIIB

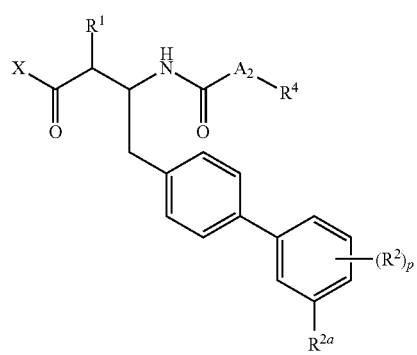

Formula VIIC

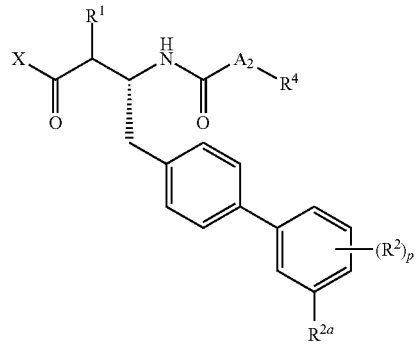

or a pharmaceutically acceptable salt thereof, wherein X, $A^2$, $R^1$, $R^2$, $R^4$ have the definitions of Formula I or I', supra; p is 0, 1, 2, 3 or 4 and $R^{2a}$ is halo.

A further aspect of this embodiment include compounds according to anyone of Formulae VII to VIIC, or a pharmaceutically acceptable salt thereof, wherein $A^2$ is $(CH_2)_p$ and p is 0, 1, 2, 3. In one aspect of this embodiment p is 0, therefore $A^2$ is a bond. In another aspect of this embodiment $A^2$ is $CH_2$ or $CH_2$—$CH_2$.

In another aspect of this embodiment the invention provide compounds according to anyone of Formulae VII to VIIC, or a pharmaceutically acceptable salt thereof, wherein $R^4$ is optionally substituted $C_{6-10}$aryl. Representative examples of aryl are benzoimidazolone, benzoisothiazolone or phenyl. In one further aspect of this embodiment, $R^4$ is phenyl. Substituents on the phenyl ring include for example, halo (e.g. F, Cl), hydroxy, halo-$C_{1-7}$alkyl (e.g. $CF_3$), —NHS(O)$_2$—$C_{1-7}$alkyl, heteroaryl, $C_{1-7}$alkoxy or $C_{1-7}$alkyl.

In yet another aspect of this embodiment the invention provides compounds according to anyone of Formula VII to VI IC or a pharmaceutically acceptable salt thereof, wherein $R^4$ is an optionally substituted bicyclic heteroaryl.

In yet another aspect of this embodiment the invention provide compounds according to anyone of Formulae VII to VIIC or a pharmaceutically acceptable salt thereof wherein $R^4$ is optionally substituted 5- or 6-membered heteroaryl. In one aspect of this embodiment, $R^4$ is a 6-membered ring heteroaryl selected from the group consisting of pyrazinyl, pyridinyl, pyrimidinyl, oxo-pyranyl (e.g. pyranone, optionally substituted pyran-4-one, pyran-2-one such as 3-hydroxy-pyran-4-one, 3-hydroxy-pyran-2-one), and oxo-pyridinyl (e.g. pyridinone, optionally substituted pyridin-4-one or pyridin-2-one such as for example 3-hydroxy-1-methyl-pyridin-4-one or 1-benzyl-pyridin-2-one), or pyrimidinone (i.e oxo-pyrimidinyl). In another aspect of this embodiment $R^4$ is a 5-membered ring heteroaryl selected from the group consisting of oxazole, pyrrole, pyrazole, isooxazole, triazole, tetrazole, oxadiazole (e.g. 1-oxa-3,4-diazole, 1-oxa-2,4-diazole), oxadiazolone (e.g. oxadiazol-2-one), thiazole, isothiazole, thiophene, imidazole and thiadiazole. Other representative examples of $R^4$ are oxazolone, thiazolone, oxadiazolone, triazolone, oxazolone, imidazolone, pyrazolone. In a further embodiment, the optional substituents on $C_{6-10}$aryl and heteroaryl are selected from hydroxy, $C_{1-7}$alkyl, $C_{1-7}$alkoxy, halo, halo-$C_{1-7}$alkyl or benzyl.

In yet another aspect of the above embodiment the invention provide compounds according to anyone of Formulae VII to VIIC or a pharmaceutically acceptable salt thereof, wherein $R^4$ is a bicyclic heteroaryl. A further embodiment includes compounds according to anyone of Formulae VII to VIIC, or a pharmaceutically acceptable salt thereof, wherein $R^4$ is indole, benzothiazole or benzimidazole. Representative examples of $R^4$ are the following:

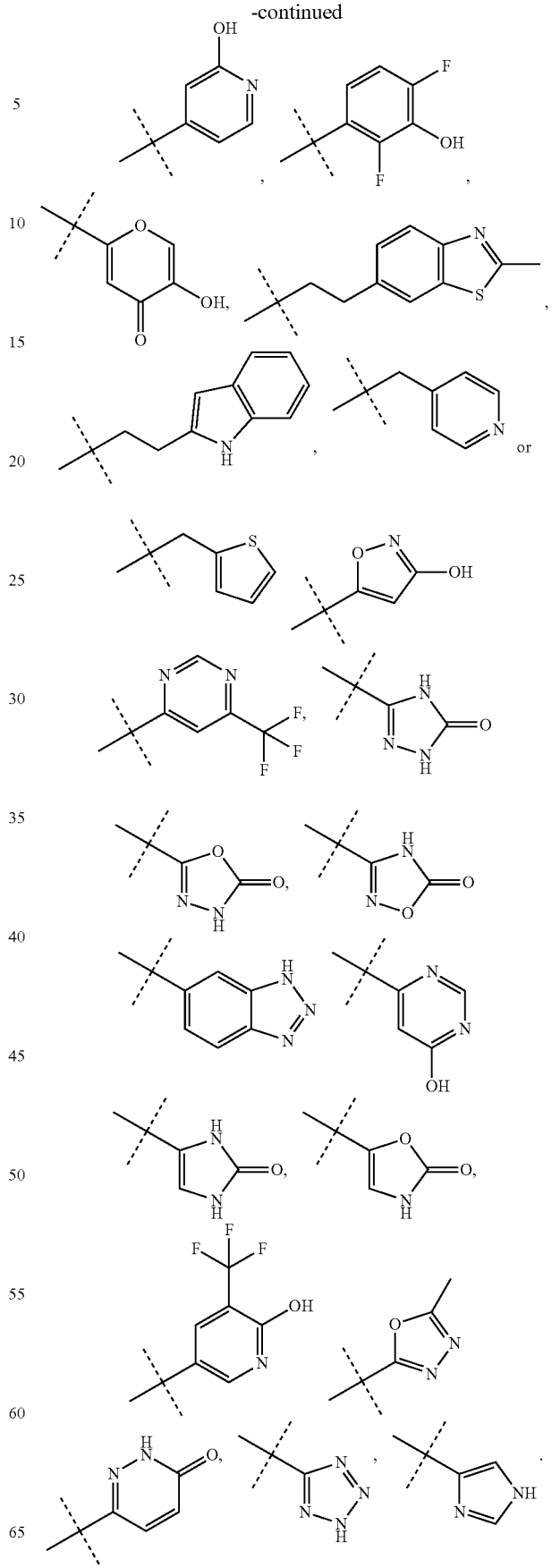

In yet another aspect of the above embodiment the invention provide compounds according to anyone of Formulae VII to VIIC, or a pharmaceutically acceptable salt thereof, wherein $R^4$ is a monocyclic saturated or partially saturated heterocyclyl, which heterocyclyl contains at least one heteroatom selected from nitrogen, sulfur and oxygen, and which heterocyclyl is optionally substituted with one or more substituents independently selected from the group consisting of oxo, hydroxy, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl. In one particular aspect of this embodiment, $R^4$ is pyrrolidine or imidazolidine, wherein the heterocyclyl may be linked to the carbonyl (C(O)-A$^2$) moiety via a carbon or a nitrogen and the heterocyclyl is optionally substituted with oxo.

In one embodiment the invention provide compounds according to anyone of Formulae I', I to IC, II to IIC, III to IIIC, IV, IVA, V, VA, VI, VIA and VII to VIIC or a pharmaceutically acceptable salt thereof, wherein $R^1$ is H.

In another embodiment the invention provide compounds according to anyone of Formulae I', I to IC, II to IIC, III to IIIC, IV, IVA, V, VA, VI, VIA and VII to VIIC, or a pharmaceutically acceptable salt thereof, wherein each $R^2$ is independently halo, $C_{1-7}$alkyl, $C_{1-7}$alkoxy, hydroxy, halo-$C_{1-7}$alkyl and n is 0, 1 or 2. In a further embodiment n is 1, 2, 3, 4 or 5, $R^2$ is halo in the meta position and the other optional $R^2$ groups are independently halo, $C_{1-7}$alkyl, $C_{1-7}$alkoxy, hydroxy or haloalkyl. In yet a further embodiment, the invention provide compounds according to anyone of Formulae I', I to IC, II to IIC, III to IIIC, IV, IVA, V, VA, VI, VIA and VII to VIIC, or a pharmaceutically acceptable salt thereof, wherein n is 1 or 2, $R^2$ is meta-chloro or meta-fluoro and the other optional $R^2$ group is halo, $C_{1-7}$alkyl, $C_{1-7}$alkoxy, hydroxy or haloalkyl.

In yet another embodiment the invention provide compounds according to anyone of Formulae I', I to IC, II to IIC, III to IIIC, I, IVA, V, VA, VI, VIA and VII to VIIC, or a pharmaceutically acceptable salt thereof, wherein X and $X^1$ are independently OH or —O—$C_{1-7}$alkyl (e.g. —O-ethyl, —O-methyl or —O-nbutyl). In one particular aspect of this embodiment X and $X^1$ are OH. In another aspect of this embodiment, X and $X^1$ are independently —O—$C_{1-7}$alkyl in which alkyl is substituted with $C_{6-10}$aryl, heteroaryl, heterocyclyl, C(O)NH$_2$, C(O)NH—$C_{1-6}$alkyl, or C(O)N($C_{1-6}$alkyl)$_2$. Representative examples of X or $X^1$ are —O—CH$_2$—C(O)N(CH$_3$)$_2$, —O—CH$_2$—CH$_2$-morpholine, —O—CH$_2$-dioxolone or —O-benzyl. In yet another aspect of this embodiment, X and $X^1$ are —O—$C_{6-10}$aryl. A representative examples of —O—$C_{6-10}$aryl is —O-(2,3-dihydro-1H-indene).

In another embodiment X, $X^1$, $B^1$, $A^1$, $A^2$, $R^2$, $R^1$ and $R^4$ groups are those defined by the X, $X^1$, $A^1$, $A^2$, $B^1$, $R^2$, $R^1$ and $R^4$ groups in the Examples section below.

In another embodiment individual compounds according to the invention are those listed in the Examples section below, or a pharmaceutically acceptable salt thereof.

Definition

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-7}$alkyl" refers to a hydrocarbon having one to seven carbon atoms. Moreover, the term alkenyl includes both "unsubstituted alkyls" and "substituted alkyls". The term "alkylene" refers to a divalent alkyl radical, wherein alkyl is as previously defined.

The term "alkenyl" refers to a branched or unbranched hydrocarbon having at least one carbon-carbon double bond. The term "$C_{2-7}$alkenyl" refers to a hydrocarbon having two to seven carbon atoms and comprising at least one carbon-carbon double bond. Representative examples of alkenyl are vinyl, prop-1-enyl, allyl, butenyl, isopropenyl or isobutenyl. The term "alkeylene" refers to a divalent alkenyl radical, wherein alkenyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "cycloalkyl" refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$cycloakyl" refers to a cyclic hydrocarbon groups having 3 to 7 carbon atoms. The term "cycloalkylalkyl" refers to an alkyl substituted with cycloalkyl.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-$CH_2CH_2$—. The term also includes substituted arylalkyl moiety.

The term "Heteroaryl" includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, oxa-2,3-diazolyl, oxa-2,4-diazolyl, oxa-2,5-diazolyl, oxa-3,4-diazolyl, thia-2,3-diazolyl, thia-2,4-diazolyl, thia-2,5-diazolyl, thia-3,4-diazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring or on the fused aryl ring. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, thieno[2,3-b] furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a] pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d] pyrimidinyl, pyrazino[2,3-b]pyrazinyl, or pyrimido[4,5-d] pyrimidinyl.

When a heteroaryl moiety is substituted with hydroxy, the invention also pertains to its oxo tautomeric. For example, an oxadiazole substituted with hydroxy also includes oxo-oxadiazole or also known as oxadiazolone. The tautomerisation is represented as follow:

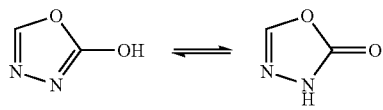 [SMILES: Oc1nnco1 ; O=c1[nH]nco1]

As used herein, the term "heterocyclyl" or "heterocyclo" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "hydroxyalkyl" refers to alkyl groups, as described above, in which the alkyl group is substituted with one or more hydroxy.

The term "halogen" includes fluorine, bromine, chlorine and iodine. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In another embodiment, the heteroatom is nitrogen, oxygen or sulfur.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g. by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C; $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atom may be enriched in $^2$H; or/and one or more carbon atom may be enriched in $^{11}$C, $^{13}$C or $^{14}$C; or/and one or more nitrogen may be enriched in $^{14}$N. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to anyone of the formulae I' and I to VIIC. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds of formulae I' or I to VIIC can generally be prepared by conventional techniques known to those skilled in the art or by processes analogous to those described in the accompanying Examples and Preparations using an appropriate isotopically-enriched reagent in place of the non-enriched reagent previously employed Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds according to anyone of formulae I' and I to VIIC, that contain groups capable of acting as donors and/or acceptors for hydrogen bonds may be capable of forming co-crystals with suitable co-crystal formers. These co-crystals may be prepared from compounds according to anyone of formulae I' and I to VIIC by known co-crystal forming procedures. Such procedures include grinding, heating, co-subliming, co-melting, or contacting in solution compounds according to anyone of formulae I' and I to VIIC with the co-crystal former under crystallization conditions and isolating co-crystals thereby formed. Suitable co-crystal formers include those described in WO 2004/078163. Hence the invention further provides co-crystals comprising a compound according to anyone of formulae I' and I to VIIC.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by neutral endopeptidase EC 3.4.24.11 or (ii) associated with neutral endopeptidase EC 3.4.24.11 activity, or (iii) characterized by abnormal activity of neutral endopeptidase EC 3.4.24.11; or (2) reducing or inhibiting the activity of neutral endopeptidase EC 3.4.24.11; or (3) reducing or inhibiting the expression of neutral endopeptidase EC 3.4.24.11. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of neutral endopeptidase EC 3.4.24.11; or at least partially reducing or inhibiting the expression of neutral endopeptidase EC 3.4.24.11.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

The term "hypertension" refers to a condition where the pressure of blood within the blood vessels is higher than normal as it circulates through the body. When the systolic pressure exceeds 150 mmHg or the diastolic pressure exceeds 90 mmHg for a sustained period of time, damage is done to the body. For example, excessive systolic pressure can rupture blood vessels anywhere, and when it occurs within the brain, a stroke results. Hypertension may also cause thickening and narrowing of the blood vessels which ultimately could lead to atherosclerosis.

The term "type 2 diabetes" including type 2 diabetes associated with hypertension refers to a disease in which the pancreas does not secrete sufficient insulin due to an impairment of pancreatic beta-cell function and/or in which there is to insensitivity to produced insulin (insulin resistance). Typically, the fasting plasma glucose is less than 126 mg/dL, while pre-diabetes is, e.g., a condition which is characterized by one of following conditions: impaired fasting glucose (110-125 mg/dL) and impaired glucose tolerance (fasting glucose levels less than 126 mg/dL and post-prandial glucose level between 140 mg/dL and 199 mg/dL). Type 2 diabetes mellitus can be associated with or without hypertension. Diabetes mellitus occurs frequently, e.g., in African American, Latino/Hispanic American, Native American, Native American, Asian American and Pacific Islanders. Markers of insulin resistance include HbA1C, HOMA IR, measuring collagen fragments, TGF-β in urine, PAI-1 and prorenin.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspects

The compounds of the invention can be synthesized using the methods described in the following schemes, examples, and by using art recognized techniques. All compounds described herein are included in the invention as compounds. Compounds of the invention may be synthesized according to at least one of the methods described in schemes 1-4.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The compounds of the invention according to anyone of formulae I' and I to VIIC can be prepared by the procedure described in the following sections.

Abbreviations:

| | |
|---|---|
| ATP: adenosine 5'-triphosphate | AS: Aldosterone Synthase |
| Alloc: allyloxycarbonyl | BOC: tertiary butyl carboxy |
| BOP: benzotriazole1-yloxy)tris(dimethylamino) phosphonium hexafluorophosphate | BINAP: racemic 2,2'-bis(diphenyl phosphino)-1,1'-binaphthyl |
| br: broad | bs: broad singlet |
| Ac: Acetyl | Atm: atmosphere |
| Aq: aqueous | calcd: calculated |
| Bn: benzyl | Cbz: benzyloxycarbonyl |
| Bu, i-bu and t-Bu: butyl, isobutyl and t-butyl | Pr and i-Pr: propyl and isopropyl |
| CDI: 1,1'-carbonyldiimidazole | COD: 1,5-cyclooctadiene |
| DBU: 1,8-diazabicyclo[5.4.0]undec-7-ene | DCC: 1,3-dicyclohexylcarbodiimide |
| DIAD: diisopropyl azodicarboxylate | DAST: (diethylamino)sulfur trifluoride |
| d: doublet dd: doublet of doublets | DCM: dichloromethane |
| DIEA: diethylisopropylamine | DME: 1,4-dimethoxyethane |
| DMF: N,N-dimethylformamide | DMSO: dimethylsulfoxide |
| DIPEA: N,N-diisopropylethylamine | DMAP: N,N-dimethylaminopyridine |
| Dppb: 1,2-bis(diphenylphosphino)butane | Dppe: 1,2-bis(diphenylphosphino)ethane |
| DAD: diode array detector | DTT: dithiothreitol |
| DPPA: diphenylphosphorylazide | EDCI, EDIC: N-Ethyl-N'-(3-dimethylaminopropyl)carbodiimide hydrochloride |

| | |
|---|---|
| EDTA: ethylenediamine tetraacetic acid | ESI: electrospray ionization |
| Et and EtOAc: ethyl and ethyl acetate | EDC: N-Ethyl-N'-(3-dimethylaminopropyl)carbodiimide hydrochloride |
| HATU: O-(7-azobenzotriazol-1-yl)-1,1,3,3-tetramethyluroniumhexafluorophosphate | HOBt: 1-hydroxy-7-azabenzotriazole |
| HPLC: high pressure liquid chromatography | LC and LCMS: liquid chromatography and liquid chromatography and mass spectrometry |
| H: Hour(s) | HOAt: 1-hydroxy-7-azabezotriazole |
| IR: infrared | LDA: lithium diisopropylamide |
| KHMDS: potassium bis(trimethylsilyl)amide | LHMDS: lithium bis(trimethylsilyl)amide |
| LTA: lead tetraacetate | NHMDS: sodium bis(trimethylsilyl)amide |
| MeOD: methanol-d4 | MeOH: methanol |
| MS: mass spectrometry | m: multiplet |
| min: minutes | m/z: mass to charge ratio |
| Ms: mesyl | Me: methyl |
| M and mM: Molar and millimolar | Mg: milligram |
| n.d.: not determined | NMR: nuclear magnetic resonance |
| ppm: parts per million | Pr and iPr: propyl and isopropyl |
| Ph: Phenyl | Pd/C: Palladium on Carbom |
| PyBOP: benzotriazol-1-yloxy Tripyrrolidinophosphoniumhexafluorophosphate | RT: room temperature |
| PIDA: iodobenzene bis(trifluoroacetate) | PIFA: iodobenzene diacetate |
| PS: polymer supported | RP: reverse phase |
| s: singlet and t: triplet | Ts tosyl |
| TFA: trifluoroacetic acid | THF: tetrahydrofuran |
| Tf: triflate | tBu: tert-butyl |
| TLC: thin layer chromatography | Tris•HCl: aminotris(hydroxymethyl) methane hydrochloride |
| μL, mL and L: microliter, milliliter and liter | TMS: Trimethylsilyl |
| WSC: water soluble carbodiimide (N-Ethyl-N'-(3-dimethylaminopropyl)carbodiimide | UV: ultraviolet |

The compounds of the invention of formula II can be prepared by hydrolysis of intermediates A to C wherein X, X¹, A¹, R¹, R² and n have the definition of Formula I or I', supra; and P¹ and P² are appropriate protecting groups selected from, but not limited to, methyl, ethyl, isopropyl, tert-butyl, methoxybenzyl or benzyl.

Intermediate A

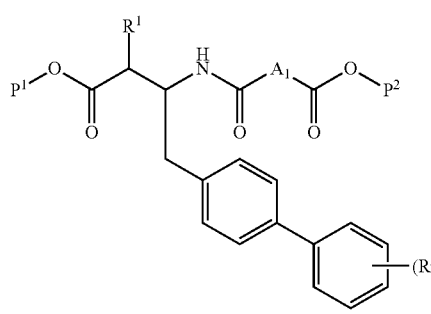

Intermediate B

Intermediate C

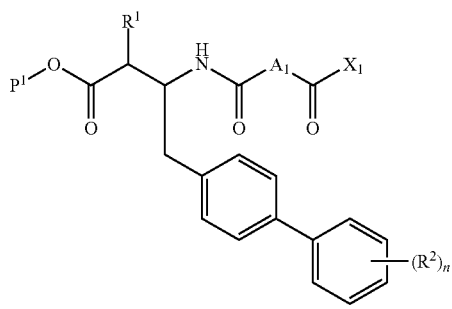

The compounds of the invention of formula III can be prepared by hydrolysis of intermediate D, E or F wherein X, X¹, A¹, R¹, R² and n have the definition of Formula I or I', supra; and P¹ and P² can be appropriate protecting groups selected from, but not limited to, methyl, ethyl, isopropyl, tert-butyl, methoxybenzyl or benzyl.

Intermediate D

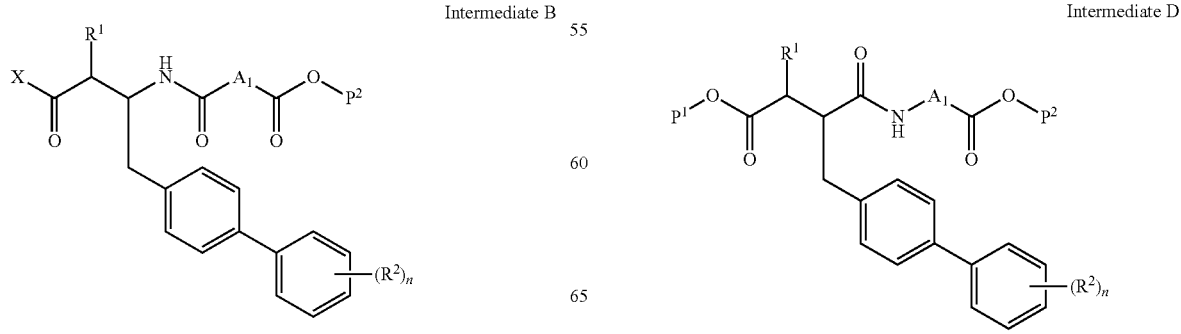

Intermediate E

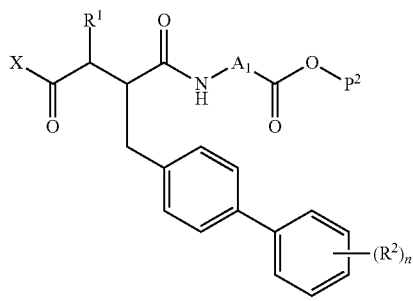

Intermediate H

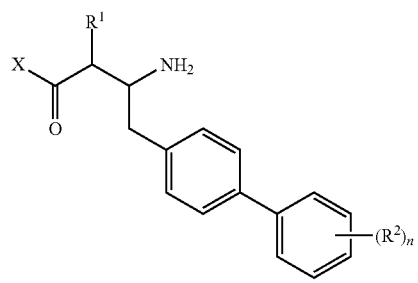

Intermediate F

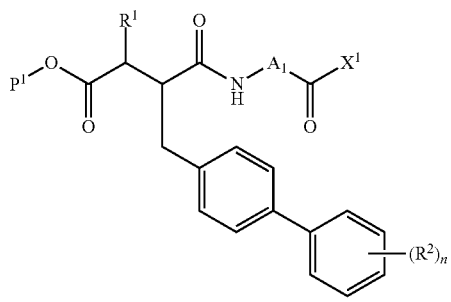

Intermediate I

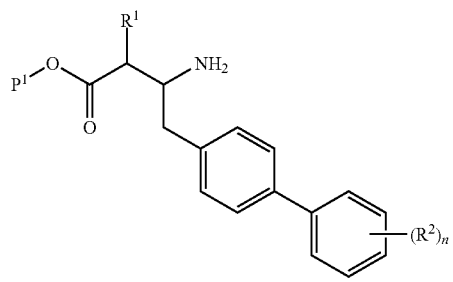

with an intermediate J, K or L wherein $X^1$, $A^1$, $A^2$, $R^4$ and $P^2$ are previously described.

The compounds of the invention of formula VII can be prepared by hydrolysis of intermediate G wherein $A^2$, $R^1$, $R^2$, $R^4$ and n have the definition of Formula I or I', supra; and $P^1$ can be appropriate protecting group selected from, but not limited to, methyl, ethyl, isopropyl, tert-butyl, methoxybenzyl or benzyl.

Intermediate J

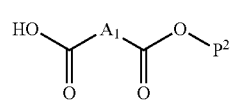

Intermediate K

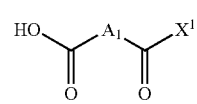

Intermediate G

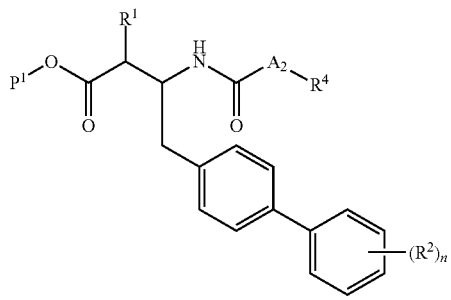

Intermediate L

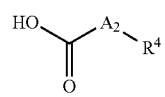

Standard methods can be applied for the hydrolysis of Intermediates A to G using a base selected from, but not limited to, NaOH, KOH or LiOH, or an acid selected from, but not limited to, TFA or HCl. When $P^1$ or $P^2$ is benzyl or methoxybenzyl, preferable method of deprotection is hydrogenation in the presence of a catalyst such as, but not limited to, palladium-on-carbon under hydrogen.

The intermediate A, B, C or G can be prepared using the following process comprising: condensing an intermediate H or I wherein X, $P^1$, $R^1$, $R^2$ and n are as previously described:

Known condensation methods may be applied including, but not limited to, conversion of the intermediate J, K or L to their corresponding acid halide, using reagents such as thionyl chloride or oxalyl chloride, or conversion of intermediate J, K or L to mixed anhydride using reagents such as ClC(O)O-isobutyl or 2,4,6-trichlorobenzoyl chloride followed by reaction of the acid halide or mixed anhydride with the intermediate H or I in a presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine). Alternatively, the intermediate J, K, or L can be coupled with H or I using coupling reagents such as DCC, EDCI, PyBOP or BOP in presence or absence of a reagent such as 1-hydroxybenazotriazole, 1-hydroxy-7-azabenzotriazole or pentafluorophenol.

Intermediate G wherein $R^4$ is a tetrazole can be synthesized according to Scheme 1:

Scheme 1

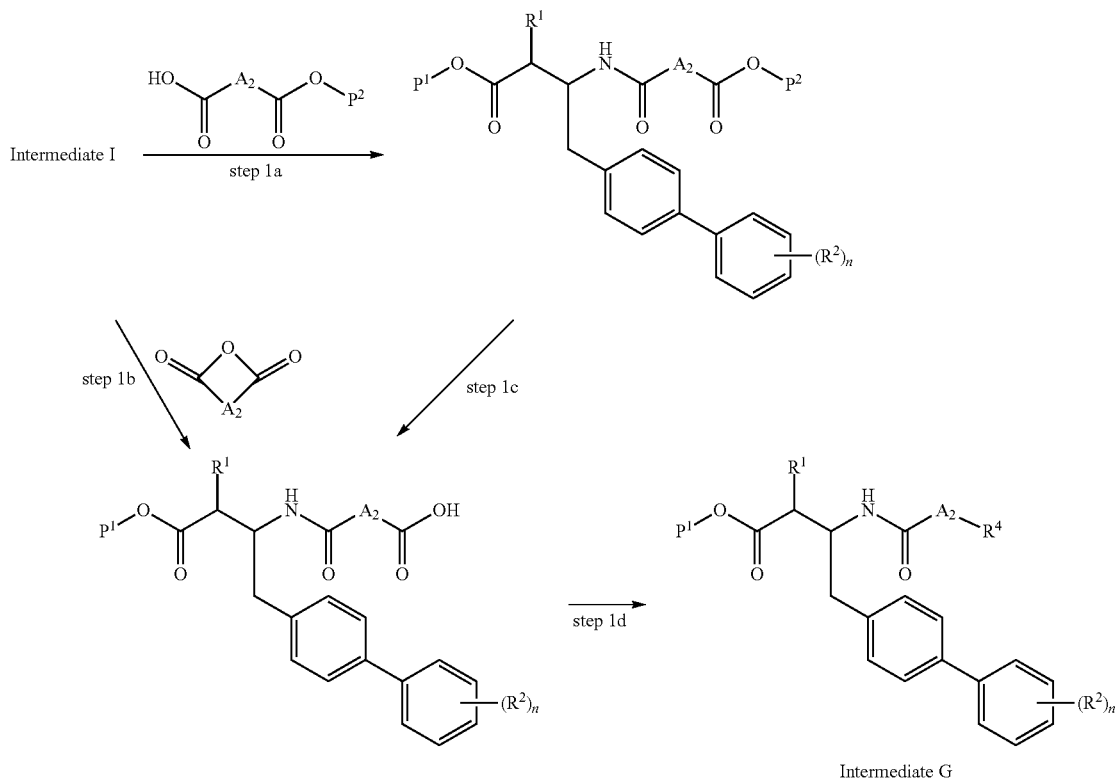

Intermediate G wherein $A^2$, $R^1$, $R^2$, $R^4$, $P^1$, $P^2$ and n are as previously defined above.

In step 1a, intermediate I is reacted with an appropriate carboxylic acid using standard coupling reagents selected from, but not limited to, DCC, EDCI, PyBOP or BOP in presence or absence of a reagent such as 1-hydroxybenazotriazole, 1-hydroxy-7-azabenzotriazole or pentafluorophenol; followed by removal of $P^2$ protecting group in step 1c using a base selected from, but not limited to, NaOH, KOH or LiOH, or an acid selected from, but not limited to, TFA or HCl, or hydrogenation with a catalyst such as, but not limited to, palladium-on-carbon under hydrogen. Alternatively, intermediate I is reacted with an appropriate anhydride in the presence of a base selected from, but not limited to, pyridine, triethylamine or diisopropylethylamine (step 1b); followed by conversion of the carboxylic acid into a tetrazole (step 1b) using similar method as described in *Journal of Medicinal Chemistry* 1998, 41, 1513.

The intermediate D, E or F can be prepared using the following process comprising: condensing an intermediate M wherein $X$, $P^1$, $R^1$, $R^2$ and n are as defined above;

Intermediate M

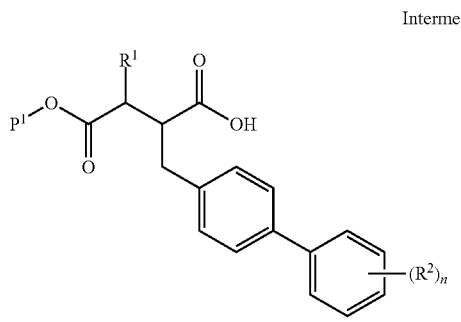

-continued

Intermediate N

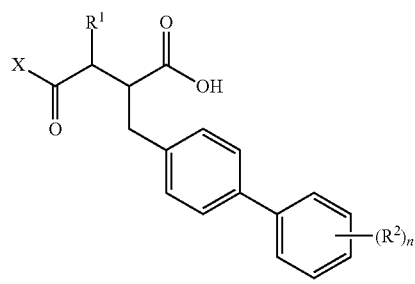

with an intermediate Q or S wherein $X^1$, $A^1$ and $P^2$ have the meaning as defined above.

Intermediate Q

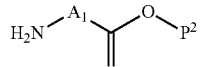

Intermediate S

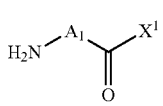

Known condensation methods may be applied including, but not limited to, conversion of the intermediate M or N to acid halide, using reagents such as thionyl chloride or oxalyl chloride, or conversion of intermediate M or N to mixed anhydride using reagents such as ClC(O)O-isobutyl or 2,4,6- trichlorobenzoyl chloride followed by reaction of the acid chloride or mixed anhydride with the intermediate Q or S in a presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine); Alternatively, the intermediate M or N can be coupled with the intermediate Q or S using a reagent such as DCC, EDCI, PyBOP or BOP in presence or absence of a reagent such as 1-hydroxybenazotriazole, 1-hydroxy-7-azabenzotriazole or pentafluorophenol.

The intermediate M or N can be prepared according to the following general procedures described in Scheme 2:

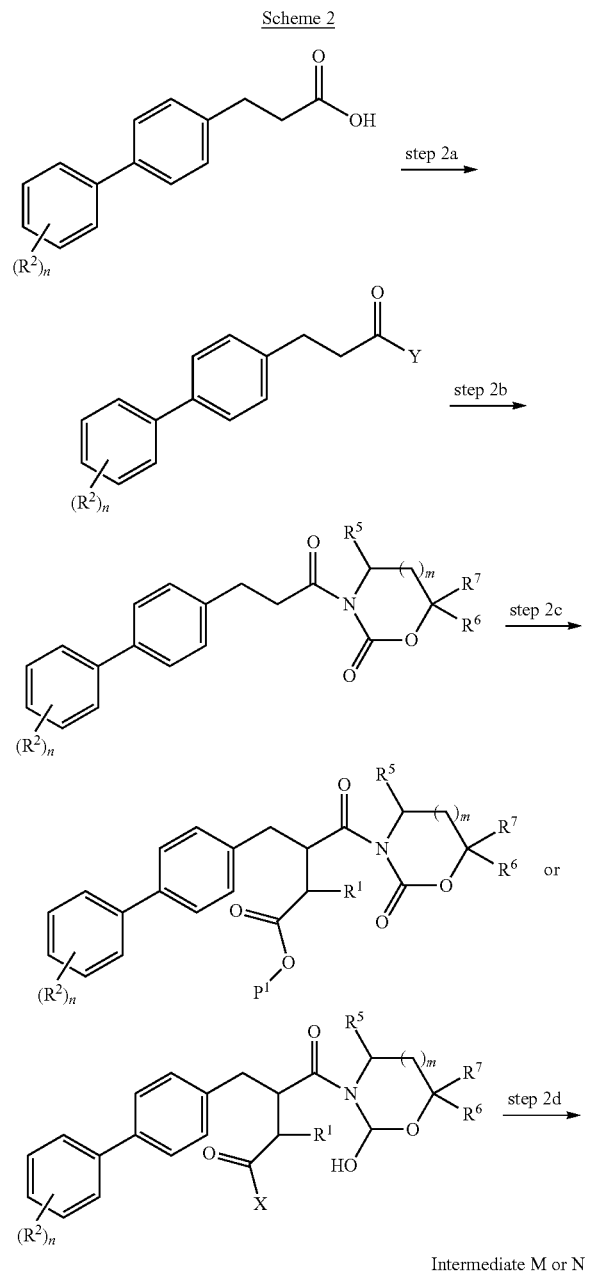

wherein $R^1$, $R^2$, X and n are as defined above and wherein m=0 or 1; $P^1$ is a protecting group selected from, but not limited to, hydrogen, methyl, ethyl, propyl, tert-butyl, methoxymethyl, tert-butyldimethylsilyl, tetrahydrofuranyl, benzyl, allyl or phenyl; $R^5$ is for example hydrogen, methyl, ethyl, isopropyl, benzyl or phenyl; $R^6$ and $R^7$ are independently hydrogen, methyl, ethyl, isopropyl, benzyl or phenyl. Y is selected from, but not limited to, chloro, bromo, iodo, benzotriazoloxy, pyridinium, N,N-dimethylaminopyridinium, pentafluorophenoxy, phenoxy, 4-chlorophenoxy, —OCO$_2$Me, —OCO$_2$Et, tert-butoxycarbonyl or —OCC(O)O-isobutyl.

In step (2a), standard methods can be applied to prepare the corresponding acid halide, such as the use of thionyl chloride, oxalyl chloride; or standard methods to prepare the mixed anhydride or the acyl pyridinium cation can be applied, such as the use of pivaloyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), 2,4,6-trichlorobenzoyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), or ClC(O)O-i-Bu with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine); or standard methods to prepare the activated ester can be applied, such as the use of 1-hydroxybenazotriazole, 1-hydroxy-7-azabenzotriazole or pentafluorophenol in the presence of a coupling reagent (e.g. DCC, EDCI) or BOP.

In step (2b), standard methods to prepare the N-acyloxazolidinones (m=0) can be employed. Illustrative examples of this chemistry are outlined in *Aldrichchimica Acta* 1997, Vol. 30, pp. 3-12 and the references therein; or standard methods to prepare the N-acyloxazinanone (m=1) can be employed. An illustrative example of this chemistry is outlined in *Organic and Biomolecular Chemistry* 2006, Vol. 4, No. 14, pp. 2753-2768.

In step (2c), standard methods for alkylation can be employed. An illustrative example is outlined in *Chemical Reviews* 1996, 96(2), 835-876 and the references therein.

In step (2d), standard methods for cleavage of N-acyloxazolidinone or N-acyloxazinanone can be employed. Illustrative examples of this chemistry are outlined in *Aldrichchimica Acta* 1997, Vo. 30, pp. 3-12 and the references therein.

The intermediate H or I can be prepared according to the following general procedures described in Schemes 3 and 4:

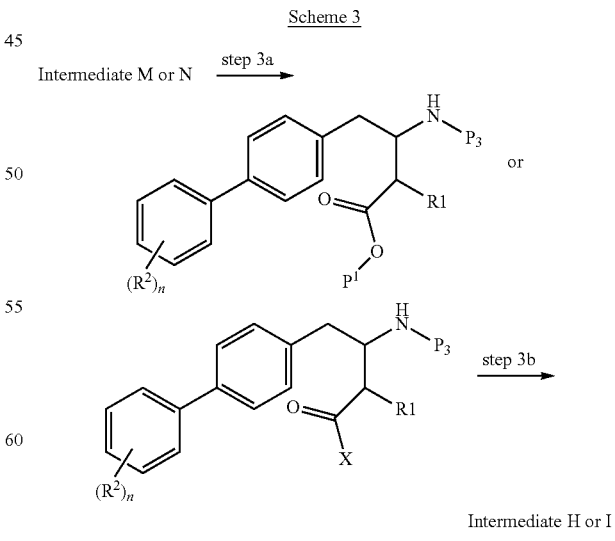

wherein $R^1$, $R^2$, X and n are as defined above and wherein $P_3$ is a protecting group selected from, but not limited to, tert-butyl, benzyl, triphenylphosphynyl, tert-butoxycarbonyl, benzyloxycarbonyl, allyloxycarbonyl, acetyl or trifluoroacetyl.

In step (3a), standard methods for introduction of the amine part can be employed, such as using: either simultaneous treatment with or stepwise treatment via the corresponding acyl azide formation by using thionyl chloride (or $ClCO_2R^8$), $NaN_3$ (or $TMSN_3$) and $R^9OH$ (wherein $R^8$ and $R^9$ are hydrogen, methyl, ethyl, tert-butyl, allyl, benzyl or 4-methoxybenzyl); or either simultaneous treatment with or stepwise treatment via the corresponding acyl azide formation with DPPA and $R^9OH$ (wherein $R^9$ is defined as above); or standard methods for conversion to the corresponding carboxamide followed by treatment with $NH_3$ equivalent and either simultaneous treatment with or stepwise treatment with LTA or hypervalent iodine reagents (e.g. PIDA, PIFA, PhI(OH)OTs, PhIO) and $R^9OH$ (wherein $R^9$ is defined as above); or standard methods for conversion to the corresponding carboxamide and either simultaneous treatment with or stepwise treatment with $Br_2$ and MOH (wherein M is defined herein e.g. Na, K, Ba or Ca); or standard methods for conversion to the corresponding carboxamide and treatment with MOZ or $NaBrO_2$ (wherein Z is defined herein e.g. Cl or Br); or standard methods for conversion to the corresponding carboxamide and treatment with $Pb(OAc)_4$ and $R^9OH$ (wherein $R^9$ is defined as above); or standard methods for conversion to the corresponding hydroxamic acid followed by treatment with $H_2NOH$ or $H_2NOTMS$ and treatment with $Ac_2O$, $Boc_2O$, $R^{10}COCl$, $R^{10}SO_2Cl$, $R^{10}PO_2Cl$ (wherein $R^{10}$ is defined herein e.g. Me, Et, tBu or phenyl), thionyl chloride, EDCl, DCC, or 1-chloro-2,4-dinitrobenzene in the presence or absence of a base (e.g. pyridine, $Na_2CO_3$aq, triethylamine, DIPEA) and treatment with $R^9OH$ in the presence of a base (e.g. DBU, ZOH, DIPEA) (wherein $R^9$ and Z are defined as above).

In step (3b), standard methods for removing $P_3$ protecting groups can be applied, such as base hydrolysis using NaOH, KOH, or LiOH, acid hydrolysis using TFA or HCl, or hydrogenation using palladium-on-carbon under hydrogen.

Scheme 4 describes an alternative synthesis of Intermediate H or I:

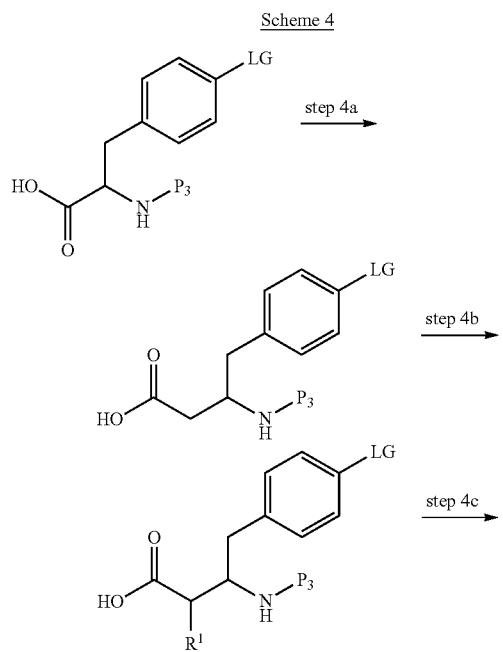

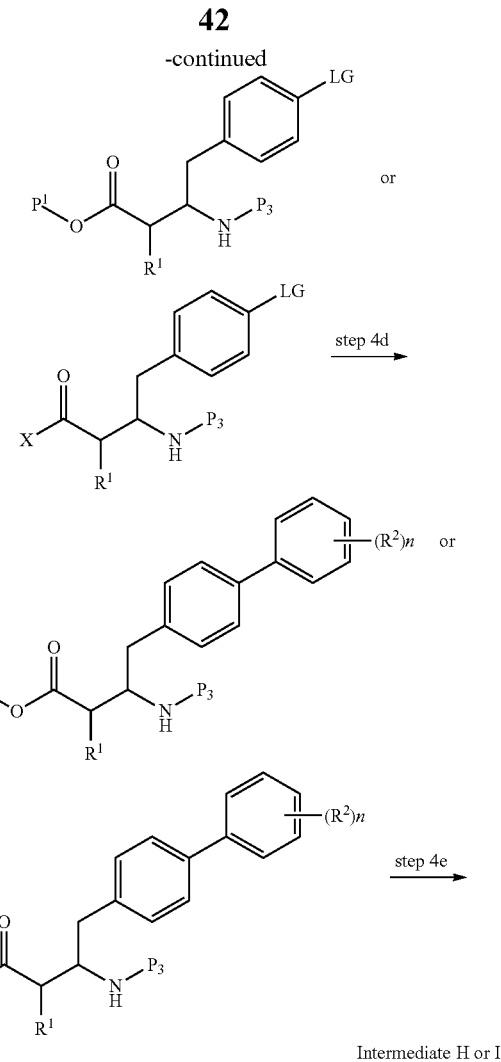

Intermediate H or I wherein LG is a leaving group selected from, but not limited to, Cl, Br, I, OMs, OTs or OTf.

In step (4a), standard methods for Arndt-Eistert homologation can be employed. An illustrative example of this chemistry is outlined in "Enantioselective synthesis of β-amino acids, $2^{nd}$ Edition", John Wiley and Sons, Inc., NJ (2005), either directly or analogously.

In step (4b), standard methods for alkylation can be employed, such as using $R^1LG$ in the presence of a base such as LDA, NHMDS, LHMDS or KHMDS.

In step (4c), standard methods to protect the carboxylic acid can be employed, such as using $TMSCHN_2$ (for methyl ester), $P^1LG$/base (e.g. $K_2CO_3$, $NaHCO_3$, $Cs_2CO_3$ or $K_3PO_4$), thionyl chloride (or oxalyl chloride)/$R^9OH$, DCC (or EDCl)/DMAP/$R^9OH$, BOP/$R^9OK$ (or $R^9ONa$), $(R^{90})_2CHNMe_2$, CDI/DBU/$R^9OH$ wherein $R^9$ has the same meaning as defined above, or isobutylene/$H_2SO_4$ (for tert-butyl ester).

In step (4d), standard methods for Suzuki coupling reaction can be applied, such as using a palladium (or nickel) species [e.g. $Pd(PPh_3)_4$, $PdCl_2(dppf)$, $Pd(OAc)_2$/a phosphine (e.g. $PPh_3$, dppf, $PCy_3$, $P(tBu)_3$, XPhos), Pd/C, $Pd_2(dba)_3$/a phosphine (e.g. $PPh_3$, dppf, $PCy_3$, $P(tBu)_3$, XPhos), $Ni(COD)_2$/a phosphine (or dppe, dppb, $PCy_3$), $Ni(dppf)Cl_2$], a base (e.g. KF, CsF, $K_3PO_4$, $Na_2CO_3$, $K_2CO_3$, $Cs_2CO_3$, NaOH, KOH, NaO-t-Bu, KO-t-Bu), and $(R^2)n$-$PhB(OH)_2$ [or $(R^2)n$-$PhBF_3K$].

In step (4e), standard methods for removing $P_3$ protecting groups can be applied, such as base hydrolysis using NaOH, KOH, or LiOH, acid hydrolysis using TFA or HCl, or hydrogenation using palladium-on-carbon under hydrogen.

Alternatively, the intermediate H or I may be prepared be following the synthetic routes outlined in *Tetrahedron Letters,* 2008, Vol. 49, No. 33, pp. 4977-4980 either directly or analogously and converting the obtained boronic acid into a substituted biphenyl by methods outlined in *Organic Letters,* 2002, Vol. 4, No. 22, pp. 3803-3805.

Alternatively, the intermediate H or I may be prepared be following the synthetic routes outlined in *Tetrahedron: Asymmetry,* 2006, Vol. 17, No. 2, pp. 205-209 either directly or analogously.

Alternatively, the intermediate H or I may be prepared by methods of Mannich reaction. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate H or I may be prepared by enolate addition. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate H or I may be prepared by methods of aza-Michael reaction. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate H or I may be prepared following the synthetic route outlined in Synlett, 2006, No. 4, pp. 539-542, either directly or analogously.

The synthesis of intermediates J, K and L is also described in US patent application Ser. No. 61/324,938 which was filed on Apr. 16, 2010, which application is incorporated herein by reference.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention or a pharmaceutically acceptable salt thereof, and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I' and I to VIIC in free form or in pharmaceutically acceptable salt form, exhibit valuable pharmacological properties, e.g. neutral endopeptidase EC 3.4.24.11 modulating properties, e.g. as indicated in in vitro and in vivo tests as provided in the next sections and are therefore indicated for therapy.

Compounds of the invention, or a pharmaceutically acceptable salt thereof, may be useful in the treatment of an indication selected from: cardiovascular disorders, such hypertension, pulmonary hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, cyclical oedema, Menieres disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, diabetic complications and atherosclerosis, male and female sexual dysfunction.

Thus, as a further embodiment, the present invention provides the use of a compound according to anyone of formulae I' and I to VIIC, or a pharmaceutically acceptable salt thereof. In a further embodiment, the therapy is selected from a disease which is ameliorated by inhibition of neutral endopeptidase EC 3.4.24.11. In another embodiment, the disease is selected from the afore-mentioned list, suitably hypertension, pulmonary hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, type-2 diabetis, and diabetic complications and most suitably cardiovascular disorders, such as hypertension, renal insufficiency including edema and congestive heart failure.

In another embodiment, the invention provides a method of treating a disease which is ameliorated by the inhibition of neutral endopeptidase EC 3.4.24.11 comprising administration of a therapeutically acceptable amount of a compound according to anyone of formulae I', I, IA, II, IIA, III, IIIA, IV, IVA, V, VA, VI, VIA and VII to VIIC, or a pharmaceutically acceptable salt thereof. In a further embodiment, the disease is selected from the afore-mentioned list, suitably hypertension, pulmonary hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, type-2 diabetes, and diabetic complications and most suitably cardiovascular disorders, such as hypertension, renal insufficiency including edema and congestive heart failure.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods and/or by the following in vitro & in vivo methods well-described in the art. See A fluorescence lifetime-based assay for protease inhibitor profiling on human kallikrein 7 Doering K, Meder G, Hinnenberger M, Woelcke J, Mayr L M, Hassiepen U Biomol Screen. 2009 January; 14(1):1-9.

In particular, the in vitro inhibition of recombinant human neutral endopeptidase (NEP, EC 3.4.24.11) can be determined as follows:

Recombinant human neutral endopeptidase (expressed in insect cells and purified using standard methods, final concentration 7 µM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys (PT14)-Arg-Arg-Leu-Trp-OH to a final concentration of 0.7 µM. Substrate hydrolysis leads to an increase fluorescence lifetime (FLT) of PT14 measured by the means of a FLT reader as described by Doering et al. (2009). The effect of the compound on the enzymatic activity was determined after 1 hour (t=60 min) incubation at room temperature. The IC50 values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory efficacy in accordance to Table 1, provided infra.

TABLE 1

Inhibitory Activity of Compounds

| Example # | Human NEP $IC_{50}$ (nM) |
|---|---|
| Example 3-25 | 18 |
| Example 3-26 | 15 |
| Example 3-27 | 15 |
| Example 5-1 | 38 |
| Example 5-4 | 7 |
| Example 5-7 | 4 |
| Example 5-11 | 3 |
| Example 5-12 | 67 |
| Example 5-36 | 42 |
| Example 5-37 | 2.3 |
| Example 5-39 | 0.7 |
| Example 5-46 | 0.5 |
| Example 5-47 | 2.7 |
| Example 5-55 | 0.7 |
| Example 6-1 | 75 |
| Example 9-1 | 56 |
| Example 11-1 | 1.1 |
| Example 11-11 | 0.5 |
| Example 11-14 | 0.07 |
| Example 12-1 | 0.2 |
| Example 14-1 | 0.8 |
| Example 15-1 | 1.2 |

The compound of the present invention may be administered either simultaneously with, or before or after, at least one other therapeutic agent. The compound of the present invention may be administered separately, by the same or different route of administration, or together in the same pharmaceutical composition.

In one embodiment, the invention provides a product comprising a compound according to anyone of formulae I' and I to VIIC, or a pharmaceutically acceptable salt thereof, and at least one other therapeutic agent as a combined preparation for simultaneous, separate or sequential use in therapy. In one embodiment, the therapy is the treatment of a disease or condition associated with neutral endopeptidase EC 3.4.24.11 activity. Products provided as a combined preparation include a composition comprising the compound of formulae I' and I to VIIC and the other therapeutic agent(s) together in the same pharmaceutical composition, or the compound according to anyone of formulae I' and I to VIIC, or a pharmaceutically acceptable salt thereof, and the other therapeutic agent(s) in separate form, e.g. in the form of a kit.

In one embodiment, the invention provides a pharmaceutical composition comprising a compound according to anyone of formulae I' and I to VIIC, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I' and I to VIIC, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention, or a pharmaceutically acceptable salt thereof and the other therapeutic agent may be manufactured and/or formulated by the same or different manufacturers. Moreover, the compound of the invention, or a pharmaceutically acceptable salt thereof, and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound according to anyone of formulae I' and I to VIIC, or a pharmaceutically acceptable salt thereof, in the manufacture of a medicament for treating a disease or condition associated with neutral endopeptidase EC 3.4.24.11 activity, wherein the medicament is prepared for administration with another therapeutic agent. The invention also provides the use of another therapeutic agent in the manufacture of medicament for treating a disease or condition associated with neutral endopeptidase EC 3.4.24.11 activity, wherein the medicament is prepared for administration with a compound according to anyone of formulae I' and I to VIIC, or a pharmaceutically acceptable salt thereof.

The invention also provides a compound according to anyone of formulae I' and I to VIIC, or a pharmaceutically acceptable salt thereof, for use in a method of treating a disease or condition associated with neutral endopeptidase EC 3.4.24.11 activity, wherein the compound according to anyone of formulae I' and I to VIIC, or a pharmaceutically acceptable salt thereof, is prepared for administration with another therapeutic agent. The invention also provides another therapeutic agent for use in a method of treating a disease or condition associated with neutral endopeptidase EC 3.4.24.11 activity, wherein the other therapeutic agent is prepared for administration with a compound according to anyone of formulae I' and I to VIIC, or a pharmaceutically acceptable salt thereof. The invention also provides a compound according to anyone of formulae I' and I to VIIC, or a pharmaceutically acceptable salt thereof, for use in a method of treating a disease or condition associated with neutral endopeptidase EC 3.4.24.11 activity, wherein the compound according to anyone of formulae I' and I to VIIC, or a pharmaceutically acceptable salt thereof, is administered with another therapeutic agent. The invention also provides another therapeutic agent for use in a method of treating a disease or condition associated with neutral endopeptidase EC 3.4.24.11 activity, wherein the other therapeutic agent is administered with a compound according to anyone of formulae I' and I to VIIC, or a pharmaceutically acceptable salt thereof.

The invention also provides the use of a compound according to anyone of formulae I' and I to VIIC, or a pharmaceutically acceptable salt thereof, in the manufacture of a medicament for treating a disease or condition associated with neutral endopeptidase EC 3.4.24.11 activity, wherein the patient has previously (e.g. within 24 hours) been treated with another therapeutic agent. The invention also provides the use of another therapeutic agent in the manufacture of a medicament for treating a disease or condition associated with neutral endopeptidase EC 3.4.24.11 activity, wherein the patient has previously (e.g. within 24 hours) been treated with a compound according to anyone of formulae I' and I to VIIC, or a pharmaceutically acceptable salt thereof.

In one embodiment, the other therapeutic agent is selected from: HMG-Co-A reductase inhibitor, an anigiotensin receptor blocker (ARBs, angiotensin II receptor antagonist), angiotensin converting enzyme (ACE) Inhibitor, a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors (ASI), a CETP inhibitor or a phophodiesterase type 5 (PDE5) inhibitor.

The term "in combination with" a second agent or treatment includes co-administration of the compound of the invention (e.g., a compound of Formulae I' or I-VIIC or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g. a disorder or disease responsive to the inhibition of neutral endopeptidase, such as for example, hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), pulmonary arterial hypertension, renal failure (including edema and salt retension), cyclical oedema, Menieres disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction.

Examples of second agents include HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R[R*(R*)],2S*,3R]]-N[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

(A)

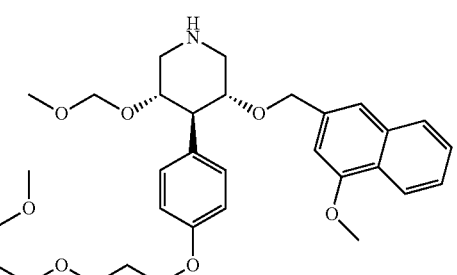

and (B)

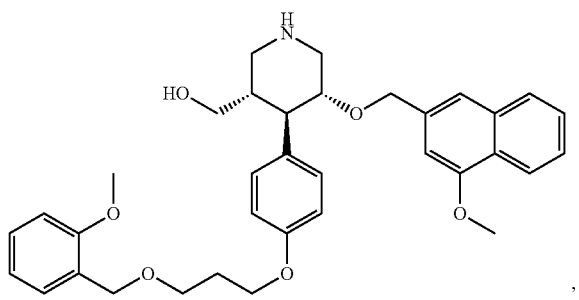

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

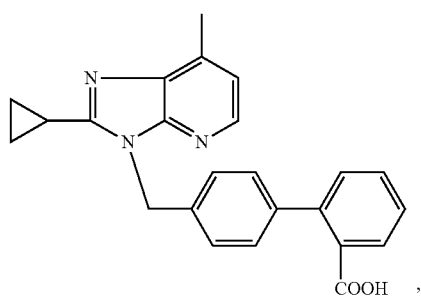 [SMILES: Cc1ccnc2c1nc(C1CC1)n2Cc1ccc(-c2ccccc2C(=O)O)cc1]

the compound with the designation SC-52458 of the following formula

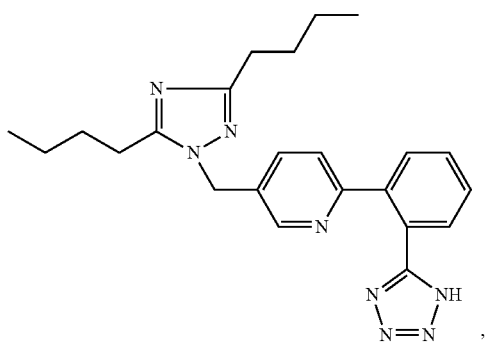 [SMILES: CCCCc1nc(CCCC)n(Cc2ccc(-c3ccccc3-c3nnn[nH]3)nc2)n1]

and the compound with the designation ZD-8731 of the following formula

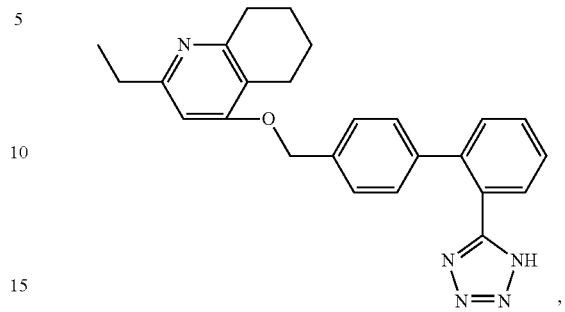

or, in each case, a pharmaceutically acceptable salt thereof.

Preferred $AT_1$-receptor antagonist are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (a g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

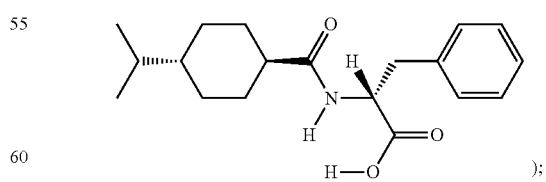

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia,* 28, 1985, 704-707 and in U.S. Pat. No. 5,705,483.

The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37) OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6 Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

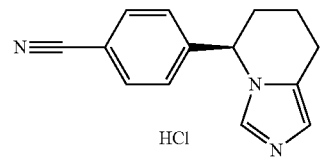

or, if appropriable, a pharmaceutically acceptable salt thereof.

A preferred steroidal aldosterone antagonist is eplerenone (cf. EP 122232 A) of the formula

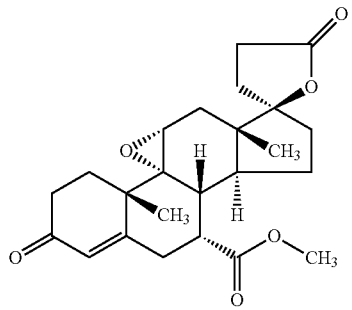

or Spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US2009/0048241 and in PCT applications WO2006/005726, WO2006/128853, WO2006/128851, WO2006/128852, WO2007/065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1 H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.;* 6:1951-1954 (1996), respectively. Furthermore, the CETP inhibitors also include those disclosed in WO2000/017165, WO2005/095409 and WO2005/097806.

A preferred PDE5 inhibitor is Sildenafil.

Second agent of particular interest include Endothelin antagonists, renin inhibitors, angiotensin II receptor antagonists, calcium channel blockers, diuretics, antidiabetic agents such as DPPIV inhibitors, and aldosterone synthase inhibitors.

EXEMPLIFICATION OF THE INVENTION

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the example 5-1 to 15-3 have been found to have $IC_{50}$ values in the range of about 0.01 nM to about 10,000 nM for NEP.

The conditions for measuring the retention times are as follows:

HPLC Condition A:
Column: INERTSIL C8-3, 3 μm×33 mm×3.0 mm at 40° C.
Flow rate: 2 ml/min
Mobile phase: A) 5 mM aqueous $HCOONH_4$, B) MeOH/$CH_3CN$ (1/1, v/v)
Gradient: linear gradient from 5% A to 95% B in 2 min
Detection: DAD-UV at 200-400 nm HPLC Condition B:
Column: INERTSIL C8-3, 3 μm×33 mm×3.0 mm at 40° C.
Flow rate: 2 ml/min
Mobile phase: A) 5 mM aqueous $HCOONH_4$, B) MeOH/$CH_3CN$ (1/1, v/v)
Gradient: linear gradient from 40% A to 95% B in 2 min
Detection: DAD-UV at 200-400 nm HPLC Condition C:
Column: INERTSIL C8-3, 3 μm×33 mm×3.0 mm at 40° C.
Flow rate: 2 ml/min
Mobile phase: A) (5 mM $NH_4^+HCOO_-$)/water, B) MeOH/$CH_3CN$ (1/1, v/v)
Gradient: linear gradient from 5 to 95% B in 2 min
Detection: DAD-UV at 200-400 nm HPLC Condition D:
Column: INERTSIL C8-3, 3 μm×33 mm×3.0 mm at 40° C.
Flow rate: 2 ml/min
Mobile phase: A) 0.1% aqueous Formic acid, B) MeOH/$CH_3CN$ (1/1, v/v)
Gradient: linear gradient from 5% B to 95% B in 2 min
Detection: DAD-UV at 200-400 nm HPLC Condition E:
Column: Inertsil C8-3, 3 μm×33 mm×3.0 mm at 40° C.
Flow rate: 2 ml/min
Mobile phase: A) methanol/acetonitrile (1/1, v/v), B) 5 mM aqueous $HCOONH_4$
Gradient: linear gradient from 40% B to 95% A in 2 min
Detection: UV at 214 nm The relative stereochemistry was determined using two dimensional NMR. Under the reaction condition, it would be unexpected that the stereocenter bearing the bisphenyl-methyl group racemize. Therefore, the absolute stereochemistry was determined based on the relative stereochemistry and the absolute stereochemistry of the stereocenter bearing the bisphenyl-methyl group.

Example 1-1

Synthesis of (R)-4-(1-(biphenyl-4-yl)-4-ethoxy-4-oxobutan-2-ylamino)-4-oxobutanoic acid

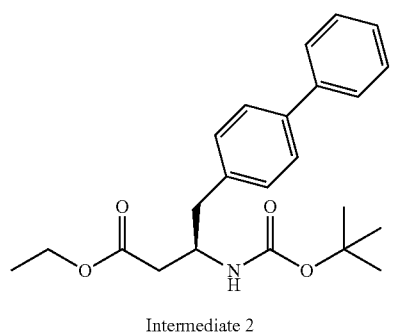

Intermediate 2

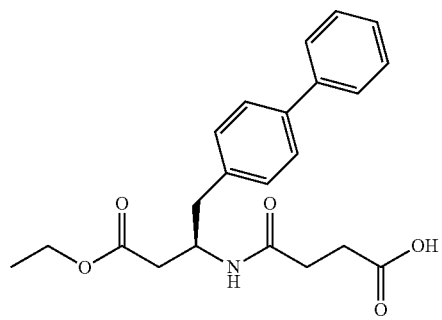

To (R)-ethyl-4-(biphenyl-4-yl)-3-(tert-butoxycarbonylamino)butanoate (230.1 mg, 0.600 mmol) is added a solution of HCl in 1,4-dioxane (3.00 mL, 12.00 mmol) at room temperature. After stirring for 1 hour, the reaction mixture is concentrated under reduced pressure to give (R)-3-amino-4-biphenyl-4-yl-butyric acid ethyl ester hydrochloride. A solution of (R)-3-amino-4-biphenyl-4-yl-butyric acid ethyl ester hydrochloride, succinic anhydride (72.1 mg, 0.720 mmol) and DIPEA (0.126 mL, 0.720 mmol) in dichloromethane (4 mL) is allowed to stir for 1 hour. The reaction is quenched with 10% aqueous citric acid and extracted with dichloromethane. The organic layer is separated and concentrated under reduced pressure. The obtained residue is purified by flash column chromatography on CN-modified silica gel (eluent: heptane/EtOAc=100:0 to 0:100) and by RP-HPLC (SunFire C18, $H_2O$ (0.1% TFA)/$CH_3CN$) to give (R)-4-(1-(biphenyl-4-yl)-4-ethoxy-4-oxobutan-2-ylamino)-4-oxobutanoic acid (148.2 mg). HPLC retention time=1.64 minutes (condition A); MS (m+1)=384.1; 1H NMR (400 MHz, ACETONITRILE-d3) δ ppm 1.21 (t, J=7.07 Hz, 3 H) 2.31-2.39 (m, 2 H) 2.40-2.56 (m, 4 H) 2.77-2.92 (m, 2 H) 4.08 (q, J=7.24 Hz, 2 H) 4.33-4.48 (m, 1 H) 6.62 (d, J=8.34 Hz, 1 H) 7.30 (d, J=8.08 Hz, 2 H) 7.32-7.39 (m, 1 H) 7.41-7.49 (m, 2 H) 7.54-7.60 (m, 2 H) 7.60-7.67 (m, 2 H) 10.02 (br. s., 1 H).

Example 1-2

Synthesis of (R)-4-(1-(3'-chlorobiphenyl-4-yl)-4-ethoxy-4-oxobutan-2-ylamino)-4-oxobutanoic acid

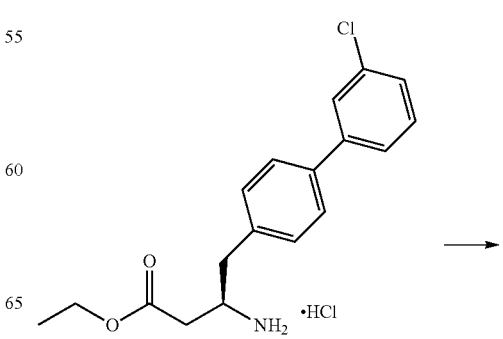

-continued

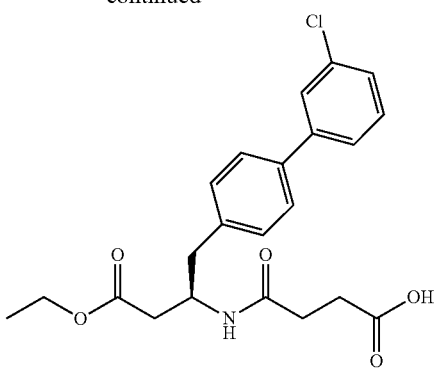

A solution of (R)-ethyl 3-amino-4-(3'-chlorobiphenyl-4-yl)butanoate hydrochloride (400 mg, 1.13 mmol), succinic anhydride (136 mg, 1.36 mmol) and DIPEA (0.237 mL, 1.36 mmol) in dichloromethane (5 mL) is allowed to stir for 2.5 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(3'-chlorobiphenyl-4-yl)-4-ethoxy-4-oxobutan-2-ylamino)-4-oxobutanoic acid (255 mg). HPLC retention time=1.15 minutes (condition B); MS (m+1)=418.0; 1H NMR (400 MHz, CHLOROFORM-d) δ ppm 1.29 (t, J=7.08 Hz, 3 H) 2.46-2.58 (m, 4 H) 2.64-2.67 (m, 2 H) 2.87 (A of ABX, $J_{ab}$=13.6 Hz, $J_{ax}$=7.8 Hz, 1 H) 2.99 (B of ABX, $J_{ab}$=13.6 Hz, $J_{bx}$=6.6 Hz, 1 H) 4.12-4.24 (m, 2 H) 4.47-4.55 (m, 1 H) 6.50 (br d, J=8.8 Hz, 1 H) 7.24-7.37 (m, 4 H) 7.43-7.46 (m, 1 H) 7.48-7.52 (m, 2 H) 7.55-7.56 (m, 1 H).

Chiral HPLC retention time=3.59 min. Column: Daicel CHIRALPAK AD-H (4.6×100 mm); flow rate=1 ml/min.; eluent: EtOH(containing 0.1% TFA)/heptane=4/6.

Following compounds are prepared using similar procedure as described in example 1-2:

| Example # | Product | Starting Material | Condition | HPLC-RT (condition) | MS (M + 1) |
|---|---|---|---|---|---|
| Example 1-3 | (R)-5-(1-(3'-chlorobiphenyl-4-yl)-4-ethoxy-4-oxobutan-2-ylamino)-5-oxopentanoic acid | | glutaric anhydride; DIPEA, DCM, RT | 1.57 min. (A) | 432.1 |
| Example 1-4 | (R)-5-(4-ethoxy-1-(5'-fluoro-2'-methoxybiphenyl-4-yl)-4-oxobutan-2-ylamino)-5-oxopentanoic acid | | glutaric anhydride; DIPEA, DCM, RT | 0.93 min. (B) | 446.3 |

-continued

| Example # | Product | Starting Material | Condition | HPLC-RT (condition) | MS (M + 1) |
|---|---|---|---|---|---|
| Example 1-5 | (R)-5-(1-(5'-chloro-2'-methoxybiphenyl-4-yl)-4-ethoxy-4-oxobutan-2-ylamino)-5-oxopentanoic acid | | glutaric anhydride; DIPEA, DCM, RT | 1.14 min. (B) | 462.5 |
| Example 1-6 | (R)-4-(1-(2'-chloro-5'-fluorobiphenyl-4-yl)-4-ethoxy-4-oxobutan-2-ylamino)-4-oxobutanoic acid | | succinic anhydride; DIPEA, DCM, RT | 0.97 min. (B) | 436.2 |

| Example # | Product | Starting Material | Condition | HPLC-RT (condition) | MS (M + 1) |
|---|---|---|---|---|---|
| Example 1-7 | (R)-4-(4-ethoxy-1-(3'-fluorobiphenyl-4-yl)-4-oxobutan-2-ylamino)-4-oxobutanoic acid | | DIPEA, DCM, RT | 1.23 min. (B) | 402.0 |
| Example 1-8 | (R)-4-(4-(benzyloxy)-1-(3'-chlorobiphenyl-4-yl)-4-oxobutan-2-ylamino)-4-oxobutanoic acid | | DIPEA, DCM, RT | 1.37 min. (B) | 480.2 |

| Example # | Product | Starting Material | Condition | HPLC-RT (condition) | MS (M + 1) |
|---|---|---|---|---|---|
| Example 1-9 | | | Pyridine, RT | 1.32 min. (C) | 490.2 |
| Example 1-10 | | | DIPEA, DCM, RT | 1.52 min. (B) | 506.4 |

Example 1-3: 1H NMR (400 MHz, CHLOROFORM-d) δ ppm 1.29 (t, J=7.2 Hz, 3 H) 1.86-1.97 (m, 2 H) 2.25-2.28 (m, 2 H) 2.34 (t, J=7.0 Hz, 2 H) 2.50 (A of ABX, $J_{ab}$=16.2 Hz, $J_{ax}$=5.6 Hz, 1 H) 2.56 (B of ABX, $J_{ab}$=16.2 Hz, $J_{bx}$=5.1 Hz, 1 H) 2.88 (A of ABX, $J_{ab}$=13.6 Hz, $J_{ax}$=7.8 Hz, 1 H) 2.98 (B of ABX, $J_{ab}$=13.6 Hz, $J_{bx}$=7.1 Hz, 1 H) 4.12-4.23 (m, 2 H) 4.50-4.58 (m, 1 H) 6.32 (br d, J=8.8 Hz, 1 H) 7.25-7.37 (m, 4 H) 7.43-7.46 (m, 1 H) 7.49-7.52 (m, 2 H) 7.55-7.56 (m, 1 H).

Example 1-4: 1H NMR (400 MHz, CHLOROFORM-d) δ ppm 1.29 (t, J=7.1 Hz, 3 H) 1.86-1.97 (m, 2 H) 2.25-2.28 (m, 2 H) 2.34 (t, J=7.0 Hz, 2 H) 2.54 (A of ABX, $J_{ab}$=16.1 Hz, $J_{ax}$=5.6 Hz, 1 H) 2.58 (B of ABX, $J_{ab}$=16.1 Hz, $J_{bx}$=5.2 Hz, 1 H) 2.88 (A of ABX, $J_{ab}$=13.5 Hz, $J_{ax}$=7.6 Hz, 1 H) 2.97 (B of ABX, $J_{ab}$=13.5 Hz, $J_{bx}$=7.0 Hz, 1 H) 3.78 (s, 3 H) 4.12-4.23 (m, 2 H) 4.50-4.59 (m, 1 H) 6.34 (br d, J=8.6 Hz, 1 H) 6.88-6.91 (m, 1 H) 6.96-7.04 (m, 2 H) 7.23 (d, J=8.3 Hz, 2 H) 7.44-7.47 (m, 2 H).

Example 1-5: 1H NMR (400 MHz, CHLOROFORM-d) δ ppm 1.29 (t, J=7.1 Hz, 3 H) 1.86-1.97 (m, 2 H) 2.25-2.36 (m, 4 H) 2.49-2.61 (m, 2 H) 2.88 (A of ABX, $J_{ab}$=13.6 Hz, $J_{ax}$=7.6 Hz, 1 H) 2.97 (B of ABX, $J_{ab}$=13.6 Hz, $J_{bx}$=6.8 Hz, 1 H) 3.79 (s, 3 H) 4.12-4.23 (m, 2 H) 4.50-4.59 (m, 1 H) 6.34-6.36 (m, 1 H) 6.89 (d, J=8.6 Hz, 1 H) 7.21-7.28 (m, 3 H) 7.43 (d, J=8.1 Hz, 2 H).

Example 1-6: 1H NMR (400 MHz, CHLOROFORM-d) δ ppm 1.29 (t, J=7.1 Hz, 3 H) 2.47-2.67 (m, 6 H) 2.89 (A of ABX, $J_{ab}$=13.7 Hz, $J_{ax}$=7.8 Hz, 1 H) 3.00 (B of ABX, $J_{ab}$=13.7 Hz, $J_{bx}$=6.7 Hz, 1 H) 4.12-4.24 (m, 2 H) 4.49-4.57 (m, 1 H) 6.51 (br d, J=8.6 Hz, 1 H) 6.97-7.07 (m, 2 H) 7.24-7.26 (m, 2 H) 7.36-7.43 (m, 3 H).

Example 1-7: 1H NMR (400 MHz, DMSO-$d_6$) δ ppm 1.16 (t, J=7.1 Hz, 3 H) 2.23-2.27 (m, 2 H) 2.34-2.38 (m, 2 H) 2.40-2.47 (m, 2 H) 2.77 (d, J=6.6 Hz, 2 H) 3.99-4.06 (m, 2 H) 4.21-4.30 (m, 1 H) 7.14-7.19 (m, 1 H) 7.29 (d, J=8.4 Hz, 2 H) 7.46-7.52 (m, 3 H) 7.63 (d, J=8.4 Hz, 2 H) 7.91 (d, J=8.3 Hz, 1 H) 12.04 (s, 1 H).

Example 1-8: 1H NMR (400 MHz, CHLOROFORM-d) δ ppm 2.41-2.45 (m, 2 H) 2.50-2.64 (m, 4 H) 2.81-2.87 (m, 1 H) 2.95-3.00 (m, 1 H) 4.49-4.56 (m, 1 H) 5.12 (A of AB, J=12.1 Hz, 1 H) 5.18 (B of AB, J=12.1 Hz, 1 H) 6.39 (d, J=8.1 Hz, 1 H) 7.18-7.54 (m, 13 H).

Example 1-9: 1H NMR (400 MHz, DMSO-$d_6$): 1H NMR (400 MHz, DMSO-$d_6$): δ ppm 1.22-1.25 (t, J=7.07 Hz, 3H), 2.61-2.63 (m, 2H), 2.91 (d, J=7.07 Hz, 2H), 4.09 (q, J=7.07 Hz, 2H), 4.52-4.59 (m, 1H), 7.32-7.34 (m, 3H), 7.04 (t, J=7.83 Hz, 1H), 7.52-7.56 (m, 3H), 7.59 (t, J=2.02 Hz, 1H).

Example 1-10: 1H NMR (400 MHz, CHLOROFORM-d) δ ppm 2.03-2.13 (m, 2 H), 2.44 (t, J=6.3 Hz, 2 H), 2.64 (t, J=6.6 Hz, 2 H), 2.70 (dd, J=16.2, 5.6 Hz, 1 H), 2.78 (dd, J=16.2, 5.1 Hz, 1 H), 2.83-2.98 (m, 5 H), 3.04 (dd, J=13.9, 6.8 Hz, 1 H), 4.57-4.69 (m, 1 H), 6.51 (d, J=8.8 Hz, 1 H), 6.79 (dd, J=8.1, 2.3 Hz, 1 H), 6.90 (d, J=1.8 Hz, 1 H), 7.18 (d, J=8.1 Hz, 1 H), 7.26-7.31 (m, 3 H), 7.34 (t, J=7.7 Hz, 1 H), 7.43 (dt, J=7.3, 1.5 Hz, 1 H), 7.49 (d, J=8.1 Hz, 2 H), 7.54 (t, J=1.8 Hz, 1 H), 9.34 (br. s., 1 H).

Example 1-11

Synthesis of (R)-4-(1-(2',5'-dichlorobiphenyl-4-yl)-4-ethoxy-4-oxobutan-2-ylamino)-4-oxobutanoic acid

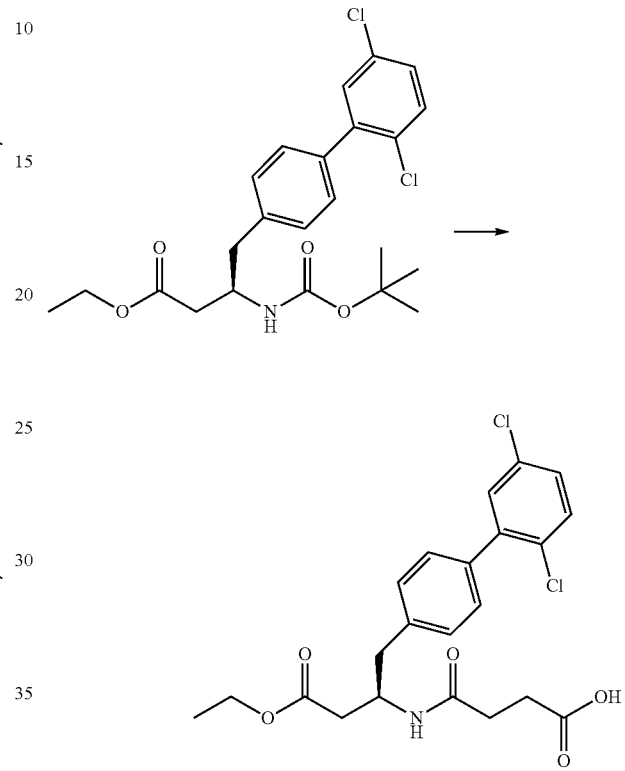

To (R)-ethyl 3-(tert-butoxycarbonylamino)-4-(2',5'-dichlorobiphenyl-4-yl)butanoate (1.09 g, 2.33 mmol) is added a solution of 4 M HCl in 1,4-dioxane (5.81 mL, 23.3 mmol) at room temperature. After stirring for 2 hours, the reaction mixture is concentrated under reduced pressure to give (R)-ethyl 3-amino-4-(2',5'-dichlorobiphenyl-4-yl)butanoate hydrochloride. Next, a solution of the product, succinic anhydride (280 mg, 2.80 mmol) and DIPEA (0.489 mL, 2.80 mmol) in dichloromethane (15 mL) is allowed to stir for 2 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(2',5'-dichlorobiphenyl-4-yl)-4-ethoxy-4-oxobutan-2-ylamino)-4-oxobutanoic acid (553 mg) as a white solid; HPLC retention time=1.02 minutes (condition B); MS (m+1)=452.14; 1H NMR (400 MHz, CHLOROFORM-d) δ ppm 1.29 (t, J=7.2 Hz, 3 H) 2.47-2.67 (m, 6 H) 2.89 (A of ABX, $J_{ab}$=13.7 Hz, $J_{ax}$=7.8 Hz, 1 H) 3.00 (B of ABX, $J_{ab}$=13.7 Hz, $J_{bx}$=6.7 Hz, 1 H) 4.12-4.24 (m, 2 H) 4.49-4.57 (m, 1 H) 6.53 (br d, J=8.8 Hz, 1 H) 7.23-7.26 (m, 3 H) 7.32-7.40 (m, 4 H).

Following compounds are prepared using similar procedure as described in example 1-11:

| Example | Product |
|---|---|
| Example 1-12 | 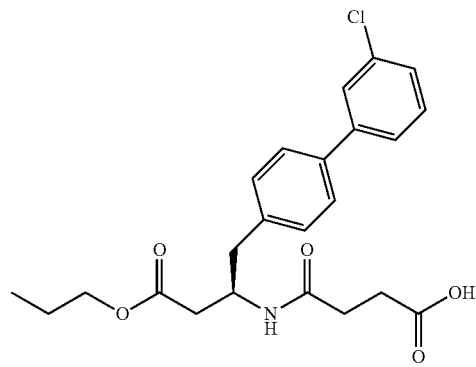<br>(R)-3-(3-Carboxy-propionxylamino)-4-(3'-chloro-biphenyl-4-yl)-butyric acid propyl ester |
| Example 1-13 | 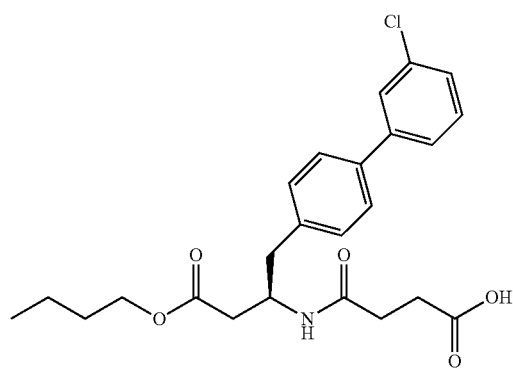<br>(R)-3-(3-Carboxy-propionylamino)-4-(3'-chloro-biphenyl-4-yl)-butyric acid butyl ester |
| Example 1-14 | 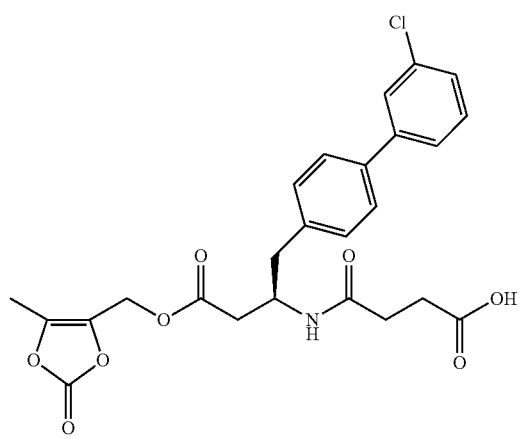<br>(R)-3-(3-Carboxy-propionylamino)-4-(3'-chloro-biphenyl-4-yl)-butyric acid 5-methyl-2-oxo-[1,3]dioxol-4-yl methyl ester |

Example 1-15
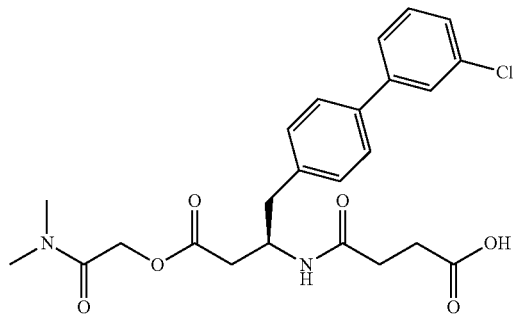
(R)-3-(3-Carboxy-
propionylamino)-4-(3'-
chloro-biphenyl-4-yl)-
butyric acid
dimethylcarbamoyl-
methyl ester
Example 1-16
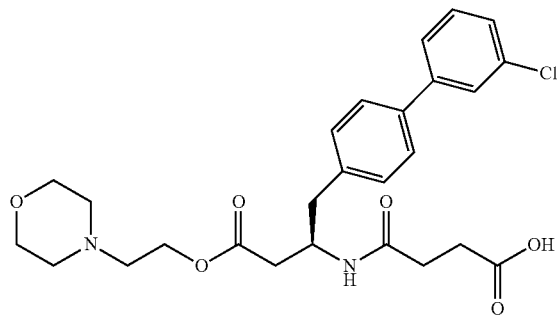
(R)-3-(3-Carboxy-
propionylamino)-4-(3'-
chloro-biphenyl-4-yl)-
butyric acid 2-
morpholin-4-yl-ethyl
ester
| Example | Srating Material | HPLC-RT (condition) | MS (M + 1) |
|---|---|---|---|
| Example 1-12 | 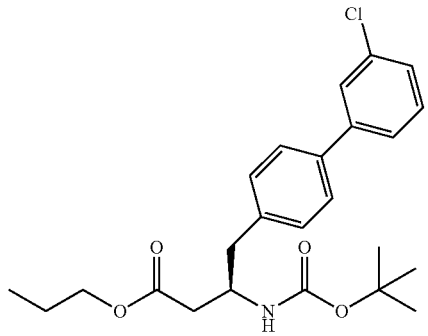 [SMILES: CCCOC(=O)C[C@@H](Cc1ccc(-c2cccc(Cl)c2)cc1)NC(=O)OC(C)(C)C] | 1.24 min. (B) | 432.3 |

| Example 1-13 | 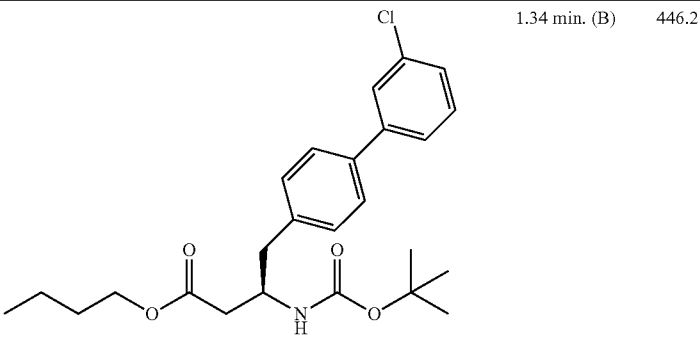 | 1.34 min. (B) | 446.2 |
| Example 1-14 | 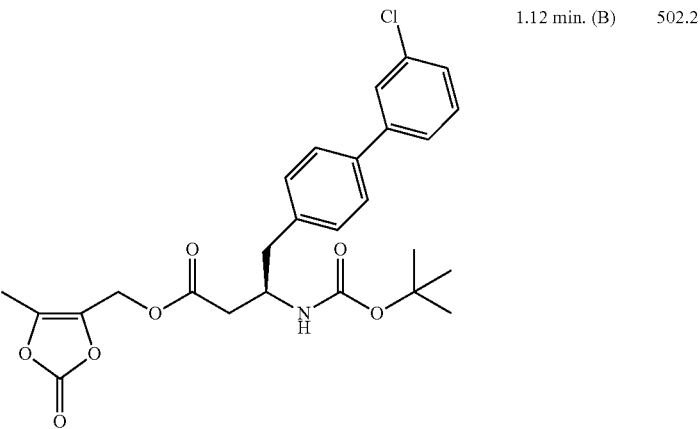 | 1.12 min. (B) | 502.2 |
| Example 1-15 | 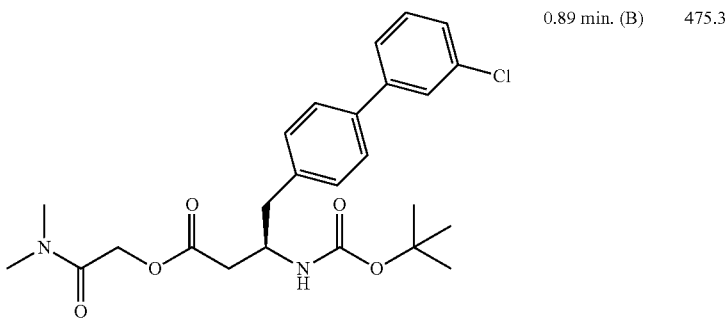 | 0.89 min. (B) | 475.3 |
| Example 1-16 | 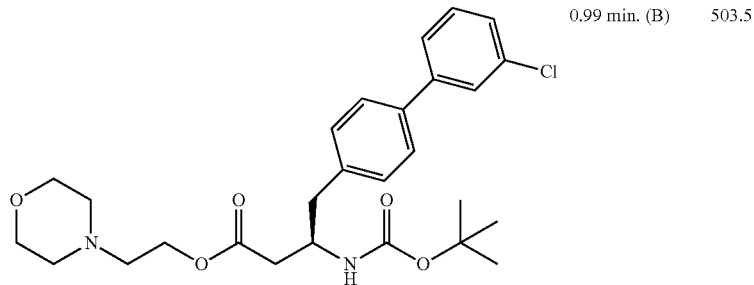 | 0.99 min. (B) | 503.5 |
Example 1-12: 1H NMR (400 MHz, DMSO-d$_6$) δ ppm 0.87 (t, J=7.5 Hz, 3 H), 1.49-1.61 (m, 2 H), 2.22-2.29 (m, 2 H), 2.32-2.39 (m, 2 H), 2.45 (dd, J=6.9, 3.4 Hz, 2 H), 2.78 (d, J=6.6 Hz, 2 H), 3.94 (t, J=6.6 Hz, 2 H), 4.21-4.33 (m, 1 H), 7.29 (d, J=8.3 Hz, 2 H), 7.37-7.42 (m, 1 H), 7.47 (t, J=7.8 Hz, 1 H), 7.58-7.65 (m, 3 H), 7.69 (t, J=1.9 Hz, 1 H), 7.92 (d, J=8.3 Hz, 1 H).
Example 1-13: 1H NMR (400 MHz, CHLOROFORM-d) δ ppm 0.94 (t, J=7.3 Hz, 3 H), 1.32-1.44 (m, 2 H), 1.56-1.67 (m, 2 H), 2.43-2.59 (m, 4 H), 2.65 (t, J=6.4 Hz, 2 H), 2.85 (dd, J=13.6, 8.1 Hz, 1 H), 2.99 (dd, J=13.6, 6.6 Hz, 1 H), 4.03-4.18 (m, 2 H), 4.43-4.56 (m, 1 H), 6.57 (d, J=8.6 Hz, 1 H), 7.25 (d, J=8.3 Hz, 2 H), 7.28-7.32 (m, 1 H), 7.35 (t, J=7.7 Hz, 1 H), 7.41-7.46 (m, 2 H), 7.48 (d, J=8.1 Hz, 2 H), 7.55 (t, J=1.8 Hz, 1 H).
Example 1-14: 1H NMR (400 MHz, CHLOROFORM-d) δ ppm 2.17 (s, 3 H), 2.44 (t, J=6.2 Hz, 2 H), 2.48-2.57 (m, 1 H), 2.57-2.73 (m, 3 H), 2.87 (dd, J=13.6, 7.6 Hz, 1 H), 2.98 (dd, J=13.9, 7.1 Hz, 1 H), 4.47-4.58 (m, 1 H), 4.84 (s, 2 H), 6.32 (d, J=8.6 Hz, 1 H), 7.23 (d, J=8.1 Hz, 2 H), 7.30 (d, 1 H), 7.35 (t, J=7.7 Hz, 1 H), 7.44 (d, J=7.3 Hz, 1 H), 7.49 (d, J=8.1 Hz, 2 H), 7.54 (s, 1 H).

Example 1-15: 1H NMR (400 MHz, CHLOROFORM-d) δ ppm 2.48-2.59 (m, 3 H), 2.61-2.71 (m, 3 H), 2.91-3.06 (m, 8 H), 4.53-4.63 (m, 1 H), 4.67 (d, J=14.7 Hz, 1 H), 5.03 (d, J=14.7 Hz, 1 H), 7.30 (dt, J=7.8, 1.8 Hz, 1 H), 7.32-7.38 (m, 3 H), 7.45 (dt, J=7.6, 1.5 Hz, 1 H), 7.50 (d, J=8.1 Hz, 2 H), 7.55 (t, J=1.8 Hz, 1 H), 8.08 (d, J=9.3 Hz, 1 H).

Example 1-16: 1H NMR (400 MHz, DMSO-d$_6$) δ ppm 2.20-2.32 (m, 2 H), 2.32-2.41 (m, 2 H), 2.42-2.50 (m, 1 H), 2.57 (dd, J=15.4, 5.6 Hz, 1 H), 2.80 (d, J=36.1 Hz, 2 H), 3.15 (br. s., 2 H), 3.31-3.50 (m, 4 H), 3.52-4.05 (m, 4 H), 4.25-4.40 (m, 3 H), 7.31 (d, J=8.3 Hz, 2 H), 7.39-7.43 (m, 1 H), 7.48 (t, J=7.8 Hz, 1 H), 7.60-7.67 (m, 3 H), 7.70 (t, J=1.8 Hz, 1 H), 8.02 (d, J=8.6 Hz, 1 H), 10.06 (br. s., 1 H), 12.17 (br. s., 1 H).

Example 1-17

Synthesis of (R)-4-(1-(5'-chloro-2'-fluorobiphenyl-4-yl)-4-ethoxy-4-oxobutan-2-ylamino)-4-oxobutanoic acid

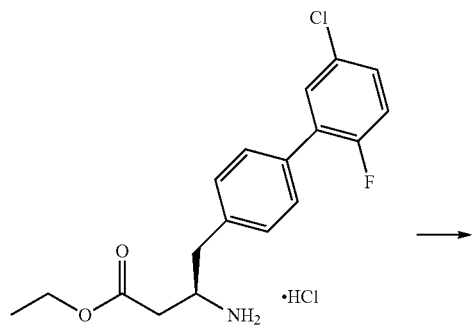

A solution of (R)-ethyl 3-amino-4-(5'-chloro-2'-fluorobiphenyl-4-yl)butanoate hydrochloride (293 mg, 0.777 mmol), succinic anhydride (93 mg, 0.932 mmol) and DIPEA (0.204 mL, 1.165 mmol) in dichloromethane (4 mL) is allowed to stir for 1.5 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(5'-chloro-2'-fluorobiphenyl-4-yl)-4-ethoxy-4-oxobutan-2-ylamino)-4-oxobutanoic acid (294 mg). HPLC retention time=1.03 minutes (condition B); MS (m+1)=436.2; 1H NMR (400 MHz, CHLOROFORM-d) δ ppm 1.28 (t, J=7.07 Hz, 3 H) 2.46-2.58 (m, 4 H) 2.64-2.68 (m, 2 H) 2.87 (A of ABX, J$_{ab}$=13.64 Hz, J$_{ax}$=7.83 Hz, 1 H) 2.99 (B of ABX, J$_{ab}$=13.64 Hz, J$_{bx}$=6.57 Hz, 1 H) 4.11-4.22 (m, 2 H) 4.47-4.56 (m, 1 H) 6.60 (br d, J=8.59 Hz, 1 H) 7.05-7.10 (m, 1 H) 7.23-7.27 (m, 3 H) 7.39-7.41 (m, 1 H) 7.44-7.46 (m, 2 H).

Following compounds are prepared using similar procedure as described in example 1-17:

| Example # | Product | Starting Material |
|---|---|---|
| Example 1-18 | (2S,3R)-3-(3-Carboxy-propionylamino)-4-(3'-chloro-biphenyl-4-yl)-2-hydroxy-butyric acid methyl ester | |

| | | |
|---|---|---|
| | 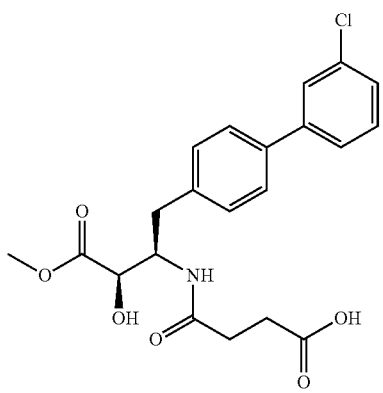<br>(2S,3R)-3-(3-Carboxy-propionylamino)-4-(3′-chloro-biphenyl-4-yl)-2-hydroxy-butyric acid methyl ester | 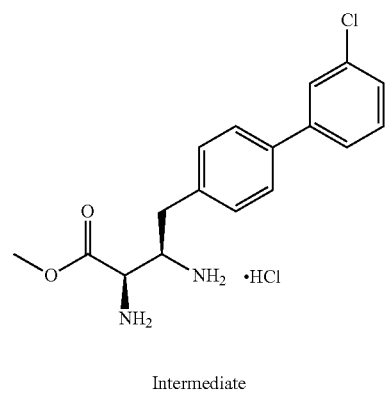<br>Intermediate 50 |
| Example 1-19 | 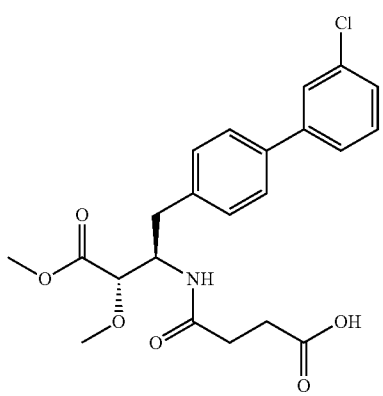<br>(2S,3R)-3-(3-Carboxy-propionylamino)-4-(3′-chloro-biphenyl-4-yl)-2-methoxy-butyric acid methyl ester | 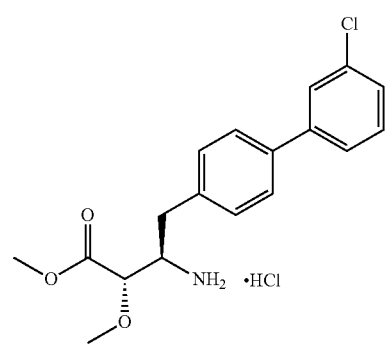 [SMILES: COC(=O)[C@@H](OC)[C@H](N)Cc1ccc(-c2cccc(Cl)c2)cc1 ; Cl] |
| | 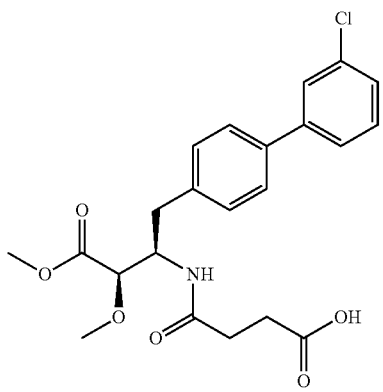<br>(2S,3R)-3-(3-Carboxy-propionylamino)-4-(3′-chloro-biphenyl-4-yl)-2-methoxy-butyric acid methyl ester | 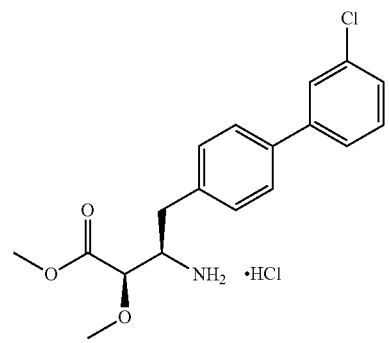<br>Intermediate 51 |

| | | |
|---|---|---|
| Example 1-20 | 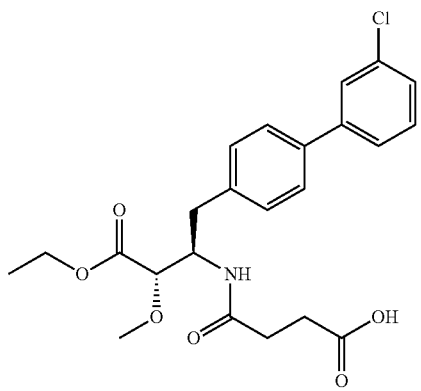<br>(2S,3R)-3-(3-Carboxy-propionylamino)-4-(3'-chloro-biphenyl-4-yl)-2-methoxy-butyric acid ethyl ester | 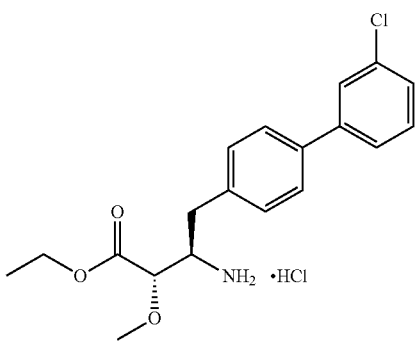 [SMILES: CCOC(=O)[C@@H](OC)[C@H](N)Cc1ccc(-c2cccc(Cl)c2)cc1 ; Cl] |
| | 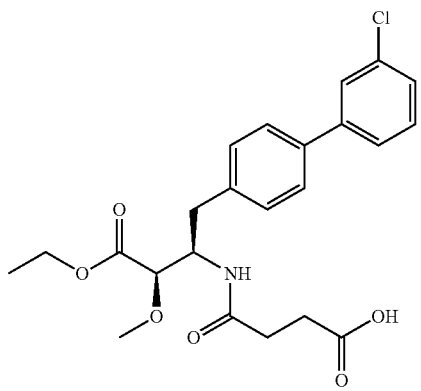<br>(2S,3R)-3-(3-Carboxy-propionylamino)-4-(3'-chloro-biphenyl-4-yl)-2-methoxy-butyric acid ethyl ester | 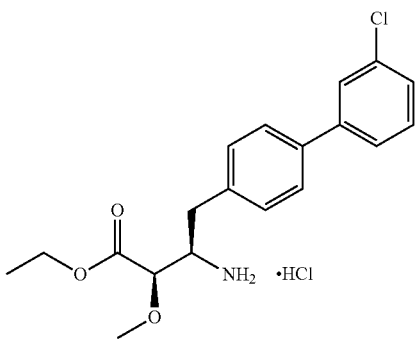<br>Intermediate 52 |
| Example 1-21 | 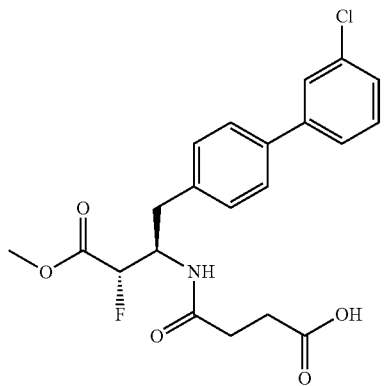<br>(2S,3R)-3-(3-Carboxy-propionylamino)-4-(3'-chloro-biphenyl-4-yl)-2-fluoro-butyric acid methyl ester | 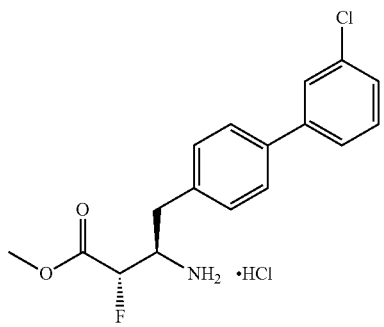 [SMILES: COC(=O)[C@@H](F)[C@H](N)Cc1ccc(-c2cccc(Cl)c2)cc1 ; Cl] |

| | | |
|---|---|---|
| | 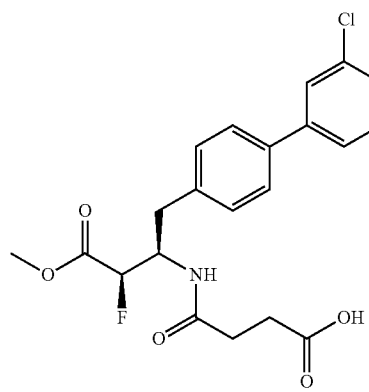<br><br>(2S,3R)-3-(3-Carboxy-propionylamino)-4-(3'-chloro-biphenyl-4-yl)-2-fluoro-butyric acid meth ester | 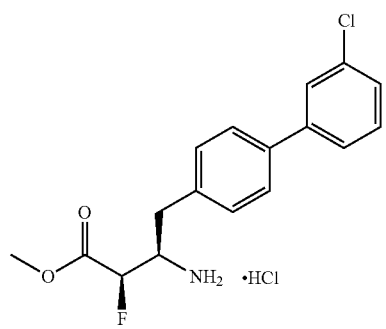<br><br>Intermediate 53 |
| Example 1-22 | 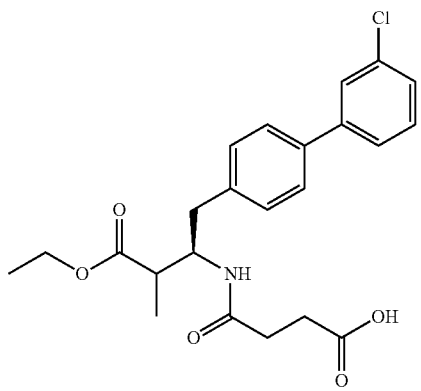<br><br>(R)-3-(3-Carboxy-propionylamino)-4-(3'-chloro-biphenyl-4-yl)-2-methyl-butyric acid ethyl ester | 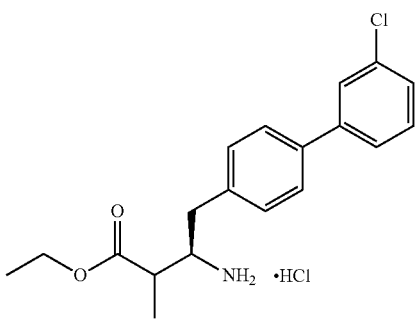<br><br>New intermediate 54 |
| Example 1-23 | 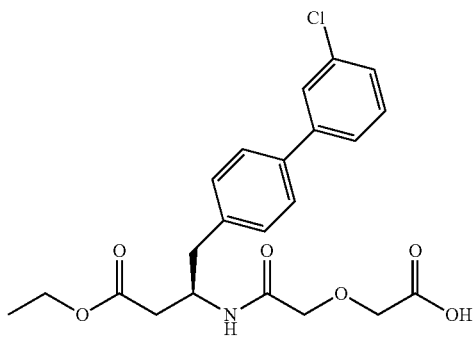<br><br>(R)-3-(2-Carboxymethoxy-acetylamino)-4-(3'-chloro-biphenyl-4-yl)-butyric acid ethyl ester | 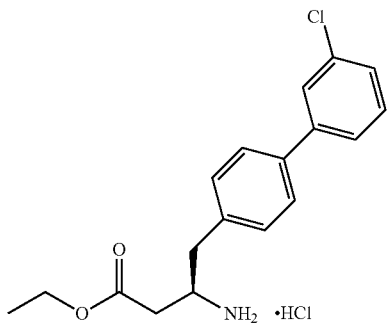 [SMILES: CCOC(=O)C[C@H](N)Cc1ccc(-c2cccc(Cl)c2)cc1 ; Cl] |

-continued
| Example # | Condition | HPLC-RT (condition) | MS (M + 1) |
|---|---|---|---|
| Example 1-18 | 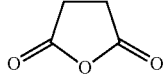 Et₃N, DCM | 1.29 min. (A) | 420.0 |
| Example 1-19 | 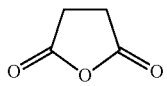 DIPEA, DCM | 1.21 min. (A) | 434.2 |
| Example 1-20 | 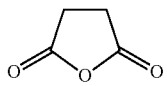 DIPEA, DCM | 1.57 min. (A) | 448.3 |
| Example 1-21 | 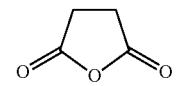 Et₃N, DCM | 0.83 min. (B) | 422.1 |
| Example 1-22 | 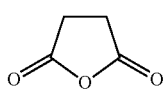 Et₃N, DCM | 0.98 min. (B) | 432 |
| Example 1-23 | 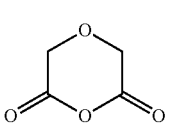 Et₃N, DCM | 0.75 min. (B) | 434 |

Example 1-20: 1H NMR (400 MHz, CDCl$_3$) δ ppm 1.15 (t, J=7.07 Hz, 3 H), 2.24-2.34 (m, 4 H), 2.74 (dd, J=8.59, 13.39 Hz), 2.88 (dd, J=6.32, 13.39 Hz), 3.34 (s, 3H), 3.75 (d, J=2.78 Hz, 1 H), 4.04 (dd, J=7.07, 13.89 Hz, 2 H), 4.33-4.43 (m, 1 H), 7.31 (d, J=8.08 Hz, 2 H), 7.38-7.43 (m, 1 H), 7.48 (t, J=7.83 Hz, 1 H), 7.63 (d, J=3.34 Hz), 7.71 (t, J=1.77 Hz, 1 H), 7.95 (d, J=9.35 Hz, 1 H).

Example 2-1

Synthesis of (R)-3-(3-carboxy-propionylamino)-4-(4'-fluoro-biphenyl-4-yl)-butyric acid ethyl ester

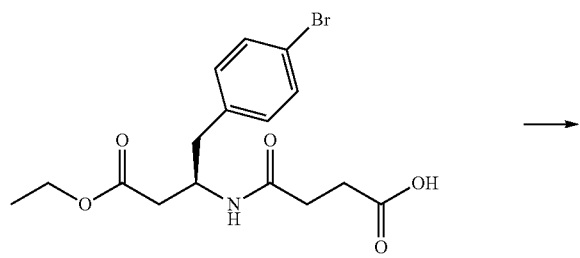

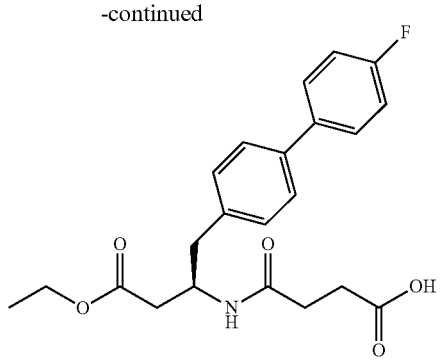

A mixture of (R)-4-(1-(4-bromophenyl)-4-ethoxy-4-oxobutan-2-ylamino)-4-oxobutanoic acid (50 mg, 0.129 mmol), 4-fluorophenylboronic acid (27.2 mg, 0.194 mmol), Pd(Ph$_3$P)$_4$ (14.96 mg, 0.013 mmol) and aqueous Na$_2$CO$_3$ (0.129 mL, 0.259 mmol) in toluene (1 mL) is allowed to stir at 95° C. under nitrogen. After stirring for 13 hours, the solution is cooled to ambient temperature and then quenched with aqueous 1 M HCl. The products are extracted with ethyl acetate, washed with brine, dried over MgSO$_4$, filtered, and concentrated under reduced pressure. The obtained residue is purified by RP-HPLC (SunFire C18, H$_2$O (0.1% TFA)/CH$_3$CN), and then lyophilized to give (R)-3-(3-carboxy-propionylamino)-4-(4'-fluoro-biphenyl-4-yl)-butyric acid ethyl ester (29.2 mg). HPLC retention time=1.26 minutes (condition B); MS (m+1)=402.2; 1H NMR (400 MHz, CHLOROFORM-d) δ ppm 1.29 (t, J=7 Hz, 3 H) 2.47-2.67 (m, 6 H) 2.87 (A of ABX, J$_{ab}$=13.7 Hz, J$_{ax}$=7.9 Hz, 1 H) 2.99 (B of ABX, J$_{ab}$=13.7 Hz, J$_{bx}$=6.6 Hz, 1 H) 4.12-4.23 (m, 2 H) 4.47-4.55 (m, 1 H) 6.52 (br d, J=8.6 Hz, 1 H) 7.08-7.14 (m, 2 H) 7.24 (d, J=8.4 Hz, 2 H) 7.46-7.55 (m, 4 H).

Following compounds are prepared using similar procedure as described in example 2-1:

| Example | Product | Reagent | HPLC-RT (condition) | MS (M + 1) |
|---|---|---|---|---|
| Example 2-2 | | Pd(PPh$_3$)$_4$, p-chlorophenylboronic acid, aq. 2M Na$_2$CO$_3$, (R)-4-(1-(4-bromophenyl)-4-ethoxy-4-oxobutan-2-ylamino)-4-oxobutanoic acid | 1.49 min. (B) | 418.1 |
| Example 2-3 | | Pd(PPh$_3$)$_4$, m-fluorophenylboronic acid, aq. 2M Na$_2$CO$_3$, (R)-ethyl 4-(4-bromophenyl)-3-(4-methoxy-4-oxobutanamido)butanoate. | 1.24 min. (B) | 416.1 |

-continued

| Example | Product | Reagent | HPLC-RT (condition) | MS (M + 1) |
|---|---|---|---|---|
| Example 2-4 | 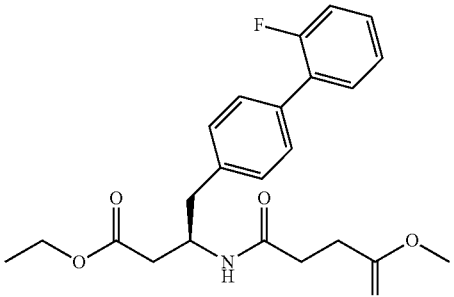 | Pd(PPh$_3$)$_4$, o-fluorophenylboronic acid, aq. 2M Na$_2$CO$_3$, (R)-ethyl 4-(4-bromophenyl)-3-(4-methoxy-4-oxobutanamido)butanoate. | 1.25 min. (B) | 416.1 |
| Example 2-5 | 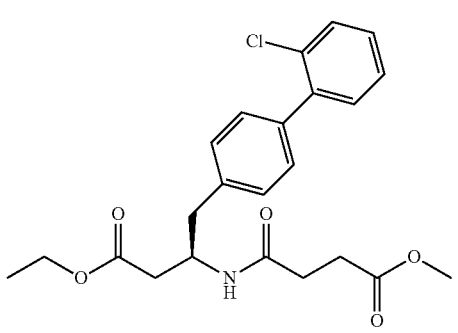 | Pd(PPh$_3$)$_4$, o-chlorophenylboronic acid, aq. 2M Na2CO3, (R)-ethyl 4-(4-bromophenyl)-3-(4-methoxy-4-oxobutanmido)butanoate. | 1.33 min. (B) | 432.1 |
| Example 2-6 | 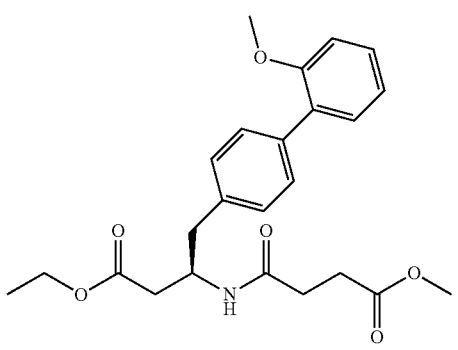 [SMILES: CCOC(=O)C[C@@H](Cc1ccc(-c2ccccc2OC)cc1)NC(=O)CCC(=O)OC] | Pd(PPh$_3$)$_4$, o-methoxyphenylboronic acid, aq. 2M Na$_2$CO$_3$, (R)-ethyl 4-(4-bromophenyl)-3-(4-methoxy-4-oxobutanamido)butanoate. | 1.22 min. (B) | 428.2 |
| Example 2-7 | 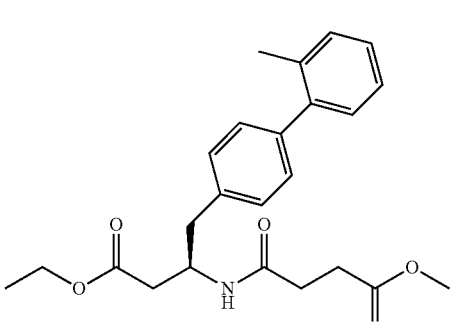 | Pd(PPh$_3$)$_4$, o-tolylboronic acid, aq. 2M Na$_2$CO$_3$, (R)-ethyl 4-(4-bromophenyl)-3-(4-methoxy-4-oxobutanamido)butanoate. | 1.35 min. (B) | 412.2 |

-continued

| Example | Product | Reagent | HPLC-RT (condition) | MS (M + 1) |
|---|---|---|---|---|
| Example 2-8 | | Pd(PPh3)4, 2-chloro-5-fluorophenylboronic acid, aq. 2M Na2CO3, (R)-ethyl 4-(4-bromophenyl)-3-(4-methoxy-4-oxobutanamido) butanoate. | 1.28 min. (B) | 450.3 |
| Example 2-9 | | Pd(PPh3)4, m-tolylboronic acid, aq. 2M Na2CO3, (R)-ethyl 4-(4-bromophenyl)-3-(4-methoxy-4-oxobutanamido) butanoate. | 1.28 min. (B) | 412.2 |
| Example 2-10 | | Pd(PPh3)4, 3,5-difluorophenylboronic acid, aq. 2M Na2CO3, (R)-ethyl 4-(4-bromophenyl)-3-(4-methoxy-4-oxobutanamido) butanoate. | 1.23 min. (B) | 434.2 |
| Example 2-11 | | Pd(PPh3)4, 3-ethylphenylboronic acid, aq. 2M Na2CO3, (R)-ethyl 4-(4-bromophenyl)-3-(4-methoxy-4-oxobutanamido) butanoate. | 1.40 min. (B) | 426.3 |

-continued

| Example | Product | Reagent | HPLC-RT (condition) | MS (M + 1) |
|---|---|---|---|---|
| Example 2-12 | | Pd(PPh3)4, 3-nitrophenylboronic acid, aq. 2M Na2CO3, (R)-ethyl 4-(4-bromophenyl)-3-(4-methoxy-4-oxobutanamido) butanoate. | 1.16 min. (B) | 443.2 |
| Example 2-13 | | 3-(trifluoromethyl)phenyl boronic acid, aq. 2M Na2CO3, (R)-ethyl 4-(4-bromophenyl)-3-(4-methoxy-4-oxobutanamido) butanoate. | 1.39 min. (G) | 466.1 |
| Example 2-14 | | Pd(PPh3)4, 3-methoxyphenylboronic acid, aq. 2M Na2CO3, (R)-ethyl 4-(4-bromophenyl)-3-(4-methoxy-4-oxobutanamido) butanoate. | 1.19 min. (G) | 428.2 |
| Example 2-15 | | Pd(PPh3)4, 3-cyanobenzeneboronic acid, aq. 2M Na2CO3, (R)-ethyl 4-(4-bromophenyl)-3-(4-methoxy-4-oxobutanamido) butanoate. | 0.98 min. (B) | 423.2 |

-continued

| Example | Product | Reagent | HPLC-RT (condition) | MS (M + 1) |
|---|---|---|---|---|
| Example 2-16 | (3-chloro-5-fluoro-biphenyl structure with ethyl ester and methyl ester amide) | Pd(PPh3)4, 3-chloro-5-fluorophenylboronic acid, aq. 2M Na2CO3, (R)-ethyl 4-(4-bromophenyl)-3-(4-methoxy-4-oxobutanamido)butanoate. | 1.45 min. (B) | 450.1 |
| Example 2-17 | (2-trifluoromethyl-biphenyl structure) | Pd(PPh3)4, 2-(trifluoromethyl)phenylboronic acid, aq. 2M Na2CO3, (R)-ethyl 4-4-bromophenyl)-3-(4-methoxy-4-oxobutanamido)butanoate. | 1.37 min. (B) | 466.1 |
| Example 2-18 | (2-cyano-biphenyl structure) | Pd(PPh3)4, 2-cyanophenylboronic acid, aq. 2M Na2CO3, (R)-ethyl 4-(4-bromophenyl)-3-(4-methoxy-4-oxobutanamido)butanoate. | 1.01 min. (B) | 423.2 |
| Example 2-19 | (2-ethoxy-biphenyl structure) | Pd(PPh3)4, 2-ethoxyphenylboronic acid, aq. 2M Na2CO3, (R)-ethyl 4-(4-bromophenyl)-3-(4-methoxy-4-oxobutanamido)butanoate. | 1.29 min. (B) | 442.2 |

| Example | Product | Reagent | HPLC-RT (condition) | MS (M + 1) |
|---|---|---|---|---|
| Example 2-20 | (structure shown) | PdCl2(dppf)·CH2Cl2 complex, phenyl-d5-boronic acid, aq. 2M Na2CO3, (R)-tert-butyl 4-(1-(4-bromophenyl)-4-ethoxy-4-oxobutan-2-ylamino)-4-oxobutanoate | 1.42 min. (B) | 445.2 |

Example 2-2: 1H NMR (400 MHz, CHLOROFORM-d) δ ppm 1.29 (t, J=7 Hz, 3 H) 2.47-2.67 (m, 6 H) 2.84-3.02 (m, 2 H) 4.12-4.24 (m, 2 H) 4.47-4.55 (m, 1 H) 6.52 (br d, J=9.3 Hz, 1 H) 7.24-7.26 (m, 2 H) 7.39-7.41 (m, 2 H) 7.48-7.51 (m, 4 H).

Example 2-3: 1H NMR (400 MHz, CHLOROFORM-d) δ ppm 1.29 (t, J=7 Hz, 3 H) 2.43-2.65 (m, 6 H) 2.84-3.02 (m, 2 H) 3.67 (s, 3 H) 4.12-4.23 (m, 2 H) 4.47-4.55 (m, 1 H) 6.30 (br d, J=8.6 Hz, 1 H) 7.00-7.05 (m, 1 H) 7.26-7.29 (m, 3 H) 7.34-7.41 (m, 2 H) 7.51 (d, J=8.3 Hz, 2 H).

Example 2-4: 1H NMR (400 MHz, CHLOROFORM-d) δ ppm 1.28 (t, J=7 Hz, 3 H) 2.44-2.65 (m, 6 H) 2.85-3.02 (m, 2 H) 3.67 (s, 3 H) 4.11-4.23 (m, 2 H) 4.48-4.56 (m, 1 H) 6.30 (br d, J=9.6 Hz, 1 H) 7.11-7.22 (m, 2 H) 7.25-7.33 (m, 3 H) 7.40-7.45 (m, 1 H) 7.48-7.50 (m, 2 H).

Example 2-5: 1H NMR (400 MHz, CHLOROFORM-d) δ ppm 1.29 (t, J=7.2 Hz, 3 H) 2.44-2.65 (m, 6 H) 2.86-3.02 (m, 2 H) 3.68 (s, 3 H) 4.12-4.23 (m, 2 H) 4.49-4.57 (m, 1 H) 6.31 (br d, J=8.8 Hz, 1 H) 7.24-7.34 (m, 5 H) 7.37-7.39 (m, 2 H) 7.45-7.47 (m, 1 H).

Example 2-6: 1H NMR (400 MHz, CHLOROFORM-d) δ ppm 1.28 (t, J=7 Hz, 3 H) 2.44-2.66 (m, 6 H) 2.84-3.01 (m, 2 H) 3.68 (s, 3 H) 3.81 (s, 3 H) 4.11-4.23 (m, 2 H) 4.48-4.56 (m, 1 H) 6.26 (br d, J=8.8 Hz, 1 H) 6.97-7.04 (m, 2 H) 7.22 (d, J=8.1 Hz, 2 H) 7.29-7.33 (m, 2 H) 7.46-7.48 (m, 2 H).

Example 2-7: 1H NMR (400 MHz, CHLOROFORM-d) δ ppm 1.29 (t, J=7.1 Hz, 3 H) 2.26 (s, 3 H) 2.44-2.69 (m, 6 H) 2.85-3.01 (m, 2 H) 3.68 (s, 3 H) 4.12-4.23 (m, 2 H) 4.48-4.57 (m, 1 H) 6.30 (br d, J=8.6 Hz, 1 H) 7.21-7.26 (m, 8 H).

Example 2-8: 1H NMR (400 MHz, CHLOROFORM-d) δ ppm 1.29 (t, J=7.2 Hz, 3 H) 2.44-2.69 (m, 6 H) 2.86-3.03 (m, 2 H) 3.68 (s, 3 H) 4.12-4.23 (m, 2 H) 4.48-4.57 (m, 1 H) 6.31 (br d, J=8.8 Hz, 1 H) 6.90-7.01 (m, 1 H) 7.05-7.08 (m, 1 H) 7.25-7.27 (m, 2 H) 7.36-7.43 (m, 3 H).

Example 2-9: 1H NMR (400 MHz, CHLOROFORM-d) δ ppm 1.28 (t, J=7.2 Hz, 3 H) 2.41-2.65 (m, 9 H) 2.84-3.00 (m, 2 H) 3.67 (s, 3 H) 4.11-4.23 (m, 2 H) 4.47-4.55 (m, 1 H) 6.29 (br d, J=8.9 Hz, 1 H) 7.16-7.39 (m, 6 H) 7.50-7.53 (m, 2 H).

Example 2-10: 1H NMR (400 MHz, CHLOROFORM-d) δ ppm 1.29 (t, J=7.2 Hz, 3 H) 2.43-2.65 (m, 6 H) 2.84-3.02 (m, 2 H) 3.67 (s, 3 H) 4.12-4.23 (m, 2 H) 4.46-4.55 (m, 1 H) 6.33 (br d, J=8.8 Hz, 1 H) 6.76-6.80 (m, 1 H) 7.06-7.12 (m, 2 H) 7.26-7.27 (m, 2 H) 7.48 (d, J=8.0 Hz, 2 H).

Example 2-11: 1H NMR (400 MHz, CHLOROFORM-d) δ ppm 1.27-1.30 (m, 6 H) 2.44-2.57 (m, 4 H) 2.62-2.74 (m, 4 H) 2.84-3.00 (m, 2 H) 3.67 (s, 3 H) 4.13-4.23 (m, 2 H) 4.47-4.55 (m, 1 H) 6.30 (br d, J=7.6 Hz, 1 H) 7.17-7.26 (m, 3 H) 7.33-7.41 (m, 3 H) 7.52 (d, J=7.8 Hz, 2 H).

Example 2-12: 1H NMR (400 MHz, CHLOROFORM-d) δ ppm 1.30 (t, J=7.1 Hz, 3 H) 2.41-2.65 (m, 6 H) 2.67-2.92 (m, 1 H) 3.00-3.05 (m, 1 H) 3.68 (s, 3 H) 4.14-4.22 (m, 2 H) 4.48-4.56 (m, 1 H) 6.33 (br d, J=8.6 Hz, 1 H) 7.32 (d, J=8.3 Hz, 2 H) 7.56-7.62 (m, 3 H) 7.89-7.91 (m, 1 H) 8.18-8.20 (m, 1 H) 8.44 (t, J=8.0 Hz, 1 H).

Example 2-13: 1H NMR (400 MHz, CHLOROFORM-d) δ ppm 1.29 (t, J=7.2 Hz, 3 H) 2.44-2.65 (m, 6 H) 2.86-2.91 (m, 1 H) 2.98-3.03 (m, 1 H) 3.67 (s, 3 H) 4.13-4.22 (m, 2 H) 4.47-4.56 (m, 1 H) 6.33 (br d, J=8.8 Hz, 1 H) 7.29 (d, J=8.2 Hz, 2 H) 7.53 (d, J=8.2 Hz, 2 H) 7.56-7.60 (m, 2 H) 7.75 (d, J=7.6 Hz, 1 H) 7.81 (s, 1 H).

Example 2-14: 1H NMR (400 MHz, CHLOROFORM-d) δ ppm 1.28 (t, J=7.2 Hz, 3 H) 2.43-2.65 (m, 6 H) 2.84-2.89 (m, 1 H) 2.96-3.01 (m, 1 H) 3.67 (s, 3 H) 3.86 (s, 3 H) 4.11-4.23 (m, 2 H) 4.47-4.55 (m, 1 H) 6.30 (br d, J=8.8 Hz, 1 H) 6.87-6.90 (m, 1 H) 7.10-7.11 (m, 1 H) 7.15-7.17 (m, 1 H) 7.24-7.26 (m, 2 H) 7.34 (t, J=7.8 Hz, 2 H) 7.51-7.53 (m, 2 H).

Example 2-15: 1H NMR (400 MHz, CHLOROFORM-d) δ ppm 1.29 (t, J=7.1 Hz, 3 H) 2.43-2.58 (m, 4 H) 2.61-2.65 (m, 2 H) 2.84-2.91 (m, 1 H) 2.98-3.03 (m, 1 H) 3.68 (s, 3 H) 4.12-4.24 (m, 2 H) 4.47-4.55 (m, 1 H) 6.34 (br d, J=8.8 Hz, 1 H) 7.30 (d, J=8.1 Hz, 2 H) 7.50 (d, J=8.1 Hz, 2 H) 7.51-7.63 (m, 2 H) 7.78-7.81 (m, 1 H) 7.85 (br s, 1 H).

Example 2-16: 1H NMR (400 MHz, CHLOROFORM-d) δ ppm 1.29 (t, J=7.1 Hz, 3 H) 2.43-2.57 (m, 4 H) 2.61-2.64 (m, 2 H) 2.87 (A of ABX, $J_{ab}$=13.6 Hz, $J_{ax}$=7.8 Hz, 1 H) 2.99 (B of ABX, $J_{ab}$=13.6 Hz, $J_{bx}$=6.6 Hz, 1 H) 3.68 (s, 3 H) 4.12-4.23 (m, 2 H) 4.46-4.55 (m, 1 H) 6.34 (br d, J=8.6 Hz, 1 H) 7.05 (dt, J=8.3 and 2.0 Hz, 1 H) 7.15-7.19 (m, 1 H) 7.26-7.28 (m, 3 H) 7.35-7.36 (m, 1 H) 7.45 (d, J=8.1 Hz, 2 H).

Example 2-17: 1H NMR (400 MHz, CHLOROFORM-d) δ ppm 1.29 (t, J=7.1 Hz, 3 H) 2.43-2.69 (m, 6 H) 2.90 (A of ABX, $J_{ab}$=13.6 Hz, $J_{ax}$=7.8 Hz, 1 H) 2.99 (B of ABX, $J_{ab}$=13.6 Hz, $J_{bx}$=6.8 Hz, 1 H) 3.68 (s, 3 H) 4.12-4.23 (m, 2 H) 4.49-4.57 (m, 1 H) 6.31 (br d, J=8.6 Hz, 1 H) 7.20-7.26 (m, 4 H) 7.32 (d, J=7.6 Hz, 1 H) 7.44-7.47 (m, 1 H) 7.53-7.57 (m, 1 H) 7.73 (d, J=7.6 Hz, 2 H).

Example 2-18: 1H NMR (400 MHz, CHLOROFORM-d) δ ppm 1.29 (t, J=7.2 Hz, 3 H) 2.44-2.65 (m, 6 H) 2.91 (A of ABX, $J_{ab}$=13.6 Hz, $J_{ax}$=7.8 Hz, 1 H) 3.01 (B of ABX, $J_{ab}$=13.6 Hz, $J_{bx}$=6.6 Hz, 1 H) 3.68 (s, 3 H) 4.12-4.24 (m, 2 H) 4.48-4.57 (m, 1 H) 6.34 (br d, J=8.6 Hz, 1 H) 7.32 (d, J=8.1 Hz, 2 H) 7.41-7.56 (m, 2 H) 7.62-7.66 (m, 1 H) 7.75-7.77 (m, 1 H) 7.81-7.84 (m, 2 H).

Example 2-19: 1H NMR (400 MHz, CHLOROFORM-d) δ ppm 1.28 (t, J=7.2 Hz, 3 H) 1.35 (t, J=6.9 Hz, 3 H) 2.44-2.53 (m, 4 H) 2.44-2.53 (m, 4 H) 2.86 (A of ABX, $J_{ab}$=13.6 Hz, $J_{ax}$=8.1 Hz, 1 H) 2.98 (B of ABX, $J_{ab}$=13.6 Hz, $J_{bx}$=6.1 Hz, 1 H) 3.67 (s, 3 H) 3.99-4.23 (m, 4 H) 4.48-4.56 (m, 1 H) 6.27 (br d, J=8.6 Hz, 1 H) 6.94-7.04 (m, 2 H) 7.20-7.22 (m, 2 H) 7.27-7.33 (m, 2 H) 7.41-7.52 (m, 2 H).

Example 2-20: 1H NMR (400 MHz, CHLOROFORM-d) δ ppm 1.28 (t, J=7.2 Hz, 3 H) 1.43 (s, 9 H) 2.36-2.56 (m, 6 H) 2.84-3.01 (m, 4 H) 4.11-4.22 (m, 2 H) 4.47-4.56 (m, 1 H) 6.30-6.35 (m, 1 H) 7.25-7.27 (m, 2 H) 7.51-7.54 (m, 2 H).

Example 2-21

Synthesis of (R)-4-(4-ethoxy-1-(5'-fluoro-2'-methoxybiphenyl-4-yl)-4-oxobutan-2-ylamino)-4-oxobutanoic acid

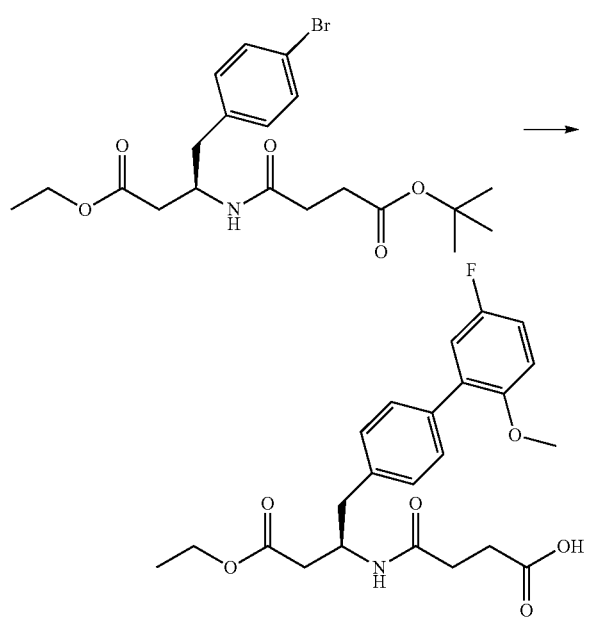

To a solution of (R)-tert-butyl 4-(1-(4-bromophenyl)-4-ethoxy-4-oxobutan-2-ylamino)-4-oxobutanoate, intermediate 9, (100 mg, 0.23 mmol) and 5-fluoro-2-methoxyphenylboronic acid (57.6 mg, 0.34 mmol) in toluene (1 mL) and EtOH (0.1 mL) is added Pd(PPh$_3$)$_4$ (26.1 mg, 0.023 mmol) and Na$_2$CO$_3$ (47.9 mg, 0.45 mmol). After stirring at 95° C. under nitrogen for 18 hours, the solution is cooled to ambient temperature and then quenched with aqueous 1 M HCl. The crude is diluted with ethyl acetate, the organic layer is washed with brine, dried over Na$_2$SO$_4$, filtered, and concentrated under reduced pressure. The obtained residue is purified by flash column chromatography on silica gel (eluent: heptane/EtOAc=100:0 to 30:70) to give (R)-tert-butyl 4-(4-ethoxy-1-(5'-fluoro-2'-methoxybiphenyl-4-yl)-4-oxobutan-2-ylamino)-4-oxobutanoate (65 mg). HPLC retention time=1.44 minutes (condition B); MS (m+1)=488.3; 1H NMR (400 MHz, CHLOROFORM-d) δ ppm 1.32 (t, J=7.1 Hz, 3 H) 1.48 (s, 9 H) 2.41-2.48 (m, 2 H) 2.51-2.63 (m, 4 H) 2.90 (dd, J=13.6, 6 Hz, 1 H) 3.02 (dd, J=13.6, 6 Hz, 1 H) 3.81 (s, 3 H) 4.14-4.29 (m, 2 H) 4.49-4.63 (m, 1 H) 6.44 (d, J=8.6 Hz, 1 H) 6.89-6.97 (m, 1 H) 6.98-7.05 (m, 1 H) 7.05-7.11 (m, 1 H) 7.27 (d, J=8.1 Hz, 2 H) 7.49 (d, J=8.1 Hz, 2 H).

A solution of (R)-tert-butyl 4-(4-ethoxy-1-(5'-fluoro-2'-methoxybiphenyl-4-yl)-4-oxobutan-2-ylamino)-4-oxobutanoate, (65 mg, 0.13 mmol) in 4M HCl in 1,4-dioxane (671 μL, 2.68 mmol) is stirred at room temperature. After stirring for 1 hour, the reaction mixture is concentrated under reduced pressure. The obtained residue is purified by RP-HPLC (SunFire C18, H$_2$O (0.1% TFA)/CH$_3$CN), and then lyophilized to give (R)-4-(4-ethoxy-1-(5'-fluoro-2'-methoxybiphenyl-4-yl)-4-oxobutan-2-ylamino)-4-oxobutanoic acid (23 mg). HPLC retention time=1.66 minutes (condition D); MS (m+1)=432.3; 1H NMR (400 MHz, DMSO-d$_6$) δ ppm 1.17 (t, J=7.1 Hz, 3 H) 2.21-2.32 (m, 2 H) 2.32-2.40 (m, 2 H) 2.40-2.48 (m, 2 H) 2.77 (d, J=6.8 Hz, 2 H) 3.74 (s, 3 H) 4.03 (q, J=7.1 Hz, 2 H) 4.19-4.33 (m, 1 H) 7.04-7.20 (m, 3 H) 7.23 (d, J=8.1 Hz, 2 H) 7.43 (d, J=8.1 Hz, 2 H) 7.93 (d, J=8.3 Hz, 1 H)

Following compounds are prepared using similar procedure as described in example 2-21:

| Example | Product | Reagent | LCMS-RT (condition) | MS (M + 1) |
|---|---|---|---|---|
| Example 2-22 | (R)-4-(1-(5'-chloro-2'-methoxybiphenyl-4-yl)-4-ethoxy-4-oxobutan-2-ylamino)-4-oxobutanoic acid | Pd(PPh$_3$)$_4$, 5-chloro-2-methoxyphenylboronic acid, aq. 2M Na$_2$CO$_3$, (R)-tert-butyl 4-(1-(4-bromophenyl)-4-ethoxy-4-oxobutan-2-ylamino)-4-oxobutanoate. | 1.63 min. (D) | 448.2 |

-continued

| Example | Product | Reagent | LCMS-RT (condition) | MS (M + 1) |
|---|---|---|---|---|
| Example 2-23 | 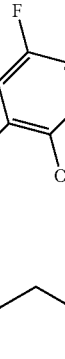<br>(R)-4-(4-ethoxy-1-(5'-fluoro-2'-hydroxybiphenyl-4-yl)-4-oxobutan-2-ylamino)-4-oxobutanoic acid | Pd(PPh$_3$)$_4$, 5-fluoro-2-hydroxyphenylboronic acid, aq. 2M Na$_2$CO$_3$, (R)-tert-butyl 4-(1-(4-bromophenyl)-4-ethoxy-4-oxobutan-2-ylamino)-4-oxobutanoate. | 1.29 min (A) | 418.3 |
| Example 2-24 | 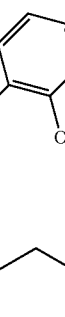<br>(R)-4-(4-ethoxy-1-(2'-hydroxybiphenyl-4-yl)-4-oxobutan-2-ylamino)-4-oxobutanoic acid | Pd(PPh$_3$)$_4$, 2-hydroxyphenylboronic acid, aq. 2M Na$_2$CO$_3$, (R)-tert-butyl 4-(1-(4-bromophenyl)-4-ethoxy-4-oxobutan-2-ylamino)-4-oxobutanoate. | 1.65 min (D) | 400.3 |

Example 2-22: 1H NMR (400 MHz, CD$_3$OD) δ ppm 1.23 (t, J=7.1 Hz, 3 H) 2.36-2.58 (m, 6 H) 2.85 (d, J=7.1 Hz, 2 H) 3.76 (s, 3 H) 4.10 (q, J=7.1 Hz, 2 H) 4.40-4.57 (m, 1 H) 7.01 (d, J=8.6 Hz, 1 H) 7.17-7.30 (m, 4 H) 7.39 (d, J=8.1 Hz, 2 H)

Example 2-23: 1H NMR (400 MHz, DMSO-d$_6$) δ ppm 1.16 (t, J=7.2 Hz, 1 H) 2.23-2.30 (m, 2 H) 2.34-2.40 (m, 2 H) 2.40-2.45 (m, 2 H) 2.75 (dd, J=6.6, 3.3 Hz, 2 H) 4.02 (q, J=7.2 Hz, 2 H) 4.19-4.30 (m, 1 H) 6.87-6.94 (m, 1 H) 6.93-7.02 (m, 1 H) 7.07 (dd, J=9.7, 3.2 Hz, 1 H) 7.22 (d, J=8.1 Hz, 2 H) 7.49 (d, J=8.1 Hz, 2 H) 7.94 (d, J=8.1 Hz, 1 H) 9.52 (s, 1 H)

Example 2-24: 1H NMR (400 MHz, DMSO-d$_6$) δ ppm 1.16 (t, J=7.1 Hz, 3 H) 2.22-2.32 (m, 2 H) 2.34-2.41 (m, 2 H) 2.43 (dd, J=6.8, 3.3 Hz, 2 H) 2.68-2.82 (m, 2 H) 4.02 (q, J=7.1 Hz, 2 H) 4.17-4.35 (m, 1 H) 6.80-6.89 (m, 1 H) 6.93 (d, J=7.1 Hz, 1 H) 7.09-7.17 (m, 1 H) 7.17-7.29 (m, 3 H) 7.46 (d, J=8.3 Hz, 2 H) 7.93 (d, J=8.1 Hz, 1 H) 9.46 (br. s., 1 H)

Example 3-1

Synthesis of (R)-6-(1-(biphenyl-4-yl)-4-ethoxy-4-oxobutan-2-ylcarbamoyl)pyrimidine-4-carboxylic acid

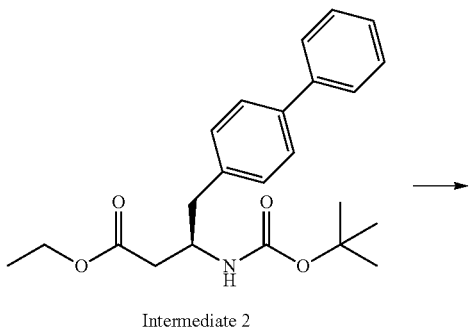

Intermediate 2

-continued

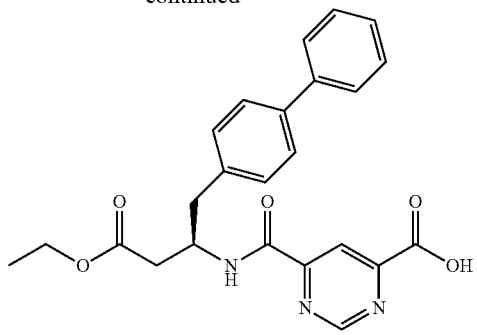

To (R)-ethyl-4-(biphenyl-4-yl)-3-(tert-butoxycarbonylamino)butanoate (300 mg, 0.782 mmol) is added a solution of 4M HCl in 1,4-dioxane (3.92 mL, 15.65 mmol) at room temperature. After stirring for 1 hour, the reaction mixture is concentrated under reduced pressure to give (R)-3-amino-4-biphenyl-4-yl-butyric acid ethyl ester hydrochloride.

Next, to a suspension of pyrimidine-4,6-dicarboxylic acid (325 mg, 1.935 mmol), (R)-3-amino-4-biphenyl-4-yl-butyric acid ethyl ester hydrochloride (250 mg, 0.774 mmol), WSC hydrochloride (148 mg, 0.774 mmol) and HOAt (105 mg, 0.774 mmol) in DMF (4 mL) and $H_2O$ (1 mL) is added DIPEA (0.135 mL, 0.774 mmol). After stirring for 14 hours, the reaction is quenched with $H_2O$, and the products are extracted with EtOAc, washed with brine, dried over $Na_2SO_4$, filtered, and concentrated under reduced pressure.

The obtained residue is purified by RP-HPLC (SunFire C18, $H_2O$ (0.1% TFA)/$CH_3CN$), and then lyophilized to give (R)-6-(1-(biphenyl-4-yl)-4-ethoxy-4-oxobutan-2-ylcarbamoyl)pyrimidine-4-carboxylic acid (84.8 mg). HPLC retention time=1.32 minutes (condition B); MS (m+1)=434.1; 1H NMR (400 MHz, DMSO-$d_6$) δ ppm 1.12 (t, J=7.0 Hz, 3 H) 2.65 (A of ABX, $J_{ab}$=15.4 Hz, $J_{ax}$=5.8 Hz, 1 H) 2.73 (B of ABX, $J_{ab}$=15.4 Hz, $J_{bx}$=7.9 Hz) 2.91 (A of ABX, $J_{ab}$=13.6 Hz, $J_{ax}$=6.1 Hz, 1 H) 3.01 (B of ABX, $J_{ab}$=13.6 Hz, $J_{bx}$=8.2 Hz, 1 H) 4.01 (q, J=7.0 Hz, 2 H) 4.59-4.68 (m, 1 H) 7.29-7.35 (m, 3 H) 7.41-7.45 (m, 2 H) 7.55-7.63 (m, 4 H) 8.32 (d, J=1.35 Hz, 1 H) 9.19 (d. J=9.1 Hz, 1 H) 9.50 (d, J=1.35 Hz, 1 H) 14.11 (br s, 1 H).

Following compounds are prepared using similar procedure as described in example 3-1:

| Example # | Product | Reagent | HPLC-RT (condition) | MS (M + 1) |
|---|---|---|---|---|
| Example 3-2 | (R)-4-biphenyl-4-yl-3-[(2-hydroxy-pyrimidine-5-carbonyl)-amino]-butyric acid ethyl ester | | 1.56 min. (A) | 406.2 |
| Example 3-3 | (R)-4-biphenyl-4-yl-3-[(pyrimidine-4-carbonyl)-amino]-butyric acid ethyl ester | | 1.73 min. (A) | 390 |

| Example # | Product | Reagent | HPLC-RT (condition) | MS (M + 1) |
|---|---|---|---|---|
| Example 3-4 | 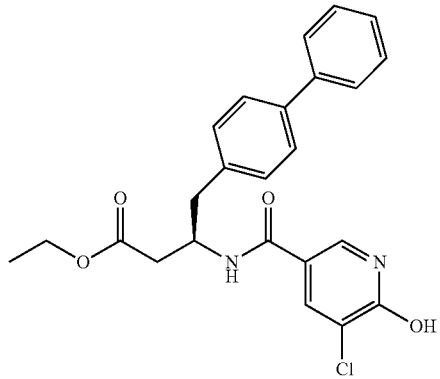<br>(R)-ethyl 4-(biphenyl-4-yl)-3-(5-chloro-6-hydroxynicotinamido)butanoate | 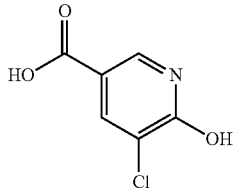<br>PyBOP instead of WSC•HCl and HOAt | 1.69 min. (D) | 439.0 |
| Example 3-5 | 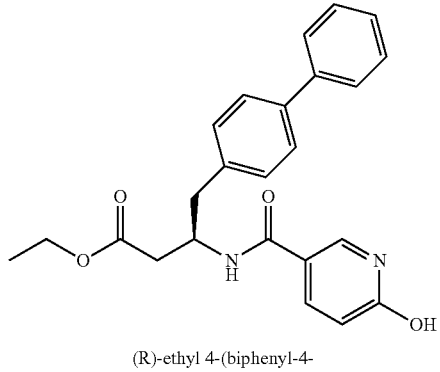<br>(R)-ethyl 4-(biphenyl-4-yl)-3-(6-hydroxynicotinamido)butanoate | 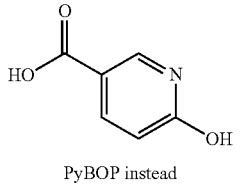<br>PyBOP instead of WSC•HCl, HOAt | 1.55 min. (B) | 405.2 |
| Example 3-6 | 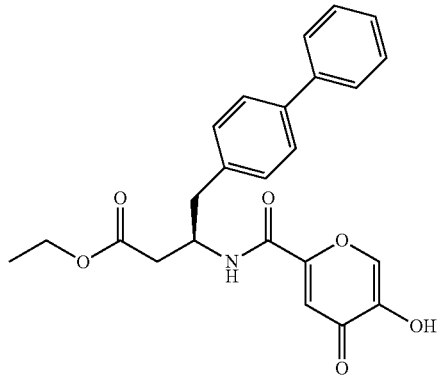<br>(R)-ethyl 4-(biphenyl-4-yl)-3-(5-hydroxy-4-oxo-4H-pyran-2-carboxamido)butanoate | 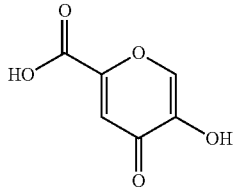 [SMILES: O=C(O)c1cc(=O)c(O)co1] | 1.65 min. (A) | 422.2 |

| Example # | Product | Reagent | HPLC-RT (condition) | MS (M + 1) |
|---|---|---|---|---|
| Example 3-7 | (R)-ethyl 3-(2-aminopyrimidine-5-carboxamido)-4-(biphenyl-4-yl)butanoate | PyBOP instead of WSC·HCl and HOAt | 1.58 min. (A) | 405.8 |
| Example 3-8 | (R)-ethyl 3-(6-aminonicotinamido)-4-(biphenyl-4-yl)butanoate | PyBOP instead of WSC·HCl and HOAt | 1.65 min. (A) | 404.3 |

Example 3-2: 1H NMR (400 MHz, DMSO-$d_6$) δ ppm 1.14 (t, J=7.1 Hz, 3 H) 2.57 (d, J=7.1 Hz, 2 H) 2.83-2.92 (m, 2 H) 4.03 (q, J=7.1 Hz, 2 H) 4.43-4.52 (m, 1 H) 7.29-7.36 (m, 3 H) 7.42-7.46 (m, 2 H) 7.58-7.65 (m, 4 H) 8.30 (d, J=8.4 Hz, 1 H) 8.64 (br s, 1 H).

Example 3-4: 1H NMR (400 MHz, DMSO-$d_6$) δ ppm 1.13 (t, J=7.1 Hz, 3 H) 2.55 (d, J=6.9 Hz, 2 H) 2.82-2.92 (m, 2 H) 4.00 (q, J=7.1 Hz, 2 H) 4.43-4.52 (m, 1 H) 7.29-7.35 (m, 3 H) 7.42-7.46 (m, 2 H) 7.58-7.65 (m, 4 H) 7.93-7.96 (m, 1H) 8.10 (d, J=2.3 Hz, 1 H) 8.25 (d, J=8.3 Hz, 1 H) 12.53 (d, J=6.1 Hz, 1 H).

Example 3-5: 1H NMR (400 MHz, DMSO-$d_6$) δ ppm 1.13 (t, J=7.1 Hz, 3 H) 2.55 (d, J=7.6 Hz, 2 H) 2.81-2.92 (m, 2 H) 4.02 (q, J=7.1 Hz, 2 H) 4.43-4.52 (m, 1 H) 7.29-7.36 (m, 3 H) 7.42-7.46 (m, 2 H) 7.57-7.65 (m, 4 H) 7.78-7.81 (m, 1H) 7.92 (d, J=2.3 Hz, 1 H) 8.16 (d, J=8.1 Hz, 1 H) 11.92 (s, 1 H).

Example 3-6: 1H NMR (400 MHz, DMSO-$d_6$) δ ppm 1.13 (t, J=7 Hz, 3 H) 2.55-2.67 (m, 2 H) 2.83-2.94 (m, 2 H) 4.02 (q, J=7 Hz, 2 H) 4.46-4.55 (m, 1 H) 6.82 (s, 1 H) 7.28-7.35 (m, 3 H) 7.42-7.46 (m, 2 H) 7.59 (d, J=8.3 Hz, 2 H) 7.63 (d, J=7.0 Hz, 2 H) 8.13 (s, 1 H) 8.89 (d, J=8.6 Hz, 1 H) 9.56 (s, 1 H).

Example 3-7: 1H NMR (400 MHz, DMSO-$d_6$) δ ppm 1.13 (t, J=7 Hz, 3 H) 2.56-2.58 (m, 2 H) 2.83-2.94 (m, 2 H) 4.02 (q, J=7 Hz, 2 H) 4.46-4.55 (m, 1 H) 7.19 (s, 2 H) 7.30-7.35 (m, 3 H) 7.42-7.46 (m, 2 H) 7.58-7.65 (m, 4H) 8.22 (d, J=8.1 Hz, 1 H) 8.60 (s, 1 H).

Example 3-9

Synthesis of (R)-benzyl 3-(4-butoxy-4-oxobutanamido)-4-(3'-chlorobiphenyl-4-yl)butanoate

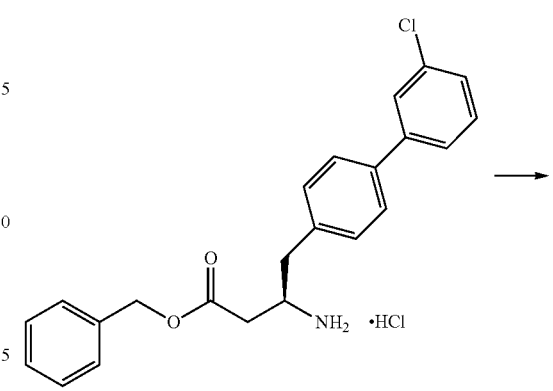

-continued

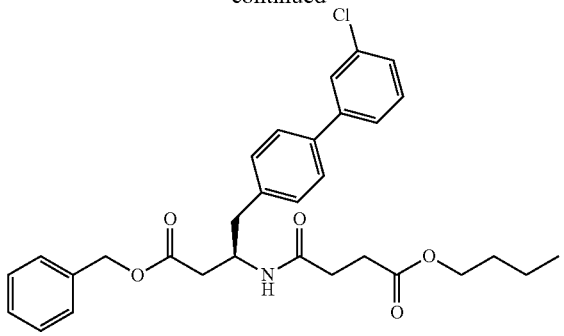

A mixture of (R)-benzyl 3-amino-4-(3'-chlorobiphenyl-4-yl)butanoate hydrochloride (150 mg, 0.360 mmol), 4-butoxy-4-oxobutanoic acid (107 mg, 0.540 mmol, 88% purity), EDCI (104 mg, 0.540 mmol), DIPEA (0.094 ml, 0.540 mmol) and HOAt (73.6 mg, 0.540 mmol) in DMF (2 ml) is allowed to stir at room temperature for 1 hour. The reaction mixture is diluted with water, and then the precipitated solid is collected on a funnel, washed with $H_2O$, and dried under reduced pressure to give crude. The obtained residue is purified by silica gel flash column chromatography (heptane/EtOAc=100:0 to 0:100) to give (R)-benzyl 3-(4-butoxy-4-oxobutanamido)-4-(3'-chlorobiphenyl-4-yl)butanoate (178.9 mg); HPLC retention time=1.47 minutes (condition B); MS (m+1)=536.42; 1H NMR (400 MHz, CHLOROFORM-d) δ ppm 0.90-0.94 (m, 3 H) 1.31-1.40 (m, 2 H) 1.56-1.63 (m, 2 H) 2.39-2.42 (m, 2 H) 2.48-2.62 (m, 4 H) 2.84 (A of ABX, $J_{ab}$=13.6 Hz, $J_{ax}$=8.1 Hz, 1 H) 2.97 (B of ABX, $J_{ab}$=13.6 Hz, $J_{bx}$=6.6 Hz, 1 H) 4.07 (t, J=6.7 Hz, 2 H) 4.48-4.56 (m, 1 H) 5.12 (A of AB, J=12.1 Hz, 1 H) 5.18 (B of AB, J=12.1 Hz, 1 H) 6.27 (br d, J=7.7 Hz, 1 H) 7.20 (d, J=8.3 Hz, 1 H) 7.29-7.39 (m, 7 H) 7.42-7.47 (m, 3 H) 7.54-7.55 (m, 1 H).

Following compounds are prepared using similar procedure as described in example 3-8:

| Example # | Product | Starting Material | Condition | HPLC-RT (condition) | MS (M + 1) |
|---|---|---|---|---|---|
| Example 3-10 | 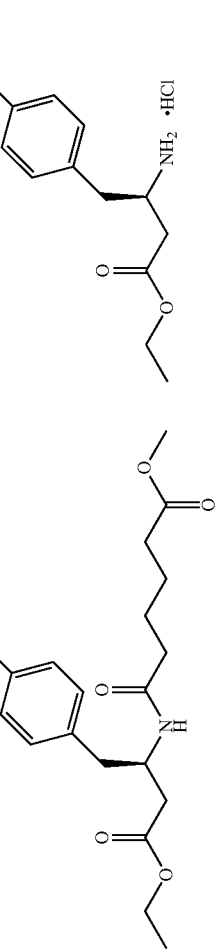 (R)-methyl 6-(1-(3'-chlorobiphenyl-4-yl)-4-ethoxy-4-oxobutan-2-ylamino)-6-oxohexanoate | 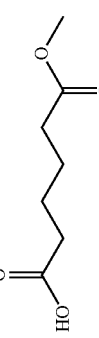 | 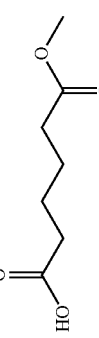 EDCI, HOAt, DIPEA, DMF, RT | 1.40 min. (B) | 460.5 |

| Example # | Product | Starting Material | Condition | HPLC-RT (condition) | MS (M+1) |
|---|---|---|---|---|---|
| Example 3-11 | 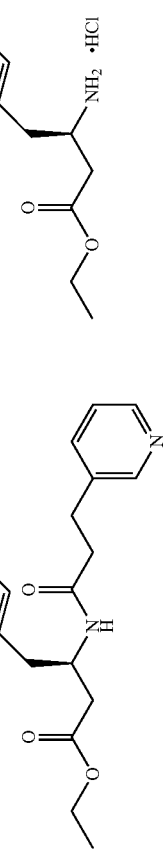<br>(R)-ethyl 4-(3'-chlorobiphenyl-4-yl)-3-(3-(pyridin-3-yl)propanamido)butanoate | 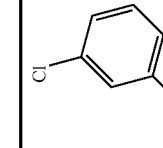 | 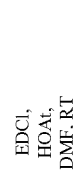<br>EDCI, HOAt, DMF, RT | 1.56 min. (A) | 451.3 |

| Example # | Product | Starting Material | Condition | HPLC-RT (condition) | MS (M + 1) |
|---|---|---|---|---|---|
| Example 3-12 | 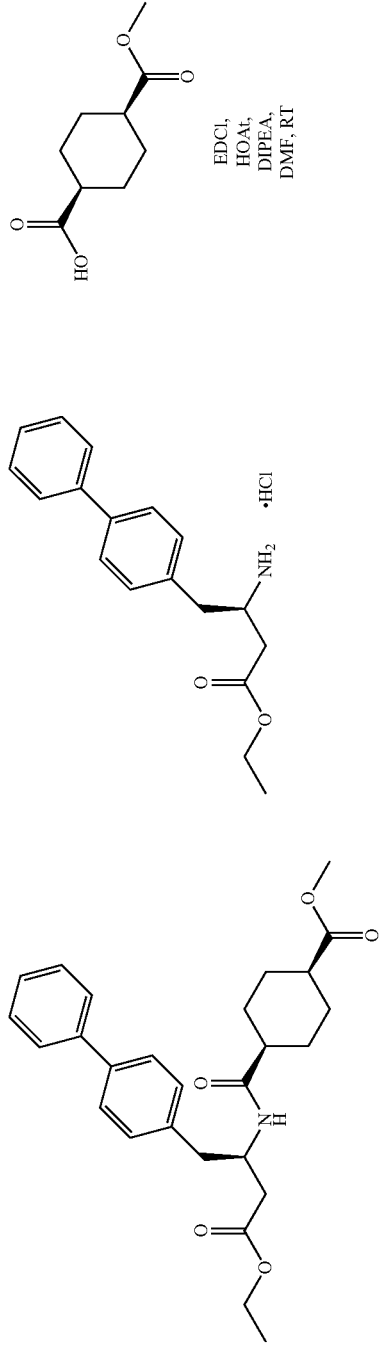 (1S,4s)-methyl 4-((R)-1-([1,1'-biphenyl]-4-yl)-4-ethoxy-4-oxobutan-2-ylcarbamoyl)cyclohexanecarboxylate | 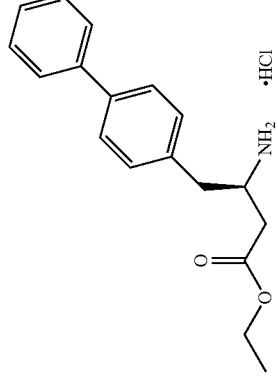 | EDCI, HOAt, DIPEA, DMF, RT | 1.42 min. (B) | 452.2 |

| Example # | Product | Starting Material | Condition | HPLC-RT (condition) | MS (M + 1) |
|---|---|---|---|---|---|
| Example 3-13 | 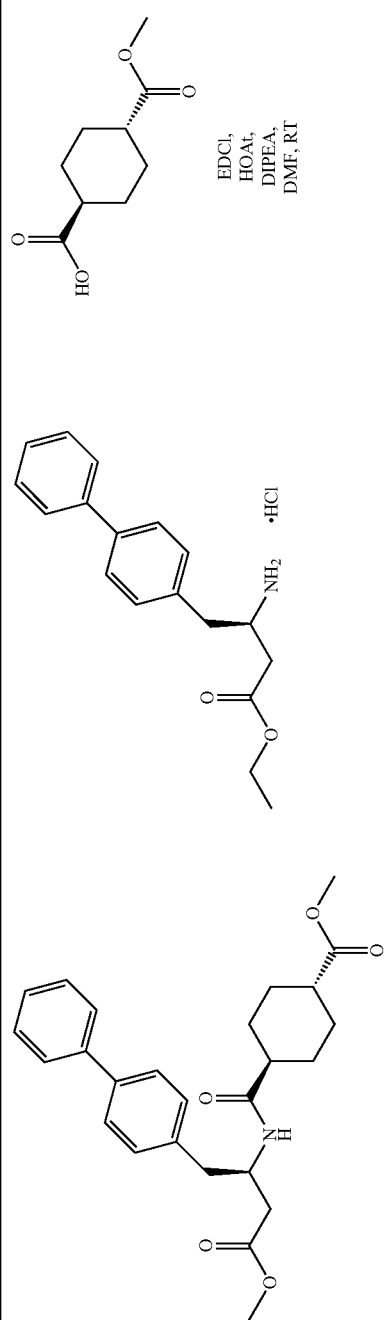 (1R,4r)-methyl 4-((R)-1-(biphenyl-4-yl)-4-ethoxy-4-oxobutan-2-ylcarbamoyl)cyclohexanecarboxylate | 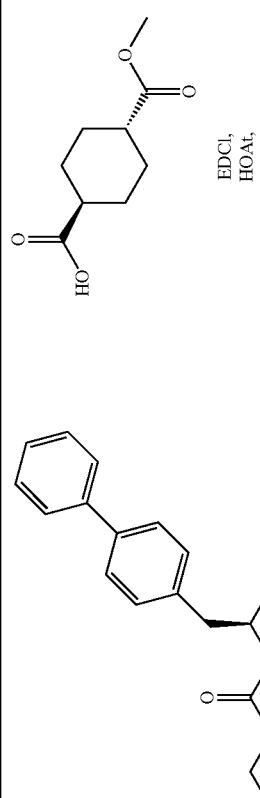 | 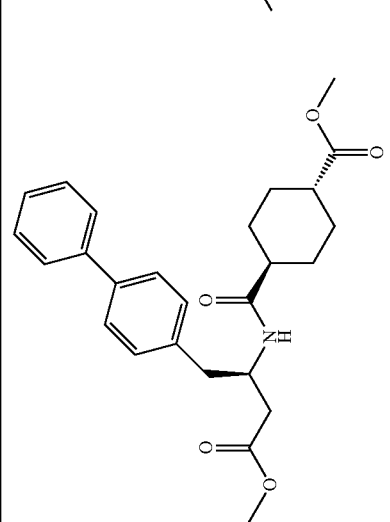 EDCI, HOAt, DIPEA, DMF, RT | 1.42 min. (B) | 452.3 |

-continued

| Example # | Starting Material | Condition | Product | HPLC-RT (condition) | MS (M+1) |
|---|---|---|---|---|---|
| Example 3-14 | [3'-chlorobiphenyl-4-yl methyl amine ethyl ester, HCl salt] | [3-(pyridin-2-yl)propanoic acid]; EDCI, HOAt, DIPEA, DMF, RT | (R)-ethyl 4-(3'-chlorobiphenyl-4-yl)-3-(3-(pyridin-2-yl)propanamido)butanoate | 1.61 min. (A) | 451.3 |

-continued

| Example # | Product | Starting Material | Condition | HPLC-RT (condition) | MS (M + 1) |
|---|---|---|---|---|---|
| Example 3-16 | (R)-benzyl 4-(3'-chlorobiphenyl-4-yl)-3-(4-ethoxy-4-oxobutanamido)butanoate | | EDCl, HOAt, DIPEA, DMF, RT | 1.56 min. (B) | 508.3 |

| Example # | Product | Starting Material | Condition | HPLC-RT (condition) | MS (M + 1) |
|---|---|---|---|---|---|
| Example 3-17 | 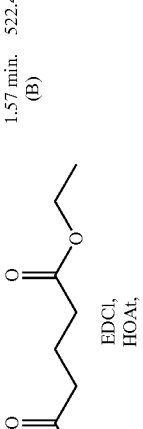 (R)-ethyl 5-(4-(benzyloxy)-1-(3'-chlorobiphenyl-4-yl)-4-oxobutan-2-ylamino)-5-oxopentanoate | 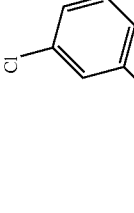 | 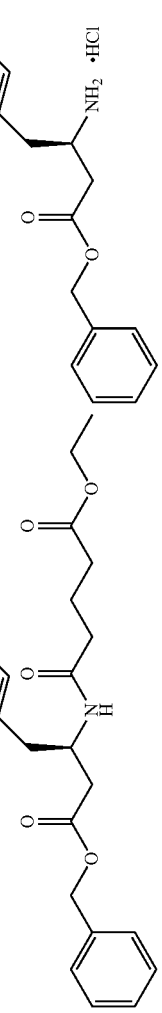 EDCl, HOAt, DIPEA, DMF, RT | 1.57 min. (B) | 522.4 |

| Example # | Product | Starting Material | Condition | HPLC-RT (condition) | MS (M + 1) |
|---|---|---|---|---|---|
| Example 3-18 | (R)-tert-butyl 2-(3-(1-(3'-chlorobiphenyl-4-yl)-4-ethoxy-4-oxobutan-2-ylamino)-3-oxopropyl)-1H-benzo[d]imidazole-1-carboxylate | | EDCI, HOAt, DIPEA, THF, RT | 0.80 min. (B) | 590.3 |

| Example # | Product | Starting Material | Condition | HPLC-RT (condition) | MS (M+1) |
|---|---|---|---|---|---|
| Example 3-19 | tert-butyl 4-(1-(3'-chloro-3-fluorobiphenyl-4-yl)-4-ethoxy-4-oxobutan-2-ylamino)-4-oxobutanoate | | EDCI, HOAt, DMF, RT | 1.46 min. (B) | 492.5 |

Example 3-10: 1H NMR (400 MHz, CHLOROFORM-d) δ ppm 1.29 (t, J=7.2 Hz, 3 H) 1.58-1.64 (m, 4 H) 2.14-2.18 (m, 2 H) 2.28-2.32 (m, 2 H) 2.49 (A of ABX, $J_{ab}$=16.2 Hz, $J_{ax}$=5.3 Hz, 1 H) 2.53 (B of ABX, $J_{ab}$=16.2 Hz, $J_{bx}$=5.3 Hz, 1 H) 2.87 (A of ABX, $J_{ab}$=13.6 Hz, $J_{ax}$=8.1 Hz, 1 H) 2.99 (B of ABX, $J_{ab}$=13.6 Hz, $J_{bx}$=6.8 Hz, 1 H) 3.65 (s, 3 H) 4.11-4.23 (m, 2 H) 4.48-4.56 (m, 1 H) 6.18 (br d, J=8.8 Hz, 1 H) 7.26-7.37 (m, 4 H) 7.43-7.52 (m, 3 H) 7.56 (br t, J=1.8 Hz, 1 H)

Example 3-11: 1H NMR (400 MHz, CHLOROFORM-d) δ ppm 1.27 (t, J=7.1 Hz, 3 H) 2.40-2.51 (m, 4 H) 2.77-2.83 (m, 1 H) 2.91-2.97 (m, 3 H) 4.08-4.20 (m, 2 H) 4.46-4.54 (m, 1 H) 6.22-6.24 (m, 1 H) 7.18-7.23 (m, 3 H) 7.29-7.37 (m, 2 H) 7.43-7.49 (m, 3 H) 7.55-7.57 (m, 2 H) 8.44 (d, J=4.8 Hz, 1 H) 8.48 (s, 1 H).

Example 3-12: 1H NMR (400 MHz, CHLOROFORM-d) δ ppm 1.29 (t, J=7.1 Hz, 3 H) 1.53-2.20 (m, 9 H) 2.46-2.57 (m, 3 H) 2.86 (A of ABX, $J_{ab}$=13.6 Hz, $J_{ax}$=7.8 Hz, 1 H) 2.98 (B of ABX, $J_{ab}$=13.6 Hz, $J_{bx}$=6.6 Hz, 1 H) 3.65 (s, 3 H) 4.11-4.23 (m, 2 H) 4.47-4.55 (m, 1 H) 6.23 (br d, J=8.6 Hz, 1 H) 7.24-7.26 (m, 2 H) 7.31-7.35 (m, 1 H) 7.41-7.45 (m, 2 H) 7.51-7.59 (m, 4 H).

Example 3-13: 1H NMR (400 MHz, CHLOROFORM-d) δ ppm 1.29 (t, J=7.2 Hz, 3 H) 1.36-1.51 (m, 4 H) 1.84-1.94 (m, 2 H) 1.98-2.06 (m, 3 H) 2.24-2.32 (m, 1H) 2.50 (A of ABX, $J_{ab}$=16.2 Hz, $J_{ax}$=5.3 Hz, 1 H) 2.53 (B of ABX, $J_{ab}$=16.2 Hz, $J_{bx}$=5.1 Hz, 1 H) 2.86 (A of ABX, $J_{ab}$=13.6 Hz, $J_{ax}$=7.8 Hz, 1 H) 2.98 (B of ABX, $J_{ab}$=13.6 Hz, $J_{bx}$=6.6 Hz, 1 H) 3.66 (s, 3 H) 4.11-4.23 (m, 2 H) 4.46-4.55 (m, 1 H) 6.19 (br d, J=8.8 Hz, 1 H) 7.24-7.26 (m, 2 H) 7.31-7.36 (m, 1 H) 7.41-7.45 (m, 2 H) 7.51-7.58 (m, 4 H).

Example 3-14: 1H NMR (400 MHz, CHLOROFORM-d) δ ppm 1.26 (t, J=7.2 Hz, 3 H) 2.41-2.51 (m, 4 H) 2.62-2.66 (m, 2 H) 2.84 (A of ABX, $J_{ab}$=13.6 Hz, $J_{ax}$=7.6 Hz, 1 H) 2.92 (B of ABX, $J_{ab}$=13.6 Hz, $J_{bx}$=6.6 Hz, 1 H) 3.06-3.10 (m, 2 H) 4.08-4.19 (m, 2 H) 4.46-4.55 (m, 1 H) 6.78 (d, J=8.9 Hz, 1 H) 7.10-7.12 (m, 1 H) 7.16 (d, J=7.8 Hz, 1 H) 7.20-7.22 (m, 2 H) 7.29-7.31 (m, 1 H) 7.35 (t, J=7.7 Hz, 1 H) 7.42-7.47 (m, 3 H) 7.54-7.59 (m, 2 H) 8.48 (d, J=1.0 Hz, 1 H).

Example 3-16: 1H NMR (400 MHz, CHLOROFORM-d) δ ppm 1.24 (t, J=7.1 Hz, 3 H) 2.38-2.42 (m, 2 H) 2.49-2.61 (m, 4 H) 2.82-3.00 (m, 2 H) 4.12 (q, J=7.1 Hz, 2 H) 4.47-4.56 (m, 1 H) 5.12 (A of AB, J=12.3 Hz, 1 H) 5.18 (B of AB, J=12.3 Hz, 1 H) 6.26 (br d, J=8.6 Hz, 1 H) 7.20 (d, J=8.3 Hz, 2 H) 7.29-7.46 (m, 10 H) 7.54-7.54 (m, 1 H).

Example 3-17: 1H NMR (400 MHz, CHLOROFORM-d) δ ppm 1.23 (t, J=7.2 Hz, 3 H) 1.86-1.92 (m, 2 H) 2.14-2.18 (m, 2 H) 2.24-2.28 (m, 2 H) 2.50-2.63 (m, 2 H) 2.82-2.99 (m, 2 H) 4.11 (q, J=7.2 Hz, 2 H) 4.53-4.54 (m, 1 H) 5.12 (A of AB, J=12.1 Hz, 1 H) 5.18 (B of AB, J=12.1 Hz, 1 H) 6.12-6.14 (m, 1 H) 7.19-7.54 (m, 13 H).

Example 3-18: 1H NMR (400 MHz, CHLOROFORM-d) δ ppm 1.26 (t, J=7.2 Hz, 3 H) 1.67 (s, 9 H) 2.46-2.57 (m, 2 H) 2.74-2.96 (m, 4 H) 3.41-3.45 (m, 2 H) 4.09-4.17 (m, 2 H) 4.50-4.59 (m, 1 H) 6.95 (br d, J=8.6 Hz, 1 H) 7.18 (d, J=8.1 Hz, 2 H) 7.27-7.42 (m, 7 H) 7.51 (t, J=1.8 Hz, 1 H) 7.61-7.65 (m, 1 H) 7.86-7.93 (m, 1 H).

Example 3-19: 1H NMR (400 MHz, CHLOROFORM-d) δ ppm 1.28 (t, J=7.2 Hz, 3 H) 1.43 (s, 9 H) 2.37-2.40 (m, 2 H) 2.50-2.59 (m, 4 H) 2.98 (d, J=7.3 Hz, 2 H) 4.13-4.21 (m, 2 H) 4.48-4.56 (m, 1 H) 6.35 (br d, J=8.8 Hz, 1 H) 7.22-7.44 (m, 6 H) 7.54-7.54 (m, 1 H).

Example 3-20

Synthesis of (R)-ethyl 4-(3'-aminobiphenyl-4-yl)-3-(4-methoxy-4-oxobutanamido)butanoate

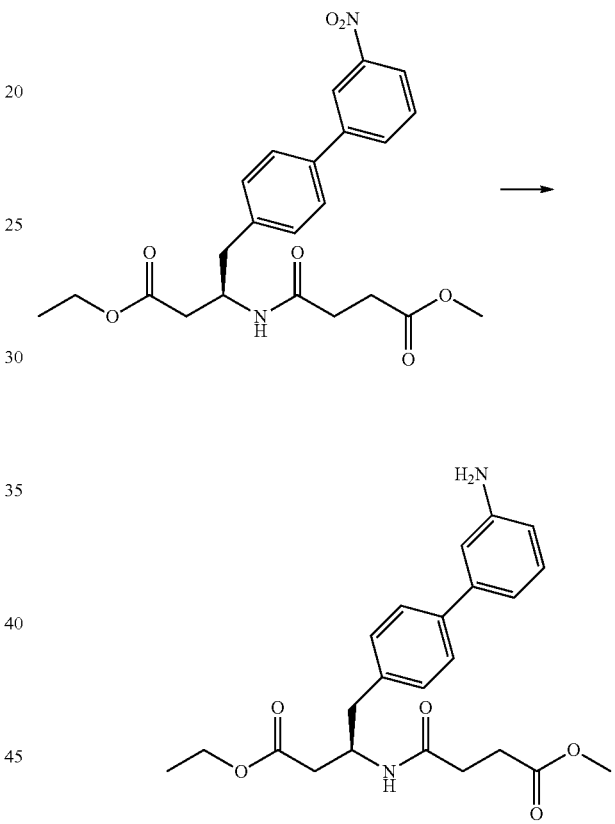

A suspension of (R)-ethyl 3-(4-methoxy-4-oxobutanamido)-4-(3'-nitrobiphenyl-4-yl)butanoate (123 mg, 0.278 mmol) and Pd/C (59.2 mg, 0.028 mmol) in EtOH (2 ml) is allowed to stir under hydrogen at room temperature for 5.5 hours. The reaction mixture is filtered, and the solution is concentrated to give (R)-ethyl 4-(3'-aminobiphenyl-4-yl)-3-(4-methoxy-4-oxobutanamido)butanoate (105 mg); HPLC retention time=0.84 minutes (condition B); MS (m+1)= 413.1; 1H NMR (400 MHz, CHLOROFORM-d) δ ppm 1.28 (t, J=7.2 Hz, 3 H) 2.41-2.65 (m, 6 H) 2.85-3.00 (m, 2 H) 3.67 (s, 3 H) 4.11-4.22 (m, 2 H) 4.46-4.54 (m, 1 H) 6.31 (br d, J=8.8 Hz, 1 H) 6.71-6.74 (m, 1 H) 6.95-7.02 (m, 2 H) 7.21-7.25 (m, 3 H) 7.48-7.50 (m, 2 H).

Following compounds are prepared using similar procedure as described in example 3-20:

| Example # | Product | Condition | HPLC-RT (condition) | MS (M+1) |
|---|---|---|---|---|
| Example 3-22 | 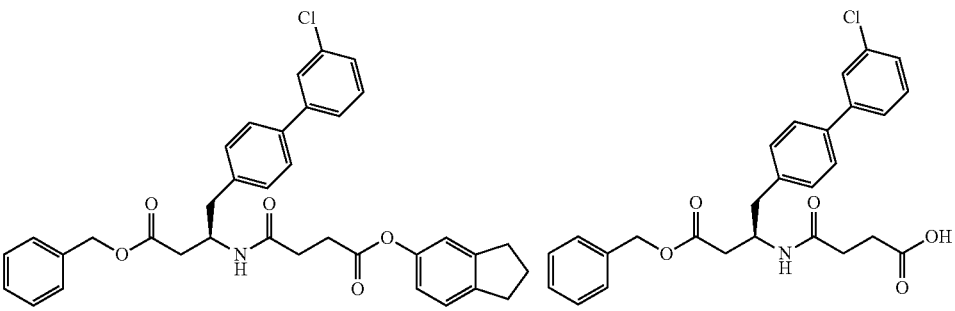<br>(R)-benzyl 4-(3'-chlorobiphenyl-4-yl)-3-(4-(2,3-dihydro-1H-inden-5-yloxy)-4-oxobutanamido)butanoate | Example BB-13, PyBOP, indanol, DCM, RT | 1.73 min. (B) | 596.5 |

Example 3-22: 1H NMR (400 MHz, CHLOROFORM-d) δ ppm 2.03-2.11 (m, 2H) 2.48-2.62 (m, 4H) 2.81-2.90 (m, 7 H) 2.95-3.00 (m, 1 H) 4.49-4.58 (m, 1 H) 5.07-5.18 (m, 2 H) 6.23 (br d, J=8.6 Hz, 1 H) 6.79-6.82 (m, 1 H) 6.92 (s, 1 H) 7.15-7.20 (m, 3 H) 7.29-7.45 (m, 10 H) 7.52-7.53 (m, 1 H)

Example 3-23

Synthesis of (S)-benzyl 1-(2-((R)-1-(biphenyl-4-yl)-4-ethoxy-4-oxobutan-2-ylamino)-2-oxoethyl)pyrrolidine-2-carboxylate trifluoroacetic acid salt

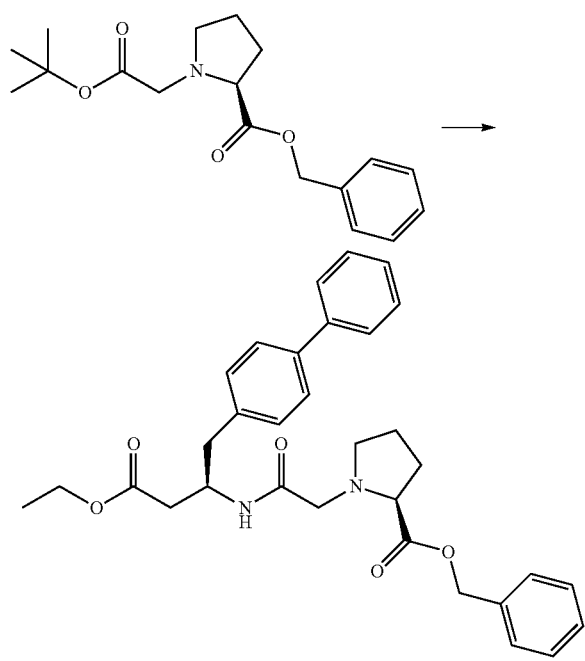

To a solution of (S)-benzyl 1-(2-tert-butoxy-2-oxoethyl)pyrrolidine-2-carboxylate (200 mg, 0.626 mmol) and triethylsilane (0.250 ml, 1.565 mmol) in DCM (3 ml), TFA (0.965 ml, 12.52 mmol) is added at room temperature. After stirring for 24 hours, the reaction is concentrated to give crude.

To a suspension of the crude, (R)-ethyl 3-amino-4-(biphenyl-4-yl)butanoate hydrochloride (266 mg, 0.832 mmol), WSC.HCl (0.180 g, 0.939 mmol) and HOAt (128 mg, 0.939 mmol) in DMF (4 ml), DIPEA (0.328 ml, 1.878 mmol) is added. After stirring for 4 hours, the reaction is diluted with $H_2O$ and EtOAc. The products are extracted with EtOAc, washed with brine, dried over $Na_2SO_4$, filtered, and concentrated. The crude is subjected twice to column chromatography (heptane/EtOAc=100:0 to 0:100). Then, the obtained product is purified by preparative HPLC using a gradient of 20% MeCN/water (0.1% TFA) to 100% MeCN to give (S)-benzyl 1-(2-((R)-1-(biphenyl-4-yl)-4-ethoxy-4-oxobutan-2-ylamino)-2-oxoethyl)pyrrolidine-2-carboxylate trifluoroacetic acid salt (28.5 mg) as a pale yellow solid; HPLC retention time=1.84 minutes (condition D); MS (m+1)= 529.3; 1H NMR (400 MHz, CHLOROFORM-d) δ ppm 1.25-1.28 (m, 3 H) 1.74-1.85 (m, 2 H) 1.91-1.98 (m, 1 H) 2.09-2.19 (m, 1 H) 2.35-2.41 (m, 1 H) 2.46 (A of ABX, $J_{ab}$=15.7 Hz, $J_{ax}$=6.6 Hz, 1 H) 2.59 (B of ABX, $J_{ab}$=13.7 Hz, $J_{bx}$=5.7 Hz, 1 H) 2.78-2.83 (m, 1 H) 2.86 (A of ABX, $J_{ab}$=13.8 Hz, $J_{ax}$=8.1 Hz, 1 H) 2.99 (B of ABX, $J_{ab}$=13.7 Hz, $J_{bx}$=6.4 Hz, 1 H) 3.08 (A of AB, J=16.5 Hz, 1 H) 3.35 (B of AB, J=16.5 Hz, 1 H) 3.41 (dd, J=9.1 and 5.1 Hz, 1 H) 4.11-4.20 (m, 2 H) 4.46-4.55 (m, 1 H) 5.10 (A of AB, J=12.4 Hz, 1 H) 5.13 (B of AB, J=12.4 Hz, 1 H) 7.26-7.27 (m, 2 H) 7.31-7.38 (m, 6 H) 7.40-7.44 (m, 2 H) 7.49-7.56 (m, 4 H) 7.74 (br d, J=8.6 Hz, 1 H).

Example 3-24

Synthesis of (R)-ethyl 4-(3'-acetamidobiphenyl-4-yl)-3-(4-methoxy-4-oxobutanamido)butanoate

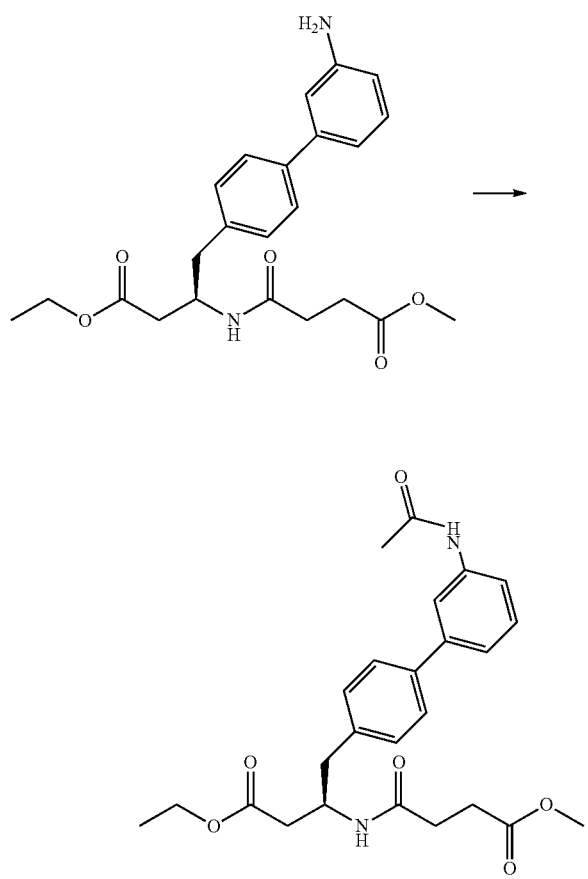

A solution of (R)-ethyl 4-(3'-aminobiphenyl-4-yl)-3-(4-methoxy-4-oxobutanamido)butanoate (70.5 mg, 0.171 mmol), Et₃N (0.027 ml, 0.205 mmol) and Ac₂O (0.019 ml, 0.205 mmol) in DCM (1.7 ml) is allowed to stir at room temperature for 65 hours. The reaction mixture is diluted with water. The products are extracted with DCM in a phase separator and concentrated to give crude (98 mg). The crude is purified by silica gel flash column chromatography (eluent: DCM/MeOH=10:1) to give (R)-ethyl 4-(3'-acetamidobiphenyl-4-yl)-3-(4-methoxy-4-oxobutanamido)butanoate (71.5 mg); HPLC retention time=1.45 minutes (condition D); MS (m+1)=455.4; 1H NMR (400 MHz, CD₃CN, mixture of rotamers, data for major rotamer) δ ppm 1.21 (t, J=7.1 Hz, 3 H) 2.07 (s, 3 H) 2.31-2.34 (m, 2 H) 2.40-2.51 (m, 4 H) 2.82-2.84 (m, 2 H) 3.58 (s, 3 H) 4.07 (q, J=7.1 Hz, 2 H) 4.34-4.43 (m, 1 H) 6.46 (br d, J=8.9 Hz, 1 H) 7.28-7.39 (m, 4 H) 7.52-7.54 (m, 3 H) 7.80 (s, 1 H) 8.37 (br s, 1 H).

Example 3-25

Synthesis of (R)-3-(4-butoxy-4-oxobutanamido)-4-(3'-chlorobiphenyl-4-yl)butanoic acid

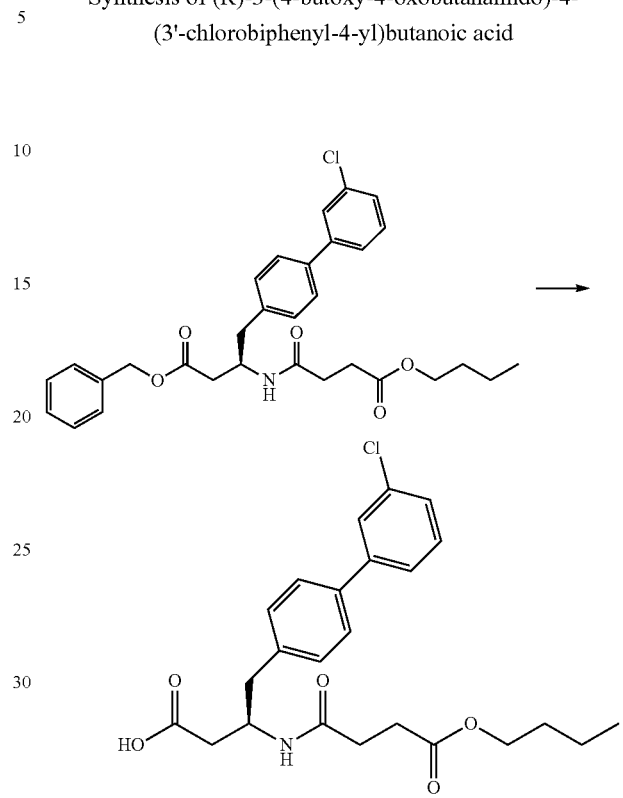

A suspension of (R)-benzyl 3-(4-butoxy-4-oxobutanamido)-4-(3'-chlorobiphenyl-4-yl)butanoate (178.9 mg, 0.334 mmol) and Pd/C (71.0 mg, 0.033 mmol) in EtOAc (3 ml) is allowed to stir under hydrogen at room temperature for 1.5 hours. The reaction mixture is filtered, and concentrated to give crude. The resulting residue is purified by preparative HPLC using a gradient of 20% MeCN/water (0.1% TFA) to 100% MeCN to give (R)-3-(4-butoxy-4-oxobutanamido)-4-(3'-chlorobiphenyl-4-yl)butanoic acid (90.7 mg) as a white solid; HPLC retention time=1.27 minutes (condition B); MS (m+1)=446.24; 1H NMR (400 MHz, CHLOROFORM-d) δ ppm 0.91 (t, J=7.5 Hz, 3 H) 1.31-1.40 (m, 2 H) 1.55-1.62 (m, 2 H) 2.43-2.47 (m, 2 H) 2.52-2.69 (m, 4 H) 2.93 (A of ABX, $J_{ab}$=13.7 Hz, $J_{ax}$=7.7 Hz, 1 H) 3.00 (B of ABX, $J_{ab}$=13.7 Hz, $J_{bx}$=6.8 Hz, 1 H) 4.07 (t, J=6.7 Hz, 2 H) 4.49-4.57 (m, 1 H) 6.31 (br d, J=8.6 Hz, 1 H) 7.26-7.37 (m, 4 H) 7.43-7.46 (m, 1 H) 7.49-7.52 (m, 2 H) 7.55 (br t, J=1.8 Hz, 1 H).

Chiral HPLC retention time=4.33 min. Column: Daicel CHIRALPAK IA (4.6×100 nm n); flow rate=1 ml/min.; eluent: EtOH(containing 0.1% TFA)/heptane=10/90 to 70/30 in 10 min. (linear gradient).

Following compounds are prepared using similar procedure as described in example 3-24:

| Example # | Product | Condition | HPLC-RT (condition) | MS (M + 1) |
|---|---|---|---|---|
| Example 3-26 | 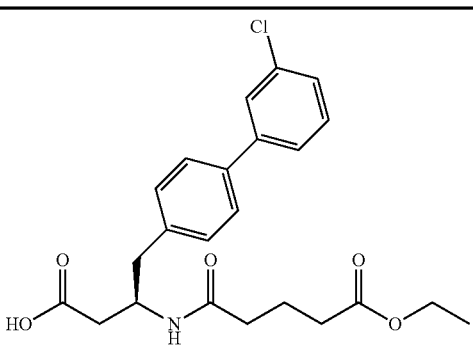<br>(R)-4-(3'-chlorobiphenyl-4-yl)-3-(5-ethoxy-5-oxopentanamido)butanoic acid | Pd/C, H₂, EtOAc, RT | 1.08 min. (B) | 432.4 |
| Example 3-27 | 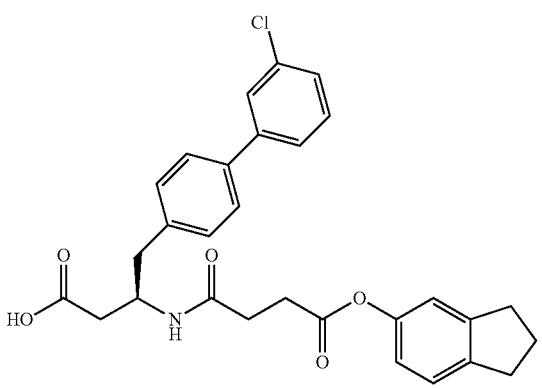<br>(R)-4-(3'-chlorobiphenyl-4-yl)-3-(4-(2,3-dihydro-1H-inden-5-yloxy)-4-oxobutanamido)butanoic acid | Pd/C, H₂, EtOAc, acetone, RT | 1.36 min. (B) | 506.4 |
| Example 3-28 | 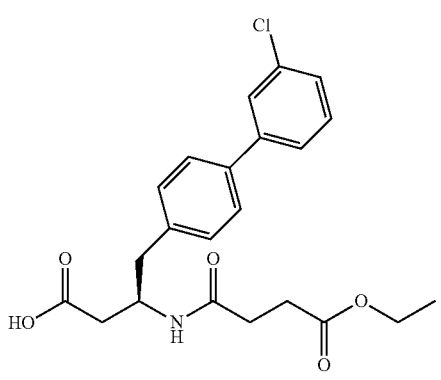<br>(R)-4-(3'-chlorobiphenyl-4-yl)-3-(4-ethoxy-4-oxobutanamido)butanoic acid | Pd/C, H₂, EtOAc, RT | 1.00 min. (B) | 418.4 |

Example 3-26: 1H NMR (400 MHz, CHLOROFORM-d) δ ppm 1.23 (t, J=7.1 Hz, 3 H) 1.86-1.93 (m, 2 H) 2.57 (A of ABX, J$_{ab}$=16.3 Hz, J$_{ax}$=5.7 Hz, 1 H) 2.64 (B of ABX, J$_{ab}$=16.3 Hz, J$_{bx}$=5.2 Hz, 1 H) 2.94 (A of ABX, J$_{ab}$=13.7 Hz, J$_{ax}$=7.6 Hz, 1 H) 2.99 (B of ABX, J$_{ab}$=13.7 Hz, J$_{bx}$=7.2 Hz, 1 H) 4.10 (q, J=7.1 Hz, 2 H) 4.51-4.60 (m, 1 H) 6.17 (br d, J=8.6 Hz, 1 H) 7.26-7.37 (m, 4 H) 7.43-7.45 (m, 1 H) 7.49-7.52 (m, 2 H) 7.55 (br t, J=1.8 Hz, 1 H).

Example 3-27: 1H NMR (400 MHz, CHLOROFORM-d) δ ppm 2.07 (quint, J=7.4 Hz, 2 H) 2.51-2.63 (m, 4 H) 2.82-3.02 (m, 8 H) 4.50-4.59 (m, 1 H) 6.28 (d, J=8.6 Hz, 1 H) 6.78-6.81 (m, 1 H) 6.91 (d, J=1.8 Hz, 1 H) 7.26-7.36 (m, 6 H) 7.41-7.44 (m, 1 H) 7.47-7.50 (m, 2 H) 7.53-7.54 (m, 1 H).

Example 3-28: 1H NMR (400 MHz, CHLOROFORM-d) δ ppm 1.24 (t, J=7.2 Hz, 3 H) 2.44-2.69 (m, 6 H) 2.93 (A of ABX, $J_{ab}$=13.7 Hz, $J_{ax}$=7.8 Hz, 1 H) 3.00 (B of ABX, $J_{ab}$=13.7 Hz, $J_{bx}$=6.7 Hz, 1 H) 4.12 (q, J=7.2 Hz, 2 H) 4.49-4.57 (m, 1 H) 6.35 (br d, J=8.6 Hz, 1 H) 7.26-7.37 (m, 4 H) 7.43-7.46 (m, 1 H) 7.49-7.52 (m, 2 H) 7.55 (br t, J=1.6 Hz, 1 H).

Example 3-29

Synthesis of (R)-3-(4-(benzyloxy)-4-oxobutanamido)-4-(3'-chlorobiphenyl-4-yl)butanoic acid

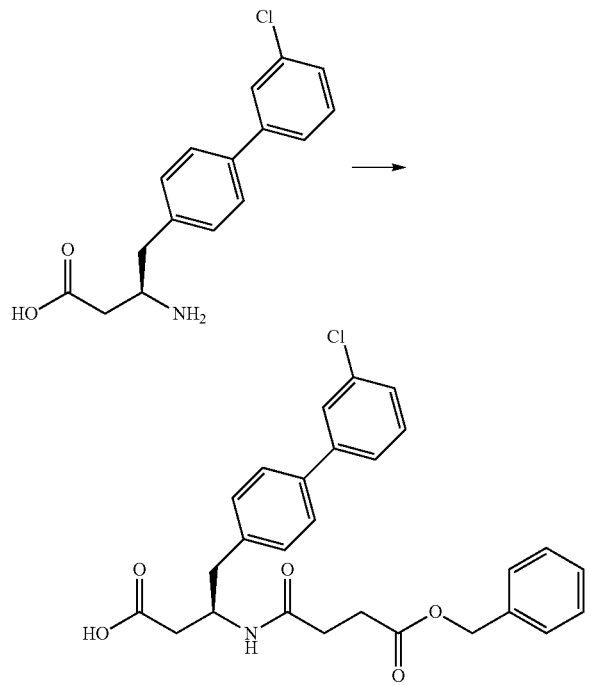

A solution of succinic acid mono-benzyl ester (71.1 mg, 0.342 mmol), EDCI (65.5 mg, 0.342 mmol) and HOAt (46.5 mg, 0.342 mmol) in DMF (1 ml), which is allowed to stir at room temperature for 1 hour, is added to a solution of (R)-3-amino-4-(3'-chlorobiphenyl-4-yl)butanoic acid (66 mg, 0.228 mmol) and DIPEA (0.080 ml, 0.456 mmol) in a mixed solvent DMF (2 ml) and water (2 ml). The reaction mixture is allowed to stir for 3 hours, and then diluted with H$_2$O. The products are extracted twice with EtOAc. The combined organic layer is washed with brine, dried over Na$_2$SO$_4$, filtered, and concentrated to give crude. The resulting residue is purified by preparative HPLC using a gradient of 20% MeCN/water (0.1% TFA) to 100% MeCN to give (R)-3-(4-(benzyloxy)-4-oxobutanamido)-4-(3'-chlorobiphenyl-4-yl) butanoic acid (42.4 mg) as a white solid; HPLC retention time=1.22 minutes (condition B); MS (m+1)=480.35; 1H NMR (400 MHz, CHLOROFORM-d) δ ppm 2.44-2.75 (m, 6 H) 2.86-2.99 (m, 2 H) 4.48-4.56 (m, 1 H) 5.11 (s, 2 H) 6.29 (br d, J=8.6 Hz, 1 H) 6.97-7.07 (m, 10 H) 7.25-7.36 (m, 2 H) 7.42-7.50 (m, 2 H) 7.54 (br t, J=1.6 Hz, 1 H).

Example 3-30

Synthesis of 4-(biphenyl-4-yl)-3-(1-(carboxymethyl) cyclopentanecarboxamido)butanoic acid

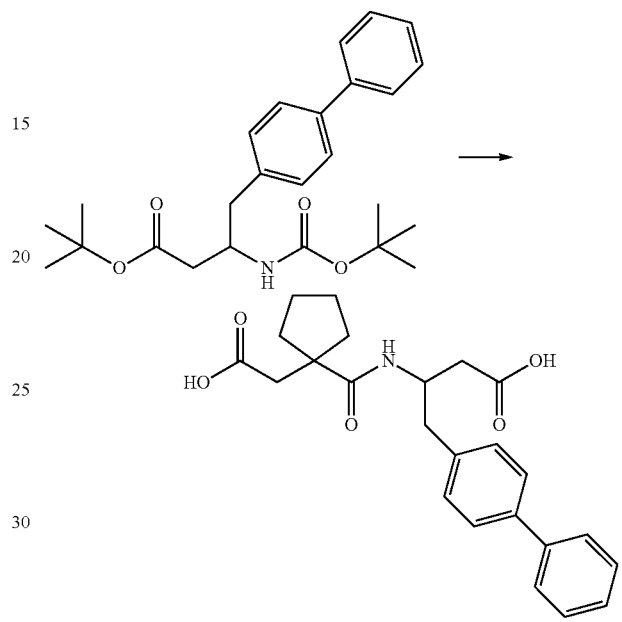

To tert-butyl 4-(biphenyl-4-yl)-3-(tert-butoxycarbonylamino)butanoate (110 mg, 0.267 mmol), a solution of 4 M HCl in 1,4-dioxane (0.668 ml, 2.67 mmol) is added. After stirring for 1 h, the reaction mixture is concentrated to give crude 3-amino-4-biphenyl-4-yl-butyric acid tert-butyl ester hydrochloride.

Next, to a solution of EDCI (51.2 mg, 0.267 mmol), 1-hydroxy-7-azabenzotriazole (36.4 mg, 0.267 mmol) and 6:1 mixture of 1-(2-(benzyloxy)-2-oxoethyl)cyclopentanecarboxylic acid and 2-(1-(benzyloxycarbonyl)cyclopentyl)acetic acid (65.6 mg, 0.214 mmol) in DMF (1 ml), which is stirred for 1.5 hours in advance, the crude 3-amino-4-biphenyl-4-yl-butyric acid tert-butyl ester hydrochloride and DIPEA (0.093 ml, 0.535 mmol) are added. After stirring for 2.5 hours, the reaction mixture is diluted with H$_2$O, and the products are extracted with EtOAc. The organic layer is washed with brine, dried over Na$_2$SO$_4$, filtered, and concentrated. The obtained residue is purified by silica gel flash column chromatography (heptane/EtOAc=100:0 to 0:100) to give crude tert-butyl 3-(1-(2-(benzyloxy)-2-oxoethyl)cyclopentanecarboxamido)-4-(biphenyl-4-yl)butanoate (38 mg).

Next, to the solution of the crude tert-butyl 3-(1-(2-(benzyloxy)-2-oxoethyl)cyclopentanecarboxamido)-4-(biphenyl-4-yl)butanoate (38 mg) in DCM (0.7 ml), TFA (0.263 ml, 3.42 mmol) is added. After stirring for 1 hour, the reaction mixture is concentrated to give crude 3-(1-(2-(benzyloxy)-2-oxoethyl)cyclopentanecarboxamido)-4-(biphenyl-4-yl)butanoic acid (39 mg).

Next, A suspension of the crude (39 mg) and Pd/C (16.6 mg, 7.8 μmol) in EtOH (1 ml) is allowed to stir under hydrogen at room temperature for 4 hours. The reaction mixture is filtered, and concentrated to give crude. The resulting residue is purified by preparative HPLC using a gradient of 20% MeCN/water (0.1% TFA) to 100% MeCN to give 4-(biphenyl-4-yl)-3-(1-(carboxymethyl)cyclopentanecarboxamido)butanoic acid (12.7 mg); HPLC retention time=1.16 minutes (condition B); MS (m+1)=410.1; 1H NMR (400 MHz, DMSO-d$_6$) δ ppm 1.39-1.53 (m, 6 H) 1.83-1.98 (m, 2 H) 2.34-2.45 (m, 2 H) 2.53 (s, 2 H) 2.73-2.86 (m, 2 H) 4.21-4.33 (m, 1 H) 7.27 (d, J=8.1 Hz, 2 H) 7.32-7.37 (m, 2 H) 7.43-7.46 (m, 2 H) 7.55-7.58 (m, 2 H) 7.62-7.64 (m, 2 H) 7.84 (br d, J=8.9 Hz, 1 H).

Example 3-31

Synthesis of (R)-ethyl 4-(3'-chlorobiphenyl-4-yl)-3-(2-oxo-2,3-dihydrooxazole-5-carboxamido)butanoate

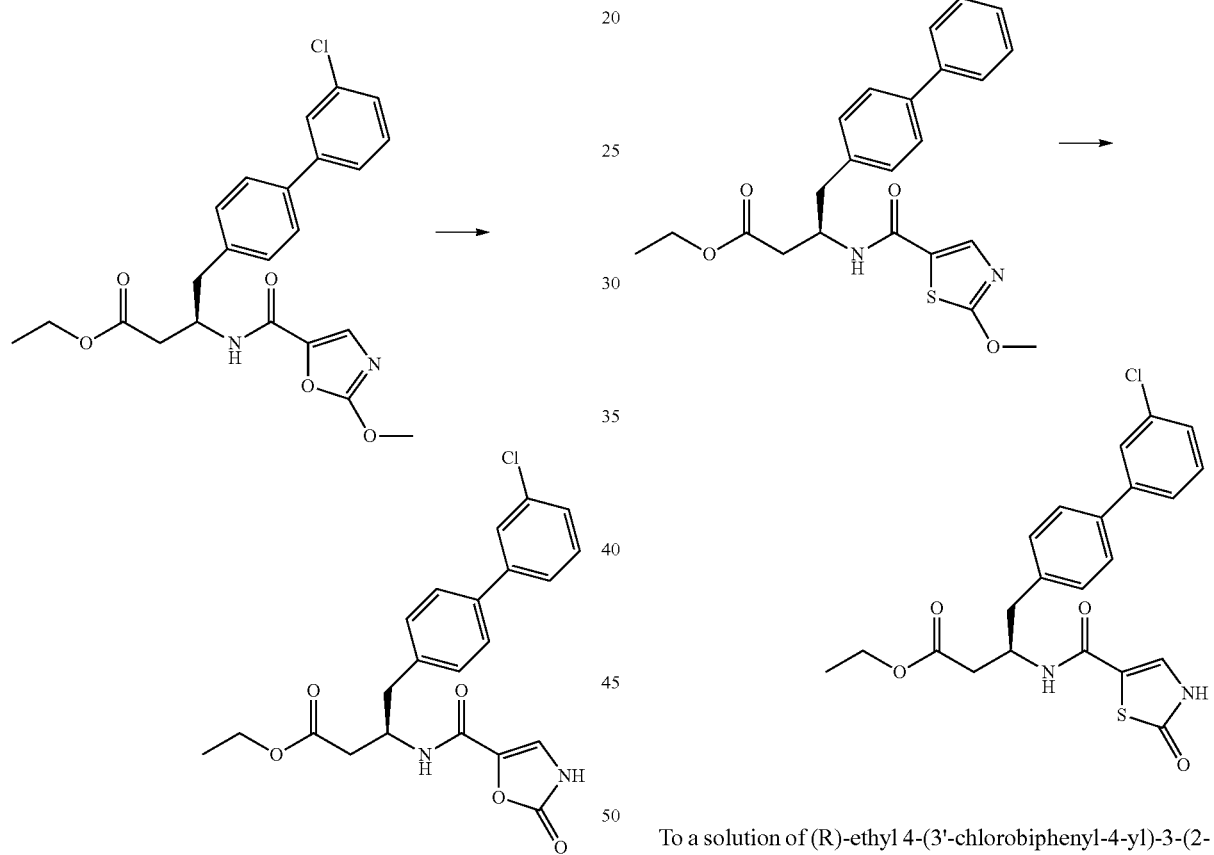

To a solution of (R)-ethyl 4-(3'-chlorobiphenyl-4-yl)-3-(2-methoxyoxazole-5-carboxamido)butanoate, intermediate 14, (103 mg, 0.23 mmol) in dioxane (3 mL) is added 4 N solution of HCl in dioxane (0.29 mL, 1.16 mmol). The crude was stirred at room temperature for 2 hrs. The crude is concentrated and is diluted in water and EtOAc. The organic layer is washed with brine, dried over MgSO$_4$, filtered, and concentrated. 50% of the crude is purified via RP-HPLC (SunFire C18, H$_2$O (0.1% TFA)/CH$_3$CN) to give (R)-ethyl 4-(3'-chlorobiphenyl-4-yl)-3-(2-oxo-2,3-dihydrooxazole-5-carboxamido)butanoate (38 mg) as a white solid. HPLC retention time=1.66 minutes (condition A); MS (m+1)=429.4; 1H NMR (400 MHz, CHLOROFORM-d) δ ppm 1.29 (t, J=7.1 Hz, 3 H) 2.51-2.69 (m, 2 H) 2.95 (dd, 1 H) 3.05 (dd, 1 H) 4.19 (q, 2 H) 4.58-4.75 (m, 1 H) 6.83 (d, J=8.8 Hz, 1 H) 7.26-7.33 (m, 4 H) 7.35 (t, J=7.7 Hz, 1 H) 7.45 (dt, J=7.6, 1.5 Hz, 1 H) 7.51 (d, J=8.3 Hz, 2 H) 7.56 (t, J=1.8 Hz, 1 H) 8.45 (br. s., 1 H).

Example 3-32

Synthesis of (R)-ethyl 4-(3'-chlorobiphenyl-4-yl)-3-(2-oxo-2,3-dihydrothiazole-5-carboxamido)butanoate

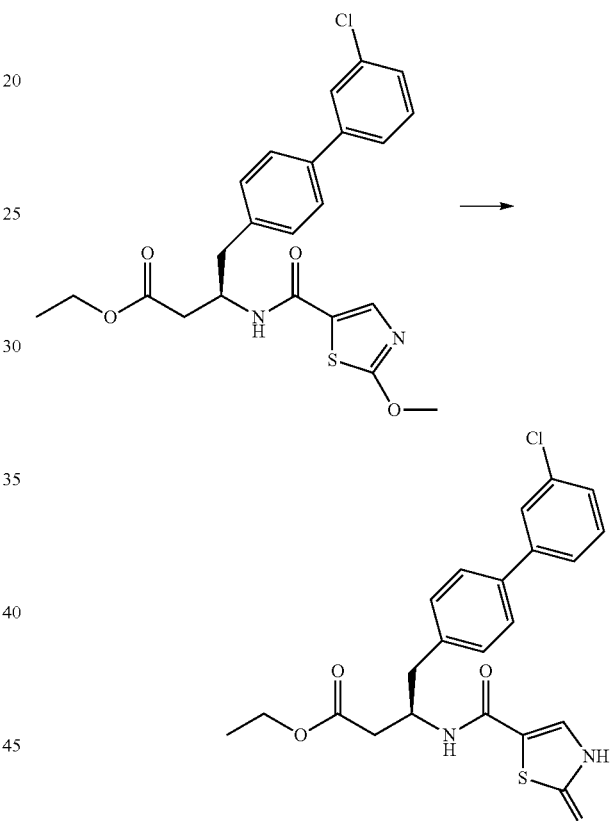

To a solution of (R)-ethyl 4-(3'-chlorobiphenyl-4-yl)-3-(2-methoxythiazole-5-carboxamido)butanoate, intermediate 13, (170 mg, 0.37 mmol) in dioxane (5 mL) is added a solution of 4 M HCl in dioxane (0.5 mL, 2.00 mmol). The crude is stirred at room temperature for 3 hrs. The crude is concentrated. Part of the crude is purified via RP-HPLC (SunFire C18, H$_2$O (0.1% TFA)/CH$_3$CN) to give (95 mg) of (R)-ethyl 4-(3'-chlorobiphenyl-4-yl)-3-(2-oxo-2,3-dihydrothiazole-5-carboxamido)butanoate as a white solid. HPLC retention time=1.82 minutes (condition D); MS (m+1)=445.2. 1H NMR (400 MHz, CHLOROFORM-d) δ ppm 1.29 (t, J=7.1 Hz, 3 H) 2.46-2.70 (m, 2 H) 2.78-2.97 (m, 1 H) 3.07 (dd, J=13.0, 6.2 Hz, 1 H) 4.11-4.28 (m, 2 H) 4.51-4.69 (m, 1 H) 6.64 (d, J=8.1 Hz, 1 H), 7.19-7.42 (m, 5 H) 7.44 (d, J=6.1 Hz, 1 H) 7.48-7.62 (m, 3 H), 9.54 (br. s., 1 H).

Example 3-33

Synthesis of (R)-ethyl 4-(3'-chlorobiphenyl-4-yl)-3-(5-oxo-4,5-dihydro-1,3,4-oxadiazole-2-carboxamido)butanoate

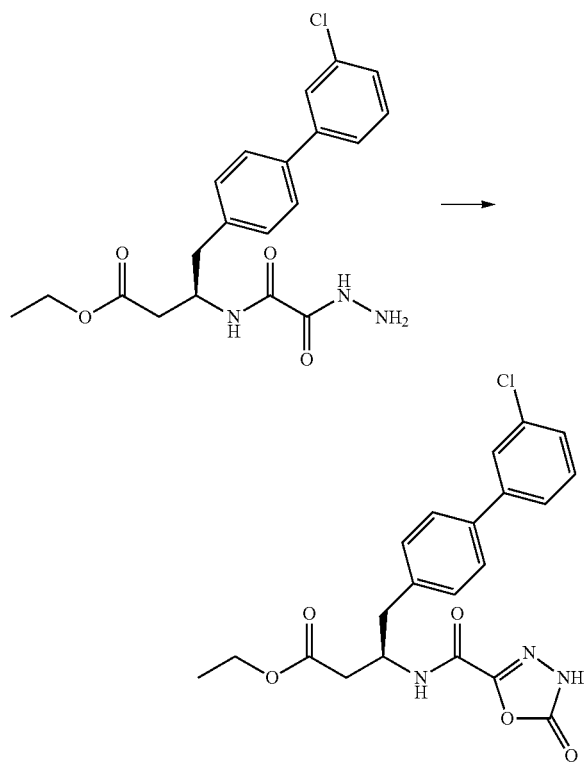

To a solution of (R)-ethyl 4-(3'-chlorobiphenyl-4-yl)-3-(2-hydrazinyl-2-oxoacetamido)butanoate, intermediate 12, (289 mg, 0.72 mmol) in THF (8.5 mL) is added CD (139 mg, 0.86 mmol) at room temperature. After stirring for 18 hour at room temperature, the reaction is quenched with $H_2O$ and 1M HCl, and the crude is diluted with EtOAc. The organic layer is washed with brine, dried over $Na_2SO_4$, filtered, and concentrated under reduced pressure. The obtained residue is purified by RP-HPLC (SunFire C18, $H_2O$ (0.1% TFA)/$CH_3CN$) and then lyophilized to give (R)-ethyl 4-(3'-chloro-biphenyl-4-yl)-3-(5-oxo-4,5-dihydro-1,3,4-oxadiazole-2-carboxamido)butanoate (100 mg). HPLC retention time=1.67 minutes (condition A); MS (m+1)=430.2; 1H NMR (400 MHz, DMSO-$d_6$) δ ppm 1.14 (t, J=7.1 Hz, 3 H) 2.52-2.70 (m, 2 H) 2.84 (dd, J=13.7, 8.4 Hz, 1 H) 2.90 (dd, J=13.7, 8.4 Hz, 1 H) 4.02 (q, J=7.1 Hz, 2 H) 4.42-4.58 (m, 1 H) 7.30 (d, J=8.1 Hz, 2 H) 7.37-7.43 (m, 1 H) 7.47 (t, J=7.8 Hz, 1 H) 7.57-7.66 (m, 3 H) 7.70 (t, J=1.9 Hz, 1 H) 8.98 (d, J=8.8 Hz, 1 H) 12.94 (s, 1 H).

Example 3-34

Synthesis of (R)-3-(3-Carboxymethyl-ureido)-4-(3'-chloro-biphenyl-4-yl)-butyric acid ethyl ester

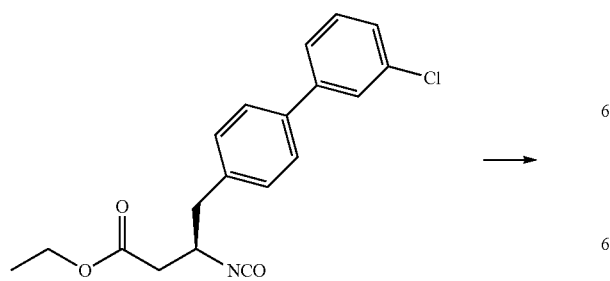

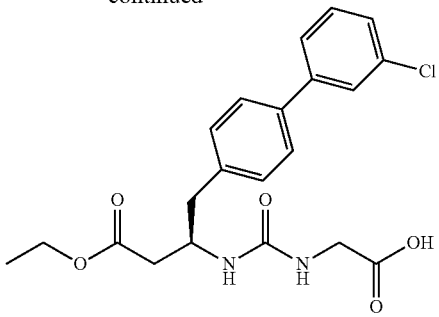

To a solution of t-butyl 2-aminoacetate (19.08 mg, 0.145 mmol) and DIEA (18.8 mg, 0.145 mmol) in DMF (1 mL) is added Intermediate 45 (50 mg, 0.145 mmol) and the mixture is stirred at room temperature for 2 hours. The solvent is removed under reduced pressure to give (R)-3-(3-tert-butoxycarbonylmethyl-ureido)-4-(3'-chloro-biphenyl-4-yl)-butyric acid ethyl ester.

Next, to a solution of the above diester (70 mg, 0.147 mmol) in methylene chloride (2 mL) is added TFA (4 mL) and the mixture is stirred at room temperature for 18 hours. The solvents are removed under reduced pressure and the residue is purified by preparative HPLC using a gradient of 35% MeCN/water to 100% MeCN (+0.1% TFA). Lyophilization of the proper fractions gives the title compound; HPLC Retention time 1.42 minutes (condition C); MS 419.1 (M+1); 1H NMR (400 MHz, DMSO-$d_6$): δ ppm 1.17 (t, J=7.07 Hz, 3H), 2.41 (d, J=7.07 Hz, 2H), 2.77-2.79 (m, 2H), 3.66-3.68 (m, 2H), 4.04 (q, J=7.07 Hz, 2H), 4.08-4.15 (m, 1H), 6.13 (t, J=5.81 Hz, 1H), 6.24 (d, J=8.59 Hz, 1H), 7.28-7.30 (m, 2H), 7.39-7.42 (m, 1H), 7.48 (t, J=7.83 Hz, 1H), 7.62-7.64 (m, 3H), 7.71 (t, J=1.77 Hz, 1H), 12.42 (s, 1H).

Example 4-1

Synthesis of (R)-4-biphenyl-4-yl-3-(2-1H-tetrazol-5-yl-acetylamino)-butyric acid ethyl ester

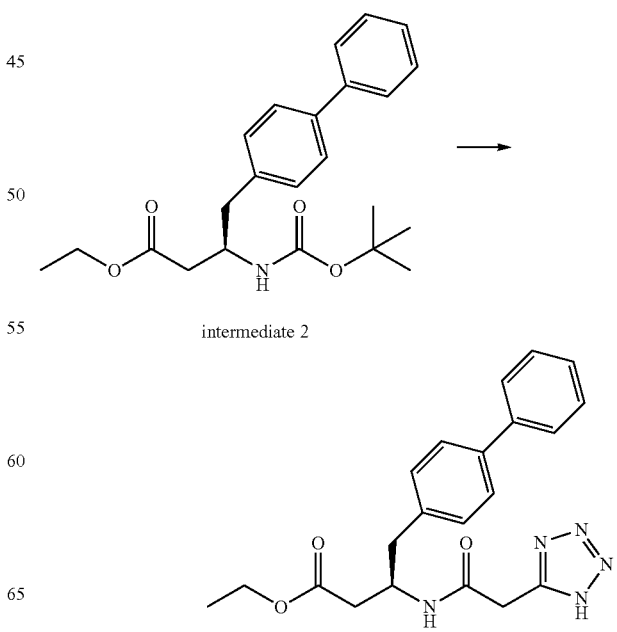

intermediate 2

To a solution of (R)-4-biphenyl-4-yl-3-tert-butoxycarbonylamino-butyric acid ethyl ester (100 mg, 0.261 mmol) in DCM (3 mL) at room temperature is added TFA (1 mL, 12.98 mmol) and the mixture is stirred at room temperature for 0.5 hour. The mixture is concentrated under reduced pressure to give (R)-3-amino-4-biphenyl-4-yl-butyric acid ethyl ester trifluoroacetic salt. HPLC retention time=1.50 minutes (condition C); MS (m+1)=384.

Next, to a suspension of (R)-3-amino-4-biphenyl-4-yl-butyric acid ethyl ester trifluoroacetic salt (0.074 g, 0.261 mmol) in DCM (10 mL) at room temperature is added 1H-tetrazole-5-acetic acid (0.050 g, 0.392 mmol). To the mixture at ice bath temperature is added bis(2-oxo-3-oxazolidinyl)phosphinic chloride (0.100 g, 0.392 mmol) and quickly followed by DIPEA (0.137 ml, 0.783 mmol). The reaction mixture is slowly warmed up to room temperature and stirred overnight. The reaction is extracted with DCM. The combined organic layer is washed with saturated $NaHCO_3$, saturated $NH_4Cl$, brine and dried over anhydrous sodium sulfate, filtered and concentrated under reduced pressure to give (R)-4-biphenyl-4-yl-3-(2-1H-tetrazol-5-yl-acetylamino)-butyric acid ethyl ester. HPLC retention time=1.04 minutes (condition E); MS (m+1)=394.

Example 4-2

Synthesis of (R)-ethyl 4-(biphenyl-4-yl)-3-(6-(methylsulfonamido)nicotinamido)butanoate

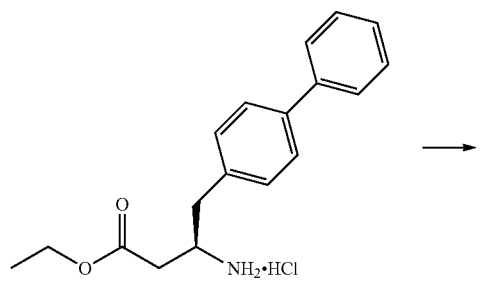

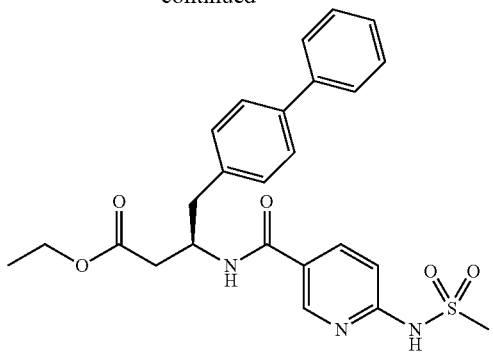

To a solution of (R)-ethyl 3-amino-4-(3'-chlorobiphenyl-4-yl)butanoate hydrochloride (103 mg, 0.32 mmol) and 6-(methylsulfonamido)nicotinic acid, intermediate 15, (84 mg, 0.39 mmol) in $CH_2Cl_2$ (2 mL) and DMF (2 mL) is added TEA (0.18 mL, 1.29 mmol) and HATU (159 mg, 0.42 mmol) at room temperature. The crude is stirred at room temperature for 2 hrs. The crude is quenched with saturated $NaHCO_3$, diluted in EtOAc. The organic layer is washed with six times with water, brine, dried over $MgSO_4$, filtered, and concentrated. The crude is purified via RP-HPLC (SunFire C18, $H_2O$ (0.1% TFA)/$CH_3CN$) to give (R)-ethyl 4-(biphenyl-4-yl)-3-(6-(methylsulfonamido)nicotinamido)butanoate as a white solid (4.1 mg). HPLC retention time=1.61 minutes (condition A); MS (m+1)=482.3. 1H NMR (400 MHz, CHLOROFORM-d) δ ppm 1.22 (t, J=7.2 Hz, 3 H), 2.56 (t, J=4.8 Hz, 2 H), 2.84-2.92 (m, 1 H), 3.05 (dd, J=13.6, 6.1 Hz, 1 H), 3.16 (s, 3 H), 4.08-4.18 (m, 2 H), 4.57-4.71 (m, 1 H), 7.03 (d, J=8.3 Hz, 1 H), 7.10 (d, J=8.3 Hz, 1 H), 7.22 (d, J=8.3 Hz, 2 H), 7.26-7.31 (m, 1 H), 7.33-7.40 (m, 2 H), 7.44-7.54 (m, 5 H), 7.98 (dd, J=8.8, 2.3 Hz, 1 H), 8.52 (s, 1 H).

Following compounds are prepared using similar procedure as described in example 4-2:

| Example # | Product | Reagent | LCMS-RT (condition) | MS (M + 1) |
|---|---|---|---|---|
| Example 4-3 | (R)-ethyl 4-(3'-chlorobiphenyl-4-yl)-3-(4-(methylsulfonamido)benzamido)butanoate | EDCl and HOAt used instead of HATU | 1.68 min (A) | 515.2 |

-continued

| Example # | Product | Reagent | LCMS-RT (condition) | MS (M + 1) |
|---|---|---|---|---|
| Example 4-4 | 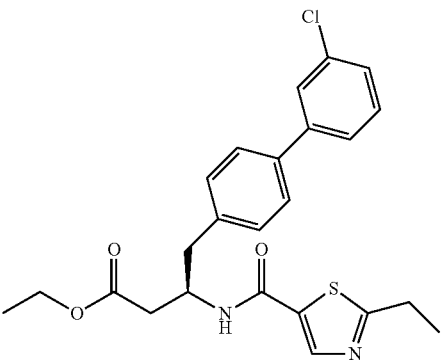<br>(R)-ethyl 4-(3'-chlorobiphenyl-4-yl)-3-(2-ethylthiazole-5-carboxamido)butanoate | 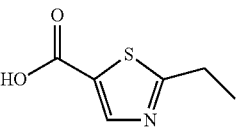<br>intermediate 26 | 1.63 min (A) | 457.2 |
| Example 4-5 | 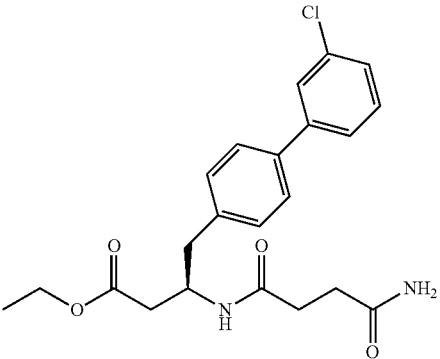<br>(R)-ethyl 3-(4-amino-4-oxobutanamido)-4-(3'-chlorobiphenyl-4-yl)butanoate | 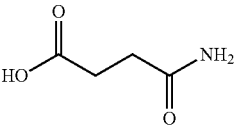<br>EDCl and HOAt used instead of HATU | 1.49 min (A) | 417.3 |
| Example 4-6 | 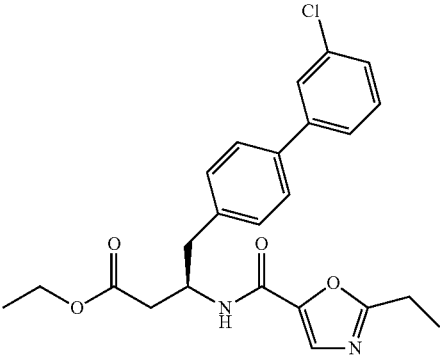<br>(R)-ethyl 4-(3'-chlorobiphenyl-4-yl)-3-(2-ethyloxazole-5-carboxamido)butanoate | 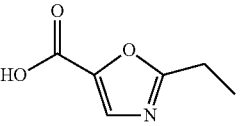<br>intermediate 23 | 1.60 min (A) | 441.3 |

-continued

| Example # | Product | Reagent | LCMS-RT (condition) | MS (M + 1) |
|---|---|---|---|---|
| Example 4-7 | (R)-ethyl 4-(3'-chlorobiphenyl-4-yl)-3-(3-hydroxy-1H-pyrazole-5-carboxamido)butanoate | | 1.82 min (A) | 428.2 |
| Example 4-8 | (R)-ethyl 4-(3'-chlorobiphenyl-4-yl)-3-(5-oxo-4,5-dihydro-1H-1,2,4-triazole-3-carboxamido)butanoate | EDCl and HOAt used instead of HATU | 1.86 min (D) | 429.2 |
| Example 4-9 | (R)-ethyl 4-(3'-chlorobiphenyl-4-yl)-3-(6-hydroxypyridazine-3-carboxamido)butanoate | EDCl and HOAt used instead of HATU | 1.82 min (D) | 440.2 |

-continued

| Example # | Product | Reagent | LCMS-RT (condition) | MS (M + 1) |
|---|---|---|---|---|
| Example 4-10 | 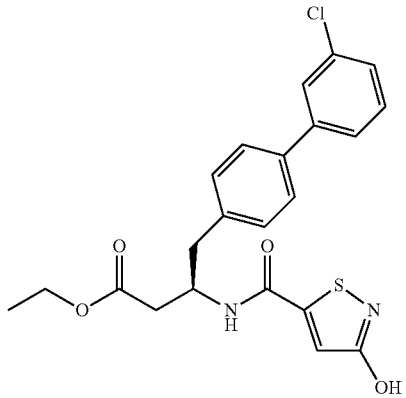<br>(R)-ethyl 4-(3'-chlorobiphenyl-4-yl)-3-(3-hydroxyisothiazole-5-carboxamido)butanoate | 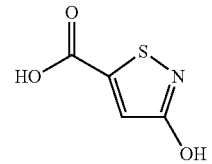<br>intermediate 20<br>EDCl and HOAt used instead of HATU | 1.56 min (A) | 445.3 |
| Example 4-11 | 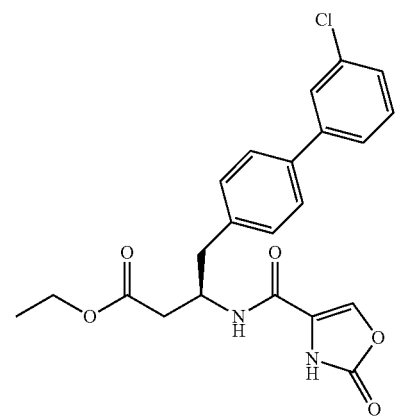<br>(R)-ethyl 4-(3'-chlorobiphenyl-4-yl)-3-(2-oxo-2,3-dihydrooxazole-4-carboxamido)butanoate | 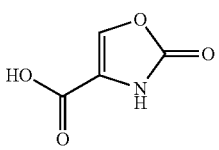<br>Intermediate 19<br>EDCl and HOAt used instead of HATU | 1.79 min (D) | 429.1 |
| Example 4-12 | 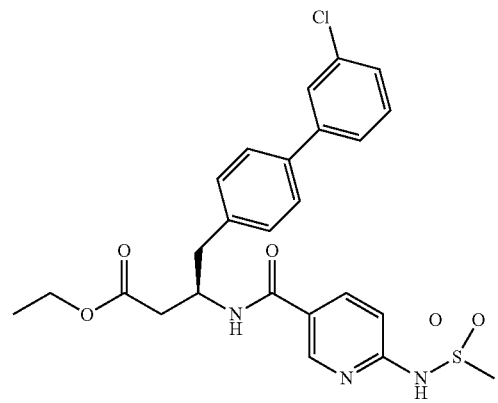<br>(R)-ethyl 4-(3'-chlorobiphenyl-4-yl)-3-(6-(methylsulfonamido)nicotinamido)butanoate | 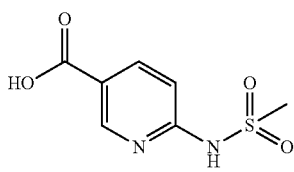<br>intermediate 15 | 1.81 min. (D) | 516.2 |

Example 4-3: 1H NMR (400 MHz, DMSO-d$_6$) δ ppm 1.13 (t, J=7.1 Hz, 3 H) 2.52-2.67 (m, 2 H) 2.88 (dd, J=13.3, 8.0 Hz, 1 H) 2.95 (dd, J=13.3, 8.0 Hz, 1 H) 3.05 (s, 3 H) 4.02 (q, J=7.1 Hz, 2 H) 4.46-4.65 (m, 1 H) 7.23 (d, J=8.8 Hz, 2 H) 7.34 (d, J=8.1 Hz, 2 H) 7.36-7.42 (m, 1 H) 7.46 (t, J=7.8 Hz, 1 H) 7.59-7.66 (m, 3 H) 7.69 (t, J=1.8 Hz, 1 H) 7.75 (d, J=8.6 Hz, 2 H) 8.31 (d, J=8.3 Hz, 1 H) 10.07 (s, 1 H)

Example 4-4: 1H NMR (400 MHz, DMSO-d$_6$) δ ppm 1.13 (t, J=7.1 Hz, 3 H) 1.28 (t, J=7.5 Hz, 3 H) 2.59 (d, J=7.1 Hz, 2 H) 2.81-2.94 (m, 2 H) 2.97 (q, J=7.6 Hz, 2 H) 4.03 (q, J=7.1 Hz, 2 H) 4.40-4.55 (m, 1 H) 7.32 (d, J=8.1 Hz, 2 H) 7.36-7.42 (m, 1 H) 7.46 (t, J=7.8 Hz, 1 H) 7.58-7.65 (m, 3 H) 7.69 (t, J=1.9 Hz, 1 H) 8.18 (s, 1 H) 8.52 (d, J=8.3 Hz, 1 H)

Example 4-5: 1H NMR (400 MHz, CD$_3$OD) δ ppm 1.24 (t, J=7.1 Hz, 3 H) 2.38-2.60 (m, 6 H) 2.78-2.94 (m, 2 H) 4.10 (q, J=7.1 Hz, 2 H) 4.42-4.55 (m, 1 H) 7.32 (d, J=8.3 Hz, 2 H) 7.40 (t, J=7.83 Hz, 1 H) 7.50-7.53 (m, 4 H) 7.60 (t, J=1.89 Hz, 1 H)

Example 4-6: 1H NMR (400 MHz, DMSO-d$_6$) δ ppm 1.13 (t, J=7.2 Hz, 3 H) 1.25 (t, J=7.6 Hz, 3 H) 2.53-2.65 (m, 2 H) 2.80 (q, J=7.6 Hz, 2 H) 2.84-2.96 (m, 2 H) 4.02 (q, J=7.1 Hz, 2 H) 4.42-4.60 (m, 1 H) 7.31 (d, J=8.3 Hz, 2 H) 7.37-7.42 (m, 1 H) 7.47 (t, J=7.8 Hz, 1 H) 7.59 (s, 1 H) 7.60-7.65 (m, 3 H) 7.69 (t, J=1.9 Hz, 1 H) 8.48 (d, J=8.6 Hz, 1 H)

Example 4-7: 1H NMR (400 MHz, DMSO-d$_6$) δ ppm 1.13 (t, J=7.1 Hz, 3 H) 2.52-2.65 (m, 2 H) 2.85 (dd, J=13.6, 5.8 Hz, 1 H) 2.91 (dd, J=13.6, 5.8 Hz, 1 H) 4.02 (q, J=7.1 Hz, 2 H) 4.38-4.60 (m, 1 H) 5.89 (s, 1 H) 7.31 (d, J=8.3 Hz, 2 H) 7.37-7.42 (m, 1 H) 7.46 (t, J=7.8 Hz, 1 H) 7.58-7.65 (m, 3 H) 7.69 (t, J=1.8 Hz, 1 H) 8.10 (d, J=8.6 Hz, 1 H)

Example 4-8: 1H NMR (400 MHz, CD$_3$OD) δ ppm 1.22 (t, J=7.2 Hz, 3 H) 2.56-2.72 (m, 2 H) 2.95 (d, J=7.3 Hz, 2 H) 4.11 (q, J=7.2 Hz, 2 H) 4.53-4.73 (m, 1 H) 7.28-7.36 (m, 3 H) 7.39 (t, J=7.8 Hz, 1 H) 7.48-7.55 (m, 3 H) 7.58 (t, J=1.8 Hz, 1 H)

Example 4-9: 1H NMR (400 MHz, DMSO-d$_6$) δ ppm 1.13 (t, J=7.1 Hz, 3 H) 2.53-2.71 (m, 2 H) 2.85 (dd, J=13.7, 8.3 Hz, 1 H) 2.96 (dd, J=13.7, 8.3 Hz, 1 H) 4.02 (q, J=7.1 Hz, 2 H) 4.45-4.63 (m, 1 H) 6.93 (dd, J=9.9, 2.3 Hz, 1 H) 7.30 (d, J=8.1 Hz, 2 H) 7.36-7.42 (m, 1 H) 7.47 (t, J=7.8 Hz, 1 H) 7.61 (d, J=8.3 Hz, 3 H) 7.69 (t, J=1.8 Hz, 1 H) 7.75 (d, J=9.9 Hz, 1 H) 8.45 (d, J=9.1 Hz, 1 H) 13.41 (d, J=2.0 Hz, 1 H)

Example 4-10: 1H NMR (400 MHz, DMSO-d$_6$) δ ppm 1.13 (t, J=7.1 Hz, 3 H) 2.60 (d, J=7.6 Hz, 2 H) 2.90 (d, J=6.8 Hz, 2 H) 4.02 (q, J=7.2 Hz, 2 H) 4.39-4.53 (m, 1 H) 7.11 (s, 1 H) 7.32 (d, J=8.1 Hz, 2 H) 7.37-7.43 (m, 1 H) 7.47 (t, J=7.8 Hz, 1 H) 7.60-7.66 (m, 3 H) 7.70 (t, J=1.9 Hz, 1 H) 8.72 (d, J=8.3 Hz, 1 H) 11.76 (br. s., 1 H)

Example 4-11: 1H NMR (400 MHz, CHLOROFORM-d) δ ppm 1.27 (t, J=7.1 Hz, 3 H) 2.47-2.69 (m, 2 H) 2.90 (dd, J=13.6, 7.8 Hz, 1 H) 3.06 (dd, J=13.6, 6.6 Hz, 1 H) 3.06 (broad s, 1H) 4.07-4.28 (m, 2 H) 4.52-4.74 (m, 1 H) 7.21-7.37 (m, 5 H) 7.38-7.44 (m, 1 H) 7.48 (d, J=8.1 Hz, 2 H) 7.53 (t, J=1.6 Hz, 1 H) 9.50 (br. s., 1 H).

Example 4-12: 1H NMR (400 MHz, DMSO-d$_6$) δ ppm 1.13 (t, J=7.1 Hz, 3 H) 2.59 (d, J=7.3 Hz, 2 H) 2.76-3.03 (m, 2 H) 4.03 (q, J=7.1 Hz, 2 H) 4.39-4.66 (m, 1 H) 7.02 (d, 1 H) 7.28-7.54 (m, 4 H) 7.54-7.80 (m, 4 H) 8.05 (dd, J=8.6, 2.3 Hz, 1 H) 8.45 (d, J=8.3 Hz, 1 H) 8.61 (br. s., 1 H).

Example 4-13

Synthesis of (R)-ethyl 4-(5'-fluoro-2'-methoxybiphenyl-4-yl)-3-(oxazole-5-carboxamido)butanoate

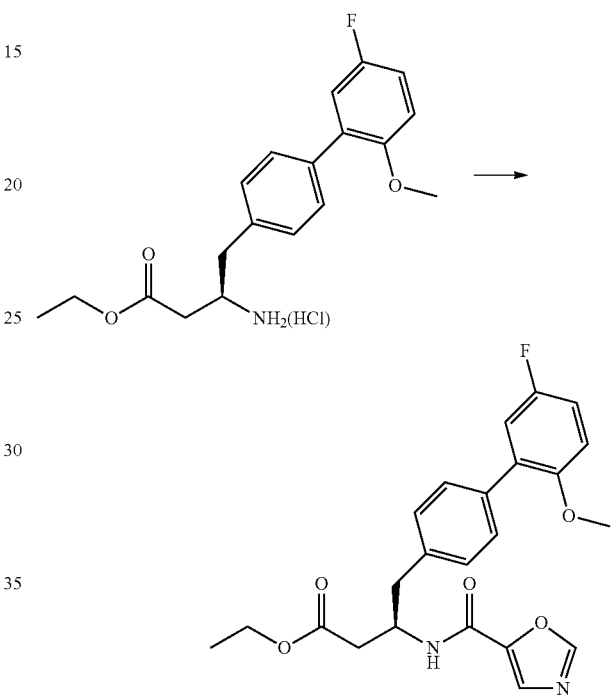

To a solution of oxazole-5-carboxylic acid (70 mg, 0.61 mmol) in DMF (1.5 mL) and DCM (1.5 mL) is added (R)-ethyl 3-amino-4-(5'-fluoro-2'-methoxybiphenyl-4-yl)butanoate hydrochloride, intermediate 10, (150 mg, 0.41 mmol), HATU (233 mg, 0.61 mmol), and TEA (284 μL, 2.04 mmol). After stirring for 2 hours, the reaction is quenched with H$_2$O, and the crude is diluted with EtOAc, the organic layer is washed with brine, dried over Na$_2$SO$_4$, filtered, and concentrated under reduced pressure. The obtained residue is purified by RP-HPLC (SunFire C18, H$_2$O (0.1% TFA)/CH$_3$CN), and then lyophilized to give (R)-ethyl 4-(5'-fluoro-2'-methoxybiphenyl-4-yl)-3-(oxazole-5-carboxamido)butanoate (157 mg). HPLC retention time=1.50 minutes (condition A); MS (m+1)=427.4; 1H NMR (400 MHz, CHLOROFORM-d) δ ppm 1.19 (t, J=7.2 Hz, 3 H) 2.46-2.62 (m, 2 H) 2.86 (dd, J=13.6, 8.1 Hz, 1 H) 3.02 (dd, J=13.6, 6.1 Hz, 1 H) 3.67 (s, 3 H) 4.05-4.15 (m, 2 H) 4.52-4.69 (m, 1 H) 6.76-6.82 (m, 1 H) 6.83-6.96 (m, 2 H) 7.11-7.21 (m, 3 H) 7.37 (d, J=8.1 Hz, 2 H) 7.61 (s, 1 H) 7.80 (s, 1 H)

Following compounds are prepared using similar procedure as described in example 4-13:

| Example 4-14 | 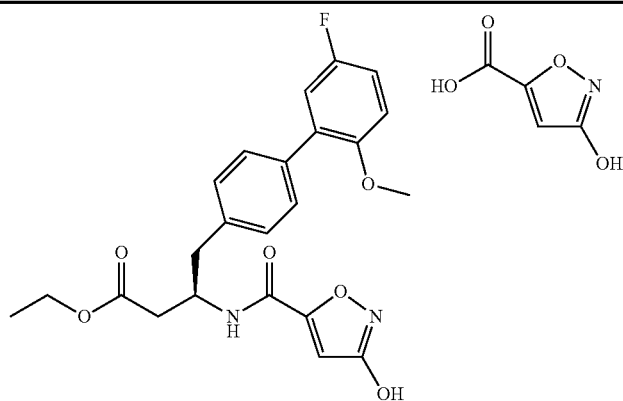 (R)-ethyl 4-(5'-fluoro-2'-methoxybiphenyl-4-yl)-3-(3-hydroxyisoxazole-5-carboxamido)butanoate | 1.43 min. 443.3 (A) |
|---|---|---|

Example 4-14: 1H NMR (400 MHz, CD$_3$OD) δ ppm 1.21 (t, J=7.1 Hz, 3 H) 2.61-2.68 (m, 2 H) 2.95 (d, J=7.1 Hz, 2 H) 3.74 (s, 3 H) 4.10 (q, J=7.1 Hz, 2 H) 4.60-4.73 (m, 1 H) 6.43 (s, 1 H) 6.98-7.06 (m, 3 H) 7.27 (d, J=8.1 Hz, 2 H) 7.38-7.48 (m, 2 H) 8.78 (d, J=8.8 Hz, 1 H)

Example 4-15

Synthesis of 5-[(R)-1-(3'-Chloro-biphenyl-4-ylmethyl)-2-ethoxycarbonyl-ethylcarbamoyl]-1H-pyrazole-3-carboxylic acid

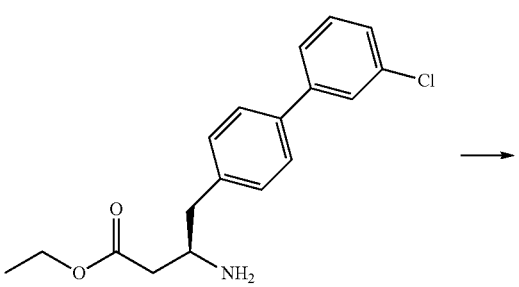

→

-continued

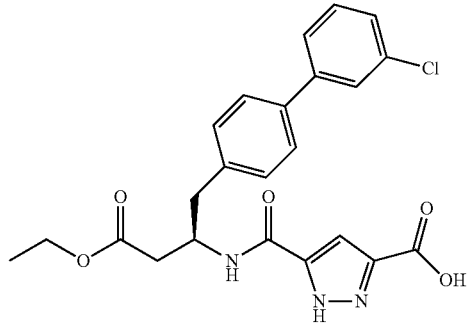

To a mixture of Intermediate 17-1 (130 mg, 0.367 mmol), 1H-pyrazole-3,5-dicarboxylic acid (74.5 mg, 0.477 mmol), EDCI (91 mg, 0.477 mmol) and HOBt (64.5 mg, 0.477 mmol) in DMF (3 mL) is added triethylamine (149 mg, 0.203 mmol) and the mixture is stirred at room temperature for 18 hours. Any insoluble material is removed by filtration and the filtrate is chromatographed by HPLC using a gradient of 10% MeCN/water to 100% MeCN (+0.1% TFA). Lyophilization of the proper fractions gives the title compound; HPLC Retention time 1.31 minutes (condition C); MS 456.2 (M+1); 1H NMR (400 MHz, DMSO-d$_6$) δ ppm 1.12 (t, J=7.07 Hz, 3H), 2.54-2.67 (m, 2H), 2.84-2.97 (m, 2H), 4.02 (q, J=7.07 Hz, 2H), 4.54 (m, 1H), 7.11 (s, broad, 1H), 7.32 (d, J=8.08 Hz, 2H), 7.39 (m, 1H), 7.46 (t, 1H), 7.62 (d, J=8.08 Hz, 3H), 7.69 (s, 1H), 8.41 (s, broad, 1H).

The following compounds are prepared using the procedure described for Example 4-15.

| Example # | Product | Reagent | HPLC-RT (condition) | MS (M + 1) |
|---|---|---|---|---|
| Example 4-16 | 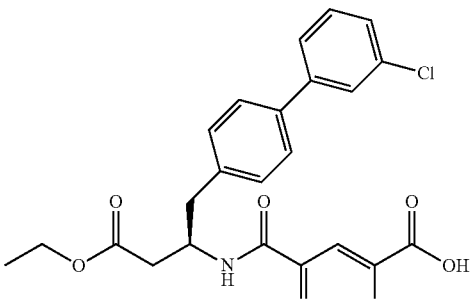<br>6-[(R)-1-(3'-Chloro-biphenyl-4-ylmethyl)-2-ethoxycarbonyl-ethylcarbamoyl]-pyrimidine-4-carboxylic acid | 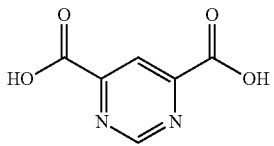 [SMILES: O=C(O)c1cc(C(=O)O)ncn1] | 1.31 min. (C) | 468.2 |

Example 4-16: 1H NMR (400 MHz, DMSO-d$_6$): δ ppm 1.11 (t, J=7.07 Hz, 3H), 2.59-2.79 (m, 2H), 2.87-2.92 (m, 1H), 2.98-3.04 (m, 1H), 4.01 (q, J=7.33 Hz, 2H), 4.57-4.66 (m, 1H), 7.30-7.32 (m, 2H), 7.37-7.40 (m, 1H), 7.45 (t, J=7.58 Hz, 1H), 7.59-7.61 (m, 3H), 7.68 (t, J=1.77 Hz, 1H), 8.16 (s, 1H), 9.10 (d, J=9.35 Hz, 1H), 9.31 (s, 1H).

Example 4-17

(R)-4-(3'-Chloro-biphenyl-4-yl)-3-[(3-hydroxy-isoxazole-5-carbonyl)-amino]-butyric acid ethyl ester

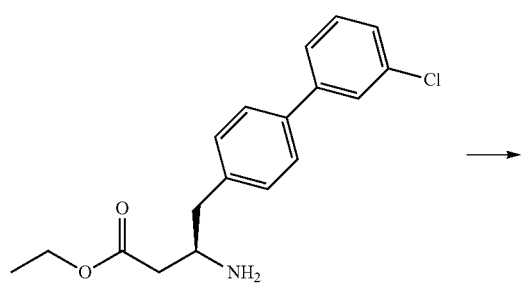

→

-continued

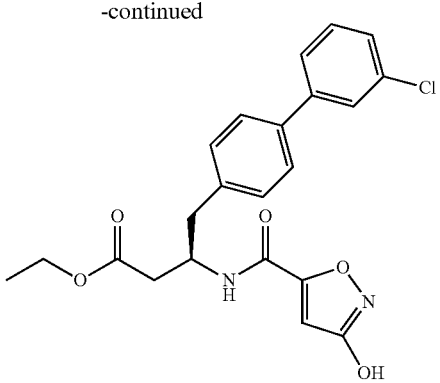

To a solution of intermediate 16-1 (40.6 mg, 0.315 mmol) and HATU (144 mg, 0.378 mmol) in DMF (2 mL) is added pyridine (74.7 mg, 0.76 mL, 0.944 mmol) and the mixture is stirred at room temperature for 15 minutes. Then Intermediate 17-1 is added and stirring is continued for 2 hours. Any insoluble is removed by filtration and the filtrate is chromatographed by HPLC using a gradient of 10% MeCN/water to 100% MeCN (+0.1% TFA). Lyophilization of the proper fractions gives the title compound. HPLC Retention time 1.36 minutes (condition C); MS 429.1 (M+1); 1H NMR (400 MHz, DMSO-d$_6$) δ ppm 1.13 (t, J=7.07 Hz, 3 H) 2.60 (dd, J=6.95, 3.66 Hz, 2 H) 2.81-2.95 (m, 2 H) 4.02 (q, J=7.24 Hz, 2 H) 4.49 (d, J=7.83 Hz, 1 H) 6.49 (s, 1 H) 7.31 (d, J=8.34 Hz, 2 H) 7.37-7.43 (m, 1 H) 7.47 (t, J=7.83 Hz, 1 H) 7.59-7.66 (m, 3 H) 7.70 (t, J=1.89 Hz, 1 H) 8.83 (d, J=8.84 Hz, 1 H).

The following compounds are prepared using the procedure described for Example 4-17

| Example # | Product | Reagent | HPLC-RT (condition) | MS (M + 1) |
|---|---|---|---|---|
| Example 4-18 | (R)-4-(3'-Chloro-biphenyl-4-yl)-3-[(oxazole-5-carbonyl)-amino]-butyric acid ethyl ester | | 1.48 min. (C) | 413.1 |
| Example 4-19 | (R)-4-(3'-Fluoro-biphenyl-4-yl)-3-[(3-hydroxy-isoxazole-5-carbonyl)-amino]-butyric acid ethyl ester | | 1.22 min. (C) | 413.1 |

Example 4-18: 1H NMR (400 MHz, DMSO-d$_6$) δ ppm 1.12 (t, J=7.07 Hz, 3 H) 2.60 (dd, J=6.95, 2.65 Hz, 2 H) 2.82-2.96 (m, 2 H) 4.02 (q, J=7.07 Hz, 2 H) 4.45-4.58 (m, 1 H) 7.31 (d, J=8.34 Hz, 2 H) 7.37-7.42 (m, 1 H) 7.47 (t, J=7.83 Hz, 1 H) 7.58-7.65 (m, 3 H) 7.69 (t, J=1.77 Hz, 1 H) 7.72 (s, 1 H) 8.55 (s, 1 H) 8.63 (d, J=8.59 Hz, 1 H).

Example 4-19: 1H NMR (400 MHz, DMSO-d$_6$) δ ppm 1.13 (t, J=7.07 Hz, 3 H) 2.54-2.75 (m, 2 H) 2.76-3.02 (m, 2 H) 4.02 (q, J=7.07 Hz, 2 H) 4.29-4.70 (m, 1 H) 6.49 (s, 1 H) 6.96-7.23 (m, 1 H) 7.30 (d, J=8.08 Hz, 2 H) 7.44-7.58 (m, 3 H) 7.64 (d, J=8.08 Hz, 2 H) 8.83 (d, J=8.59 Hz, 1 H) 11.68 (s, 1 H).

Example 4-20

(R)-3-[(5-Carboxymethyl-furan-2-carbonyl)-amino]-4-(3'-chloro-biphenyl-4-yl)-butyric acid ethyl ester and Example 4-21

(R)-3-[(5-Carboxymethyl-furan-2-carbonyl)-amino]-4-(3'-chloro-biphenyl-4-yl)-butyric acid

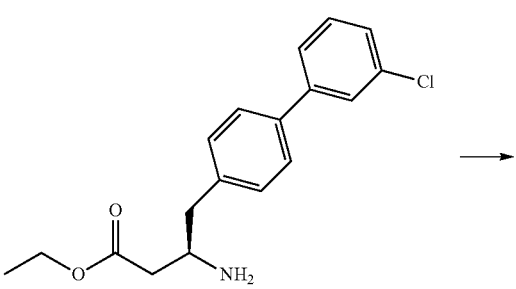

-continued

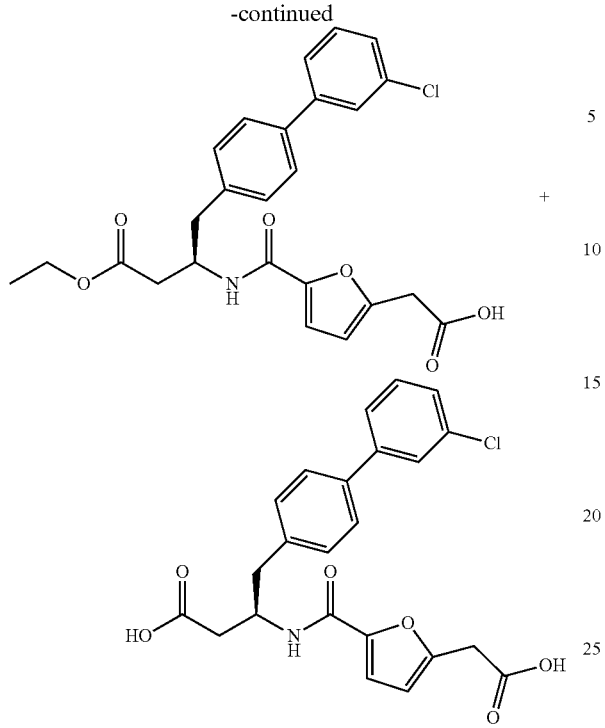

The reaction is performed similar to Example 4-15 using Intermediate 16-1 and Intermediate 44 to give (R)-4-(3'-chloro-biphenyl-4-yl)-3-[(5-methoxycarbonylmethyl-furan-2-carbonyl)-amino]-butyric acid ethyl ester. HPLC Retention time 1.38 minutes (condition C). Next, to a solution of the above diester (235 mg, 0.486 mmol) in EtOH (5 mL) is added 1N NaoH (0.486 mL) and the mixture is stirred at room temperature for 4 hours. The solvent is removed under reduced pressure and water (4 mL) is added. The solution is acidified with 1N HCl and the mixture is extracted with EtOAc. The organic phase is dried over sodium sulfate and the solvent is removed under reduced pressure. The residue is purified by preparative HPLC using a gradient of 10% MeCN/water to 100% MeCN (+0.1% TFA). Lyophilization of the proper fractions gives the title compounds. (R)-3-[(5-Carboxymethyl-furan-2-carbonyl)-amino]-4-(3'-chloro-biphenyl-4-yl)-butyric acid ethyl ester. HPLC Retention time 1.35 minutes (condition C); MS 470.0 (M+1); 1H NMR (400 MHz, DMSO-d$_6$) δ ppm 1.13 (t, J=7.07 Hz, 3H), 2.50-2.64 (m, 2H), 2.81-2.95 (m, 2H), 3.74 (s, 2H), 4.01 (q, J=7.07 Hz, 2H), 4.51 (m, 1H), 6.99 (d, J=3.28 Hz, 1H), 7.31 (d, J=8.34 Hz, 2H), 7.38-7.41 (m, 1H), 7.47 (t, 1H), 7.62 (d, J=8.08 Hz, 3H), 7.69 (t, 1H), 8.24 (d, J=8.84 Hz, 1H).

(R)-3-[(5-Carboxymethyl-furan-2-carbonyl)-amino]-4-(3'-chloro-biphenyl-4-yl)-butyric acid. HPLC Retention time 0.94 minutes (condition C); MS 442.0 (M+1); 1H NMR (400 MHz, DMSO-d$_6$) δ ppm 2.44-2.58 (m, 2H), 2.81-2.94 (m, 2H), 3.74 (s, 2H), 4.48 (m, 1H), 6.39 (d, J=3.28 Hz, 1H), 6.99 (d, J=3.54 Hz, 1H), 7.30 (d, J=8.34 Hz, 2H), 7.38-7.41 (m, 1H), 7.47 (t, 1H), 7.62 (d, J=8.34 Hz, 3H), 7.70 (t, J=1.77 Hz, 1H), 8.22 (d, J=8.84 Hz, 1H).

Example 4-22

(R)-4-(3'-Chloro-biphenyl-4-yl)-3-[(2H-tetrazole-5-carbonyl)-amino]-butyric acid ethyl ester

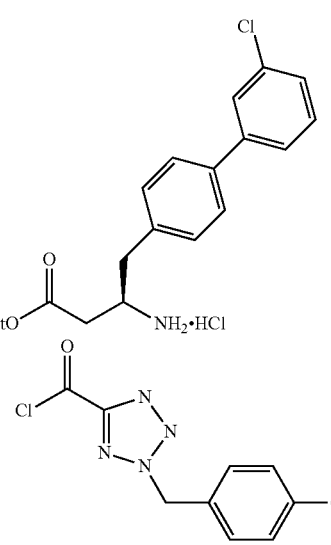

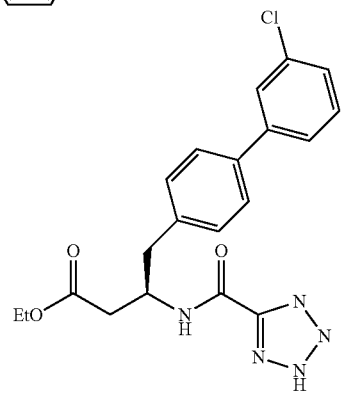

To a solution of intermediate 16-1 in DCM (8 ml) at room temperature is added 2-(4-methoxy-benzyl)-2H-tetrazole-5-carbonyl chloride and followed by TEA (0.293 ml, 2.100 mmol). The Reaction is stirred at room temperature for 5 min. The reaction is quenched by brine and is extracted with DCM. The combined organic layer is washed with brine and dried over anhydrous sodium sulfate, filtered and concentrated under reduced pressure. The residue is purified by column chromatography (15% to 40% EtOAc/Heptane). The obtained residue in TFA (5 ml, 64.9 mmol) is heated at 80° C. for 0.5 hours. The reaction is concentrated under reduced pressure to give (R)-4-(3'-chloro-biphenyl-4-yl)-3-[(2H-tetrazole-5-carbonyl)-amino]-butyric acid ethyl ester.

HPLC retention time=1.31 minutes (condition B); MS (m+1)=414.1; 1H NMR (400 MHz, DMSO-d$_6$) δ ppm 1.11 (t, J=7.1 Hz, 3 H), 2.63 (dd, J=15.4, 5.6 Hz, 1 H), 2.72 (dd, J=15.4, 8.3 Hz, 1 H), 2.86-2.99 (m, 2 H), 4.02 (q, J=7.1 Hz, 2 H), 4.55-4.67 (m, 1 H), 7.32 (d, J=8.1 Hz, 2 H), 7.37-7.42 (m, 1 H), 7.46 (t, J=7.8 Hz, 1 H), 7.60 (d, J=8.1 Hz, 3 H), 7.68 (t, J=1.8 Hz, 1 H), 9.37 (d, J=8.8 Hz, 1 H).

Following compounds are prepared using similar procedure as described in example 4-22:

| Example # | Product | Starting Material | Deprotection Condition | HPLC-RT (condition) | MS (M + 1) |
|---|---|---|---|---|---|
| Example 4-23 | 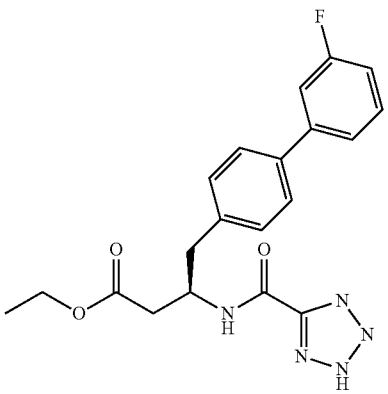<br>(R)-4-(3'-Fluoro-biphenyl-4-yl)-3-[(2H-tetrazole-5-carbonyl)-amino]-butyric acid ethyl ester | 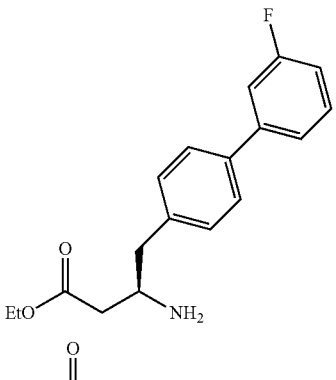 | 1 atm. H₂, 10% Pd/C, EtOH, RT | 1.12 min. (B) | 398.2 |
| Example 4-24 | 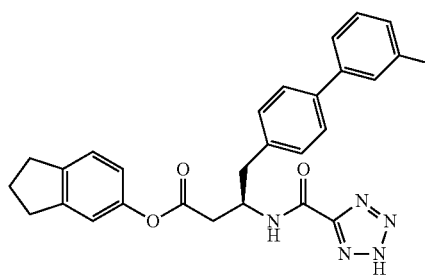<br>(R)-4-(3'-Chloro-biphenyl-4-yl)-3-[(2H-tetrazole-5-carbonyl)-amino]-butyric acid indan-5-yl ester | 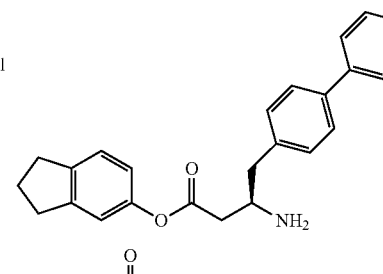 | TFA, 80° C. | 1.68 min. (B) | 502.3 |

Example 4-23: 1H NMR (400 MHz, DMSO-$d_6$) δ ppm 1.12 (t, J=7.2 Hz, 3 H), 2.59-2.67 (m, J=15.4, 5.6 Hz, 1 H), 2.72 (dd, J=15.4, 8.3 Hz, 1 H), 2.85-3.01 (m, 2 H), 4.02 (q, J=7.1 Hz, 2 H), 4.55-4.67 (m, 1 H), 7.11-7.19 (m, 1 H), 7.32 (d, J=8.3 Hz, 2 H), 7.42-7.51 (m, 3 H), 7.61 (d, J=8.3 Hz, 2 H), 9.34 (d, J=8.8 Hz, 1 H).

Example 4-24: 1H NMR (400 MHz, DMSO-$d_6$) δ ppm 1.95-2.06 (m, 2 H), 2.75-2.92 (m, 6 H), 2.95 (dd, J=13.5, 5.9 Hz, 1 H), 3.06 (dd, J=13.6, 8.1 Hz, 1 H), 4.64-4.76 (m, 1 H), 6.78 (dd, J=8.1, 2.3 Hz, 1 H), 6.88 (d, J=1.5 Hz, 1 H), 7.17 (d, J=8.1 Hz, 1 H), 7.34-7.41 (m, 3 H), 7.46 (t, J=7.8 Hz, 1 H), 7.59-7.65 (m, 3 H), 7.70 (t, J=1.8 Hz, 1 H), 8.43 (d, J=8.8 Hz, 1 H).

Example 4-25

2-((R)-1-Biphenyl-4-ylmethyl-2-ethoxycarbonyl-ethylamino)-oxazole-4-carboxylic acid ethyl ester

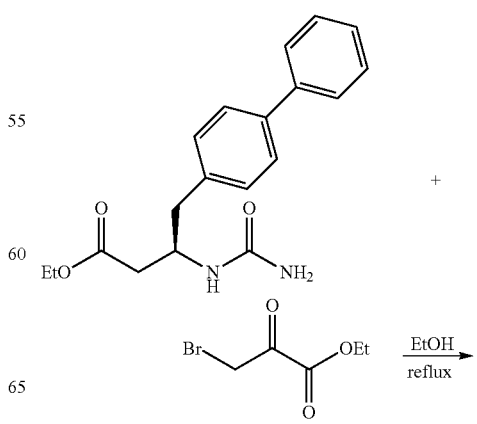

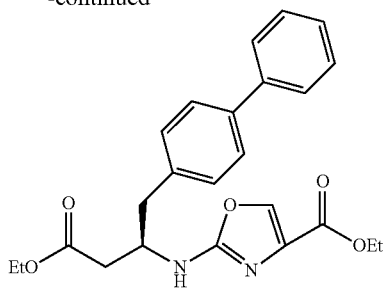

To a suspension of (R)-4-biphenyl-4-yl-3-ureido-butyric acid ethyl ester (169 mg, 0.518 mmol) in EtOH (5 ml) at ice bath is added ethyl bromopyruvate (0.098 ml, 0.777 mmol). The reaction is warmed up slowly to room temperature and stirred at reflux overnight. The reaction is concentrated and the residue is taken up in EtOAc and H$_2$O. The combined organic layer is washed with brine and dried over anhydrous sodium sulfate, filtered and concentrated under reduced pressure to give 2-(R)-1-biphenyl-4-ylmethyl-2-ethoxycarbonyl-ethylamino)-oxazole-4-carboxylic acid ethyl ester. HPLC retention time=1.42 minutes (condition B); MS (m+1)=423.

Example 4-26

Synthesis of (R,E)-ethyl 4-(4-(benzyloxy)-1-(3'-chlorobiphenyl-4-yl)-4-oxobutan-2-ylamino)-4-oxobut-2-enoate

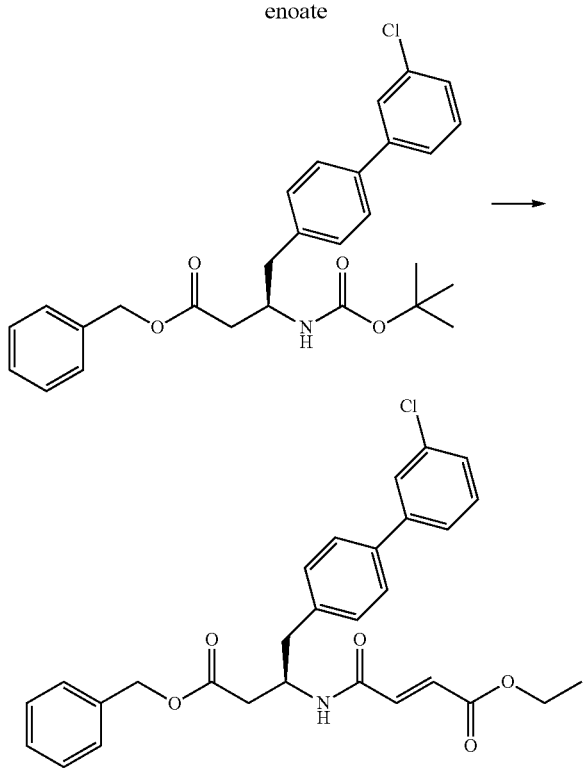

To (R)-benzyl 3-amino-4-(3'-chlorobiphenyl-4-yl)butanoate (87.6 mg, 0.183 mmol) is added a solution of HCl in 1,4-dioxane (0.456 mL, 1.825 mmol) at room temperature. After stirring for 3 hours, the reaction mixture is concentrated under reduced pressure to give (R)-benzyl 3-amino-4-(3'-chlorobiphenyl-4-yl)butanoate hydrochloride. A mixture of (R)-benzyl 3-amino-4-(3'-chlorobiphenyl-4-yl)butanoate hydrochloride, fumaric acid monoethyl ester (33.4 mg, 0.220 mmol), EDCI (63.3 mg, 0.330 mmol), DIPEA (0.058 ml, 0.330 mmol) and HOAt (44.9 mg, 0.330 mmol) in DMF (1.8 ml) is allowed to stir at room temperature for 3 hour. The reaction mixture is diluted with water, and then the products are extracted with EtOAc. The organic layer is washed with NH$_4$OH, 1M HCl aq and brine, dried over Na$_2$SO$_4$, filtered, and concentrated to give crude. The obtained residue is purified by silica gel flash column chromatography (heptane/EtOAc=100:0 to 0:100) to give (R,E)-ethyl 4-(4-(benzyloxy)-1-(3'-chlorobiphenyl-4-yl)-4-oxobutan-2-ylamino)-4-oxobut-2-enoate (72.9 mg); HPLC retention time=1.40 minutes (condition B); MS (m+1)=506.3; 1H NMR (400 MHz, CHLOROFORM-d) δ ppm 1.31 (t, J=7.1 Hz, 3 H) 2.58 (A of ABX, J$_{ab}$=16.4 Hz, J$_{ax}$=5.3 Hz, 1 H) 2.6 (B of ABX, J$_{ab}$=16.4 Hz, J$_{bx}$=5.1 Hz, 1 H) 2.88 (A of ABX, J$_{ab}$=13.6 Hz, J$_{ax}$=8.1 Hz, 1 H) 3.03 (B of ABX, J$_{ab}$=13.6 Hz, J$_{bx}$=6.3 Hz, 1 H) 4.24 (q, J=7.1 Hz, 2 H) 4.56-4.64 (m, 1 H) 5.12 (A of AB, J=12.1 Hz, 1 H) 5.18 (B of AB, J=12.1 Hz, 1 H) 6.57 (br d, J=9.1 Hz, 1 H) 6.77 (A of AB, J=15.4 Hz, 1 H) 6.81 (B of AB, J=15.4 Hz, 1 H) 7.19 (br d, J=8.1 Hz, 2 H) 7.29-7.47 (m, 10 H) 7.53-7.54 (m, 1 H).

Example 4-27

Synthesis of (R)-ethyl 4-(3'-chlorobiphenyl-4-yl)-3-(2-(ethoxycarbonylamino)acetamido)butanoate

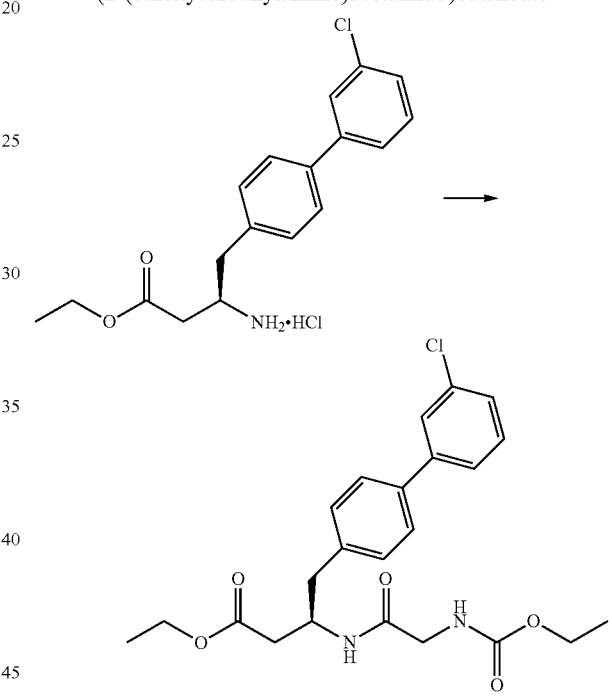

A mixture of (R)-ethyl 3-amino-4-(3'-chlorobiphenyl-4-yl)butanoate hydrochloride (173 mg, 0.488 mmol), 2-(ethoxycarbonylamino)acetic acid (86 mg, 0.488 mmol), EDCI (140 mg, 0.732 mmol), DIPEA (0.128 ml, 0.732 mmol) and HOAt (100 mg, 0.732 mmol) in DMF (2.5 ml) is allowed to stir at room temperature for 1 hour. The reaction mixture is diluted with water, and then the precipitated solid is collected on a funnel, washed with H$_2$O, and dried under reduced pressure to give crude. The obtained residue is purified by silica gel flash column chromatography (heptane/EtOAc=100:0 to 0:100) to give (R)-ethyl 4-(3'-chlorobiphenyl-4-yl)-3-(2-(ethoxycarbonylamino)acetamido)butanoate (161 mg); HPLC retention time=1.16 minutes (condition B); MS (m+1)=447.3; 1H NMR (400 MHz, CHLOROFORM-d) δ ppm 1.25 (t, J=7.07 Hz, 3 H) 1.29 (t, J=7.07 Hz, 3 H) 2.50 (A of ABX, J$_{ab}$=16.2 Hz, J$_{ax}$=5.3 Hz, 1 H) 2.54 (B of ABX, J$_{ab}$=16.2 Hz, J$_{bx}$=5.3 Hz, 1 H) 2.89 (A of ABX, J$_{ab}$=13.6 Hz, J$_{ax}$=7.8 Hz, 1 H) 2.99 (B of ABX, J$_{ab}$=13.6 Hz, J$_{bx}$=6.6 Hz, 1 H) 3.80 (be d, J=5.8 Hz, 2 H) 4.12-4.23 (m, 4 H) 4.48-4.56 (m, 1 H) 5.15 (br s, 1 H) 6.64 (br d, J=8.8 Hz, 1 H) 7.25-7.27 (m, 2 H) 7.29-7.38 (m, 2 H) 7.43-7.46 (m, 1 H) 7.49-7.52 (m, 2 H) 7.55-7.56 (m, 1 H).

Following compounds are prepared using similar procedure as described in example 4-27:

| Example # | Product | Starting Material | Condition | HPLC-RT (condition) | MS (M + 1) |
|---|---|---|---|---|---|
| Example 4-28 | (R)-2-(tert-butoxycarbonyl(2-(1-(3'-chlorobiphenyl-4-yl)-4-ethoxy-4-oxobutan-2-ylamino)-2-oxoethyl)amino)acetic acid | | EDCI, HOAT, DIPEA, DMF, rt | 1.53 min. (A) | 533.2 |
| Example 4-29 | (R,E)-4-(3'-chlorobiphenyl-4-yl)-3-(4-ethoxy-4-oxobut-2-enamido)butanoic acid | | EDCI, HOAT, DIPEA, DMF, rt | 1.00 min. (B) | 416.1 |

-continued

| Example # | Product | Starting Material | Condition | HPLC-RT (condition) | MS (M + 1) |
|---|---|---|---|---|---|
| Example 4-30 | (R)-4-(2',5'-dichloro-biphenyl-4-yl)-3-[(2-ethyl-oxazole-5-carbonyl)-amino]-butyric acid ethyl ester | | HATU, TEA, DMF/DCM, rt | 1.64 min. (A) | 476.2 |

-continued

| Example # | Product | Starting Material | Condition | HPLC-RT (condition) | MS (M + 1) |
|---|---|---|---|---|---|
| Example 4-31 | (R)-4-(3'-chloro-biphenyl-4-yl)-3-[(5-methyl-2H-pyrazole-3-carbonyl)-amino]-butyric acid ethyl ester | | HATU, TEA, DMF/DCM, rt | 1.66 min. (A) | 426.1 |

-continued

| Example # | Product | Starting Material | Condition | HPLC-RT (condition) | MS (M + 1) |
|---|---|---|---|---|---|
| Example 4-32 | (R)-4-(3'-chloro-biphenyl-4-yl)-3-[(2-methyl-thiazole-5-carbonyl)-amino]-butyric acid ethyl ester | | HATU, TEA, DMF/DCM, rt | 1.69 min. (A) | 443.2 |

-continued

| Example # | Product | Starting Material | Condition | HPLC-RT (condition) | MS (M + 1) |
|---|---|---|---|---|---|
| Example 4-33 | (R)-4-(3'-chloro-biphenyl-4-yl)-3-[(2-methyl-pyrimidine-5-carbonyl)-amino]-butyric acid ethyl ester | | HATU, TEA, DMF/DCM, rt | 1.66 min. (A) | 438.2 |

-continued
| Example # | Product | Starting Material | Condition | HPLC-RT (condition) | MS (M + 1) |
|---|---|---|---|---|---|
| Example 4-34 | 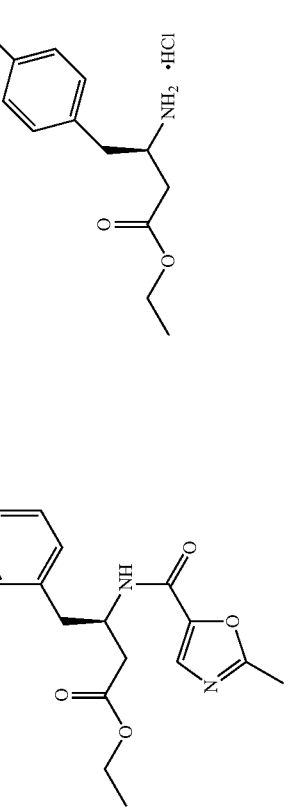 (R)-4-(3'-chloro-biphenyl-4-yl)-3-[(2-methyl-oxazole-5-carbonyl)-amino]-butyric acid ethyl ester | 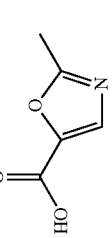 | 2-methyloxazole-5-carboxylic acid, HATU, TEA, DMF/DCM, rt | 1.71 min. (A) | 427.1 |

| Example # | Product | Starting Material | Condition | HPLC-RT (condition) | MS (M + 1) |
|---|---|---|---|---|---|
| Example 4-35 | (R)-4-(5'-chloro-2'-fluoro-biphenyl-4-yl)-3-[(oxazole-5-carbonyl)-amino]-butyric acid ethyl ester | | oxazole-5-carboxylic acid, HATU, TEA, DMF/DCM, rt | 1.75 min. (A) | 431.1 |

| Example # | Product | Starting Material | Condition | HPLC-RT (condition) | MS (M + 1) |
|---|---|---|---|---|---|
| Example 4-36 | (R)-4-(5'-chloro-2'-fluoro-biphenyl-4-yl)-3-[(2-ethyl-oxazole-5-carbonyl)-amino]-butyric acid ethyl ester | | HATU, TEA, DMF/DCM, rt | 1.81 min. (A) | 459.1 |

-continued

| Example # | Product | Starting Material | Condition | HPLC-RT (condition) | MS (M + 1) |
|---|---|---|---|---|---|
| Example 4-37 | (R)-ethyl 4-(3'-chlorobiphenyl-4-yl)-3-(2-(prop-1-en-2-yl)oxazole-5-carboxamido)butanoate | | HATU, TEA, DMF/DCM, rt | 1.86 min. (A) | 453.2 |

Example 4-29: 1H NMR (400 MHz, CHLOROFORM-d) δ ppm 1.31 (t, J=7.2 Hz, 3 H) 2.64 (A of ABX, $J_{ab}$=16.8 Hz, $J_{ax}$=5.1 HZ, 1 H) 2.68 (B of ABX, $J_{ab}$=16.8 Hz, $J_{bx}$=5.1 Hz, 1 H) 2.97 (A of ABX, $J_{ab}$=13.7 Hz, $J_{ax}$=8.1 HZ, 1 H) 3.08 (B of ABX, $J_{ab}$=13.7 Hz, $J_{bx}$=6.7 Hz, 1 H) 4.25 (q, J=7.2 Hz, 2 H) 4.58-4.67 (m, 1 H) 6.66 (d, J=8.8 Hz, 1 H) 6.80 (A of AB, J=15.4 Hz, 1 H) 6.97 (B of AB, J=15.4 Hz, 1 H) 7.27-7.37 (m, 4 H) 7.43-7.45 (m, 1 H) 7.51 (d, J=8.3 Hz, 2 H) 7.55-7.56 (m, 1 H).

Example 4-30: 1H NMR (400 MHz, CD$_3$OD) δ ppm 1.21 (t, J=7.2 Hz, 3 H) 1.34 (t, J=7.6 Hz, 3 H) 2.68 (d, J=6.8 Hz, 2 H) 2.84-2.87 (m, 2 H) 2.98-3.00 (m, 2 H) 4.10 (q, J=7.1 Hz, 2 H) 4.66-4.78 (m, 1 H) 7.27-7.37 (m, 6 H) 7.41-7.47 (m, 1 H) 7.54 (s, 1 H).

Example 4-31: 1H NMR (400 MHz, CD$_3$OD) δ ppm 1.20 (t, J=7.1 Hz, 3 H) 2.28 (s, 3 H) 2.62 (d, J=7.1 Hz, 2 H) 2.93 (dd, J=13.6, 6.8 Hz, 1 H) 3.00 (dd, J=13.6, 7.3 Hz, 1 H) 4.09 (q, J=7.1 Hz, 2 H) 4.60-4.76 (m, 1 H) 6.45 (s, 1 H) 7.24-7.40 (m, 4 H) 7.42-7.51 (m, 3 H) 7.54 (t, J=1.8 Hz, 1 H).

Example 4-32: 1H NMR (400 MHz, CD$_3$OD) δ ppm 1.20 (t, J=7.2 Hz, 3 H) 2.58-2.66 (m, 2 H) 2.68 (s, 3 H) 2.94 (dd, J=14.2, 7.8 Hz, 1 H) 2.99 (dd, J=13.6, 6.8 Hz, 1 H) 4.09 (q, J=7.2 Hz, 2 H) 4.58-4.76 (m, 1 H) 7.27-7.31 (m, 1 H) 7.33 (d, J=8.3 Hz, 2 H) 7.37 (t, J=7.8 Hz, 1 H) 7.46-7.49 (m, 1 H) 7.51 (d, J=8.1 Hz, 2 H) 7.55 (t, J=1.9 Hz, 1 H) 8.06 (s, 1 H) 8.49 (d, J=8.6 Hz, 1 H).

Example 4-33: 1H NMR (400 MHz, CD$_3$OD) δ ppm 1.21 (t, J=7.1 Hz, 3 H) 2.60-2.70 (m, 2 H) 2.72 (s, 3 H) 2.97 (dd, J=13.6, 8.1 Hz, 1 H) 3.03 (dd, J=13.9, 6.6 Hz, 1 H) 4.11 (q, J=7.2 Hz, 2 H) 4.67-4.81 (m, 1 H) 7.27-7.33 (m, 1 H) 7.33-7.41 (m, 3 H) 7.48-7.52 (m, 1 H) 7.54 (d, J=8.3 Hz, 2 H) 7.57 (t, J=1.8 Hz, 1 H) 8.70 (d, J=8.3 Hz, 1 H) 8.92 (s, 2 H).

Example 4-34: 1H NMR (400 MHz, CD$_3$OD) δ ppm 1.21 (t, J=7.2 Hz, 3 H) 2.43 (s, 3 H) 2.63 (d, J=6.6 Hz, 2 H) 2.94 (dd, J=13.9, 7.1 Hz, 1 H) 2.99 (dd, J=13.6, 7.6 Hz, 1 H) 4.10 (q, J=7.1 Hz, 2 H) 4.62-4.74 (m, 1 H) 7.26-7.30 (m, 1 H) 7.30-7.39 (m, 3 H) 7.43-7.51 (m, 3 H) 7.53 (t, J=1.8 Hz, 1 H) 8.15 (s, 1 H).

Example 4-35: 1H NMR (400 MHz, CD$_3$OD) δ ppm 1.20 (t, J=7.1 Hz, 3 H) 2.64 (dd, J=15.4, 7.3 Hz, 1 H) 2.70 (dd, J=15.9, 6.3 Hz, 1 H) 2.99 (d, J=7.3 Hz, 2 H) 4.10 (q, J=7.2 Hz, 2 H) 4.65-4.79 (m, 1 H) 7.14 (dd, J=10.2, 8.7 Hz, 1 H) 7.30 (ddd, J=8.8, 4.1, 2.8 Hz, 1 H) 7.32-7.37 (m, 2 H) 7.37-7.46 (m, 3 H) 7.67 (s, 1 H) 8.28 (s, 1 H) 8.62 (d, J=8.6 Hz, 1 H).

Example 4-36: 1H NMR (400 MHz, CD$_3$OD) δ ppm 1.20 (t, J=7.2 Hz, 3 H) 1.33 (t, J=7.7 Hz, 3 H) 2.66 (d, J=6.8 Hz, 2 H) 2.83 (q, J=7.6 Hz, 2 H) 2.98 (d, J=7.1 Hz, 2 H) 4.10 (q, J=7.1 Hz, 2 H) 4.65-4.79 (m, 1 H) 7.14 (dd, J=10.2, 8.7 Hz, 1 H) 7.30 (ddd, J=8.8, 4.1, 2.8 Hz, 1 H) 7.32-7.37 (m, 2 H) 7.37-7.46 (m, 3 H) 7.54 (s, 1 H) 8.49 (d, J=8.8 Hz, 1 H).

Example 4-37: 1H NMR (400 MHz, CHLOROFORM-d) δ ppm 1.33 (t, J=7.1 Hz, 3 H) 2.22 (s, 3 H) 2.57-2.72 (m, 2 H) 2.99 (dd, J=13.6, 8.1 Hz, 1 H) 3.16 (dd, J=13.6, 6.3 Hz, 1 H) 4.15-4.33 (m, 2 H) 4.60-4.82 (m, 1 H) 5.55 (s, 1 H) 6.10 (s, 1 H) 7.15 (d, J=8.8 Hz, 1 H) 7.34 (d, J=8.1 Hz, 3 H) 7.39 (t, J=7.7 Hz, 1 H) 7.48 (dt, J=7.6, 1.5 Hz, 1 H) 7.54 (d, J=8.1 Hz, 2 H) 7.58 (t, J=1.8 Hz, 1 H) 7.72 (s, 1 H).

Example 5-1

Synthesis of (R)-4-(biphenyl-4-yl)-3-(3-carboxypropanamido)butanoic acid

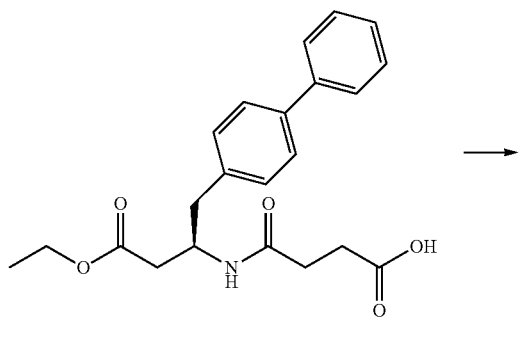

Example 1-1

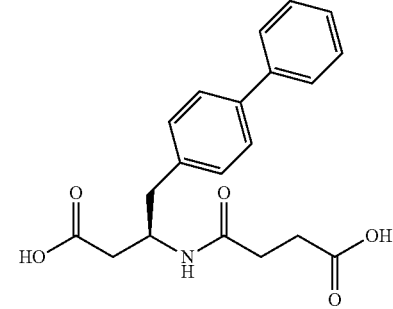

To a solution of (R)-4-(1-(biphenyl-4-yl)-4-ethoxy-4-oxobutan-2-ylamino)-4-oxobutanoic acid (61.2 mg, 0.160 mmol) in THF (1.6 mL) and methanol (0.2 mL), aqueous 1M NaOH solution (0.638 mL, 0.638 mmol) is added at room temperature. After stirring for 45 minutes, the reaction is quenched with aqueous 0.1 M HCl and is extracted with ethyl acetate. The organic layer is washed with brine, dried over Na$_2$SO$_4$, filtered, and concentrated under reduced pressure to give (R)-4-(biphenyl-4-yl)-3-(3-carboxypropanamido)butanoic acid (54.9 mg). HPLC retention time=1.33 minutes (condition A); MS (m+1)=356.1; 1H NMR (400 MHz, CD$_3$OD) δ ppm 2.40-2.56 (m, 6 H) 2.83-2.94 (m, 2 H) 4.43-4.50 (m, 1 H) 7.29-7.32 (m, 3 H) 7.41 (t, 2 H, J=7.7 Hz) 7.53-7.60 (m, 4 H).

Following compounds are prepared using similar procedure as described in example 5-1:

| Example # | Product | Starting Material | Hydrolysis Condition | HPLC-RT (condition) | MS (M + 1) |
|---|---|---|---|---|---|
| Example 5-2 | (R)-3-(3-carboxy-propionylamino)-4-(4'-chloro-biphenyl-4-yl)-butyric acid | Example 2-2 | Aq. NaOH, THF, MeOH, rt | 1.10 min. (A) | 389.9 |
| Example 5-3 | (R)-3-(3-carboxy-propionylamino)-4-(4'-fluoro-biphenyl-4-yl)-butyric acid | Example 2-1 | Aq. NaOH, THF, MeOH, rt | 0.87 min. (A) | 373.9 |
| Example 5-4 | (R)-3-(3-carboxy-propionylamino)-4-(3'-fluoro-biphenyl-4-yl)-butyric acid | Example 2-3 | Aq. NaOH, THF, MeOH, rt | 0.69 min. (B) | 374.0 |
| Example 5-5 | (R)-3-(3-carboxy-propionylamino)-4-(2'-fluoro-biphenyl-4-yl)-butyric acid | Example 2-4 | Aq. NaOH, THF, MeOH, rt | 0.80 min. (B) | 373.9 |

-continued

| Example # | Product | Starting Material | Hydrolysis Condition | HPLC-RT (condition) | MS (M + 1) |
|---|---|---|---|---|---|
| Example 5-6 | (R)-3-(3-carboxy-propionylamino)-4-(2′-chloro-biphenyl-4-yl)-butyric acid | Example 2-5 | Aq. NaOH, THF, MeOH, rt | 0.74 min. (B) | 390.0 |
| Example 5-7 | (R)-3-(3-carboxy-propionylamino)-4-(2′-methoxy-biphenyl-4-yl)-butyric acid | Example 2-6 | Aq. NaOH, THF, MeOH, rt | 0.61 min. (B) | 386.1 |
| Example 5-8 | (R)-3-(3-carboxy-propionylamino)-4-(2′-methyl-biphenyl-4-yl)-butyric acid | Example 2-7 | Aq. NaOH, THF, MeOH, rt | 0.94 min. (B) | 370.0 |
| Example 5-9 | (R)-4-biphenyl-4-yl-3-[(pyrimidine-4-carbonyl)-amino]-butyric acid | Example 3-3 | Aq. LiOH, EtOH, rt. | 0.67 min. (B) | 362.0 |

-continued

| Example # | Product | Starting Material | Hydrolysis Condition | HPLC-RT (condition) | MS (M + 1) |
|---|---|---|---|---|---|
| Example 5-10 | (R)-4-biphenyl-4-yl-3-(2-1H-tetrazol-5-yl-acetylamino)-butyric acid | Example 4-1 | aq. NaOH, MeOH, RT | 1.19 min. (C) | 366.0 |
| Example 5-11 | (R)-4-Biphenyl-4-yl-3-[(2-hydroxy-pyrimidine-5-carbonyl)-amino]-butyric acid | Example 3-2 | aq. NaOH, THF, MeOH, RT | 1.28 min. (A) | 377.9 |
| Example 5-12 | 6-((R)-1-Biphenyl-4-ylmethyl-2-carboxy-ethylcarbamoyl)-pyrimidine-4-carboxylic acid | Example 3-1 | aq. NaOH, THF, MeOH, RT | 0.80 min. (B) | 406.0 |
| Example 5-13 | (R)-4-(1-carboxy-3-(2'-chloro-5'-fluorobiphenyl-4-yl)propan-2-ylamino)-4-oxobutanoic acid | Example 2-8 | aq. NaOH, THF, MeOH, RT | 0.74 min. (B) | 408.2 |

-continued

| Example # | Product | Starting Material | Hydrolysis Condition | HPLC-RT (condition) | MS (M + 1) |
|---|---|---|---|---|---|
| Example 5-14 | (R)-4-(1-carboxy-3-(3'-methylbiphenyl-4-yl)propan-2-ylamino)-4-oxobutanoic acid | Example 2-9 | aq. NaOH, THF, MeOH, RT | 0.55 min. (B) | 370.1 |
| Example 5-15 | (R)-4-(1-carboxy-3-(3',5'-difluorobiphenyl-4-yl)propan-2-ylamino)-4-oxobutanoic acid | Example 2-10 | aq. NaOH, THF, MeOH, RT | 0.46 min. (B) | 392.1 |
| Example 5-16 | (R)-4-(1-carboxy-3-(3'-ethylbiphenyl-4-yl)propan-2-ylamino)-4-oxobutanoic acid | Example 2-11 | aq. NaOH, THF, MeOH, RT | 0.70 min. (B) | 384.3 |

-continued

| Example # | Product | Starting Material | Hydrolysis Condition | HPLC-RT (condition) | MS (M + 1) |
|---|---|---|---|---|---|
| Example 5-17 | (R)-4-(biphenyl-4-yl)-3-(5-chloro-6-hydroxynicotinamido)butanoic acid | Example 3-4 | aq. NaOH, THF, MeOH, RT | 1.40 min. (A) | 411.2 |
| Example 5-18 | (R)-4-(3'-aminobiphenyl-4-yl)-3-(3-carboxypropanamido)butanoic acid | Example 3-20 | aq. NaOH, THF, MeOH, RT | 0.88 min. (A) | 371.2 |
| Example 5-19 | (R)-4-(1-carboxy-3-(3'-nitrobiphenyl-4-yl)propan-2-ylamino)-4-oxobutanoic acid | Example 2-12 | aq. NaOH, THF, MeOH, RT | 1.41 min. (D) | 401.2 |

-continued

| Example # | Product | Starting Material | Hydrolysis Condition | HPLC-RT (condition) | MS (M + 1) |
|---|---|---|---|---|---|
| Example 5-20 | 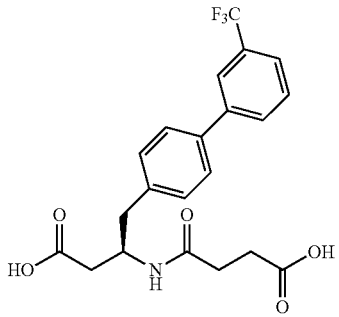<br>(R)-4-(1-carboxy-3-(3'-(trifluoromethyl)biphenyl-4-yl)propan-2-ylamino)-4-oxobutanoic acid | 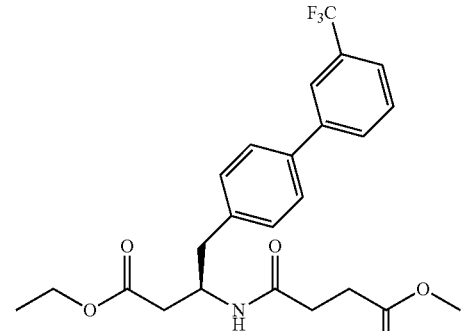<br>Example 2-13 | aq. NaOH, THF, MeOH, RT | 1.59 min. (H) | 424.2 |
| Example 5-21 | 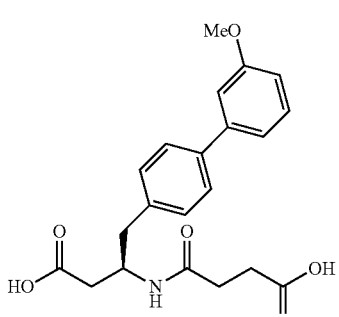<br>(R)-4-(1-carboxy-3-(3'-methoxybiphenyl-4-yl)propan-2-ylamino)-4-oxobutanoic acid | 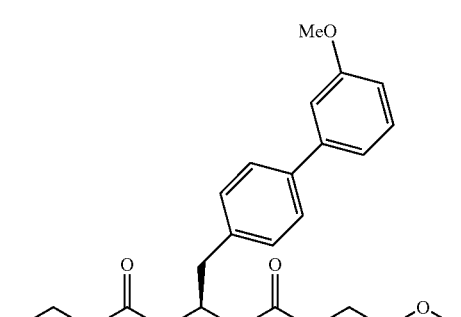<br>Example 2-14 | aq. NaOH, THF, MeOH, RT | 1.44 min. (H) | 386.2 |
| Example 5-22 | 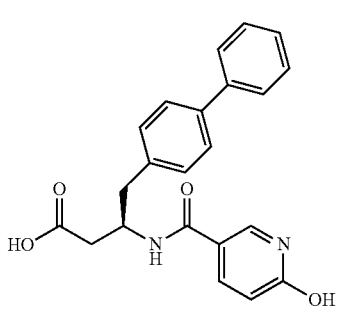<br>(R)-4-(biphenyl-4-yl)-3-(6-hydroxynicotinamido)butanoic acid | 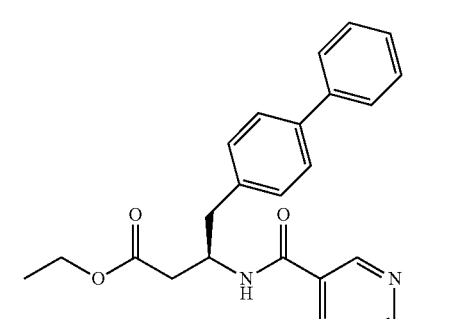<br>Example 3-5 | aq. NaOH, THF, MeOH, RT | 1.29 min. (B) | 377.1 |
| Example 5-23 | 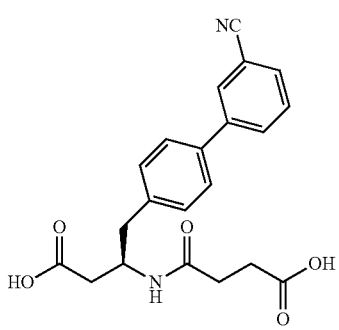<br>(R)-4-(1-carboxy-3-(3'-cyanobiphenyl-4-yl)propan-2-ylamino)-4-oxobutanoic acid | 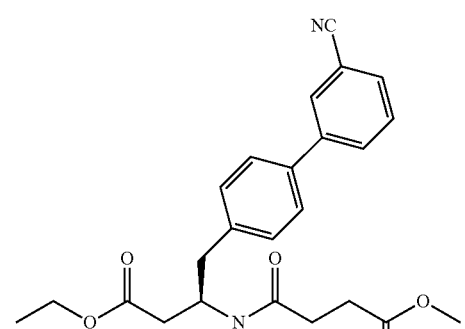<br>Example 2-15 | aq. NaOH, THF, MeOH, RT | 0.49 min. (B) | 381.1 |

-continued

| Example # | Product | Starting Material | Hydrolysis Condition | HPLC-RT (condition) | MS (M + 1) |
|---|---|---|---|---|---|
| Example 5-24 | 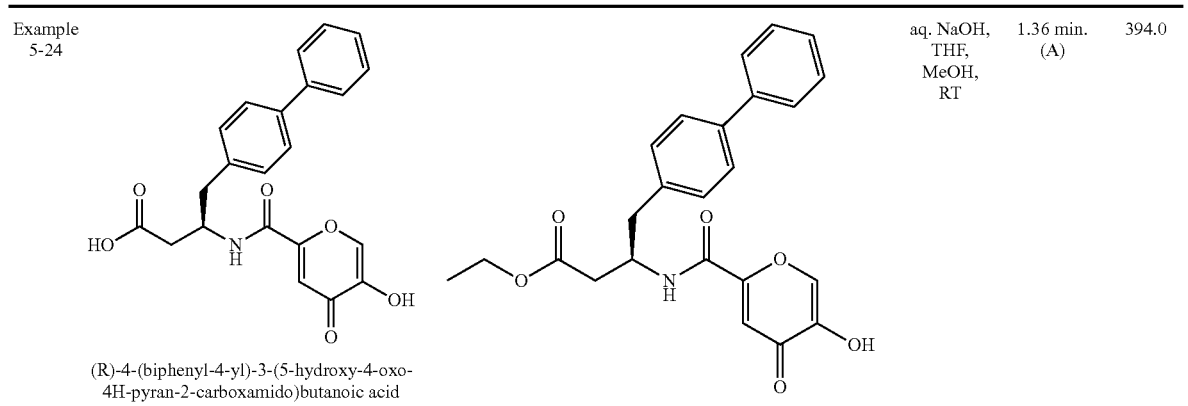(R)-4-(biphenyl-4-yl)-3-(5-hydroxy-4-oxo-4H-pyran-2-carboxamido)butanoic acid | Example 3-6 | aq. NaOH, THF, MeOH, RT | 1.36 min. (A) | 394.0 |
| Example 5-26 | 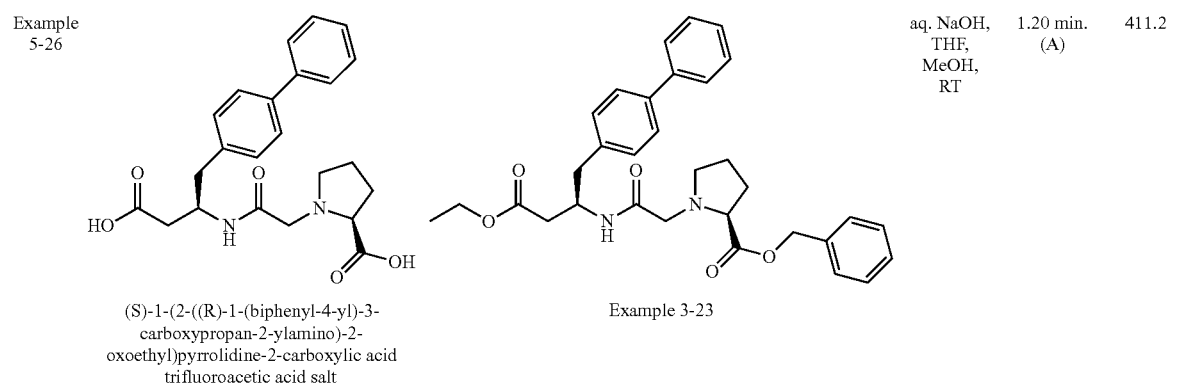(S)-1-(2-((R)-1-(biphenyl-4-yl)-3-carboxypropan-2-ylamino)-2-oxoethyl)pyrrolidine-2-carboxylic acid trifluoroacetic acid salt | Example 3-23 | aq. NaOH, THF, MeOH, RT | 1.20 min. (A) | 411.2 |
| Example 5-27 | 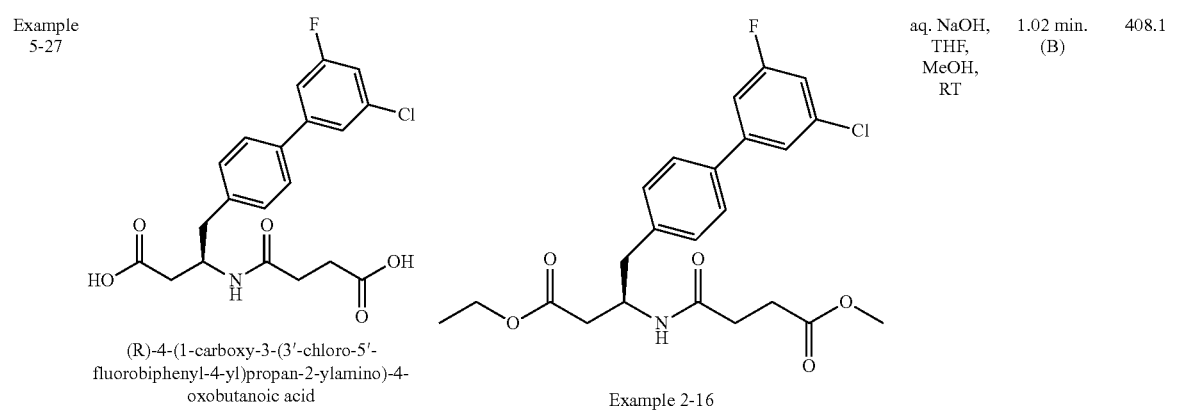(R)-4-(1-carboxy-3-(3'-chloro-5'-fluorobiphenyl-4-yl)propan-2-ylamino)-4-oxobutanoic acid | Example 2-16 | aq. NaOH, THF, MeOH, RT | 1.02 min. (B) | 408.1 |

-continued

| Example # | Product | Starting Material | Hydrolysis Condition | HPLC-RT (condition) | MS (M + 1) |
|---|---|---|---|---|---|
| Example 5-28 | (1S,4s)-4-((R)-1-(biphenyl-4-yl)-3-carboxypropan-2-ylcarbamoyl)cyclohexanecarboxylic acid | Example 3-12 | aq. NaOH, THF, MeOH, RT | 0.82 min. (B) | 410.1 |
| Example 5-29 | (R)-4-(1-carboxy-3-(2'-(trifluoromethyl)biphenyl-4-yl)propan-2-ylamino)-4-oxobutanoic acid | Example 2-17 | aq. NaOH, THF, MeOH, RT | 0.53 min. (B) | 424.0 |
| Example 5-30 | (R)-3-(2-aminopyrimidine-5-carboxamido)-4-(biphenyl-4-yl)butanoic acid | Example 3-7 | aq. NaOH, THF, MeOH, RT | 1.36 min. (A) | 377.0 |
| Example 5-31 | (R)-4-(1-carboxy-3-(2'-cyanobiphenyl-4-yl)propan-2-ylamino)-4-oxobutanoic acid | Example 2-18 | aq. NaOH, THF, MeOH, RT | 1.11 min. (A) | 381.1 |

-continued

| Example # | Product | Starting Material | Hydrolysis Condition | HPLC-RT (condition) | MS (M + 1) |
|---|---|---|---|---|---|
| Example 5-32 | (1R,4r)-4-((R)-1-(biphenyl-4-yl)-3-carboxypropan-2-ylcarbamoyl)cyclohexanecarboxylic acid | Example 3-13 | aq. NaOH, THF, MeOH, RT | 0.61 min. (B) | 410.1 |
| Example 5-33 | (R)-3-(6-aminonicotinamido)-4-(biphenyl-4-yl)butanoic acid | Example 3-8 | aq. NaOH, THF, MeOH, RT | 1.28 min. (A) | 376.2 |
| Example 5-34 | (R)-4-(1-carboxy-3-(2'-ethoxybiphenyl-4-yl)propan-2-ylamino)-4-oxobutanoic acid | Example 2-19 | aq. NaOH, THF, MeOH, RT | 1.51 min. (D) | 400.5 |

| Example # | Product | Starting Material | Hydrolysis Condition | HPLC-RT (condition) | MS (M + 1) |
|---|---|---|---|---|---|
| Example 5-35 | 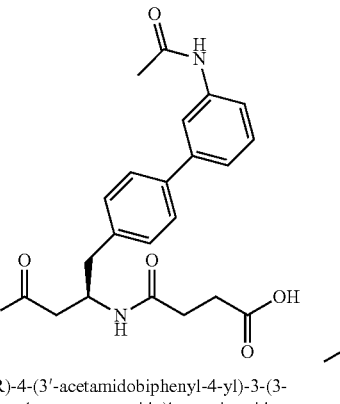<br>(R)-4-(3'-acetamidobiphenyl-4-yl)-3-(3-carboxypropanamido)butanoic acid | 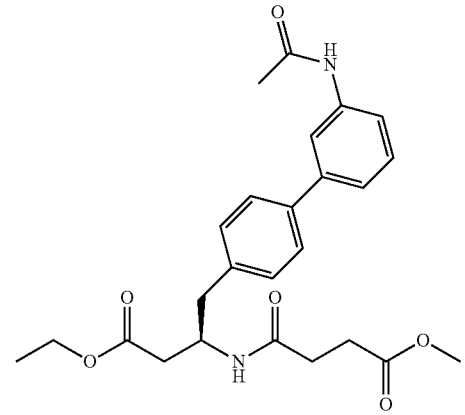<br>Example 3-24 | aq. NaOH, THF, MeOH, RT | 1.18 min. (D) | 413.2 |
| Example 5-36 | 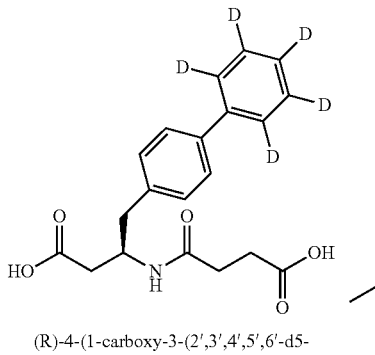<br>(R)-4-(1-carboxy-3-(2',3',4',5',6'-d5-biphenyl-4-yl)propan-2-ylamino)-4-oxobutanoic acid | 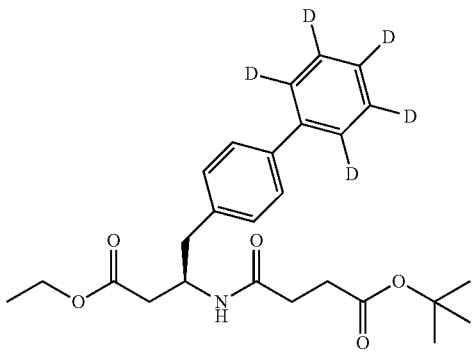<br>Example 2-20 | aq. NaOH, THF, MeOH, 50° C. | 0.68 min. (B) | 361.2 |

Example 5-2: 1H NMR (400 MHz, CD$_3$OD) δ ppm 2.38-2.42 (m, 2 H) 2.45-2.54 (m, 4 H) 2.82-2.94 (m, 2 H) 4.42-4.48 (m, 1 H) 7.12-7.16 (m, 2 H) 7.31 (d, J=8.4 Hz, 2 H) 7.41 (d, J=8.6 Hz, 2 H) 7.54 (d, J=8.1 Hz, 2 H) 7.58 (d, J=8.6 Hz, 2 H).

Example 5-3: 1H NMR (400 MHz, CD$_3$OD) δ ppm 2.39-2.42 (m, 2 H) 2.45-2.54 (m, 4 H) 2.85 (A of ABX, $J_{ab}$=13.6 Hz, $J_{ax}$=7.6 HZ, 1 H) 2.91 (B of ABX, $J_{ab}$=13.6 Hz, $J_{bx}$=6.2 HZ, 1 H) 4.42-4.48 (m, 1 H) 7.12-7.16 (m, 2 H) 7.31 (A of AB, J=8.2 Hz, 2 H) 7.52 (B of AB, J=8.2 Hz, 2 H) 7.58-7.62 (m, 2 H)

Example 5-4: 1H NMR (400 MHz, CD$_3$OD) δ ppm 2.39-2.44 (m, 2 H) 2.46-2.55 (m, 4 H) 2.86 (A of ABX, $J_{ab}$=13.6 Hz, $J_{ax}$=7.6 HZ, 1 H) 2.92 (B of ABX, $J_{ab}$=13.6 Hz, $J_{bx}$=6.3 HZ, 1 H) 4.42-4.49 (m, 1 H) 7.01-7.06 (m, 1 H) 7.32 (br d, J=8.1 Hz, 2 H) 7.39-7.45 (m, 2 H) 7.55 (d, J=8.1 Hz, 2 H)

Example 5-5: 1H NMR (400 MHz, CD$_3$OD) δ ppm 2.40-2.43 (m, 2 H) 2.46-2.56 (m, 4 H) 2.87 (A of ABX, $J_{ab}$=13.5 Hz, $J_{ax}$=7.7 HZ, 1 H) 2.93 (B of ABX, $J_{ab}$=13.5 Hz, $J_{bx}$=6.2 HZ, 1 H) 4.43-4.50 (m, 1 H) 7.13-7.18 (m, 1 H) 7.20-7.24 (m, 1 H) 7.31-7.35 (m, 3 H) 7.44-7.48 (m, 3 H) 7.99 (br d, J=8.3 Hz, 1 H)

Example 5-6: 1H NMR (400 MHz, CD$_3$OD) δ ppm 2.39-2.43 (m, 2 H) 2.45-2.57 (m, 4 H) 2.87 (A of ABX, $J_{ab}$=13.6 Hz, $J_{ax}$=7.6 HZ, 1 H) 2.94 (B of ABX, $J_{ab}$=13.6 Hz, $J_{bx}$=6.1 HZ, 1 H) 4.44-4.51 (m, 1 H) 7.28-7.35 (m, 7 H) 7.46 (br d, J=7.9 Hz, 1 H)

Example 5-7: 1H NMR (400 MHz, CD$_3$OD) δ ppm 2.40-2.52 (m, 6 H) 2.83-2.92 (m, 2 H) 3.77 (s, 3 H) 4.44-4.47 (m, 1 H) 6.96-7.05 (m, 2 H) 7.23-7.30 (m, 4 H) 7.39-7.41 (m, 2 H)

Example 5-8: 1H NMR (400 MHz, CD$_3$OD) δ ppm 2.21 (s, 3 H) 2.41-2.55 (m, 6 H) 2.82-2.94 (m, 2 H) 3.77 (s, 3 H) 4.45-4.48 (m, 1 H) 7.15-7.28 (m, 8 H)

Example 5-9: 1H NMR (400 MHz, DMSO-d$_6$) δ ppm 2.56 (dd, J=5.81, 15.92 Hz, 1H), 2.66 (dd, J=7.07, 15.92 Hz, 1H), 2.90 (dd, J=6.06, 13.64 Hz, 1H), 3.00 (dd, J=8.08, 13.64 Hz, 1H), 4.53-4.64 (m, 1H), 7.30 (d, J=8.34 Hz, 2H), 7.33 (t, J=7.58, 1H), 7.56 (d, J=8.34 Hz, 2H), 7.62 (d, J=7.07 Hz, 2H), 7.95 (dd, J=1.26, 5.05 Hz, 1H), 9.01-9.07 (m, 2H), 9.33 (d, J=1.52 Hz, 1H), 12.28 (s, 1H).

Example 5-10: 1H NMR (400 MHz, DMSO-$d_6$) δ ppm 2.36-2.49 (m, 2 H), 2.75-2.86 (m, 2 H), 3.83 (s, 2 H), 4.19-4.31 (m, 1 H), 7.26 (d, J=8.3 Hz, 2 H), 7.31-7.38 (m, 1 H), 7.45 (t, J=7.6 Hz, 2 H), 7.56 (d, J=8.3 Hz, 2 H), 7.61-7.67 (m, 2 H), 8.40 (d, J=8.1 Hz, 1 H), 12.26 (br. s., 1 H), 16.02 (br. s., 1 H).

Example 5-11: 1H NMR (400 MHz, DMSO-$d_6$) δ ppm 2.46-2.59 (m, 2 H), 2.86-2.88 (m, 2 H), 4.41-4.49 (m, 1 H), 7.29-7.36 (m, 3 H), 7.42-7.46 (m, 2 H), 7.58-7.65 (m, 4 H), 8.26 (d, J=8 Hz, 1 H), 8.64 (br s, 2 H) 12.24 (br. s., 1 H).

Example 5-12: 1H NMR (400 MHz, DMSO-$d_6$) δ ppm 2.54-2.70 (m, 2 H), 2.88-3.03 (m, 2 H), 4.56-4.65 (m, 1 H), 7.29-7.34 (m, 3 H), 7.41-7.45 (m, 2 H), 7.55-7.63 (m, 4 H), 8.33 (s, 1 H), 9.15 (d, J=9.1 Hz, 1 H), 9.49 (s, 1 H), 12.30 (br s, 1 H), 14.11 (br s, 1 H).

Example 5-13: 1H NMR (400 MHz, CD$_3$OD) δ ppm 2.38-2.57 (m, 6 H) 2.87 (A of ABX, $J_{ab}$=13.6 Hz, $J_{ax}$=7.6 Hz, 1 H) 2.95 (B of ABX, $J_{ab}$=13.6 Hz, $J_{bx}$=6.1 Hz, 1 H) 4.44-4.51 (m, 1 H) 7.06-7.14 (m, 2 H) 7.31-7.37 (m, 5 H) 7.48 (dd, J=8.8 and 5.1 Hz, 1 H).

Example 5-14: 1H NMR (400 MHz, CD$_3$OD) δ ppm 2.39 (s, 3 H) 2.39-2.55 (m, 6 H) 2.85 (A of ABX, $J_{ab}$=13.5 Hz, $J_{ax}$=7.5 HZ, 1 H) 2.90 (B of ABX, $J_{ab}$=13.5 Hz, $J_{bx}$=6.4 Hz, 1 H) 4.42-4.49 (m, 1 H) 7.13 (br d, J=7.3 Hz, 1 H) 7.26-7.30 (m, 3 H) 7.36-7.40 (m, 2 H) 7.52 (d, J=8.3 Hz, 2 H).

Example 5-15: 1H NMR (400 MHz, CD$_3$OD) δ ppm 2.38-2.55 (m, 6 H) 2.86 (A of ABX, $J_{ab}$=13.6 Hz, $J_{ax}$=7.8 HZ, 1 H) 2.93 (B of ABX, $J_{ab}$=13.6 Hz, $J_{bx}$=6.1 Hz, 1 H) 4.42-4.49 (m, 1 H) 6.86-6.92 (m, 1 H) 7.19-7.25 (m, 2 H) 7.33-7.35 (m, 2 H) 7.55-7.58 (m, 2 H).

Example 5-16: 1H NMR (400 MHz, CD$_3$OD) δ ppm 1.27 (t, J=7.6 Hz, 3 H) 2.39-2.55 (m, 6 H) 2.70 (q, J=7.6 Hz, 2 H) 2.85 (A of ABX, $J_{ab}$=13.6 Hz, $J_{ax}$=7.5 HZ, 1 H) 2.90 (B of ABX, $J_{ab}$=13.6 Hz, $J_{bx}$=6.4 HZ, 1 H) 4.42-4.49 (m, 1 H) 7.16 (br d, J=7.6 Hz, 1 H) 7.28-7.33 (m, 3 H) 7.38-7.42 (m, 2 H) 7.52-7.54 (m, 2 H).

Example 5-17: 1H NMR (400 MHz, DMSO-$d_6$) δ ppm 2.47-2.50 (m, 2 H) 2.82-2.91 (m, 2 H) 4.40-4.49 (m, 1 H) 7.29 (d, J=8.3 Hz, 2 H) 7.31-7.36 (m, 1 H) 7.42-7.46 (m, 2 H) 7.59 (d, J=8.4 Hz, 2 H) 7.63-7.65 (m, 2 H) 7.95 (br d, J=2.3 Hz, 1 H) 8.11 (br d, J=2.3 Hz, 1 H) 8.25-8.27 (m, 1 H) 12.24 (br s, 1 H) 12.48 (br s, 1 H).

Example 5-18: 1H NMR (400 MHz, CD$_3$OD) δ ppm 2.38-2.55 (m, 6 H) 2.86 (A of ABX, $J_{ab}$=13.6 Hz, $J_{ax}$=7.8 Hz, 1 H) 2.92 (B of ABX, $J_{ab}$=13.6 Hz, $J_{bx}$=6.3 Hz, 1 H) 4.43-4.50 (m, 1 H) 7.26 (br d, J=7.3 Hz, 1 H) 7.35 (d, J=8.1 Hz, 2 H) 7.51-7.58 (m, 4 H) 7.64 (br d, J=7.8 Hz, 1 H).

Example 5-19: 1H NMR (400 MHz, CD$_3$OD) δ ppm 2.39-2.42 (m, 2 H) 2.45-2.56 (m, 4 H) 2.88 (A of ABX, $J_{ab}$=13.6 Hz, $J_{ax}$=7.6 Hz, 1 H) 2.95 (B of ABX, $J_{ab}$=13.6 Hz, $J_{bx}$=6.2 Hz, 1 H) 4.44-4.51 (m, 1 H) 6.86-6.89 (m, 1 H) 7.38-7.41 (m, 2 H) 7.63-7.70 (m, 3 H) 8.02-8.04 (m, 1 H) 8.18-8.21 (m, 1 H) 8.45 (br t, J=1.9 Hz, 1 H).

Example 5-20: 1H NMR (400 MHz, CD$_3$OD) δ ppm 2.39-2.56 (m, 6 H) 2.87 (A of ABX, $J_{ab}$=13.6 Hz, $J_{ax}$=7.6 Hz, 1 H) 2.93 (B of ABX, $J_{ab}$=13.6 Hz, $J_{bx}$=6.3 Hz, 1 H) 4.43-4.50 (m, 1 H) 7.36 (d, J=8.3 Hz, 2 H) 7.58-7.62 (m, 4 H) 7.85-7.87 (m, 2 H).

Example 5-21: 1H NMR (400 MHz, CD$_3$OD) δ ppm 2.39-2.54 (m, 6 H) 2.85 (A of ABX, $J_{ab}$=13.6 Hz, $J_{ax}$=7.5 Hz, 1 H) 2.91 (B of ABX, $J_{ab}$=13.6 Hz, $J_{bx}$=6.3 HZ, 1 H) 3.84 (s, 3 H) 4.42-4.49 (m, 1 H) 6.86-6.89 (m, 1 H) 7.11-7.17 (m, 2 H) 7.29-7.34 (m, 3 H) 7.52-7.54 (m, 2 H).

Example 5-22: 1H NMR (400 MHz, DMSO-$d_6$) δ ppm 2.43-2.46 (m, 2 H), 2.81-2.91 (m, 2 H) 4.40-4.49 (m, 1 H) 6.33 (d, J=9.6 Hz, 1 H) 7.28-7.35 (m, 3 H) 7.42-7.46 (m, 2 H) 7.58 (d, J=8.1 Hz, 2 H) 7.63-7.65 (m, 2 H) 7.81 (dd, J=9.6, 2.8 Hz, 1 H) 7.93 (br s, 1 H) 8.14 (d, J=8.3 Hz, 1 H) 11.92 (br s, 1 H) 12.19 (br s, 1 H).

Example 5-23: 1H NMR (400 MHz, CD$_3$OD) δ ppm 2.39-2.42 (m, 2 H) 2.44-2.55 (m, 4 H) 2.86 (A of ABX, $J_{ab}$=13.6 Hz, $J_{ax}$=7.6 Hz, 1 H) 2.93 (B of ABX, $J_{ab}$=13.6 Hz, $J_{bx}$=6.3 HZ, 1 H) 4.43-4.50 (m, 1 H) 7.36 (d, J=8.3 Hz, 2 H) 7.58-7.63 (m, 3 H) 7.66-7.69 (m, 1 H) 7.91-7.94 (m, 1 H) 7.97 (br t, J=1.5 Hz, 1 H).

Example 5-24: 1H NMR (400 MHz, DMSO-$d_6$) δ ppm 2.50-2.61 (m, 2 H) 2.83-2.94 (m, 2 H) 4.43-4.52 (m, 1 H) 6.82 (s, 1 H) 7.28-7.35 (m, 3 H) 7.44 (t, J=7.7 Hz, 2 H) 7.58-7.65 (m, 4 H) 8.12 (s, 1 H) 8.86 (d, J=8.3 Hz, 1 H) 9.55 (s, 1 H) 12.25 (br s, 1 H).

Example 5-25: 1H NMR (400 MHz, DMSO-$d_6$) δ ppm 1.66-2.47 (m, 10 H) 2.71-2.83 (m, 2 H) 3.31-3.46 (m, 3 H) 4.18-4.49 (m, 2 H) 7.26-7.28 (m, 2 H) 7.32-7.36 (m, 1 H) 7.43-7.47 (m, 2 H) 7.57-7.66 (m, 4 H) 7.86 (d, J=8.3 Hz, 1 H) 12.31 (br s, 2 H).

Example 5-26: 1H NMR (400 MHz, DMSO-$d_6$) δ ppm 1.80-2.03 (m, 3 H) 2.27-2.31 (m, 1 H) 2.39-2.52 (m, 2 H) 2.75-2.81 (m, 1 H) 2.85-2.89 (m, 1 H) 2.95-3.03 (m, 1 H) 3.41-3.78 (m, 2 H) 3.90-3.99 (m, 1 H) 4.14-4.20 (m, 1 H) 4.28-4.35 (m, 1 H) 7.28-7.37 (m, 3 H) 7.44-7.48 (m, 2 H) 7.58-7.65 (m, 2 H) 8.45 (br s, 1 H) 12.34 (br s, 1 H).

Example 5-27: 1H NMR (400 MHz, CD$_3$OD) δ ppm 2.38-2.54 (m, 6 H) 2.86 (A of ABX, $J_{ab}$=13.6 Hz, $J_{ax}$=7.6 Hz, 1 H) 2.93 (B of ABX, $J_{ab}$=13.6 Hz, $J_{bx}$=6.2 HZ, 1 H) 4.42-4.49 (m, 1 H) 7.13-7.17 (m, 1 H) 7.31-7.37 (m, 3 H) 7.46-7.47 (m, 1 H) 7.54-7.57 (m, 2 H).

Example 5-28: 1H NMR (400 MHz, CD$_3$OD) δ ppm 1.49-1.71 (m, 6 H) 2.01-2.11 (m, 2 H) 2.14-2.21 (m, 1 H) 2.44-2.56 (m, 3 H) 2.83 (A of ABX, $J_{ab}$=13.6 Hz, $J_{ax}$=8.0 Hz, 1 H) 2.91 (B of ABX, $J_{ab}$=13.6 Hz, $J_{bx}$=6.3 HZ, 1 H) 4.43-4.51 (m, 1 H) 7.28-7.32 (m, 3 H) 7.38-7.42 (m, 2 H) 7.52 (d, J=8.1 Hz, 2 H) 7.56-7.59 (m, 2 H) 7.71 (br d, J=8.6 Hz, 1 H).

Example 5-29: 1H NMR (400 MHz, CD$_3$OD) δ ppm 2.39-2.42 (m, 2 H) 2.45-2.56 (m, 4 H) 2.87 (A of ABX, $J_{ab}$=13.6

Hz, $J_{ax}$=7.8 Hz, 1 H) 2.94 (B of ABX, $J_{ab}$=13.6 Hz, $J_{bx}$=6.1 Hz, 1 H) 4.44-4.51 (m, 1 H) 7.23 (A of AB, J=8.0 Hz, 2 H) 7.28 (B of AB, J=8.0 Hz, 2 H) 7.35 (d, J=7.6 Hz, 1 H) 7.50-7.53 (m, 1 H) 7.60-7.63 (m, 1 H) 7.75 (d, J=7.8 Hz, 1 H)

Example 5-30: 1H NMR (400 MHz, DMSO-$d_6$) δ ppm 2.45-2.56 (m, 2 H) 2.83-2.93 (m, 2 H) 4.43-4.52 (m, 1 H) 7.18 (s, 2 H) 7.29-7.35 (m, 3 H) 7.42-7.46 (m, 2 H) 7.58-7.65 (m, 4 H) 8.19 (d, J=8.1 Hz, 1 H) 8.60 (s, 2 H) 12.21 (br s, 1 H).

Example 5-31: 1H NMR (400 MHz, CD$_3$OD) δ ppm 2.39-2.43 (m, 2 H) 2.46-2.57 (m, 4 H) 2.90 (A of ABX, $J_{ab}$=13.6 Hz, $J_{ax}$=7.8 Hz, 1 H) 2.97 (B of ABX, $J_{ab}$=13.6 Hz, $J_{bx}$=6.1 Hz, 1 H) 4.45-4.52 (m, 1 H) 7.37-7.39 (m, 2 H) 7.49-7.53 (m, 3 H) 7.57-7.59 (m, 1 H) 7.70-7.74 (m, 1 H) 7.80-7.82 (m, 1 H).

Example 5-32: 1H NMR (400 MHz, CD$_3$OD) δ ppm 1.33-1.49 (m, 4 H) 1.68-1.72 (m, 1 H) 1.79-1.83 (m, 1 H) 1.96-2.01 (m, 2 H) 2.05-2.13 (m, 1 H) 2.17-2.25 (m, 1 H) 2.43-2.55 (m, 2 H) 2.80-2.95 (m, 2 H) 4.42-4.49 (m, 1 H) 7.28-7.32 (m, 3 H) 7.38-7.43 (m, 2 H) 7.52-7.59 (m, 4 H).

Example 5-33: 1H NMR (400 MHz, DMSO-$d_6$) δ ppm 2.48-2.55 (m, 2 H) 2.84-2.96 (m, 2 H) 4.44-4.53 (m, 1 H) 6.94 (br s, 1 H) 7.30-7.35 (m, 3 H) 7.42-7.46 (m, 2 H) 7.57-7.64 (m, 4 H) 8.17-8.60 (br m, 5 H) 12.27 (br s, 1 H).

Example 5-34: 1H NMR (400 MHz, CD$_3$OD) δ ppm 1.30 (t, J=7.0 Hz, 3 H) 2.39-2.56 (m , 6 H) 2.82-2.93 (m, 2 H) 4.02 (q, J=7.0 Hz, 2 H) 4.42-4.49 (m, 1 H) 6.96-7.03 (m, 2 H) 7.23-7.28 (m, 4 H) 7.44 (d, J=8.4 Hz, 2 H).

Example 5-35: 1H NMR (400 MHz, CD$_3$OD) δ ppm 2.14 (s, 3 H) 2.39-2.43 (m, 2 H) 2.45-2.56 (m, 4 H) 2.82-2.94 (m, 2 H) 4.02 (q, J=7.0 Hz, 2 H) 4.42-4.49 (m, 1 H) 7.30-7.38 (m, 4 H) 7.49-7.55 (m, 3 H) 7.80 (br s, 1 H).

Example 5-36: 1H NMR (400 MHz, CD$_3$OD) δ ppm 2.39-2.55 (m, 6 H) 2.85 (A of ABX, $J_{ab}$=13.6 Hz, $J_{ax}$=7.5 HZ, 1 H) 2.90 (B of ABX, $J_{ab}$=13.6 Hz, $J_{bx}$=6.3 HZ, 1 H) 4.42-4.49 (m, 1 H) 6.86-6.92 (m, 1 H) 7.31 (d, J=8.1 Hz, 2 H) 7.53-7.55 (m, 2 H).

Example 5-37

Synthesis of (R)-4-(1-carboxy-3-(5'-fluoro-2'-methoxybiphenyl-4-yl)propan-2-ylamino)-4-oxobutanoic acid

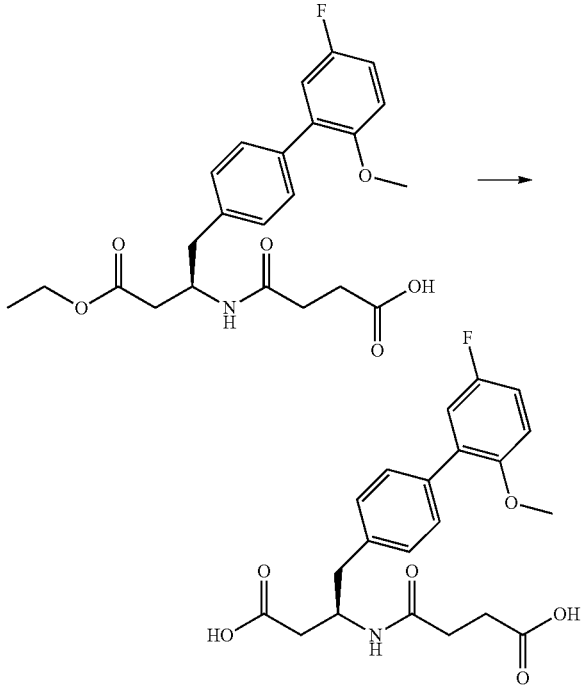

To a solution of (R)-4-(4-ethoxy-1-(5'-fluoro-2'-methoxybiphenyl-4-yl)-4-oxobutan-2-ylannino)-4-oxobutanoic acid (83 mg, 0.192 mmol) in MeOH (2 mL) is added 1N NaOH (4 mL, 4 mmol) After stirring at room temperature for 2 hours, the crude is concentrated under reduced pressure to remove MeOH and is diluted with EtOAc. The organic layer is washed with brine, dried over Na$_2$SO$_4$, filtered and concentrated under reduced pressure. The obtained residue is purified by RP-HPLC (SunFire C18, H$_2$O (0.1% TFA)/CH$_3$CN), and then lyophilized to give (R)-4-(1-carboxy-3-(5'-fluoro-2'-methoxybiphenyl-4-yl)propan-2-ylamino)-4-oxobutanoic acid (58 mg). HPLC retention time=1.46 minutes (condition D); MS (m+1)=404.2; 1H NMR (400 MHz, CD$_3$OD) δ ppm 2.36-2.59 (m, 6 H) 2.84 (dd, J=13.4, 6.3 Hz, 1 H) 2.91 (dd, J=13.4, 6.3 Hz, 1 H) 3.75 (s, 3 H) 4.34-4.56 (m, 1 H) 6.95-7.08 (m, 3 H) 7.26 (d, J=8.1 Hz, 2 H) 7.42 (d, J=8.3 Hz, 2 H)

Following compounds are prepared using similar procedure as described in example 5-37:

| Example # | Product | Starting Material | Hydrolysis Condition | LCMS-RT (condition) | MS (M + 1) |
|---|---|---|---|---|---|
| Example 5-38 | R-4-(3'-chlorobiphenyl-4-yl)-3-(6-(methylsulfonamido)nicotinamido)butanoic acid | | Aq. NaOH, MeOH, rt | 1.68 min. (D) | 488.1 |

-continued

| Example # | Product | Starting Material | Hydrolysis Condition | LCMS-RT (condition) | MS (M + 1) |
|---|---|---|---|---|---|
| Example 5-39 | R-4-(1-carboxy-3-(5'-chloro-2'-methoxybiphenyl-4-yl)propan-2-ylamino)-4-oxobutanoic acid | | Aq. NaOH, MeOH, rt | 1.52 min. (D) | 420.1 |
| Example 5-40 | R-4-(3'-chlorobiphenyl-4-yl)-3-(4-(methylsulfonamido)benzamido)butanoic acid | | Aq. NaOH, MeOH, rt | 1.57 min. (D) | 487.2 |
| Example 5-41 | R-4-(3'-chlorobiphenyl-4-yl)-3-(2-ethylthiazole-5-carboxamido)butanoic acid | | Aq. NaOH, MeOH, rt | 1.65 min. (D) | 429.1 |

-continued

| Example # | Product | Starting Material | Hydrolysis Condition | LCMS-RT (condition) | MS (M + 1) |
|---|---|---|---|---|---|
| Example 5-42 | R-4-(1-carboxy-3-(5'-fluoro-2'-hydroxybiphenyl-4-yl)propan-2-ylamino)-4-oxobutanoic acid | | Aq. NaOH, MeOH, rt | 1.42 min. (D) | 390.2 |
| Example 5-43 | R-4-(1-carboxy-3-(3'-chloro-2'-methoxybiphenyl-4-yl)propan-2-ylamino)-4-oxobutanoic acid | | Aq. NaOH, MeOH, rt | 1.53 min. (D) | 420.2 |
| Example 5-44 | R-4-(biphenyl-4-yl)-3-(6-hydroxypyrimidine-4-carboxamido)butanoic acid | | Aq. NaOH, MeOH, rt | 1.45 min. (D) | 378.1 |

-continued

| Example # | Product | Starting Material | Hydrolysis Condition | LCMS-RT (condition) | MS (M + 1) |
|---|---|---|---|---|---|
| Example 5-45 | 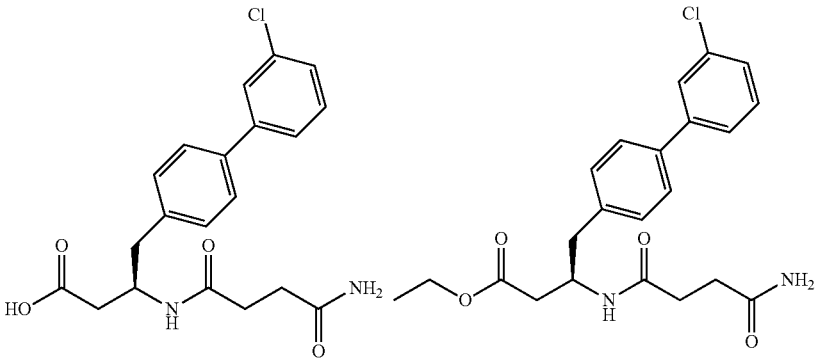<br>(R)-3-(4-amino-4-oxobutanamido)-4-(3'-chlorobiphenyl-4-yl)butanoic acid | 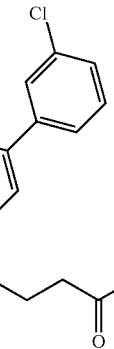 | Aq. NaOH, MeOH, rt | 1.26 min. (A) | 389.3 |
| Example 5-46 | 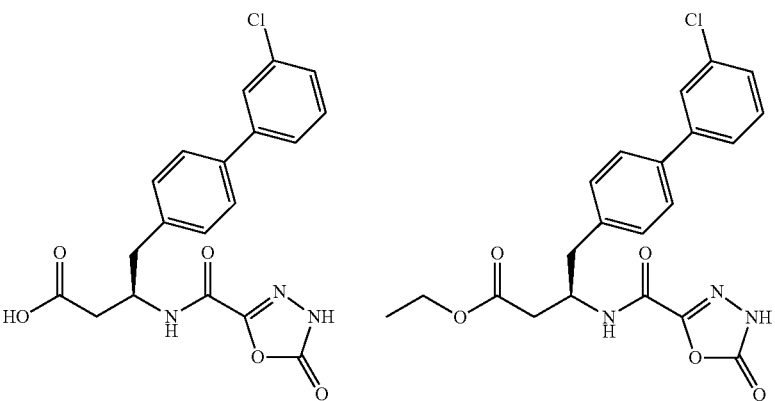<br>(R)-4-(3'-chlorobiphenyl-4-yl)-3-(5-oxo-4,5-dihydro-1,3,4-oxadiazole-2-carboxamido)butanoic acid | 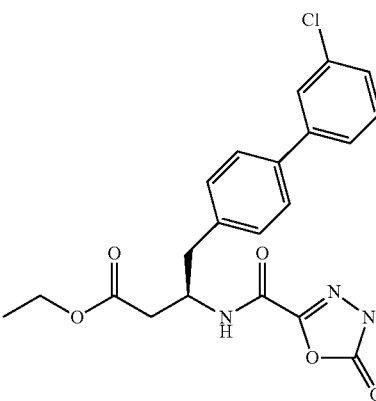 | Aq. NaOH, MeOH, rt | 1.53 min. (D) | 402.2 |
| Example 5-47 | 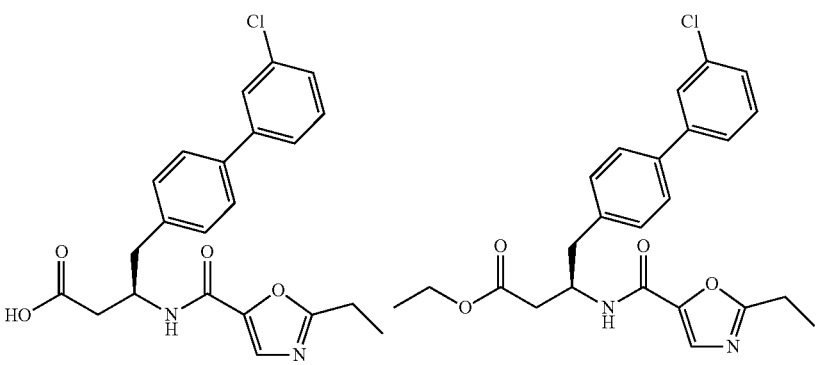<br>R-4-(3'-chlorobiphenyl-4-yl)-3-(2-ethyloxazole-5-carboxamido)butanoic acid | 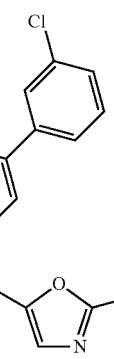 | Aq. NaOH, MeOH, rt | 1.60 min. (D) | 413.3 |

-continued

| Example # | Product | Starting Material | Hydrolysis Condition | LCMS-RT (condition) | MS (M + 1) |
|---|---|---|---|---|---|
| Example 5-48 | R-3-(2-ethyloxazole-5-carboxamido)-4-(5'-fluoro-2'-methoxybiphenyl-4-yl)butanoic acid | | Aq. NaOH, MeOH, rt | 1.38 min. (D) | 427.2 |
| Example 5-49 | R-4-(5'-fluoro-2'-methoxybiphenyl-4-yl)-3-(oxazole-5-carboxamido)butanoic acid | | Aq. NaOH, MeOH, rt | 1.37 min. (D) | 399.3 |
| Example 5-50 | R-3-(1H-benzo[d][1,2,3]triazole-5-carboxamido)-4-(biphenyl-4-yl)butanoic acid | | Aq. NaOH, MeOH, rt | 1.50 min. (D) | 401.1 |

-continued

| Example # | Product | Starting Material | Hydrolysis Condition | LCMS-RT (condition) | MS (M + 1) |
|---|---|---|---|---|---|
| Example 5-51 | R-4-(biphenyl-4-yl)-3-(5-oxo-4,5-dihydro-1H-1,2,4-triazole-3-carboxamido)butanoic acid | | Aq. NaOH, MeOH, rt | 1.39 min. (D) | 367.1 |
| Example 5-52 | R-4-(1-carboxy-3-(3'-(trifluoromethoxy)biphenyl-4-yl)propan-2-ylamino)-4-oxobutanoic acid | | Aq. NaOH, MeOH, rt | 1.57 min. (D) | 440.1 |
| Example 5-53 | (3R)-4-(3'-chlorobiphenyl-4-yl)-3-(5-oxopyrrolidine-3-carboxamido)butanoic acid | | Aq. NaOH, MeOH, rt | 1.37 min. (D) | 401.3 |

-continued

| Example # | Product | Starting Material | Hydrolysis Condition | LCMS-RT (condition) | MS (M + 1) |
|---|---|---|---|---|---|
| Example 5-54 | 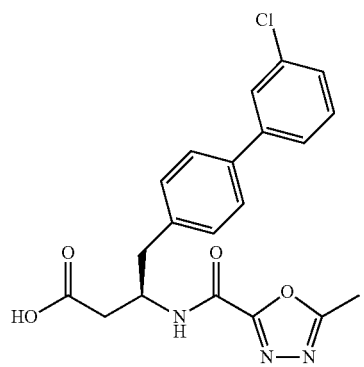<br>R-4-(3'-chlorobiphenyl-4-yl)-3-(5-methyl-1,3,4-oxadiazole-2-carboxamido)butanoic acid | 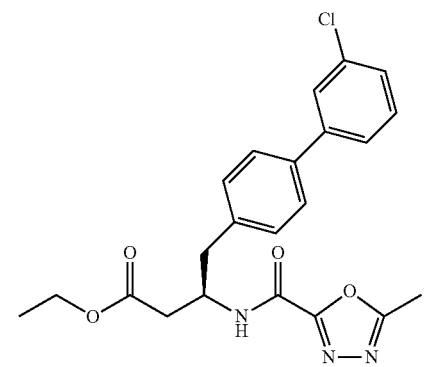 [SMILES: CCOC(=O)C[C@@H](Cc1ccc(-c2cccc(Cl)c2)cc1)NC(=O)c1nnc(C)o1] | Aq. NaOH, MeOH, rt | 1.44 min. (D) | 400.2 |
| Example 5-55 | 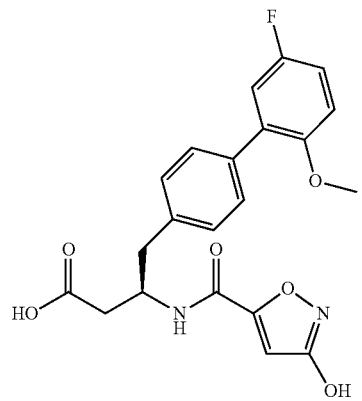<br>R-4-(5'-fluoro-2'-methoxybiphenyl-4-yl)-3-(3-hydroxyisoxazole-5-carboxamido)butanoic acid | 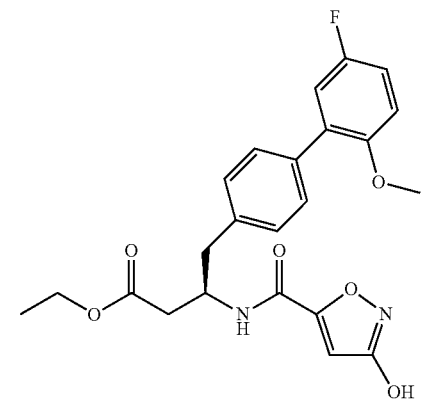 [SMILES: CCOC(=O)C[C@@H](Cc1ccc(-c2cc(F)ccc2OC)cc1)NC(=O)c1cc(O)no1] | Aq. NaOH, MeOH, rt | 1.37 min. (D) | 415.1 |
| Example 5-56 | 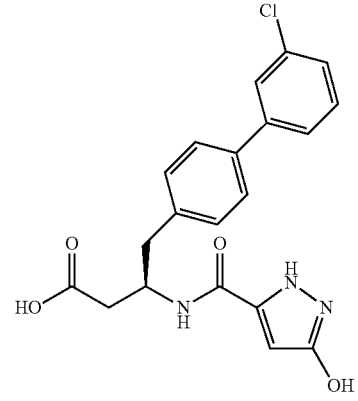<br>R-4-(3'-chlorobiphenyl-4-yl)-3-(3-hydroxy-1H-pyrazole-5-carboxamido)butanoic acid | 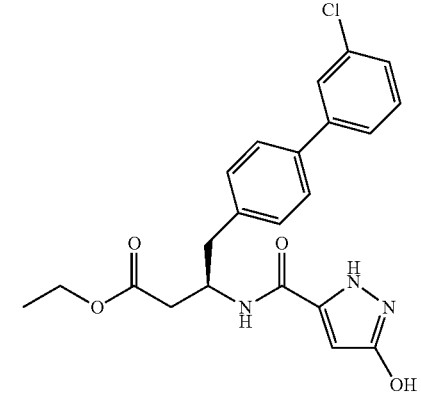 [SMILES: CCOC(=O)C[C@@H](Cc1ccc(-c2cccc(Cl)c2)cc1)NC(=O)c1cc(O)n[nH]1] | Aq. NaOH, MeOH, rt | 1.52 min. (D) | 400.2 |

-continued

| Example # | Product | Starting Material | Hydrolysis Condition | LCMS-RT (condition) | MS (M + 1) |
|---|---|---|---|---|---|
| Example 5-57 | R-4-(biphenyl-4-yl)-3-(5-oxo-4,5-dihydro-1,2,4-oxadiazole-3-carboxamido)butanoic acid | | Aq. NaOH, MeOH, rt | 1.77 min. (D) | 368.2 |
| Example 5-58 | R-4-(3'-chlorobiphenyl-4-yl)-3-(5-oxo-4,5-dihydro-1H-1,2,4-triazole-3-carboxamido)butanoic acid | | Aq. NaOH, MeOH, rt | 1.63 min. (D) | 401.1 |
| Example 5-59 | R-4-(biphenyl-4-yl)-3-(2-oxo-2,3-dihydro-1H-benzo[d]imidazole-5-carboxamido)butanoic acid | | Aq. NaOH, MeOH, rt | 1.46 min. (D) | 416.0 |

-continued

| Example # | Product | Starting Material | Hydrolysis Condition | LCMS-RT (condition) | MS (M + 1) |
|---|---|---|---|---|---|
| Example 5-60 | R-4-(1-carboxy-3-(2'-(trifluoromethoxy)biphenyl-4-yl)propan-2-ylamino)-4-oxobutanoic acid | | Aq. NaOH, MeOH, rt | 1.41 min. (D) | 440.0 |
| Example 5-61 | R-4-(1-carboxy-3-(2'-hydroxybiphenyl-4-yl)propan-2-ylamino)-4-oxobutanoic acid | | Aq. NaOH, MeOH, rt | 1.16 min. (D) | 372.2 |
| Example 5-62 | R-4-(1-carboxy-3-(2',3'-difluoro-6'-methoxybiphenyl-4-yl)propan-2-ylamino)-4-oxobutanoic acid | | Aq. NaOH, MeOH, rt | 1.34 min. (D) | 422.2 |

-continued

| Example # | Product | Starting Material | Hydrolysis Condition | LCMS-RT (condition) | MS (M + 1) |
|---|---|---|---|---|---|
| Example 5-63 | R-4-(3'-chlorobiphenyl-4-yl)-3-(2-oxo-2,3-dihydro-1H-imidazole-4-carboxamido)butanoic acid | | Aq. NaOH, MeOH, rt | 1.16 min. (D) | 400.1 |
| Example 5-64 | R-4-(1-carboxy-3-(3'-fluoro-2'-methoxybiphenyl-4-yl)propan-2-ylamino)-4-oxobutanoic acid | | Aq. NaOH, MeOH, rt | 1.29 min. (D) | 404.1 |
| Example 5-65 | R-4-(1-carboxy-3-(4-pyridine-2-yl)phenyl)propan-2-ylamino)-4-oxobutanoic acid | | Aq. NaOH, MeOH, rt | 1.43 min. (D) | 356.2 |

-continued

| Example # | Product | Starting Material | Hydrolysis Condition | LCMS-RT (condition) | MS (M + 1) |
|---|---|---|---|---|---|
| Example 5-66 | 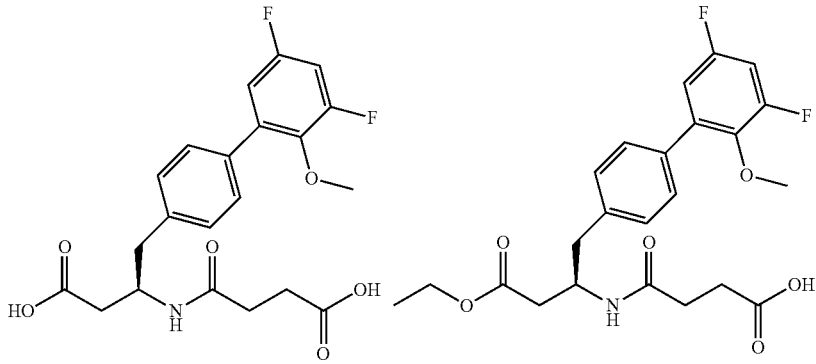<br>R-4-(1-carboxy-3-(3',5'-difluoro-2'-methoxybiphenyl-4-yl)propan-2-ylamino)-4-oxobutanoic acid | 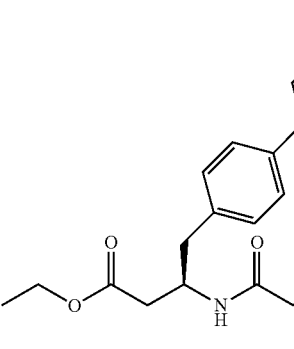 | Aq. NaOH, MeOH, rt | 1.42 min. (D) | 422.0 |
| Example 5-67 | 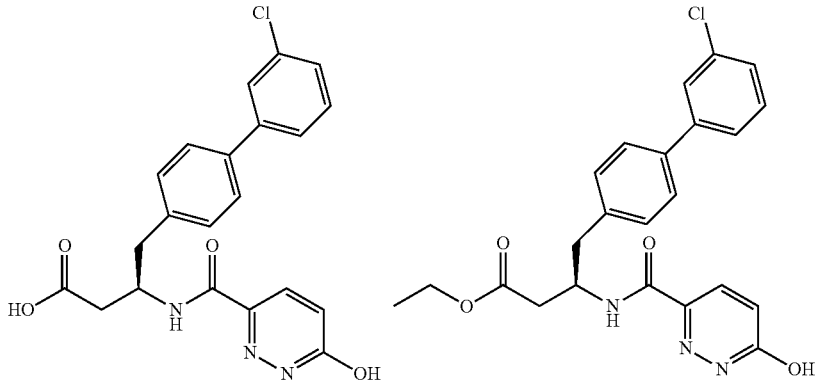<br>R-4-(3'-chlorobiphenyl-4-yl)-3-(6-hydroxypyridazine-3-carboxamido)butanoic acid | 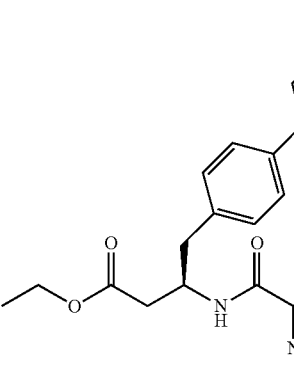 | Aq. NaOH, MeOH, rt | 1.78 min. (D) | 412.1 |
| Example 5-68 | 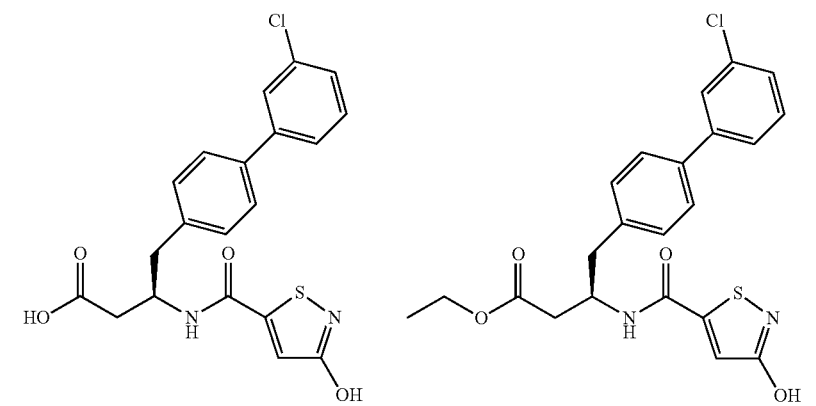<br>R-4-(3'-chlorobiphenyl-4-yl)-3-(3-hydroxyisothiazole-5-carboxamido)butanoic acid | 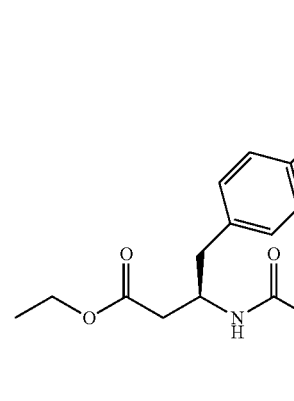 | Aq. NaOH, MeOH, rt | 1.53 min. (D) | 417.1 |

-continued

| Example # | Product | Starting Material | Hydrolysis Condition | LCMS-RT (condition) | MS (M + 1) |
|---|---|---|---|---|---|
| Example 5-69 | R-4-(3′-chlorobiphenyl-4-yl)-3-(2-oxo-2,3-dihydrooxazole-5-carboxamido)butanoic acid | | Aq. NaOH, MeOH, rt | 1.79 min. (D) | 401.2 |
| Example 5-70 | R-4-(3′-chlorobiphenyl-4-yl)-3-(2-oxo-2,3-dihydrooxazole-4-carboxamido)butanoic acid | | Aq. NaOH, MeOH, rt | 1.62 min. (D) | 401.1 |
| Example 5-71 | R-4-(3′-chlorobiphenyl-4-yl)-3-(2-oxo-2,3-dihydrothiazole-5-carboxamido)butanoic acid | | Aq. NaOH, MeOH, rt | 1.73 min. (D) | 417.2 |

| Example # | Product | Starting Material | Hydrolysis Condition | LCMS-RT (condition) | MS (M + 1) |
|---|---|---|---|---|---|
| Example 5-72 | R-4-(biphenyl-4-yl)-3-(6-(methylsulfonamido)nicotinamido)butanoic acid | | Aq. NaOH, MeOH, rt | 1.49 min. (D) | 454.2 |
| Example 5-73 | 2-((R)-1-Biphenyl-4-ylmethyl-2-carboxy-(R)-4-(1-carboxy-ethylamino)-oxazole-4-carboxylic acid | | Aq. NaOH, MeOH, rt | 1.28 min. (A) | 367.0 |

Example 5-38: 1H NMR (400 MHz, CD$_3$OD) δ ppm 2.65 (d, J=7.1 Hz, 2 H) 2.91-3.07 (m, 2 H) 3.26 (s, 3 H) 4.70 (m, 1 H) 7.04 (d, J=8.8 Hz, 1 H) 7.26-7.33 (m, 1 H) 7.33-7.44 (m, 3 H) 7.47-7.56 (m, 3 H) 7.57 (t, J=1.9 Hz, 1 H) 8.02 (dd, J=8.8, 2.5 Hz, 1 H) 8.55 (d, J=1.78 Hz, 1 H).

Example 5-39: 1H NMR (400 MHz, CD$_3$OD) δ ppm 2.36-2.60 (m, 6 H) 2.84 (dd, J=13.4, 6.1 Hz, 1 H) 2.91 (dd, J=13.4, 6.1 Hz, 1 H) 3.77 (s, 3 H) 4.34-4.58 (m, 1 H) 7.03 (d, J=8.6 Hz, 1 H) 7.18-7.31 (m, 4 H) 7.39 (d, J=8.1 Hz, 2 H)

Example 5-40: 1H NMR (400 MHz, DMSO-d$_6$) δ ppm 2.51-2.70 (m, 2 H) 2.79-2.99 (m, 2 H) 3.05 (s, 3 H) 4.41-4.62 (m, 1 H) 7.22 (d, J=8.8 Hz, 2 H) 7.33 (d, J=8.1 Hz, 2 H) 7.36-7.43 (m, 1 H) 7.46 (t, J=7.8 Hz, 1 H) 7.56-7.66 (m, 3 H) 7.69 (t, J=1.8 Hz, 1 H) 7.76 (d, J=8.6 Hz, 2 H) 8.30 (d, J=8.3 Hz, 1 H) 10.09 (s, 1 H) 12.24 (s, 1 H)

Example 5-41: 1H NMR (400 MHz, DMSO-d$_6$) δ ppm 1.28 (t, J=7.6 Hz, 3 H) 2.51-2.60 (m, 2 H) 2.84-2.94 (m, 2 H) 2.97 (q, J=7.6 Hz, 2 H) 4.36-4.56 (m, 1 H) 7.32 (d, J=8.3 Hz, 2 H) 7.37-7.42 (m, 1 H) 7.47 (t, J=7.8 Hz, 1 H) 7.60-7.66 (m, 3 H) 7.70 (t, J=1.8 Hz, 1 H) 8.23 (s, 1 H) 8.60 (d, J=8.3 Hz, 1 H) 12.30 (br. s., 1 H)

Example 5-42: 1H NMR (400 MHz, DMSO-d$_6$) δ ppm 2.23-2.31 (m, 2 H) 2.31-2.43 (m, 4 H) 2.76 (d, J=6.6 Hz, 2 H) 4.16-4.30 (m, 1 H) 6.87-7.02 (m, 2 H) 7.07 (dd, J=9.6, 3.0 Hz, 1 H) 7.21 (d, J=8.3 Hz, 2 H) 7.50 (d, J=8.1 Hz, 2 H) 7.90 (d, J=8.1 Hz, 1 H) 9.51 (br. s., 1 H)

Example 5-43: 1H NMR (400 MHz, CD$_3$OD) δ ppm 2.33-2.60 (m, 6 H) 2.85 (dd, J=13.7, 6.1 Hz, 1 H) 2.94 (dd, J=13.7, 6.1 Hz, 1 H) 3.45 (s, 3 H) 4.35-4.57 (m, 1 H) 7.14 (t, J=7.8 Hz, 1 H) 7.21-7.34 (m, 3 H) 7.38 (dd, J=8.0, 1.6 Hz, 1 H) 7.47 (d, J=8.3 Hz, 2 H)

Example 5-44: 1H NMR (400 MHz, CD$_3$OD) δ ppm 2.64 (d, J=5.8 Hz, 2 H) 3.01 (d, J=6.8 Hz, 2 H) 4.51-4.74 (m, 1 H) 7.00 (br. s., 1 H) 7.25-7.35 (m, 3 H) 7.40 (t, J=7.6 Hz, 2 H) 7.53 (d, J=8.1 Hz, 2 H) 7.58 (d, J=8.1 Hz, 2 H) 8.21 (br. s., 1 H)

Example 5-45: 1H NMR (400 MHz, CD$_3$OD) δ ppm 2.38-2.55 (m, 6 H) 2.85 (dd, J=13.6, 6.3, Hz, 1 H) 2.93 (dd, J=13.6, 6.3, Hz, 1 H) 4.40-4.56 (m, 1 H) 7.27-7.37 (m, 3 H) 7.40 (t, J=7.8 Hz, 1 H) 7.54-7.56 (m, 3 H) 7.60 (t, J=1.8 Hz, 1 H)

Example 5-46: 1H NMR (400 MHz, DMSO-d$_6$) δ ppm 2.51-2.63 (m, 2 H) 2.84 (dd, J=13.6, 8.3 Hz, 1 H) 2.89 (dd, J=13.6, 8.3 Hz, 1 H) 4.40-4.55 (m, 1 H) 7.30 (d, J=8.3 Hz, 2 H) 7.37-7.42 (m, 1 H) 7.47 (t, J=7.8 Hz, 1 H) 7.58-7.66 (m, 3 H) 7.70 (t, J=1.9 Hz, 1 H) 8.95 (d, J=8.6 Hz, 1 H) 12.93 (s, 1 H)

Example 5-47: 1H NMR (400 MHz, DMSO-d$_6$) δ ppm 1.25 (t, J=7.6 Hz, 3 H) 2.51-2.59 (m, 2 H) 2.80 (q, J=7.6 Hz, 2 H) 2.84-2.94 (m, 2 H) 4.41-4.56 (m, 1 H) 7.31 (d, J=8.1 Hz, 2 H) 7.37-7.42 (m, 1 H) 7.47 (t, J=7.8 Hz, 1 H) 7.59 (s, 1 H) 7.63 (d, J=8.3 Hz, 3 H) 7.70 (t, J=1.9 Hz, 1 H) 8.45 (d, J=8.6 Hz, 1 H) 12.27 (br. s., 1 H)

Example 5-48: 1H NMR (400 MHz, CD₃OD) δ ppm 1.33 (t, J=7.6 Hz, 3 H) 2.64 (d, J=6.8 Hz, 2 H) 2.84 (q, J=7.6 Hz, 2 H) 2.98 (d, J=7.01 Hz, 2 H) 3.72 (s, 3 H) 4.62-4.75 (m, 1 H) 6.94-7.06 (m, 3 H) 7.27 (d, J=8.1 Hz, 2 H) 7.40 (d, J=8.3 Hz, 2 H) 7.54 (s, 1 H)

Example 5-49: 1H NMR (400 MHz, DMSO-d₆) δ ppm 2.51-2.62 (m, 2 H) 2.84 (dd, J=13.7, 7.9 Hz, 1 H) 2.91 (dd, J=13.7, 7.9 Hz, 1 H) 3.73 (s, 3 H) 4.42-4.55 (m, 1 H) 7.05-7.19 (m, 3 H) 7.25 (d, J=8.1 Hz, 2 H) 7.42 (d, J=8.1 Hz, 2 H) 7.73 (s, 1 H) 8.55 (s, 1 H) 8.63 (d, J=8.6 Hz, 1 H)

Example 5-50: 1H NMR (400 MHz, CD₃OD) δ ppm 2.69 (d, J=6.8 Hz, 2 H) 2.95-3.10 (m, 2 H) 4.68-4.79 (m, 1 H) 7.21-7.33 (m, 1 H) 7.33-7.47 (m, 4 H) 7.49-7.65 (m, 4 H) 7.76-7.97 (m, 2 H) 8.20-8.42 (m, 1 H)

Example 5-51: 1H NMR (400 MHz, CD₃OD) δ ppm 2.62 (d, J=6.6 Hz, 2 H) 2.96 (d, J=7.3 Hz, 2 H) 4.54-4.68 (m, 1 H) 7.28-7.36 (m, 3 H) 7.40 (t, J=7.7 Hz, 2 H) 7.56 (dd, J=17.2, 7.8 Hz, 4 H)

Example 5-52: 1H NMR (400 MHz, CD₃OD) δ ppm 2.34-2.45 (m, 2 H) 2.45-2.59 (m, 4 H) 2.86 (dd, J=13.4, 6.0 Hz, 1 H) 2.93 (dd, J=13.4, 6.0 Hz, 1 H) 4.40-4.55 (m, 1 H) 7.19-7.26 (m, 1 H) 7.34 (d, J=8.1 Hz, 2 H) 7.46-7.49 (m, 1 H) 7.51 (t, J=8.0 Hz, 1 H) 7.56 (d, J=8.3 Hz, 2 H) 7.61 (d, J=7.8 Hz, 1 H)

Example 5-53: 1H NMR (400 MHz, DMSO-d₆) δ ppm 2.04-2.26 (m, 2 H) 2.31-2.46 (m, 2 H) 2.69-2.88 (m, 2 H) 2.94-3.21 (m, 2 H) 4.18-4.37 (m, 1 H) 7.28 (d, J=7.1 Hz, 2 H) 7.35-7.43 (m, 1 H) 7.43-7.54 (m, 2 H) 7.63 (d, J=8.2 Hz, 3 H) 7.70 (t, J=1.9 Hz, 1 H) 7.98 (dd, J=8.3, 2.3 Hz, 1 H) 12.22 (br. s., 1 H)

Example 5-54: 1H NMR (400 MHz, CD₃OD) δ ppm 2.57 (s, 3 H) 2.68 (d, J=6.6 Hz, 2 H) 2.92-3.08 (m, 2 H) 4.64-4.74 (m, 1 H) 7.25-7.33 (m, 1 H) 7.33-7.44 (m, 3 H) 7.44-7.55 (m, 3 H) 7.57 (t, J=1.8 Hz, 1 H)

Example 5-55: 1H NMR (400 MHz, CD₃OD) δ ppm 2.64 (d, J=6.3 Hz, 2 H) 2.97 (d, J=7.1 Hz, 2 H) 3.74 (s, 3 H) 4.58-4.73 (m, 1 H) 6.43 (s, 1 H) 6.96-7.08 (m, 3 H) 7.27 (d, J=8.1 Hz, 2 H) 7.42 (d, J=8.1 Hz, 2 H) 8.71 (d, J=8.3 Hz, 1 H)

Example 5-56: 1H NMR (400 MHz, DMSO-d₆) δ ppm 2.52-2.67 (m, 2 H) 2.80-2.96 (m, 2 H) 4.38-4.54 (m, 1 H) 5.90 (br. s., 1 H) 7.30 (d, J=8.1 Hz, 2 H) 7.35-7.42 (m, 1 H) 7.46 (t, J=7.8 Hz, 1 H) 7.61 (d, J=8.3 Hz, 3 H) 7.69 (t, J=1.9 Hz, 1 H) 8.08 (br. s., 1 H)

Example 5-57: 1H NMR (400 MHz, CD₃OD) δ ppm 2.48-2.55 (m, 1 H) 2.64 (d, J=6.8 Hz, 1 H) 2.88-3.00 (m, 2 H) 4.32-4.69 (m, 1 H) 7.26-7.35 (m, 3 H) 7.41 (t, J=7.5 Hz, 2 H) 7.49-7.65 (m, 4 H)

Example 5-58: 1H NMR (400 MHz, CD₃OD) δ ppm 2.62 (d, J=6.6 Hz, 2 H) 2.92-3.01 (m, 2 H) 4.59-4.64 (m, 1 H) 7.28-7.43 (m, 4 H) 7.48-7.56 (m, 3 H) 7.59 (t, J=1.9 Hz, 1 H)

Example 5-59: 1H NMR (400 MHz, CD₃OD) δ ppm 2.64 (d, J=6.6 Hz, 2 H) 3.01 (d, J=7.1 Hz, 2 H) 4.63-4.75 (m, 1 H) 7.05 (d, J=8.1 Hz, 1 H) 7.26-7.32 (m, 1 H) 7.35 (d, J=8.3 Hz, 2 H) 7.37-7.43 (m, 2 H) 7.44 (d, J=1.0 Hz, 1 H) 7.48 (dd, J=8.1, 1.77 Hz, 1 H) 7.52-7.60 (m, 4 H)

Example 5-60: 1H NMR (400 MHz, CD₃OD) δ ppm 2.30-2.44 (m, 2 H) 2.44-2.64 (m, 4 H) 2.87 (dd, J=13.7, 6.4 Hz, 1 H) 2.95 (dd, J=13.7, 6.4 Hz, 1 H) 4.42-4.53 (m, 1 H) 7.27-7.52 (m, 8 H)

Example 5-61: 1H NMR (400 MHz, DMSO-d₆) δ ppm 2.22-2.32 (m, 2 H) 2.32-2.44 (m, 4 H) 2.76 (d, J=6.6 Hz, 2 H) 4.16-4.29 (m, 1 H) 6.82-6.88 (m, 1 H) 6.89-6.97 (m, 1 H) 7.08-7.17 (m, 1 H) 7.17-7.28 (m, 3 H) 7.47 (d, J=8.1 Hz, 2 H) 7.90 (d, J=8.1 Hz, 1 H) 9.47 (br. s., 1 H) 12.14 (br. s., 1 H)

Example 5-62: 1H NMR (400 MHz, DMSO-d₆) δ ppm 2.22-2.31 (m, 2 H) 2.33-2.42 (m, 4 H) 2.72-2.85 (m, 2 H) 3.72 (s, 3 H) 4.16-4.34 (m, 1 H) 6.92 (ddd, J=9.4, 3.79, 1.8 Hz, 1 H) 7.21-7.33 (m, 4 H) 7.34-7.45 (m, 1 H) 7.92 (d, J=8.1 Hz, 1 H) 12.14 (br. s., 2 H)

Example 5-63: 1H NMR (400 MHz, DMSO-d₆) δ ppm 2.42-2.48 (m, 2 H) 2.85 (d, J=6.8 Hz, 2 H) 4.30-4.46 (m, 1 H) 6.99 (s, 1 H) 7.30 (d, J=8.1 Hz, 2 H) 7.36-7.42 (m, 1 H) 7.47 (t, J=7.8 Hz, 1 H) 7.63 (d, J=8.1 Hz, 3 H) 7.67-7.77 (m, 2 H) 10.13 (br. s., 1 H) 10.22 (br. s., 1 H) 12.26 (br. s., 1 H)

Example 5-64: 1H NMR (400 MHz, CD₃OD) δ ppm 2.35-2.60 (m, 6 H) 2.85 (dd, J=13.7, 6.4 Hz, 1 H) 2.93 (dd, J=13.7, 6.4 Hz, 1 H) 3.65 (s, 3 H) 4.37-4.58 (m, 1 H) 7.05-7.18 (m, 3 H) 7.30 (d, J=8.1 Hz, 2 H) 7.44 (d, J=8.3 Hz, 2 H)

Example 5-65: 1H NMR (400 MHz, CD₃OD) δ ppm 2.38-2.56 (m, 6 H) 2.85 (dd, J=13.4, 7.3 Hz, 1 H) 2.89 (dd, J=13.4, 7.3 Hz, 1 H) 4.40-4.52 (m, 1 H) 7.26-7.35 (m, 3 H) 7.36-7.46 (m, 2 H) 7.52-7.61 (m, 3 H)

Example 5-66: 1H NMR (400 MHz, CD₃OD) δ ppm 2.31-2.58 (m, 6 H) 2.68-2.99 (m, 2 H) 3.63 (s, 3 H) 4.33-4.56 (m, 1 H) 6.92-7.18 (m, 3 H) 7.30-7.38 (m, 1 H) 7.38-7.46 (m, 2 H)

Example 5-67: 1H NMR (400 MHz, DMSO-d₆) δ ppm 2.51-2.65 (m, 2 H) 2.86 (dd, J=13.7, 8.1 Hz, 1 H) 2.95 (dd, J=13.7, 8.1 Hz, 1 H) 4.42-4.61 (m, 1 H) 6.89-6.99 (m, 1 H) 7.30 (d, J=8.3 Hz, 2 H) 7.37-7.42 (m, 1 H) 7.42-7.51 (m, 1 H) 7.62 (d, J=8.1 Hz, 3 H) 7.69 (t, J=1.8 Hz, 1 H) 7.76 (d, J=9.9 Hz, 1 H) 8.41 (d, J=9.1 Hz, 1 H) 12.26 (br. s., 1 H) 13.40 (s, 1 H)

Example 5-68: 1H NMR (400 MHz, DMSO-d₆) δ ppm 2.51-2.57 (m, 2 H) 2.90 (d, J=6.8 Hz, 2 H) 4.34-4.52 (m, 1 H) 7.15 (s, 1 H) 7.31 (d, J=8.1 Hz, 2 H) 7.39 (dd, J=7.6, 1.77 Hz, 1 H) 7.47 (t, J=7.8 Hz, 1 H) 7.59-7.66 (m, 3 H) 7.70 (t, J=1.8 Hz, 1 H) 8.74 (d, J=8.6 Hz, 1 H)

Example 5-69: 1H NMR (400 MHz, CD₃OD) δ ppm 2.61 (d, J=6.6 Hz, 2 H) 2.89-3.02 (m, 2 H) 4.53-4.71 (m, 1 H) 7.16-7.37 (m, 4 H) 7.39 (t, J=7.8 Hz, 1 H) 7.45-7.57 (m, 3 H) 7.59 (t, J=1.8 Hz, 1 H) 8.20 (d, 1 H).

Example 5-70: 1H NMR (400 MHz, DMSO-d₆) δ ppm 2.41-2.57 (m, 2 H) 2.73-2.96 (m, 2 H) 4.35-4.46 (m, 1 H) 7.30 (d, J=8.3 Hz, 2 H) 7.35-7.44 (m, 1 H) 7.47 (t, J=7.8 Hz, 1 H) 7.57-7.67 (m, 4 H) 7.70 (t, J=1.9 Hz, 1 H) 8.23 (d, J=8.3 Hz, 1 H) 11.14 (s, 1 H) 12.29 (br. s., 1 H).

Example 5-71: 1H NMR (400 MHz, CD₃OD) δ ppm 2.58 (dd, J=6.8, 1.8 Hz, 2 H) 2.95 (dd, J=7.0, 3.4 Hz, 2 H) 4.53-4.66 (m, 1 H) 7.27-7.36 (m, 3 H) 7.36-7.43 (m, 2 H) 7.49-7.57 (m, 3 H) 7.59 (t, J=1.7 Hz, 1 H).

Example 5-72: 1H NMR (400 MHz, CD₃OD) δ ppm 2.60-2.71 (m, 2 H), 3.03 (dd, J=6.9, 4.7 Hz, 2 H), 3.28 (s, 3 H), 4.65-4.76 (m, 1 H), 7.06 (d, J=8.8 Hz, 1 H), 7.23-7.38 (m, 3 H), 7.38-7.47 (m, 2 H), 7.50-7.64 (m, 5 H), 8.03 (dd, J=8.8, 2.3 Hz, 1 H), 8.17 (d, 1 H), 8.56 (br. s., 1 H).

Example 5-73: 1H NMR (400 MHz, DMSO-d₆) δ ppm 2.43-2.59 (m, 2 H), 2.82-2.95 (m, 2 H), 4.04-4.16 (m, 1 H), 7.30 (d, J=8.3 Hz, 2 H), 7.34 (t, J=7.3 Hz, 1 H), 7.45 (t, J=7.6 Hz, 2 H), 7.59 (d, J=8.1 Hz, 3 H), 7.64 (d, J=8.6 Hz, 2 H), 8.03 (s, 1 H), 12.45 (br. s., 2 H).

Example 6-1

Synthesis of (R)-3-(biphenyl-4-ylmethyl)-4-(2-carboxyethylamino)-4-oxobutanoic acid

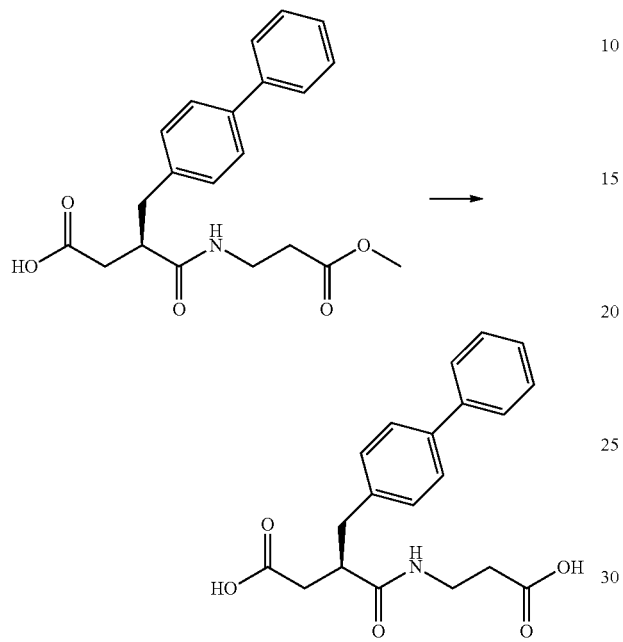

To a solution of (R)-3-(biphenyl-4-ylmethyl)-4-(3-methoxy-3-oxopropylamino)-4-oxobutanoic acid (22.1 mg, 0.060 mmol) in THF (0.6 mL) and methanol (0.1 mL), aqueous 1M NaOH (0.12 mL, 0.12 mmol) is added at room temperature. After stirring for 3 hours, additional aqueous 1M NaOH (0.12 mL, 0.12 mmol) is added. The reaction mixture is allowed to stir for 30 minutes and quenched with 0.5 mL of aqueous 1M HCl and 0.5 mL of brine. The mixture is extracted twice with ethyl acetate, and the organic layer is concentrated under reduced pressure to give (R)-3-(biphenyl-4-ylmethyl)-4-(2-carboxyethylamino)-4-oxobutanoic acid (16.4 mg). HPLC retention time=1.04 minutes (condition A); MS (m+1)= 356.1; 1H NMR (400 MHz, DMSO-$d_6$) δ ppm 2.13-2.31 (m, 3 H) 2.59-2.65 (m, 1 H) 2.81-2.90 (m, 2 H) 3.12-3.27 (m, 2 H) 7.26 (d, 2 H, J=8 Hz) 7.34 (t, 1 H, J=7.4 Hz) 7.45 (t, 2 H, J=7.7 Hz) 7.57 (d, 2 H, J=8.1 Hz) 7.63-7.65.

Example 7-1

Synthesis of (R)-3-biphenyl-4-ylmethyl-N-carboxymethyl-succinamic acid

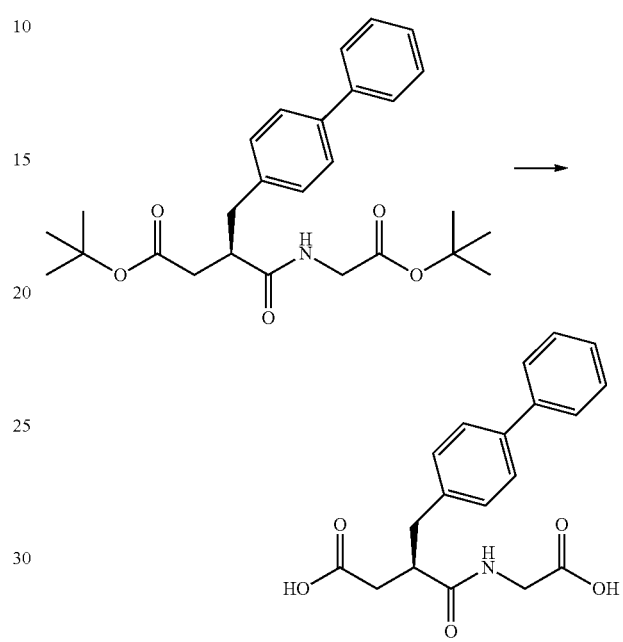

A solution of (R)-tert-butyl 3-(biphenyl-4-ylmethyl)-4-(2-tert-butoxy-2-oxoethylamino)-4-oxobutanoate (40 mg, 0.088 mmol) and TFA (0.5 mL, 6.49 mmol) in DCM (1.5 mL) is allowed to stir for 2 hours at room temperature. The reaction is concentrated under reduced pressure, and the obtained residue is suspended in DCM (0.5 mL) and heptane (2 mL), and collected on a funnel, giving (R)-3-biphenyl-4-ylmethyl-N-carboxymethyl-succinamic acid (9.6 mg). HPLC retention time=1.26 minutes (condition A); MS (m+1)=342.0; 1H NMR (400 MHz, CD$_3$OD) δ ppm 2.39 (dd, J=16.67, 5.31 Hz, 1 H) 2.63-2.82 (m, 2 H) 2.98-3.14 (m, 2 H) 3.84 and 3.95 (AB, 2 H, J=17.8 Hz) 7.26-7.33 (m, 3 H) 7.40 (t, J=7.71 Hz, 2 H) 7.56 (dd, J=19.96, 8.08 Hz, 4 H).

Following compounds are prepared using similar procedure as described in example 7-1:

| Example # | Product | Starting Material | Hydrolysis Condition | HPLC-RT (condition) | MS (M + 1) |
|---|---|---|---|---|---|
| Example 7-2 | (R)-3-biphenyl-4-ylmethyl-N-(3-carboxypropyl)-succinamic acid | Intermediate 3 | TFA, DCM, rt | 1.35 min. (A) | 370.0 |

Example 7-2: 1H NMR (400 MHz, DMSO-d$_6$) δ ppm 1.51-1.58 (m, 2 H) 2.12-2.21 (m, 3 H) 2.49-2.65 (m, 2 H) 2.81-2.89 (m, 2 H) 2.94-3.08 (m, 2 H) 7.26 (d, 2 H, J=8.1 Hz) 7.32-7.36 (m, 1 H) 7.43-7.46 (m, 2 H) 7.57 (d, 2 H, J=8.0 Hz) 7.63-7.65 (m, 2 H).

Example 8-1

Synthesis of (R)-4-(2-biphenyl-4-ylmethyl-3-carboxy-propionylamino)-2-methyl-pentanoic acid

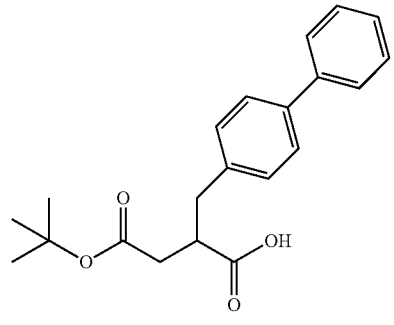

Intermediate 10

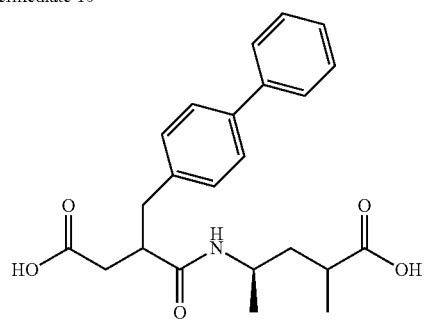

To a stirred solution of 2-biphenyl-4-ylmethyl-succinic acid 4-tert-butyl ester (100 mg, 0.29 mmol) in DMF (10 mL) is added HOBt (45 mg, 0.29 mmol) and EDCI (56 mg, 0.29 mmol) and the mixture is stirred at room temperature for 10 minutes then (2R,4R)-4-amino-2-methyl-pentanoic acid ethyl ester trifluoroacetate (47 mg, 0.29 mmol) and triethylamine (89 mg, 0.87 mmol) is added and the mixture is stirred at room temperature for 5 hours. The mixture is quenched with water and extracted with ethyl acetate. The organic layer is washed with water, brine, dried over magnesium sulfate and filtered. The solvent is removed under reduced pressure to give (2R,4R)-7-biphenyl-4-ylmethyl-2,4-dimethyl-6-oxo-nonanedioic acid 9-tert-butyl ester 1-ethyl ester.

Next, to a solution of (2R,4R)-7-biphenyl-4-ylmethyl-2,4-dimethyl-6-oxo-nonanedioic acid 9-tert-butyl ester 1-ethyl ester EtOH (4 mL) is added aqueous 1M NaOH (4 mL) and the mixture is stirred at room temperature for 30 minutes. The mixture is acidified to pH 2-3 with aqueous 1M HCl and is extracted with ethyl acetate. The solvent is removed under reduced pressure and the residue is purified by preparative HPLC using a gradient of 10-100% MeCN/water (0.1% TFA). Lyophilization of the proper fractions furnished (R)-4-(2-biphenyl-4-ylmethyl-3-carboxy-propionylamino)-2-methyl-pentanoic acid. HPLC retention time=1.13 minutes (condition C); MS 398.2 (M+1); $^1$H-NMR (400 MHz, DMSO-d$_6$) δ ppm 0.93 (m, 6H), 1.23 (m, 1H), 1.59 (m, 1H), 2.17 (m, 1H), 2.63 (m, 1H), 2.82 (m, 1H), 3.72 (m, 1H), 7.27 (m, 2H), 7.33 (m, 1H), 7.45 (m, 2H), 7.56 (m, 2H), 7.62 (m, 2H), 7.71 (m, 1H), 12.07 (s, 1H).

Example 9-1

Synthesis of (R)-4-biphenyl-4-yl-3-[(1H-tetrazole-5-carbonyl)-amino]-butyric acid

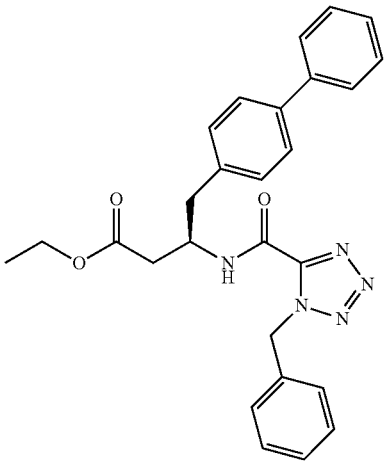

+

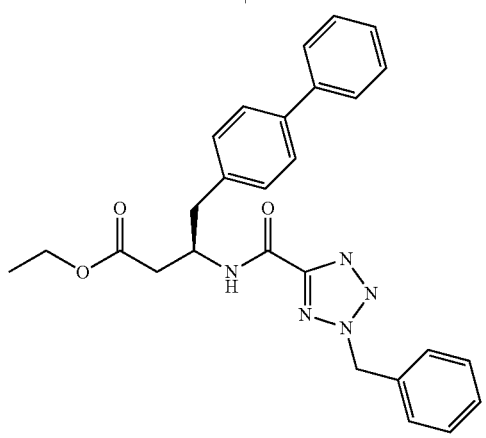

Intermediate 8

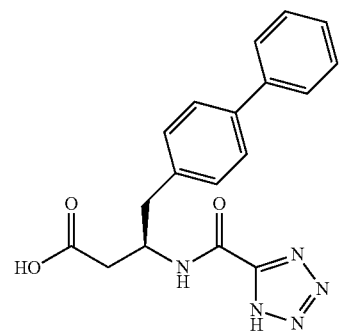

To a mixture of (R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester (180 mg, 0.383 mmol) in EtOH (1 mL) and THF (1 mL) is added aqueous 1M LiOH (2 mL). After stirring for 0.5 hour, the reaction mixture is acidified with aqueous 1M HCl. The mixture is extracted with ethyl acetate, dried over Na$_2$SO$_4$, and concentrated under reduced pressure. The residue is dissolved in MeOH and hydrogenated with 10% Pd/C at room temperature for 3 hours and at 40° C. for 2 hours. The reaction mixture is concentrated and purified by reverse phase HPLC to give (R)-4-biphenyl-4-yl-3-[(1H-tetrazole-5-carbonyl)-amino]-butyric acid. HPLC retention time=1.18 minutes (condition D); MS (m+1)=352; $^1$H NMR (400 MHz, DMSO-$d_6$) ppm 2.56 (dd, J=5.81, 15.92 Hz, 1H), 2.67 (dd, J=7.58, 15.92 Hz, 1H), 2.85-2.99 (m, 2H), 4.55-4.64 (m, 1H), 7.26-7.35 (m, 3H), 7.43 (dd, J=7.83, 7.83 Hz, 2H), 7.56 (d, J=8.08 Hz, 2H), 7.62 (d, J=7.07 Hz, 2H), 9.28 (d, 8.84 Hz, 1H), 12.28 (s, 1H).

Example 10-1

(R)-4-bipheyl-4-yl-3-(3-1H-tetrazol-5-yl-propionylamino)-butyric acid

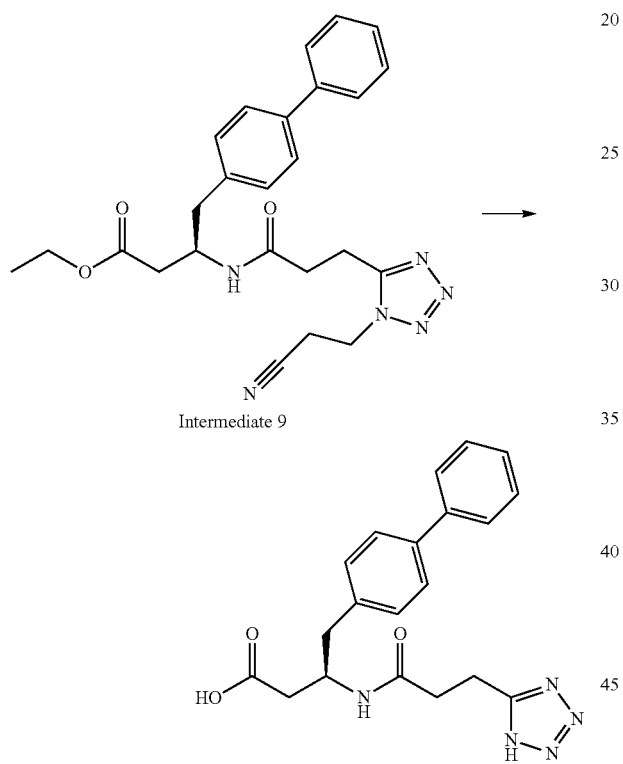

Intermediate 9

To a solution of (R)-4-biphenyl-4-yl-3-{3-[1-(2-cyanoethyl)-1H-tetrazol-5-yl]-propionylamino}-butyric acid ethyl ester (137 mg, 0.297 mmol) in DCM (8 mL) at room temperature is added DBU (1.507 mL, 10.00 mmol) and the mixture is stirred at room temperature for 2 hours. The reaction is extracted with DCM. The combined organic layer is washed with saturated NH$_4$Cl, brine and dried over anhydrous sodium sulfate, filtered and concentrated under reduced. The obtained residue is purified by flash chromatography (silica gel, 2% to 10% EtOH/DCM) to give (R)-4-biphenyl-4-yl-3-(3-1H-tetrazol-5-yl-propionylamino)-butyric acid ethyl ester (37 mg). To the obtained ester in EtOH (2 mL) at room temperature is added aqueous 1M NaOH (1 mL, 1.0 mmol) and the mixture is stirred at room temperature for 1 hour. To the reaction is added 1 mL of aqueous 1M HCl to pH=4, and the mixture is purified by reverse phase HPLC [30% to 60% acetonitrile-H$_2$O (0.1% TFA)] to give (R)-4-biphenyl-4-yl-3-(3-1H-tetrazol-5-yl-propionylamino)-butyric acid. HPLC retention time=1.24 minutes (condition C); MS (m+1)=380; 1H NMR (400 MHz, DMSO-$d_6$) δ ppm 2.37 (dd, J=6.7, 2.1 Hz, 2 H), 2.53 (t, J=7.6 Hz, 2 H), 2.69-2.82 (m, 2 H), 3.02 (t, J=7.7 Hz, 2 H), 4.17-4.29 (m, 1 H), 7.22 (d, J=8.3 Hz, 2 H), 7.34 (tt, J=7.3, 1.3 Hz, 1 H), 7.42-7.48 (m, 2 H), 7.57 (d, J=8.3 Hz, 2 H), 7.64 (dd, J=8.2, 1.1 Hz, 2 H), 8.00 (d, J=8.1 Hz, 1 H), 12.21 (br. s., 1 H), 15.92 (br. s., 1 H).

Chiral HPLC retention time=5.64 min. Column: Daicel CHIRALCEL OJ-H (4.6×100 mm); flow rate=1 ml/min.; eluent: EtOH(containing 0.1% TFA)/heptane=2/8.

Example 11-1

Synthesis of (R)-4-(1-carboxy-3-(3'-chlorobiphenyl-4-yl)propan-2-ylamino)-4-oxobutanoic acid

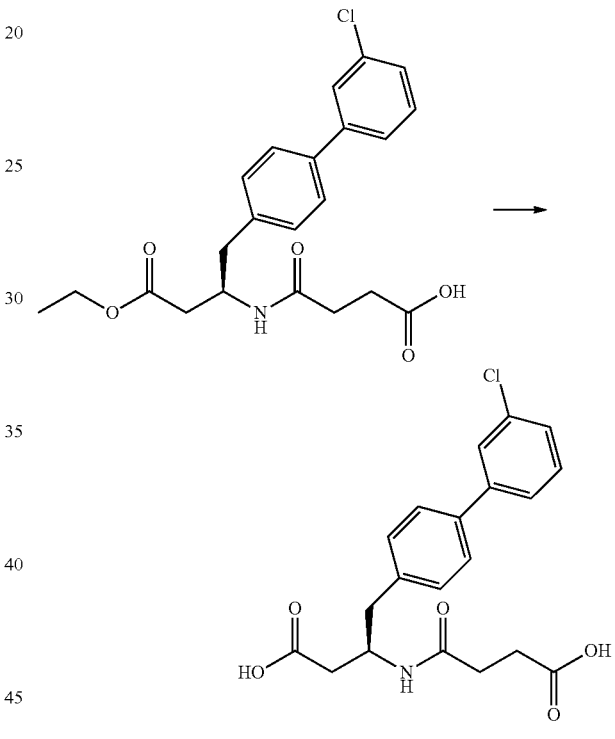

To a solution of (R)-4-(1-(biphenyl-4-yl)-4-ethoxy-4-oxobutan-2-ylamino)-4-oxobutanoic acid (110 mg, 0.263 mmol) in THF (2 mL) and methanol (0.2 mL), aqueous 1M NaOH solution (1.053 mL, 1.053 mmol) is added at room temperature. After stirring for 1 hour, the reaction is quenched with 0.1 M aqueous HCl, and the solution is diluted with DCM (15 ml) and allowed to stir for 1.5 hours. The precipitated solid is collected on a funnel, washed with water, DCM, heptane and then DCM in that order, and dried under reduced pressure to (R)-4-(1-carboxy-3-(3'-chlorobiphenyl-4-yl)propan-2-ylamino)-4-oxobutanoic acid (66 mg). HPLC retention time=0.87 minutes (condition B); MS (m+1)=390.0; 1H NMR (400 MHz, CD$_3$OD) δ ppm 2.39-2.55 (m, 6 H) 2.86 (A of ABX, J$_{ab}$=13.6 Hz, J$_{ax}$=7.6 Hz, 1 H) 2.92 (B of ABX, J$_{ab}$=13.6 Hz, J$_{bx}$=6.2 Hz, 1 H) 4.42-4.49 (m, 1 H) 7.30-7.34 (m, 3 H) 7.40 (t, J=7.4 Hz, 1 H) 7.51-7.56 (m, 3 H) 7.60 (t, J=1.8 Hz, 1 H).

Following compounds are prepared using similar procedure as described in example 11-1:

| Example # | Product | Starting Material | Hydrolysis Condition | HPLC-RT (condition) | MS (M + 1) |
|---|---|---|---|---|---|
| Example 11-2 | (R)-5-(1-carboxy-3-(3'-chlorobiphenyl-4-yl)propan-2-ylamino)-5-oxopentanoic acid | | Aq. NaOH, THF, MeOH, RT | 0.79 min. (B) | 404.1 |
| Example 11-3 | (R)-5-(1-carboxy-3-(5'-fluoro-2'-methoxybiphenyl-4-yl)propan-2-ylamino)-5-oxopentanoic acid | | Aq. NaOH, THF, MeOH, RT | 0.65 min. (B) | 418.2 |
| Example 11-4 | (R)-5-(1-carboxy-3-(5'-chloro-2'-methoxybiphenyl-4-yl)propan-2-ylamino)-5-oxopentanoic acid | | Aq. NaOH, THF, MeOH, RT | 0.63 min. (B) | 434.3 |
| Example 11-5 | (R)-6-(1-carboxy-3-(3'-chlorobiphenyl-4-yl)propan-2-ylamino)-6-oxohexanoic acid | | Aq. NaOH, THF, MeOH, RT | 1.40 min. (A) | 418.3 |

-continued

| Example # | Product | Starting Material | Hydrolysis Condition | HPLC-RT (condition) | MS (M + 1) |
|---|---|---|---|---|---|
| Example 11-6 | (R)-4-(3'-chlorobiphenyl-4-yl)-3-(3-(pyridin-3-yl)propanamido)butanoic acid | | Aq. NaOH, THF, MeOH, RT | 1.40 min. (A) | 423.3 |
| Example 11-7 | (R)-4-(3'-chlorobiphenyl-4-yl)-3-(3-(pyridin-2-yl)propanamido)butanoic acid | | Aq. NaOH, THF, MeOH, RT | 1.39 min. (A) | 423.3 |
| Example 11-9 | (R)-3-(3-(1H-benzo[d]imidazol-2-yl)propanamido)-4-(3'-chlorobiphenyl-4-yl)butanoic acid | | Aq. NaOH, THF, MeOH, RT | 1.50 min. (B) | 462.3 |
| Example 11-10 | 4-(1-carboxy-3-(3'-chloro-3-fluorobiphenyl-4-yl)propan-2-ylamino)-4-oxobutanoic acid | | Aq. NaOH, THF, MeOH, 50° C. | 0.72 min. (B) | 408.2 |

-continued

| Example # | Product | Starting Material | Hydrolysis Condition | HPLC-RT (condition) | MS (M + 1) |
|---|---|---|---|---|---|
| Example 11-11 | 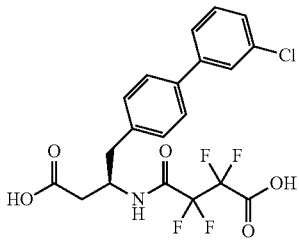<br>N-[(R)-2-Carboxy-1-(3'-chloro-biphenyl-4-ylmethyl)-ethyl]-2,2,3,3-tetrafluoro-succinamic acid | 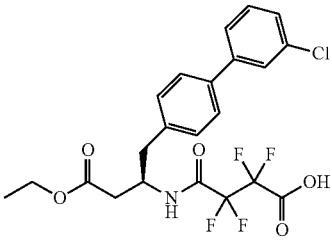 [SMILES: CCOC(=O)C[C@@H](Cc1ccc(-c2cccc(Cl)c2)cc1)NC(=O)C(F)(F)C(F)(F)C(=O)O] | Aq. NaOH, EtOH, rt | 1.16 min. (C) | 462.2 |
| Example 11-12 | 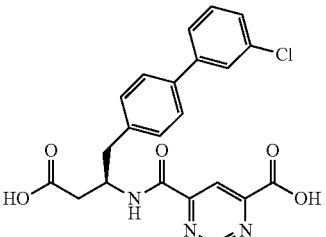<br>6-[(R)-2-Carboxy-1-(3'-chloro-biphenyl-4-ylmethyl)-ethylcarbamoyl]-pyrimidine-4-carboxylic acid | 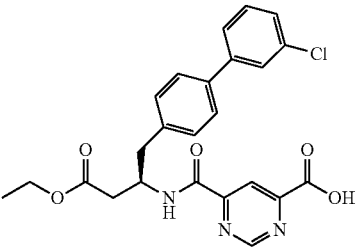 | Aq. NaOH, EtOH, rt | 1.34 min. (C) | 440.2 |
| Example 11-13 | 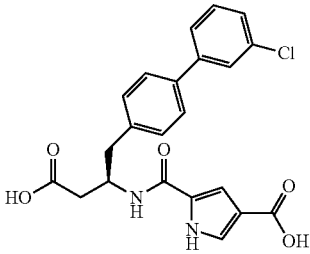<br>5-[(R)-2-Carboxy-1-(3'-chloro-biphenyl-4-ylmethyl)-ethylcarbamoyl]-1H-pyrazole-3-carboxylic acid | 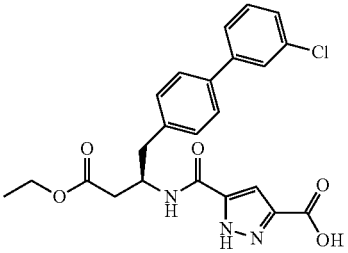 [SMILES: CCOC(=O)C[C@@H](Cc1ccc(-c2cccc(Cl)c2)cc1)NC(=O)c1cc(C(=O)O)n[nH]1] | Aq. NaOH, EtOH, 50° C. | 1.09 min. (C) | 428.2 |
| Example 11-14 | 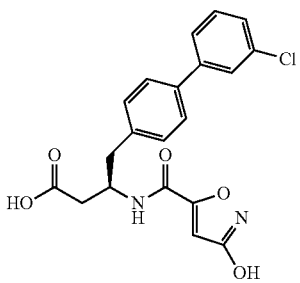<br>(R)-4-(3'-Chloro-biphenyl-4-yl)-3-[(3-hydroxy-isoxazole-5-carbonyl)amino]-butyric acid | 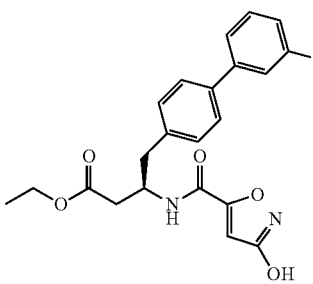 | Aq. NaOH, EtOH, rt | 1.17 min. (C) | 401.0 |

| Example # | Product | Starting Material | Hydrolysis Condition | HPLC-RT (condition) | MS (M + 1) |
|---|---|---|---|---|---|
| Example 11-15 | (R)-4-(3'-Chloro-biphenyl-4-yl)-3-[(oxazole-5-carbonyl)-amino]-butyric acid | | Aq. NaOH, EtOH, rt | 1.12 min. (C) | 385.2 |
| Example 11-16 | (R)-4-(3'-Chloro-biphenyl-4-yl)-3-[(isoxazole-5-carbonyl)-amino]-butyric acid | | BCl₃, DCM, rt | 1.15 min. (C) | 385.1 |
| Example 11-17 | (R)-4-(3'-Chloro-biphenyl-4-yl)-3-[(1H-pyrazole-3-carbonyl)-amino]-butyric acid | | Aq. NaOH, EtOH, 50° C. | 1.18 min. (C) | 384.3 |
| Example 11-18 | 5-[(R)-2-Carboxy-1-(3'-chloro-biphenyl-4-ylmethyl)-ethylcarbamoyl]-furan-2-carboxylic acid | | Aq. NaOH, EtOH, 50° C, | 1.08 min. (C) | 428.2 |

-continued

| Example # | Product | Starting Material | Hydrolysis Condition | HPLC-RT (condition) | MS (M + 1) |
|---|---|---|---|---|---|
| Example 11-19 | 2-[(R)-2-Carboxy-1-(3'-chloro-biphenyl-4-ylmethyl)-ethylcarbamoyl]-isonicotinic acid | | Aq. NaOH, EtOH, rt | 1.04 min. (C) | 439.3 |
| Example 11-20 | 4-[(R)-2-Carboxy-1-(3'-chloro-biphenyl-4-ylmethyl)-ethylcarbamoyl]-pyridine-2-carboxylic acid | | Aq. NaOH, EtOH, rt | 1.03 min. (C) | 439.2 |
| Example 11-21 | 2-[(R)-2-Carboxy-1-(3'-chloro-biphenyl-4-ylmethyl)-ethylcarbamoyl]-pyrimidine-4-carboxylic acid | | Aq. NaOH, EtOH, rt | 0.89 min. (C) | 440.1 |
| Example 11-22 | 5-[(R)-2-Carboxy-1-(3'-chloro-biphenyl-4-ylmethyl)-ethylcarbamoyl]-1H-pyrrole-2-carboxylic acid | | Aq. NaOH, EtOH, rt | 1.09 min. (C) | 427.3 |

| Example # | Product | Starting Material | Hydrolysis Condition | HPLC-RT (condition) | MS (M + 1) |
|---|---|---|---|---|---|
| Example 11-23 | (R)-4-(3'-Chloro-biphenyl-4-yl)-3-(oxalyl-amino)-butyric acid | | Aq. NaOH, EtOH, rt | 0.9 min. (C) | 362.1 |
| Example 11-24 | 5-[(R)-2-Carboxy-1-(3'-fluoro-biphenyl-4-ylmethyl)-ethylcarbamoyl]-1H-pyrazole-3-carboxylic acid | | Aq. NaOH, EtOH, 50° C. | 0.96 min. (C) | 412.1 |
| Example 11-25 | 6-[(R)-2-Carboxy-1-(3'-fluoro-biphenyl-4-ylmethyl)-ethylcarbamoyl]-pyrimidine-4-carboxylic acid | | Aq. NaOH, EtOH, rt | 0.97 min. (C) | 424.4 |
| Example 11-26 | (R)-4-(3'-Fluoro-biphenyl-4-yl)-3-[(3-hydroxy-isoxazole-5-carbonyl)-amino]-butyric acid | | Aq. NaOH, EtOH, rt | 0.83 min. (C) | 385.1 |

| Example # | Product | Starting Material | Hydrolysis Condition | HPLC-RT (condition) | MS (M + 1) |
|---|---|---|---|---|---|
| Example 11-27 | 6-[(R)-2-Carboxy-1-(2'-methoxy-biphenyl-4-ylmethyl)-ethylcarbamoyl]-pyrimidine-4-carboxylic acid | | Aq. NaOH, EtOH, rt | 1.22 min. (C) | 436.2 |
| Example 11-28 | 5-[(R)-2-Carboxy-1-(2'-methoxy-biphenyl-4-ylmethyl)-ethylcarbamoyl]-1H-pyrazole-3-carboxylic acid | | Aq. NaOH, EtOH, 50° C. | 0.98 min. (C) | 424.0 |
| Example 11-29 | (R)-4-(2',5'-Dichloro-biphenyl-4-yl)-3-[(2-ethyl-oxazole-5-carbonyl)-amino]-butyric acid | | Aq. NaOH, MeOH, rt | 1.52 min. (D) | 448.1 |
| Example 11-30 | (E)-3-[(R)-2-Carboxy-1-(3'-chloro-biphenyl-4-ylmethyl)-ethylcarbamoyl]-acrylic acid | | Aq. NaOH, THF, MeOH, rt | 1.12 min. (A) | 388.3 |

-continued

| Example # | Product | Starting Material | Hydrolysis Condition | HPLC-RT (condition) | MS (M + 1) |
|---|---|---|---|---|---|
| Example 11-31 | 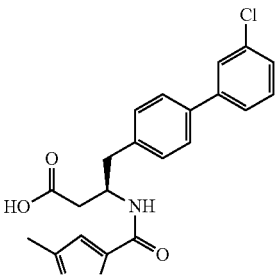<br>(R)-4-(3'-Chloro-biphenyl-4-yl)-3-[(5-methyl-2H-pyrazole-3-carbonyl)-amino]-butyric acid | 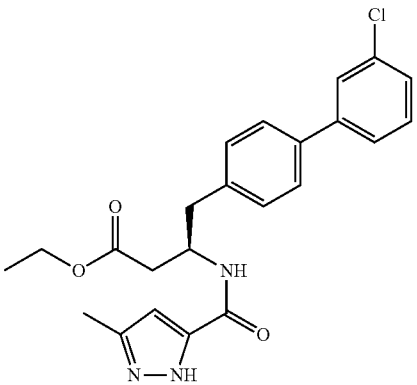 [SMILES: CCOC(=O)C[C@@H](Cc1ccc(-c2cccc(Cl)c2)cc1)NC(=O)c1cc(C)n[nH]1] | Aq. NaOH, MeOH, rt | 1.52 min. (D) | 398.1 |
| Example 11-32 | 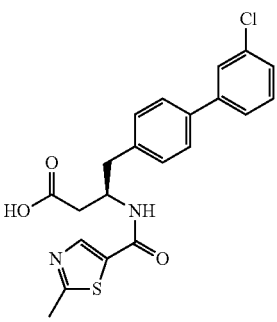<br>(R)-4-(3'-Chloro-biphenyl-4-yl)-3-[(2-methyl-thiazole-5-carbonyl)-amino]-butyric acid | 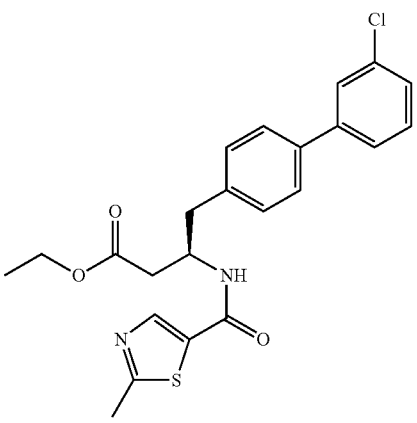 [SMILES: CCOC(=O)C[C@@H](Cc1ccc(-c2cccc(Cl)c2)cc1)NC(=O)c1cnc(C)s1] | Aq. NaOH, MeOH, rt | 1.56 min. (D) | 415.0 |
| Example 11-33 | 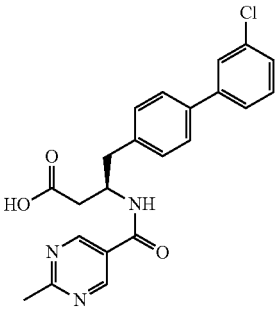<br>(R)-4-(3'-Chloro-biphenyl-4-yl)-3-[(2-methyl-pyrimidine-5-carbonyl)-amino]-butyric acid | 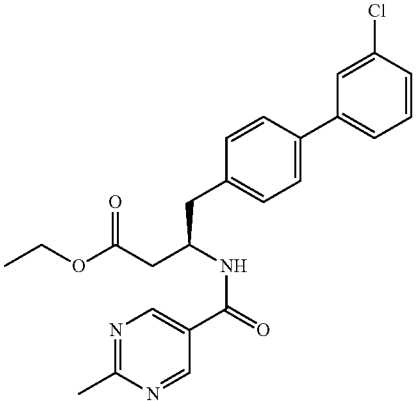 [SMILES: CCOC(=O)C[C@@H](Cc1ccc(-c2cccc(Cl)c2)cc1)NC(=O)c1cnc(C)nc1] | Aq. NaOH, MeOH, rt | 1.56 min. (D) | 410.1 |

-continued

| Example # | Product | Starting Material | Hydrolysis Condition | HPLC-RT (condition) | MS (M + 1) |
|---|---|---|---|---|---|
| Example 11-34 | 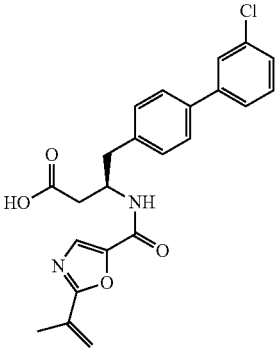<br>(R)-4-(3'-Chloro-biphenyl-4-yl)-3-[(2-isopropenyl-oxazole-5-carbonyl)-amino]-butyric acid | 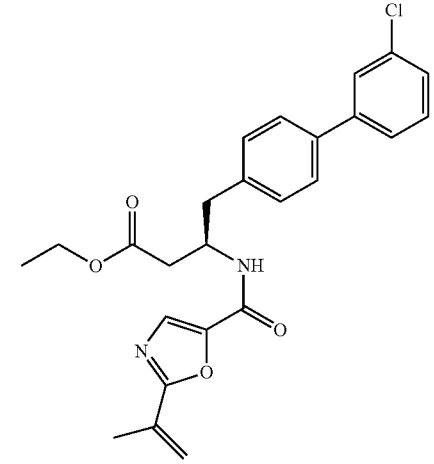 [SMILES: C=C(C)c1ncc(C(=O)N[C@@H](CC(=O)OCC)Cc2ccc(-c3cccc(Cl)c3)cc2)o1] | Aq. NaOH, MeOH, rt | 1.75 min. (D) | 425.1 |
| Example 11-35 | 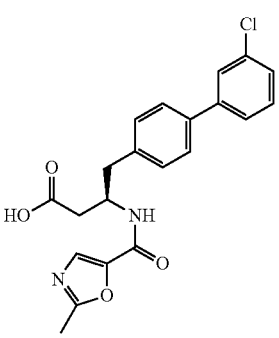<br>(R)-4-(3'-Chloro-biphenyl-4-yl)-3-[(2-methyl-oxazole-5-carbonyl)-amino]-butyric acid | 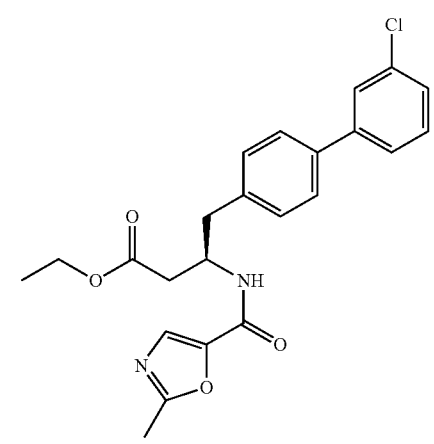 [SMILES: CCOC(=O)C[C@@H](Cc1ccc(-c2cccc(Cl)c2)cc1)NC(=O)c1cnc(C)o1] | Aq. NaOH, MeOH, rt | 1.63 min. (D) | 399.1 |
| Example 11-36 | 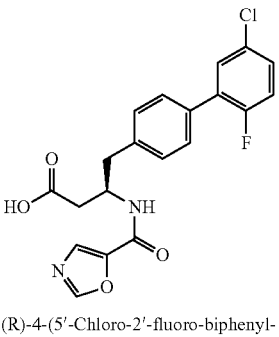<br>(R)-4-(5'-Chloro-2'-fluoro-biphenyl-4-yl)-3-[(oxazole-5-carbonyl)-amino]-butyric acid | 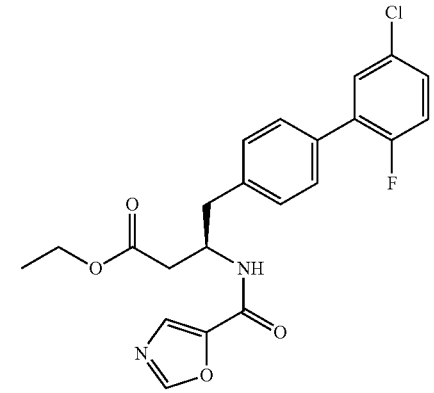 [SMILES: CCOC(=O)C[C@@H](Cc1ccc(-c2cc(Cl)ccc2F)cc1)NC(=O)c1cnco1] | Aq. NaOH, MeOH, rt | 1.62 min. (D) | 403.0 |

-continued

| Example # | Product | Starting Material | Hydrolysis Condition | HPLC-RT (condition) | MS (M + 1) |
|---|---|---|---|---|---|
| Example 11-37 | 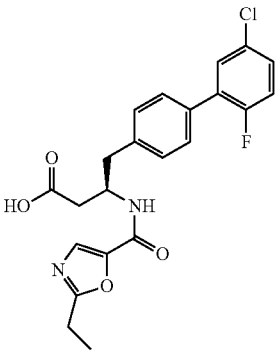<br>(R)-4-(5'-Chloro-2'-fluoro-biphenyl-4-yl)-3-[(2-ethyl-oxazole-5-carbonyl)-amino]-butyric acid | 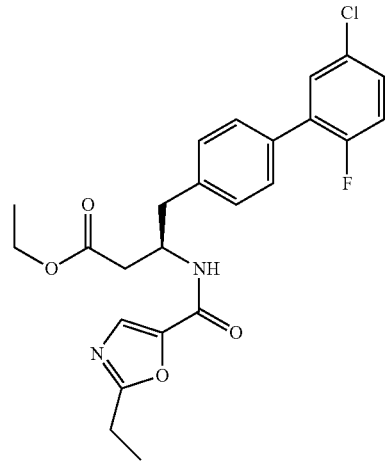 [SMILES: CCOC(=O)C[C@@H](Cc1ccc(-c2cc(Cl)ccc2F)cc1)NC(=O)c1cnc(CC)o1] | Aq. NaOH, MeOH, rt | 1.73 min. (D) | 431.1 |
| Example 11-38 | 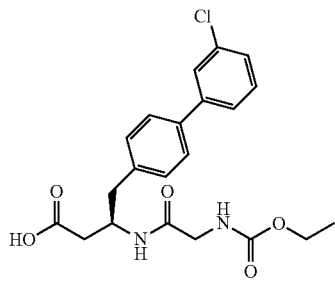<br>(R)-4-(3'-Chloro-biphenyl-4-yl)-3-(2-ethoxycarbonylamino-acetylamino)-butyric acid | 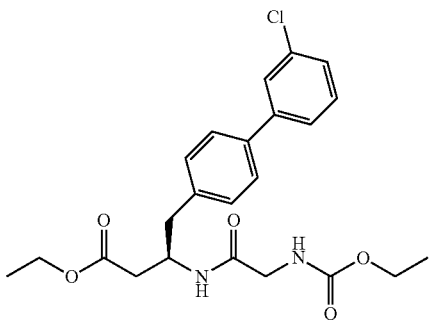 [SMILES: CCOC(=O)C[C@@H](Cc1ccc(-c2cccc(Cl)c2)cc1)NC(=O)CNC(=O)OCC] | Aq. NaOH, THF, MeOH, rt | 0.80 min. (B) | 419.2 |
| Example 11-39 | 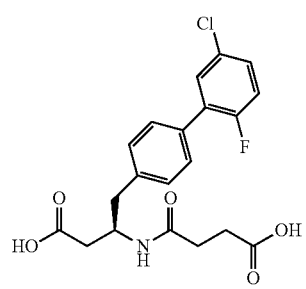<br>(R)-3-(3-Carboxy-propionylamino)-4-(5'-chloro-2'-fluoro-biphenyl-4-yl)-butyric acid | 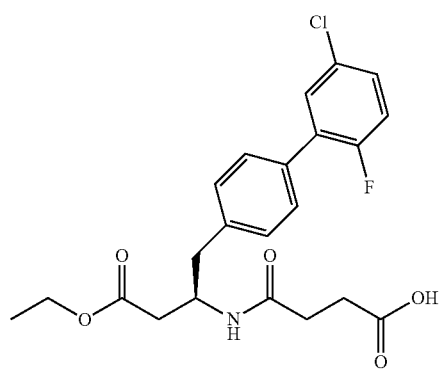 [SMILES: CCOC(=O)C[C@@H](Cc1ccc(-c2cc(Cl)ccc2F)cc1)NC(=O)CCC(=O)O] | Aq. NaOH, THF, MeOH, rt | 0.66 min. (B) | 408.1 |

| Example # | Product | Starting Material | Hydrolysis Condition | HPLC-RT (condition) | MS (M + 1) |
|---|---|---|---|---|---|
| Example 11-40 | 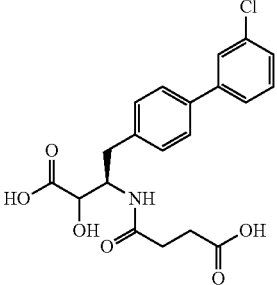<br>(major product)<br>(R)-3-(3-Carboxy-propionylamino)-4-(3'-chloro-biphenyl-4-yl)-2-hydroxy-butyric acid | 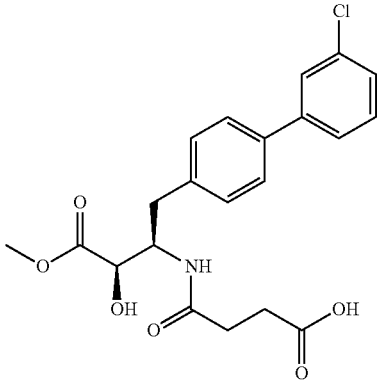 [SMILES: COC(=O)[C@H](O)[C@@H](Cc1ccc(-c2cccc(Cl)c2)cc1)NC(=O)CCC(=O)O] | Aq. NaOH, MeOH, rt | 1.07 min. (A) | 406.0 |
| Example 11-41 | 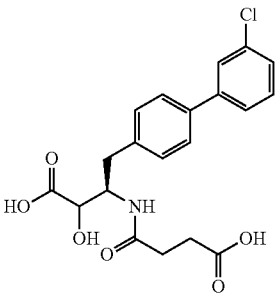<br>(minor product)<br>(R)-3-(3-Carboxy-propionylamino)-4-(3'-chloro-biphenyl-4-yl)-2-hydroxy-butyric acid | 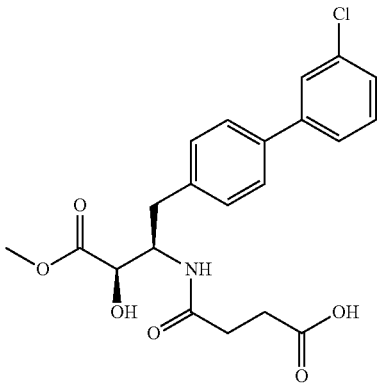 [SMILES: COC(=O)[C@H](O)[C@@H](Cc1ccc(-c2cccc(Cl)c2)cc1)NC(=O)CCC(=O)O] | Aq. NaOH, MeOH, rt | 1.04 min. (A) | 406.0 |

-continued
| Example # | Product | Starting Material | Hydrolysis Condition | HPLC-RT (condition) | MS (M + 1) |
|---|---|---|---|---|---|
| | | 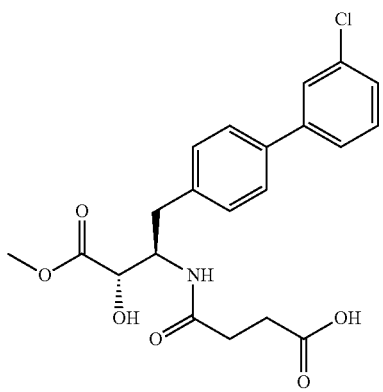 [SMILES: COC(=O)[C@@H](O)[C@@H](Cc1ccc(-c2cccc(Cl)c2)cc1)NC(=O)CCC(=O)O] | | | |
| Example 11-42 | 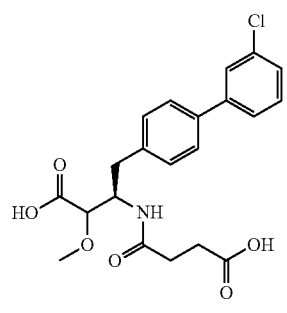<br>(major product)<br>(R)-3-(3-Carboxy-propionylamino)-4-(3'-chloro-biphenyl-4-yl)-2-methoxy-butyric acid | 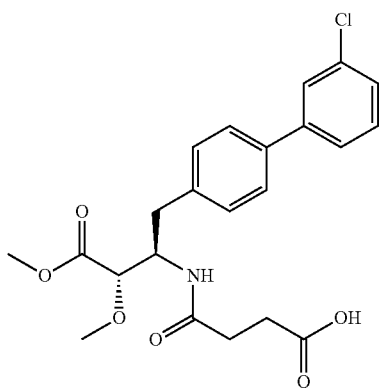 [SMILES: COC(=O)[C@@H](OC)[C@@H](Cc1ccc(-c2cccc(Cl)c2)cc1)NC(=O)CCC(=O)O] | Aq. NaOH, MeOH, rt | 0.97 min. (A) | 420.1 |
| | | 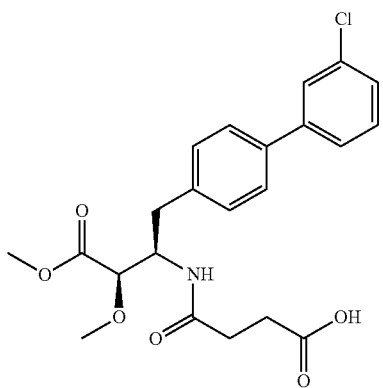 [SMILES: COC(=O)[C@H](OC)[C@@H](Cc1ccc(-c2cccc(Cl)c2)cc1)NC(=O)CCC(=O)O] | | | |

-continued
| Example # | Product | Starting Material | Hydrolysis Condition | HPLC-RT (condition) | MS (M + 1) |
|---|---|---|---|---|---|
| Example 11-43 | 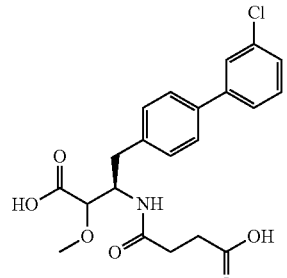<br>(minor product)<br>(R)-3-(3-Carboxy-propionylamino)-4-(3'-chloro-biphenyl-4-yl)-2-methoxy-butyric acid | 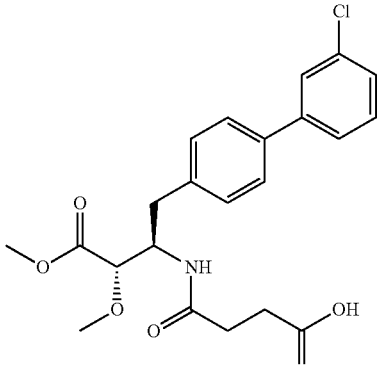 | Aq. NaOH, MeOH, rt | 0.96 min. (A) | 420.1 |
| Example 11-44 | 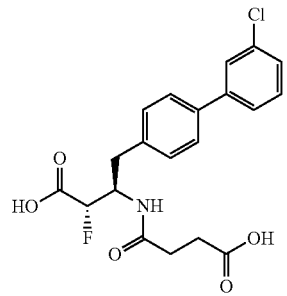 [SMILES: O=C(O)CCC(=O)N[C@H](Cc1ccc(-c2cccc(Cl)c2)cc1)[C@H](F)C(=O)O]<br>(R)-3-(3-Carboxy-propionylamino)-4-(3'-chloro-biphenyl-4-yl)-2-fluoro-butyric acid | 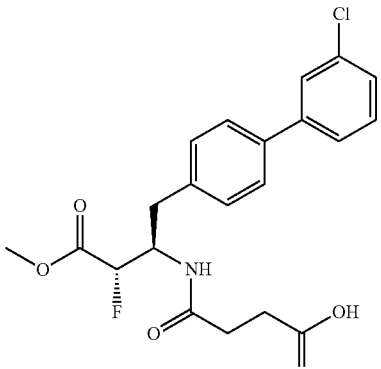 | Aq. NaOH, MeOH, rt | 1.07 min (A) | 408.1 |

| Example # | Product | Starting Material | Hydrolysis Condition | HPLC-RT (condition) | MS (M+1) |
|---|---|---|---|---|---|
| Example 11-45 | 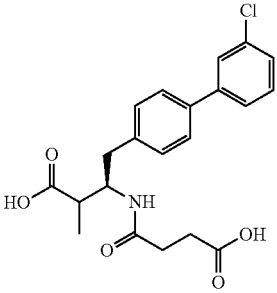 (R)-3-(3-Carboxy-propionylamino)-4-(3'-chloro-biphenyl-4-yl)-2-methyl-butyric acid | 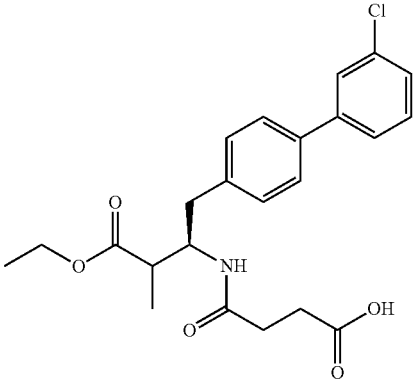 [SMILES: CCOC(=O)C(C)[C@@H](Cc1ccc(-c2cccc(Cl)c2)cc1)NC(=O)CCC(=O)O] | Aq. NaOH, MeOH, rt | 0.53 min. (B) | 404 |
| Example 11-46 | 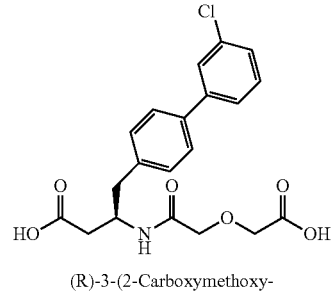 (R)-3-(2-Carboxymethoxy-acetylamino)-4-(3'-chloro-biphenyl-4-yl)-butyric acid | 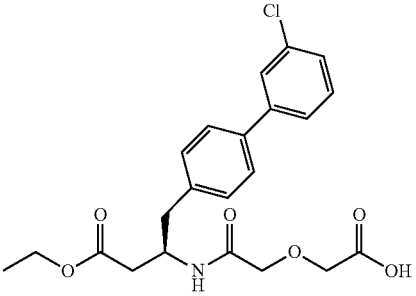 [SMILES: CCOC(=O)C[C@@H](Cc1ccc(-c2cccc(Cl)c2)cc1)NC(=O)COCC(=O)O] | Aq. NaOH, MeOH, rt | 0.37 min. (B) | 406 |

Example 11-2: 1H NMR (400 MHz, CD$_3$OD) δ ppm 1.76-1.83 (m, 2 H) 2.15-2.21 (m, 4 H) 2.49 (A of ABX, J$_{ab}$=15.7 Hz, J$_{ax}$=7.3 Hz, 1 H) 2.53 (B of ABX, J$_{ab}$=15.7 Hz, J$_{bx}$=6.1 Hz, 1 H) 2.83 (A of ABX, J$_{ab}$=13.6 Hz, J$_{ax}$=8.3 Hz, 1 H) 2.93 (B of ABX, J$_{ab}$=13.6 Hz, J$_{bx}$=5.8 Hz, 1 H) 4.46-4.53 (m, 1 H) 7.30-7.33 (m, 3 H) 7.39 (t, J=7.8 Hz, 1 H) 7.51-7.55 (m, 3 H) 7.59-7.60 (m, 1 H).

Example 11-3: 1H NMR (400 MHz, CD$_3$OD) δ ppm 1.77-1.84 (m, 2 H) 2.16-2.23 (m, 4 H) 2.39-2.42 (m, 2 H) 2.49 (A of ABX, J$_{ab}$=15.6 Hz, J$_{ax}$=7.5 Hz, 1 H) 2.53 (B of ABX, J$_{ab}$=15.6 Hz, J$_{bx}$=6.1 Hz, 1 H) 2.83 (A of ABX, J$_{ab}$=13.6 Hz, J$_{ax}$=6.1 Hz, 1 H) 2.91 (B of ABX, J$_{ab}$=13.6 Hz, J$_{bx}$=6.3 Hz, 1 H) 3.75 (s, 3 H) 4.46-4.53 (m, 1 H) 6.97-7.04 (m, 2 H) 7.26 (d, J=8.1 Hz, 2 H) 7.42 (d, J=8.1 Hz, 2 H).

Example 11-4: 1H NMR (400 MHz, CD$_3$OD) δ ppm 1.77-1.84 (m, 2 H) 2.16-2.24 (m, 4 H) 2.49 (A of ABX, J$_{ab}$=15.6 Hz, J$_{ax}$=7.5 Hz, 1 H) 2.54 (B of ABX, J$_{ab}$=15.6 Hz, J$_{bx}$=6.1 Hz, 1 H) 2.83 (A of ABX, J$_{ab}$=13.6 Hz, J$_{ax}$=8.2 Hz, 1 H) 2.91 (B of ABX, J$_{ab}$=13.6 Hz, J$_{bx}$=6.1 Hz, 1 H) 3.77 (s, 3 H) 4.45-4.52 (m, 1 H) 7.03 (d, J=8.6 Hz, 1 H) 7.24-7.28 (m, 3 H) 7.39-7.41 (m, 2 H).

Example 11-5: 1H NMR (400 MHz, CD$_3$OD) δ ppm 1.49-1.56 (m, 4 H) 2.13 (t, J=6.8 Hz, 2 H) 2.23 (t, J=6.9 Hz, 2 H) 2.45-2.56 (m, 2 H) 2.80-2.86 (m, 1 H) 2.91-2.96 (m, 1 H) 4.46-4.53 (m, 1 H) 7.31-7.33 (m, 3 H) 7.40 (t, J=8.0 Hz, 1 H) 7.52-7.55 (m, 3 H) 7.59 (br t, J=1.8 Hz, 1 H).

Example 11-6: 1H NMR (400 MHz, CD$_3$OD) δ ppm 2.39-2.57 (m, 4 H) 2.80 (A of ABX, J$_{ab}$=13.6 Hz, J$_{ax}$=8.1 Hz, 1 H) 2.89 (B of ABX, J$_{ab}$=13.6 Hz, J$_{bx}$=6.1 Hz, 1 H) 3.04 (t, J=7.1 Hz, 2 H) 3.75 (s, 3 H) 4.40-4.47 (m, 2 H) 7.27-7.29 (m, 2 H) 7.32-7.35 (m, 1 H) 7.41 (t, J=7.8 Hz, 1 H) 7.51-7.54 (m, 3 H) 7.59-7.60 (m, 1 H) 7.83-7.84 (m, 1 H) 8.28 (br d, J=7.1 Hz, 1 H) 8.55 (d, J=5.6 Hz, 1 H) 8.62 (s, 1 H).

Example 11-7: 1H NMR (400 MHz, CD$_3$OD) δ ppm 2.47 (A of ABX, J$_{ab}$=15.7 Hz, J$_{ax}$=7.7 HZ, 1 H) 2.54 (B of ABX, J$_{ab}$=15.7 Hz, J$_{bx}$=5.8 Hz, 1 H) 2.64-2.75 (m, 2 H) 2.80 (A of ABX, J$_{ab}$=13.7 Hz, J$_{ax}$=8.3 Hz, 1 H) 2.92 (B of ABX, J$_{ab}$=13.7 Hz, J$_{bx}$=5.9 Hz, 1 H) 3.17-3.21 (m, 2 H) 4.43-4.50 (m, 1 H) 7.28-7.35 (m, 3 H) 7.39-7.43 (m, 1 H) 7.51-7.54 (m, 3 H) 7.59 (br t, J=1.9 Hz, 1 H) 7.69-7.75 (m, 2 H) 8.29-8.32 (m, 1 H) 8.61 (d, J=4.6 Hz, 1 H).

Example 11-8: 1H NMR (400 MHz, CHLOROFORM-d) δ ppm 1.82-1.89 (m, 2 H) 2.29 (t, J=7.3 Hz, 2 H) 2.56 (A of ABX, J$_{ab}$=16.4 Hz, J$_{ax}$=5.6 Hz, 1 H) 2.64 (B of ABX, J$_{ab}$=16.4 Hz, J$_{bx}$=5.1 Hz, 1 H) 2.95 (A of ABX, J$_{ab}$=13.8 Hz, J$_{ax}$=7.6 Hz, 1 H) 2.99 (B of ABX, J$_{ab}$=13.8 Hz, J$_{bx}$=7.2 Hz, 1 H) 3.30 (s, 3 H) 3.38 (t, J=5.9 Hz, 2 H) 4.10 (q, J=7.1 Hz, 2 H) 4.52-4.57 (m, 1 H) 6.59 (br d, J=8.6 Hz, 1 H) 7.26-7.37 (m, 4 H) 7.42-7.45 (m, 2 H) 7.48-7.52 (m, 2 H) 7.55 (br t, J=1.6 Hz, 1 H).

Example 11-9: 1H NMR (400 MHz, CD$_3$CN+D$_2$O) δ ppm 2.43-2.56 (m, 2 H) 2.71-2.91 (m, 4 H) 3.21-3.34 (m, 2 H) 4.39-4.46 (m, 1 H) 7.27 (d, J=8.3 Hz, 2 H) 7.34-7.49 (m, 7 H) 7.55-7.56 (m, 1 H) 7.65-7.70 (m, 2 H).

Example 11-10: 1H NMR (400 MHz, CD$_3$OD) δ ppm 2.38-2.41 (m, 2 H) 2.47-2.58 (m, 4 H) 2.85-2.90 (m, 1 H) 2.99-3.04 (m, 1 H) 4.48-4.55 (m, 1 H) 7.32-7.44 (m, 5 H) 7.53-7.56 (m, 1 H) 7.62-7.63 (m, 1 H).

Example 11-11: 1H NMR (400 MHz, DMSO-d$_6$): 1H NMR (400 MHz, DMSO-d$_6$): δ ppm 2.44-2.52 (m, 2H), 2.83-2.85 (d, J=6.82 Hz, 2H), 4.29-4.38 (m, 1H), 7.28-7.30

(d, J=8.34 Hz, 2H), 7.40-7.43 (t, J=7.83 Hz, 1H), 7.62-7.65 (m, 3H), 7.71-7.72 (t, J=1.77 Hz, 1H), 9.42-9.45 (M, 1H), 12.32 (s, 1H).

Example 11-12: 1H NMR (400 MHz, DMSO-d$_6$) δ ppm 2.54-2.59 (m, 1H), 2.64-2.70 (m, 1H), 2.88-2.93 (m, 1H), 2.98-3.03 (m, 1H), 4.56-4.63 (m, 1H), 7.30-7.32 (m, 2H), 7.37-7.40 (m, 1H), 7.43-7.47 (t, J=7.83 Hz, 1H), 7.59-7.61 (m, 3H), 7.67-7.68 (1, J=2.02 Hz, 1H), 8.32 (d, J=1.26 Hz, 1H), 9.17-9.19 (d, J=9.09 Hz, 1H), 9.50 (d, J=1.52 Hz, 1H), 12.34 (s, 1H), 14.14 (s, 1H).

Example 11-13: 1H NMR (400 MHz, DMSO-d$_6$) δ ppm 2.46-2.60 (m, 2H), 2.84-2.96 (m, 2H), 4.51 (m, 1H), 7.31 (d, J=8.34 Hz, 2H), 7.38-7.41 (m, 1H), 7.46 (t, 1H), 7.62 (d, J=8.34 Hz, 3H), 7.69 (t, 1H).

Example 11-14: 1H NMR (400 MHz, DMSO-d$_6$) δ ppm) 2.75-2.99 (m, 1 H) 4.47 (d, J=7.58 Hz, 1 H) 6.49 (s, 1 H) 7.30 (d, J=8.34 Hz, 1 H) 7.37-7.43 (m, 1 H) 7.47 (t, J=7.83 Hz, 1 H) 7.63 (d, J=8.08 Hz, 2 H) 7.70 (t, J=1.77 Hz, 1 H) 8.80 (d, J=8.59 Hz, 1 H) 11.69 (s, 1 H) 12.04-12.58 (m, 1 H).

Example 11-15: 1H NMR (400 MHz, DMSO-d$_6$) δ ppm 2.81-2.96 (m, 2 H) 4.42-4.55 (m, 1 H) 7.31 (d, J=8.34 Hz, 2 H) 7.36-7.43 (m, 1 H) 7.47 (t, J=7.83 Hz, 1 H) 7.63 (d, J=8.34 Hz, 4 H) 7.69 (t, J=1.77 Hz, 1 H) 7.72 (s, 1 H) 8.54 (s, 1 H) 8.60 (d, J=8.59 Hz, 1 H) 12.29 (br. s., 1 H).

Example 11-16: 1H NMR (400 MHz, DMSO-d$_6$) δ ppm 2.53-2.64 (m, 2 H) 2.84-2.93 (m, 2 H) 4.41-4.59 (m, 1 H) 7.00 (d, J=2.02 Hz, 1 H) 7.31 (d, J=8.08 Hz, 2 H) 7.37-7.42 (m, 1H) 7.47 (t, J=7.83 Hz, 1 H) 7.58-7.65 (m, 3 H) 7.70 (t, J=1.77 Hz, 1 H) 8.72 (d, J=1.77 Hz, 1 H) 8.95 (d, J=8.59 Hz, 1 H) 12.31 (br. s., 1 H).

Example 11-17: 1H NMR (400 MHz, DMSO-d$_6$) δ ppm 2.46-2.60 (m, 2H), 2.83-2.98 (m, 2H), 4.52 (m, 1H), 6.61 (d, J=2.27 Hz, 1H), 7.31 (d, J=8.34 Hz, 2H), 7.37-7.42 (m, 1H), 7.46 (t, 1H), 7.62 (d, J=8.34 Hz, 3H), 7.69 (t, 1H), 7.74 (d, J=2.02 Hz, 1H), 8.13 (d, J=8.84 Hz, 1H).

Example 11-18: 1H NMR (400 MHz, DMSO-d$_6$) δ ppm 2.48-2.62 (m, 2H), 2.84-2.96 (m, 2H), 4.52 (m, 1H), 7.16 (d, J=3.54 Hz, 1H), 7.27 (d, J=3.79 Hz, 1H), 7.31 (d, J=8.34 Hz, 2H), 7.38-7.41 (m, 1H), 7.47 (t, 1H), 7.63 (d, J=8.34 Hz, 3H), 7.70 (t, 1H), 8.59 (d, J=8.59 Hz, 1H).

Example 11-19: 1H NMR (400 MHz, DMSO-d$_6$): 1H NMR (400 MHz, DMSO-d$_6$): δ ppm 2.54-2.67 (m, 2H), 2.88-2.92 (m, 1H), 2.99-3.05 (m, 1H), 4.53-4.62 (m, 1H), 7.31-7.33 (m, 2H), 7.37-7.39 (m, 1H), 7.43-7.47 (t, J=7.58 Hz, 1H), 7.60-7.62 (m, 3H), 7.68 (m, 1H), 7.86-7.87 (d, J=4.55 Hz, 1H), 8.30 (s, 1H), 8.62-8.63 (d, J=4.80 Hz, 1H), 8.80-8.83 (d, J=9.09 Hz, 1H).

Example 11-20: 1H NMR (400 MHz, DMSO-d$_6$): 1H NMR (400 MHz, DMSO-d$_6$): δ ppm 2.50-2.53 (m, 1H), 2.56-2.59 (t, J=6.32 Hz, 1H), 2.90-2.98 (m, 2H), 4.51-4.58 (m, 1H), 7.33-7.35 (d, J=8.34 Hz, 2H), 7.39-7.42 (m, 1H), 7.45-7.49 (t, J=7.83 Hz, 1H), 7.61-7.65 (m, 3H), 7.69-7.70 (t, J=1.77 Hz, 1H), 7.90-7.91 (dd, J=1.77 Hz, 5.05 Hz, 1H), 8.38-8.39 (m, 1H), 8.83-8.85 (dd, J=0.76 Hz, 5.05 Hz, 1H), 8.91-8.93 (d, J=8.34 Hz, 1H).

Example 11-21: 1H NMR (400 MHz, DMSO-d$_6$): 1H NMR (400 MHz, DMSO-d$_6$): δ ppm 2.45-2.55 (m, 1H), 2.59-2.67 (m, 1H), 2.88-2.93 (m, 1H), 2.99-3.05 (m, 1H), 4.51-4.61 (m, 1H), 7.32-7.34 (d, J=8.08 Hz, 2H), 7.37-7.40 (m, 1H), 7.44-7.48 (t, J=7.58 Hz, 1H), 7.60-7.62 (t, J=7.83 Hz, 1H), 7.69 (s, 1H), 7.77 (s, 1H), 8.86-8.87 (d, J=4.04 Hz, 1H), 9.06 (s, 1H).

Example 11-22: 1H NMR (400 MHz, DMSO-d$_6$): δ ppm 2.49-2.53 (m, 2H), 2.90-2.92 (d, J=6.82 Hz, 2H), 4.42-4.51 (m, 1H), 6.72-6.73 (d, J=2.27 Hz, 1H), 7.32-7.34 (m, 2H), 7.39-7.42 (m, 1H), 7.45-7.49 (t, J=7.83 Hz, 1H), 7.62-7.66 (m, 3H), 7.70-7.71 (t, J=1.77 Hz, 1H), 8.27-8.29 (d, J=8.08 Hz, 1H), 11.96 (s, 1H), 12.33 (s, 1H), 12.75 (s, 1H).

Example 11-23: 1H NMR (400 MHz, DMSO-d$_6$): 1H NMR (400 MHz, DMSO-d$_6$): δ ppm 2.44-2.55 (m, 2H), 2.79-2.89 (m, 2H), 4.29-4.38 (m, 1H), 7.27-7.29 (d, J=8.08 Hz, 2H), 7.39-7.42 (m, 1H), 7.45-7.49 (t, J=8.08 Hz, 1H), 7.62-7.64 (d, J=8.08 Hz, 3H), 7.70-7.71 (m, 1H), 8.85-8.87 (d, J=9.09 Hz, 1H), 12.30 (s, 1H).

Example 11-24: 1H NMR (400 MHz, DMSO-d$_6$) δ ppm 2.46-2.60 (m, 2H), 2.84-2.96 (m, 2H), 4.51 (m, 1H), 7.15 (m, 2H), 7.44-7.52 (m, 3H), 7.62 (d, J=8.34 Hz, 2H), 8.38 (d, broad, J=7.58 Hz, 1H).

Example 11-25: 1H NMR (400 MHz, DMSO-d$_6$): δ ppm 2.54-2.59 (m, 1H), 2.64-2.70 (m, 1H), 2.88-2.93 (m, 1H), 2.98-3.03 (m, 1H), 4.56-4.65 (m, 1H), 7.13-7.18 (m, 1H), 7.30-7.32 (d, J=8.34 Hz, 2H), 7.45-7.48 (m, 3H), 7.60-7.62 (d, J=8.34 Hz, 2H), 8.31-8.32 (d, J=1.26 Hz, 1H), 8.17-8.19 (d, J=9.09 Hz, 1H), 8.49 (d, J=1.26 Hz, 1H), 12.32 (s, 1H), 14.10 (s, 1H).

Example 11-26: 1H NMR (400 MHz, DMSO-d$_6$) δ ppm 2.52-2.62 (m, 2 H) 2.83-2.92 (m, 2 H) 4.47 (d, J=7.07 Hz, 1 H) 6.49 (s, 1 H) 7.11-7.21 (m, 1 H) 7.30 (d, J=8.34 Hz, 2 H) 7.42-7.55 (m, 3 H) 7.64 (d, J=8.34 Hz, 2 H) 8.80 (d, J=8.59 Hz, 1 H) 11.68 (br. s., 1 H) 12.30 (br. s., 1 H).

Example 11-27: 1H NMR (400 MHz, DMSO-d$_6$) δ ppm 2.51-2.57 (m, 1H), 2.64-2.70 (m, 1H), 2.84-2.89 (dd, J=6.06 Hz, 1H), 2.96-3.01 (dd, J=7.83 Hz, 1H), 3.72 (s, 3H), 4.54-4.63 (m, 1H), 6.96-7.00 (m, 1H), 7.06-7.08 (dd, J=0.76 Hz, 1H), 7.22-7.24 (m, 3H), 7.28-7.32 (m, 1H), 7.35-7.38 (m, 2H), 8.33-8.34 (d, J=1.26 Hz, 1H), 9.16-9.18 (d, J=9.09 Hz, 1H), 9.49 (d, J=1.52 Hz, 1H), 12.31 (s, 1H), 14.13 (s, 1H).

Example 11-28: 1H NMR (400 MHz, DMSO-d$_6$) δ ppm 2.52-2.60 (m, 2H), 2.73 (s, 1H), 2.89 (s, 1H), 2.81-2.95 (m, 2H), 3.74 (s, 3H), 4.50 (m, 1H), 7.00 (t, 1H), 7.08 (d, J=8.34 Hz, 1H), 7.15 (s, broad, 1H), 7.23-7.26 (m, 3H), 7.29-7.33 (m, 1H), 7.38 (d, J=8.08 Hz, 2H), 8.39 (d, broad, J=7.07 Hz, 1H).

Example 11-29: 1H NMR (400 MHz, CD$_3$OD) δ ppm 1.33 (t, J=7.6 Hz, 3 H) 2.66 (d, J=6.8 Hz, 2 H) 2.84 (q, J=7.6 Hz, 2 H) 2.98 (dd, J=13.6, 8.1 Hz, 1 H) 3.03 (dd, J=13.6, 6.6 Hz, 1 H) 4.64-4.76 (m, 1 H) 7.24-7.37 (m, 6 H) 7.40-7.45 (m, 1 H) 7.53 (s, 1 H).

Example 11-30: 1H NMR (400 MHz, DMSO-d$_6$) δ ppm 2.40-2.51 (m, 2 H) 2.79-2.90 (m, 2 H) 4.29-4.38 (m, 1 H) 6.47 (d, J=15.7 Hz, 1 H) 6.88 (d, J=15.7 Hz, 1 H) 7.28-7.30 (m, 2 H) 7.39-7.41 (m, 1 H) 7.47 (t, J=8.0 Hz, 1 H) 7.62-7.65 (m, 2 H) 7.70-7.71 (m, 1 H) 8.54 (d, J=8.1 Hz, 1 H) 7.31 (d, J=8.3 HZ, 2 H) 7.40-7.43 (m, 1 H) 7.47-7.50 (m, 1 H) 7.62-7.65 (m, 3 H) 7.69-7.71 (m, 1 H) 8.54 (d, J=8.1 Hz, 1 H)

Example 11-31: 1H NMR (400 MHz, DMSO-d$_6$) δ ppm 2.22 (s, 3 H) 2.43-2.49 (m, 1 H) 2.52-2.60 (m, 1 H) 2.84 (dd, J=13.6, 6.1 Hz, 1 H) 2.94 (dd, J=13.6, 8.1 Hz, 1 H) 4.39-4.58 (m, 1 H) 6.33 (s, 1 H) 7.30 (d, J=8.3 Hz, 2 H) 7.36-7.42 (m, 1 H) 7.46 (t, J=7.8 Hz, 1 H) 7.61 (d, J=8.3 Hz, 3 H) 7.69 (t, J=1.9 Hz, 1 H) 8.02 (d, J=7.8 Hz, 1 H).

Example 11-32: 1H NMR (400 MHz, DMSO-d$_6$) δ ppm 2.51-2.56 (m, 2 H) 2.89 (d, J=6.8 Hz, 2 H) 3.31 (s, 3 H) 4.33-4.57 (m, 1 H) 7.31 (d, J=8.1 Hz, 2 H) 7.37-7.42 (m, 1 H) 7.46 (t, J=7.8 Hz, 1 H) 7.60-7.66 (m, 3 H) 7.69 (t, J=1.8 Hz, 1 H) 8.15 (s, 1 H) 8.50 (d, J=8.3 Hz, 1 H) 12.24 (br. s., 1 H).

Example 11-33: 1H NMR (400 MHz, DMSO-d$_6$) δ ppm 2.52-2.60 (m, 2 H) 2.66 (s, 3 H) 2.93 (d, J=6.8 Hz, 2 H) 4.43-4.63 (m, 1 H) 7.33 (d, J=8.1 Hz, 2 H) 7.36-7.42 (m, 1 H) 7.46 (t, J=7.8 Hz, 1 H) 7.58-7.66 (m, 3 H) 7.69 (t, J=1.8 Hz, 1 H) 8.74 (d, J=8.3 Hz, 1 H) 8.98 (s, 2 H) 12.28 (br. s., 1 H).

Example 11-34: 1H NMR (400 MHz, MeOD) δ ppm 2.15 (s, 3 H) 2.67 (d, J=6.6 Hz, 2 H) 2.98 (dd, J=13.9, 8.3 Hz, 1 H) 3.03 (dd, J=14.1, 6.8 Hz, 1 H) 4.62-4.77 (m, 1 H) 5.57 (s, 1 H)

6.16 (s, 1 H) 7.27-7.32 (m, 1 H) 7.32-7.41 (m, 3 H) 7.46-7.54 (m, 3 H) 7.56 (t, J=1.8 Hz, 1 H) 7.65 (s, 1 H) 8.55 (d, J=8.6 Hz, 1 H).

Example 11-35: 1H NMR (400 MHz, CD$_3$OD) δ ppm 2.42 (s, 3 H) 2.63 (d, J=6.3 Hz, 2 H) 2.99 (d, J=7.1 Hz, 2 H) 4.59-4.73 (m, 1 H) 7.25-7.30 (m, 1 H) 7.30-7.37 (m, 3 H) 7.41-7.50 (m, 3 H) 7.53 (t, J=1.8 Hz, 1 H) 8.15 (s, 1 H).

Example 11-36: 1H NMR (400 MHz, DMSO-d$_6$) δ ppm 2.51-2.61 (m, 2 H) 2.87 (dd, J=13.1, 5.6 Hz, 1 H) 2.94 (dd, J=13.4, 7.6 Hz, 1 H) 4.41-4.60 (m, 1 H) 7.29-7.38 (m, 3 H) 7.45 (ddd, J=8.7, 4.2, 2.8 Hz, 1 H) 7.49 (d, J=6.8 Hz, 2 H) 7.56 (dd, J=6.8, 2.5 Hz, 1 H) 7.71 (s, 1 H) 8.53 (s, 1 H) 8.59 (d, J=8.6 Hz, 1 H) 12.26 (br. s., 1 H).

Example 11-37: 1H NMR (400 MHz, CD$_3$OD) δ ppm 1.32 (t, J=7.6 Hz, 3 H) 2.66 (d, J=6.8 Hz, 2 H) 2.83 (q, J=7.6 Hz, 2 H) 2.98 (dd, J=13.6, 7.8 Hz, 1 H) 3.03 (dd, J=14.7, 6.8 Hz, 1 H) 4.61-4.80 (m, 1 H) 7.13 (dd, J=18.9, 10.1 Hz, 1 H) 7.25-7.32 (m, 1 H) 7.32-7.37 (m, 2 H) 7.37-7.45 (m, 3 H) 7.54 (s, 1 H).

Example 11-38: 1H NMR (400 MHz, DMSO-d$_6$) δ ppm 1.15 (t, J=7.73 Hz, 3 H) 2.39 (d, J=6.8 Hz, 2 H) 2.79 (d, J=6.8 Hz, 2 H) 3.46-3.56 (m, 2 H) 3.91-4.01 (m, 2 H) 4.21-4.29 (m, 1 H) 7.14-7.17 (m, 1 H) 7.28 (d, J=8.3 Hz, 2 H) 7.39-7.42 (m, 1 H) 7.48 (t, J=7.83 Hz, 1 H) 7.61-7.64 (m, 3 H) 7.69-7.70 (m, 1 H) 7.84 (d, J=8.4 Hz, 1 H) 12.23 (br s, 1 H).

Example 11-39: 1H NMR (400 MHz, Methanol-d$_4$) δ ppm 2.39-2.56 (m, 6 H) 2.87 (A of ABX, J$_{ab}$=13.6 Hz, J$_{ax}$=7.6 Hz, 1 H) 2.94 (B of ABX, J$_{ab}$=13.6 Hz, J$_{bx}$=6.1 Hz, 1 H) 4.43-4.50 (m, 1 H) 7.15-7.20 (m, 1 H) 7.31-7.35 (m, 3 H) 7.45-7.48 (m, 3 H).

Example 11-40: 1H NMR (400 MHz, DMSO-d$_6$) δ ppm 2.24-2.37 (m, 4H), 2.73 (dd, 1H, J=7.83, 13.4 Hz), 2.88 (dd, 1H, J=7.33, 13.4 Hz), 3.93 (s, 1H), 4.26-4.36 (m, 1H), 5.35 (bs, 1H), 7.33 (d, 2H, J=8.08 Hz), 7.38-7.43 (m, 1H), 7.48 (t, 1H, J=7.83 Hz), 7.63 (d, 3H, J=8.34 Hz), 7.70 (t, 1H, J=2.02 Hz), 7.73 (d, 1H, J=9.09 Hz), 12.26 (bs, 2H).

Example 11-41: 1H NMR (400 MHz, DMSO-d$_6$) δ ppm 2.21-2.33 (m, 4H), 2.65-2.81 (m, 2H), 4.02 (d, 1H, J=4.04 Hz), 4.24-4.32 (m, 1H), 5.56 (bs, 1H), 7.27 (d, 2H, J=8.34 Hz), 7.37-7.42 (m, 1H), 7.47 (t, 1H, J=7.83 Hz), 7.58 (d, 2H, J=8.34 Hz), 7.60-7.64 (m, 1H), 7.69 (t, 1H, J=1.77 Hz), 7.96 (d, 1H, J=8.84 Hz), 12.03 (bs, 1H), 12.60 (bs, 1H).

Example 11-42: 1H NMR (400 MHz, DMSO-d$_6$) δ ppm 2.22-2.37 (m, 4H), 2.74 (dd, 1H, J=8.34, 13.4 Hz), 2.86 (dd, 1H, J=6.82, 13.4 Hz), 3.34 (s, 3H), 3.62 (d, 1H, J=2.78 Hz), 4.34-4.44 (m, 1H), 7.31 (d, 2H, J=8.34 Hz), 7.38-7.43 (m, 1H), 7.48 (t, 1H, J=7.83 Hz), 7.63 (d, 3H, J=8.34 Hz), 7.71 (s, 1H), 7.89 (d, 1H, J=9.35 Hz).

Example 11-43: 1H NMR (400 MHz, DMSO-d$_6$) δ ppm 2.17-2.37 (m, 4H), 2.64-2.81 (m, 2H), 3.37 (s, 3H), 3.77 (d, 1H, J=4.04 Hz), 4.25-4.34 (m, 1H), 7.25 (d, 2H, J=8.08 Hz), 7.38-7.42 (m, 1H), 7.47 (t, 1H, J=7.83 Hz), 7.56-7.64 (m, 3H), 7.68 (t, 1H, J=1.77 Hz), 8.05 (d, 1H, J=8.84 Hz), 12.05 (bs, 1H), 12.89 (bs, 1H).

Example 11-44: 1H NMR (400 MHz, DMSO-d$_6$) δ ppm 2.20-2.39 (m, 4H), 2.65-2.87 (m, 2H), 4.37-4.56 (m, 1H), 4.91 (d, 0.5H, J=2.78 Hz), 5.04 (d, 0.5H, J=3.03 Hz), 7.29 (d, 2H, J=8.34 Hz), 7.38-7.43 (m, 1H), 7.47 (t, 1H, J=7.83 Hz), 7.58-7.65 (m, 3H), 7.69 (t, 1H, J=1.77 Hz), 8.27 (d, 1H, J=8.59 Hz), 12.05 (bs, 1H), 13.57 (bs, 1H).

Example 11-45: 1H NMR (400 MHz, DMSO-d$_6$) δ ppm 1.10 (d, J=7.1 Hz, 3 H), 2.17-2.37 (m, 4 H), 2.57-2.78 (m, 3 H), 4.19-4.31 (m, J=9.2, 9.2, 4.5, 4.3 Hz, 1 H), 7.30 (d, J=8.1 Hz, 2 H), 7.37-7.42 (m, 1 H), 7.47 (t, J=7.8 Hz, 1 H), 7.57-7.65 (m, 3 H), 7.70 (t, J=1.8 Hz, 1 H), 7.86 (d, J=8.8 Hz, 1 H), 12.21 (br. s., 2 H).

Example 11-46: 1H NMR (400 MHz, DMSO-d$_6$) δ ppm 2.45 (dd, J=6.6, 3.5 Hz, 1 H), 2.82 (d, J=7.1 Hz, 1 H), 3.88 (dd, J=20.2, 15.2 Hz, 1 H), 4.03 (s, 1 H), 4.29-4.41 (m, 1 H), 7.29 (d, J=8.3 Hz, 1 H), 7.37-7.43 (m, 1 H), 7.48 (t, J=8.0 Hz, 1 H), 7.62 (d, J=8.3 Hz, 2 H), 7.70 (t, J=1.8 Hz, 1 H), 7.89 (d, J=8.8 Hz, 1 H), 11.65-13.45 (m, 1 H).

Example 11-47/48

(R)-3-[(S)-2-(Carboxymethyl-amino)-propionylamino]-4-(3'-chloro-biphenyl-4-yl)-butyric acid and (R)-3-[(R)-2-(Carboxymethyl-amino)-propionylamino]-4-(3'-chloro-biphenyl-4-yl)-butyric acid

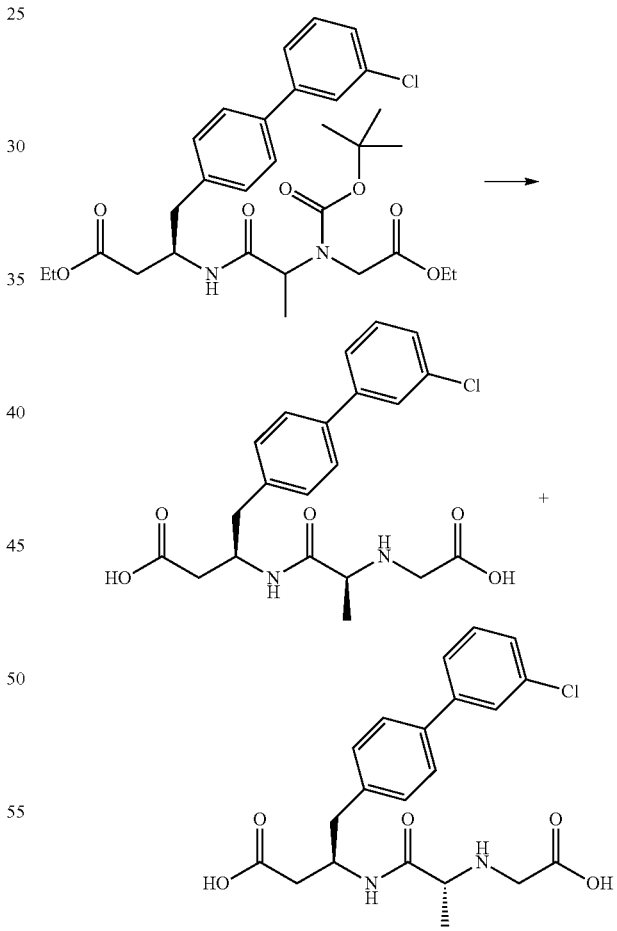

To a solution of (R)-3-[2-(tert-butoxycarbonyl-ethoxycarbonylmethyl-amino)-propionylamino]-4-(3'-chloro-biphenyl-4-yl)-butyric acid ethyl ester (290 mg, 0.504 mmol) in THF (3 ml) and MeOH (0.5 ml) at room temperature is added 2M NaOH (1.009 ml, 2.017 mmol). The reaction is stirred at room temperature over night. The mixture is concentrated to dryness and the crude i taken up in DCM (3.00 ml), to which is added TFA (3.89 ml, 50.4 mmol) and the mixture is stirred at room temperature for 2 hr. The reaction is concentrated for HPLC purification. Reverse phase HPLC [25 to 50% ACN—H₂O (0.1% TFA) over 10 min by Sunfire C18 column] give (R)-3-[(S)-2-(Carboxymethyl-amino)-propionylamino]-4-(3'-chloro-biphenyl-4-yl)-butyric acid and (R)-3-[(R)-2-(Carboxymethyl-amino)-propionylamino]-4-(3'-chloro-biphenyl-4-yl)-butyric acid.

(R)-3-[(S)-2-(Carboxymethyl-amino)-propionylamino]-4-(3'-chloro-biphenyl-4-yl)-butyric acid: 1H NMR (400 MHz, DMSO-d₆) δ ppm 1.28 (d, J=7.1 Hz, 3 H), 2.40 (dd, J=15.7, 8.3 Hz, 1 H), 2.51-2.56 (m, 1 H), 2.76 (dd, J=13.4, 8.1 Hz, 1 H), 2.87 (dd, J=13.4, 5.3 Hz, 1 H), 3.43-3.52 (m, 3 H), 3.67 (q, J=6.7 Hz, 1 H), 4.25-4.36 (m, 1 H), 7.30 (d, J=8.3 Hz, 2 H), 7.38-7.43 (m, 1 H), 7.48 (t, J=7.8 Hz, 1 H), 7.59-7.65 (m, 3 H), 7.70 (t, J=1.8 Hz, 1 H), 8.41 (d, J=8.3 Hz, 1 H). HRMS: Calcd for C₂₁H₂₃ClN₂O₅: 418.1295; found: m/z 418.1307. LCMS (condition A): 419 (M+1); retention time=0.93 min; (R)-3-[(R)-2-(Carboxymethyl-amino)-propionylamino]-4-(3'-chloro-biphenyl-4-yl)-butyric acid: 1H NMR (400 MHz, DMSO-d₆) δ ppm 1.17 (d, J=6.8 Hz, 3 H), 2.41-2.49 (m, 0 H), 2.51-2.57 (m, 1 H), 2.73 (dd, J=13.4, 9.1 Hz, 1 H), 2.91 (dd, J=13.4, 4.8 Hz, 1 H), 3.55-3.67 (m, 2 H), 3.67-3.74 (m, 1 H), 4.26-4.40 (m, 1 H), 7.29 (d, J=8.3 Hz, 2 H), 7.39-7.44 (m, 0 H), 7.48 (t, J=7.8 Hz, 0 H), 7.59-7.65 (m, 3 H), 7.69 (t, J=1.8 Hz, 1 H), 8.43 (d, J=8.6 Hz, 1 H). HRMS: Calcd for C₂₁H₂₃ClN₂O₅: 418.1295; found: m/z 418.1305. LCMS (condition A): 419 (M+1); retention time=0.99 min.

Following compounds are prepared using similar procedure as described in example 11-47/48:

| Example # | Product | Starting material | HPLC-RT (condition) | MS (M + 1) |
|---|---|---|---|---|
| Example 11-49 | (R)-3-[2-(Carboxymethyl-amino)-acetylamino]-4-(3'-chloro-biphenyl-4-yl)-butyric acid | | 1.12 min. (A) | 405.2 |

Example 11-49: 1H NMR (400 MHz, DMSO-d₆) δ ppm 2.39-2.50 (m, 2 H) 2.77-2.89 (m, 2 H) 3.61-3.71 (m, 2 H) 3.81 (s, 2 H) 4.26-4.35 (m, 1 H) 7.31 (d, J=8.3 HZ, 2 H) 7.40-7.43 (m, 1 H) 7.47-7.50 (m, 1 H) 7.62-7.65 (m, 3H) 7.69-7.70 (m, 1 H) 8.49 (d, J=7.3 Hz, 1 H).

Example 12-1

Synthesis of (R)-4-(1-carboxy-3-(3'-chlorobiphenyl-4-yl)propan-2-ylamino)-4-oxobutanoic acid

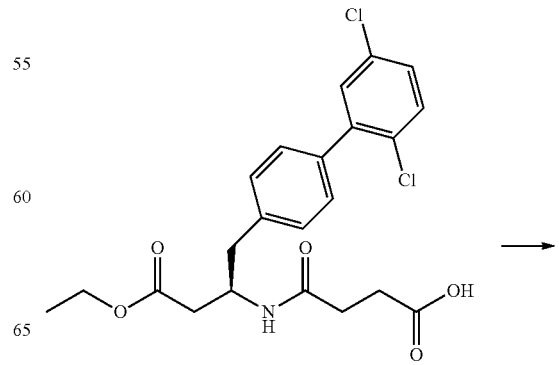

-continued

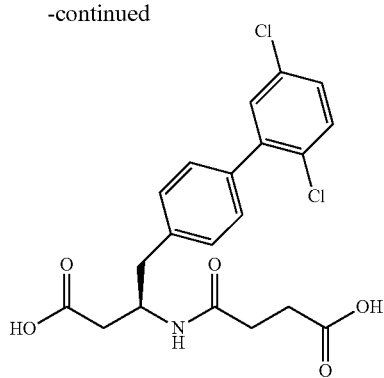

To a solution of (R)-4-(1-(2',5'-dichlorobiphenyl-4-yl)-4-ethoxy-4-oxobutan-2-ylamino)-4-oxobutanoic acid (106 mg, 0.234 mmol) in THF (2 ml) and MeOH (0.1 ml), 1M aqueous NaOH solution (1.406 mL, 1.406 mmol) is added at room temperature. After stirring for 4.5 hours, the reaction is quenched with 0.1 M aqueous HCl (3 ml), and the products are extracted with EtOAc. The combined organic layer is washed with brine, dried over $Na_2SO_4$, filtered, and concentrated under reduced pressure. The crude is triturated in DCM. The precipitates are collected on a funnel, washed with DCM, and dried under reduced pressure to give (R)-4-(1-carboxy-3-(3'-chlorobiphenyl-4-yl)propan-2-ylamino)-4-oxobutanoic acid (64.0 mg) as white solid; HPLC retention time=1.24 minutes (condition A); MS (m+1)=424.07; 1H NMR (400 MHz, $CD_3OD$) δ ppm 2.38-2.42 (m, 2 H) 2.45-2.57 (m, 4 H) 2.87 (A of ABX, $J_{ab}$=13.6 Hz, $J_{ax}$=7.6 Hz, 1 H) 2.95 (B of ABX, $J_{ab}$=13.6 Hz, $J_{bx}$=6.1 Hz, 1 H) 4.44-4.51 (m, 1 H) 7.30-7.37 (m, 6 H) 7.47 (d, J=8.4 Hz, 1 H).

Example 13-1

Synthesis of (R)-4-(1-(biphenyl-4-yl)-3-carboxypropan-2-ylcarbamoyl)picolinic acid Example 13-2

Synthesis of (R)-2-(1-(biphenyl-4-yl)-3-carboxypropan-2-ylcarbamoyl)isonicotinic acid

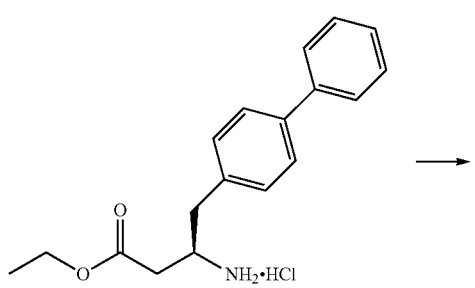

-continued

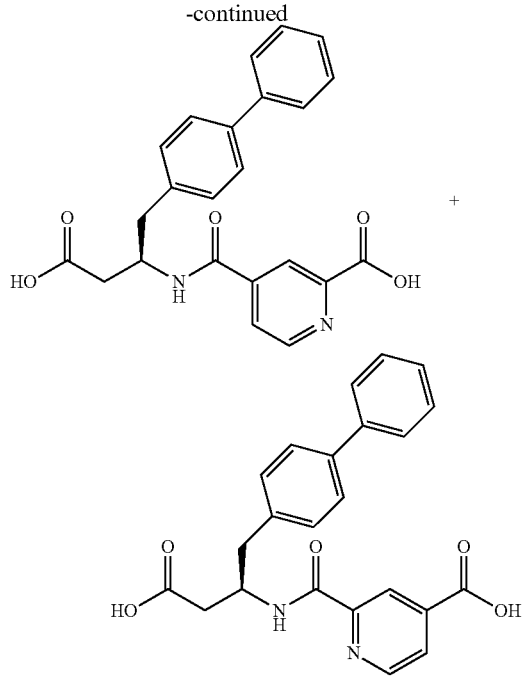

To a solution of (R)-ethyl 3-amino-4-(biphenyl-4-yl)butanoate hydrochloride (200 mg, 0.625 mmol), 2,4-pyridinedicarboxylic acid hydrate (151 mg, 0.813 mmol), EDCI (132 mg, 0.688 mmol) and 1-hydroxy-7-azabenzotriazole (94 mg, 0.688 mmol) in DMF (6 ml), DIPEA (0.164 ml, 0.938 mmol) is added. The reaction mixture is allowed to stir for 3 hours. Then, the reaction mixture is diluted with $H_2O$. The precipitated solid is collected on a funnel and dried under reduced pressure. To a solution of the crude in THF (8 ml) and MeOH (1 ml), 1 M aqueous NaOH (2.5 ml, 2.5 mmol) is added. After stirring for 1 hour, the reaction is quenched with 5% citric acid and brine, and the products are extracted with EtOAc. The organic layer is washed with brine, dried over $Na_2SO_4$, filtered, and concentrated. The resulting residue is purified by preparative HPLC using a gradient of 20% MeCN/water (0.1% TFA) to 100% MeCN to give (R)-4-(1-(biphenyl-4-yl)-3-carboxypropan-2-ylcarbamoyl)picolinic acid and (R)-2-(1-(biphenyl-4-yl)-3-carboxypropan-2-ylcarbamoyl)isonicotinic acid as white solids, respectively (Example 13-1: 33 mg; Example 13-2: 36 mg). Example 13-1, HPLC retention time=1.50 minutes (condition D); MS (m+1)=405.1; 1H NMR (400 MHz, DMSO-$d_6$) δ ppm 2.53-2.62 (m, 2 H) 2.88-2.97 (m, 2 H) 4.50-4.59 (m, 1 H) 7.31-7.35 (m, 3 H) 7.42-7.45 (m, 2 H) 7.57-7.64 (m, 4 H) 7.89 (dd, J=5, 1.6 Hz, 1 H) 8.83 (dd, J=5, 0.8 Hz, 1 H) 8.37 (dd, J=1.6, 0.8 Hz) 8.89 (d, J=8.3 Hz, 1 H). Example 13-2, HPLC retention time=1.24 minutes (condition A); MS (m+1)=405.1; 1H NMR (400 MHz, DMSO-$d_6$) δ ppm 2.52-2.68 (m, 2 H) 2.91 (A of ABX, $J_{ab}$=13.6 Hz, $J_{ax}$=6.1 Hz, 1 H) 3.01 (B of ABX, $J_{ab}$=13.6 Hz, $J_{bx}$=8.1 Hz, 1 H) 4.56-4.65 (m, 1 H) 7.29-7.34 (m, 3 H) 7.41-7.45 (m, 2 H) 7.55-7.64 (m, 4 H) 7.99 (dd, J=5, 1.6 Hz, 1 H) 8.34 (dd, J=1.6, 0.8 Hz, 1 H) 8.84 (dd, J=5, 0.8 Hz, 1 H) 8.90 (d, J=9.1 Hz, 1 H) 12.26 (br s, 1 H) 13.87 (br s, 1 H).

Following compounds are prepared using similar procedure as described in example 13-1 and 13-2:

| Example # | Product | Condition | HPLC-RT (condition) | MS (M + 1) |
|---|---|---|---|---|
| Example 13-3 | (R)-3-(2-aminopyrimidine-4-carboxamido)-4-(biphenyl-4-yl)butanoic acid | PyBOP, DIPEA, DMF, RT; aq. NaOH, THF, MeOH, RT | 1.37 min. (A) | 377.0 |

Example 13-3: 1H NMR (400 MHz, DMSO-$d_6$) δ ppm 2.55 (d, J=6.6 Hz, 2 H) 2.91 (A of ABX, $J_{ab}$=13.6 Hz, $J_{ax}$=6.3 Hz, 1 H) 2.96 (B of ABX, $J_{ab}$=13.6 Hz, $J_{bx}$=7.6 Hz, 1 H) 4.46-4.55 (m, 1 H) 6.86 (br s, 2 H) 7.02 (d, J=4.8 Hz, 1 H) 7.28-7.36 (m, 3 H) 7.42-7.46 (m, 2 H) 7.58-7.65 (m, 4 H) 8.39 (d, J=9.1 Hz, 1 H) 8.45 (d, J=4.8 Hz, 1 H).

Example 14-1

Synthesis of (R)-3-(3-Carboxymethyl-ureido)-4-(3'-chloro-biphenyl-4-yl)-butyric acid

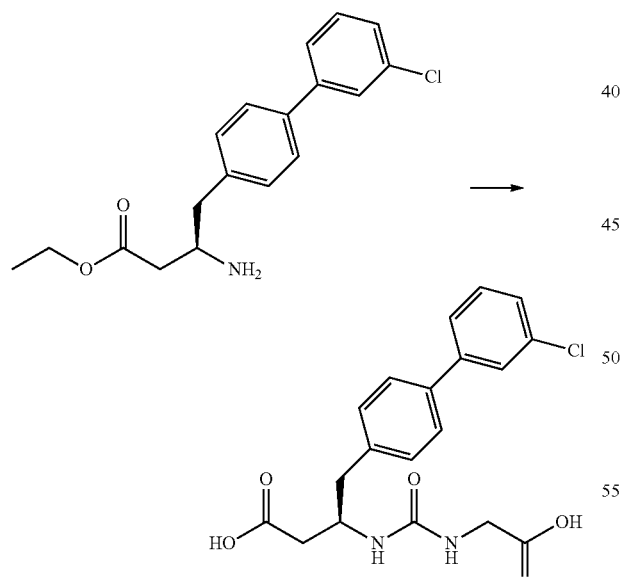

To a solution of Intermediate 16-1 (90 mg, 0.254 mmol) and ethyl isocyanatoacetate (39.4 mg, 0.305 mmol) in DMF (3 mL) is added pyridine (2.93 g, 37.1 mmol) and the mixture is stirred at room temperature for 2 hours. The solvent is removed under reduced pressure and the residue is used directly in the next step.

Next, the above residue is dissolved in EtOH (1 mL) and 1N NaOH (3 mL, 3 mmol) is added. The mixture is stirred at room temperature for 2 hours then is acidified with 1N HCl. The mixture is extracted with EtOAc and the organic phase is washed with water, brine then dried over sodium sulfate. The solvent is removed under reduced pressure and the residue purified by preparative HPLC using a gradient of 10% MeCN/water to 100% MeCN (+0.1% TFA). Lyophilization of the proper fractions gives the title compound; HPLC Retention time 0.98 minutes (condition C); MS 391.3 (M+1); 1H NMR (400 MHz, DMSO-$d_6$): δ ppm 2.34 (d, J=7.33 Hz, 2H), 2.79 (d, J=6.57 Hz, 2H), 3.67 (d, J=5.56 Hz, 2H), 4.04-4.12 (m, 1H), 6.15 (t, J=5.81 Hz, 1H), 6.23 (d, J=8.34 Hz, 1H), 7.28-7.30 (m, 2H), 7.39-7.42 (m, 1H), 7.48 (t, J=7.83 Hz, 1H), 7.62-7.65 (m, 3H), 7.71 (t, J=1.77 Hz, 1H), 12.32 (s, br, 2H).

Example 15-1

(R)-4-(3'-Chloro-biphenyl-4-yl)-3-[(2H-tetrazole-5-carbonyl)-amino]-butyric acid

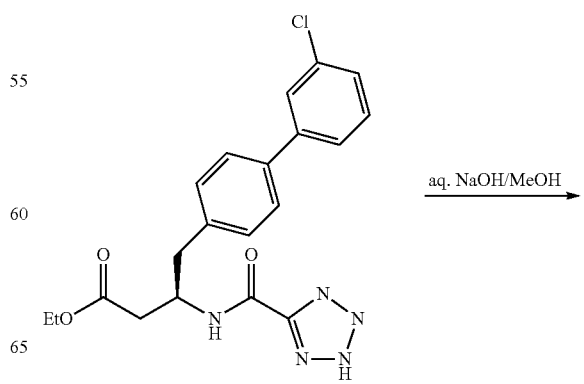

-continued

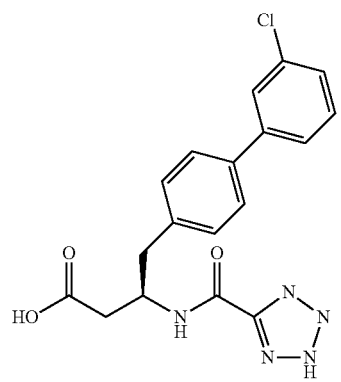

To a suspension of the starting material in MeOH (5 ml) at room temperature is added NaOH (2 mL, 6.00 mmol) and the mixture is stirred until the reaction was completed. The reaction mixture is acidified to pH<4 and purified by HPLC (15% to 60% acetonitrile-H$_2$O with 0.1% TFA) to give (R)-4-(3'-chloro-biphenyl-4-yl)-3-[(2H-tetrazole-5-carbonyl)-amino]-butyric acid (80 mg).

HPLC retention time=0.95 minutes (condition B); MS (m+1)=386.1; 1H NMR (400 MHz, DMSO-d$_6$) d ppm 2.52-2.61 (m, 1 H), 2.61-2.72 (m, 1 H), 2.84-2.99 (m, 2 H), 4.51-4.64 (m, 1 H), 7.31 (d, J=8.1 Hz, 2 H), 7.36-7.41 (m, 1 H), 7.46 (t, J=7.8 Hz, 1 H), 7.61 (d, J=8.3 Hz, 3 H), 7.68 (t, J=1.9 Hz, 1 H), 9.31 (d, J=8.8 Hz, 1 H), 12.32 (br. s., 1 H).

Following compounds are prepared using similar procedure as described in example 15-1:

| Example # | Product | Starting material and hydrolysis condition | HPLC-RT (condition) | MS (M + 1) |
|---|---|---|---|---|
| Example 15-2 | (R)-4-(3'-Fluoro-biphenyl-4-yl)-3-[(2H-tetrazole-5-carbonyl)-amino]-butyric acid | 1 atm. H2, Pd/C, EtOH, RT Followed by aq. NaOH and EtOH | 1.26 min. (A) | 370.2 |
| Example 15-3 | (R)-4-(2'-Methoxy-biphenyl-4-yl)-3-[(2H-tetrazole-5-carbonyl)-amino]-butyric acid | 1 atm. H2, Pd/C, EtOH, RT Followed by aq. NaOH and EtOH | 1.24 min. (A) | 382.2 |

Example 15-2: 1H NMR (400 MHz, DMSO-$d_6$) d ppm 2.52-2.72 (m, 2 H), 2.86-3.00 (m, 2 H), 4.52-4.65 (m, 1 H), 7.11-7.20 (m, 1 H), 7.31 (d, J=8.1 Hz, 2 H), 7.43-7.51 (m, 3 H), 7.61 (d, J=8.3 Hz, 2 H), 9.28 (d, J=8.8 Hz, 1 H), 12.29 (br. s., 1 H).

Example 15-3: 1H NMR (400 MHz, DMSO-$d_6$) δ ppm 2.52-2.60 (m, J=15.9, 5.8 Hz, 1 H), 2.67 (dd, J=15.9, 7.8 Hz, 1 H), 2.87 (dd, J=13.6, 5.8 Hz, 1 H), 2.95 (dd, J=13.6, 8.3 Hz, 1 H), 3.73 (s, 3 H), 4.52-4.64 (m, 1 H), 7.00 (td, J=7.4, 1.1 Hz, 1 H), 7.08 (d, J=9.1 Hz, 1 H), 7.22-7.27 (m, 3 H), 7.28-7.34 (m, 1 H), 7.37 (d, J=8.3 Hz, 2 H), 9.30 (d, J=8.8 Hz, 1 H), 12.28 (br. s., 1 H).

Example 16-1

N-[(R)-1-(3'-chloro-biphenyl-4-ylmethyl)-3-methanesulfonylamino-3-oxo-propyl]-succinamic acid

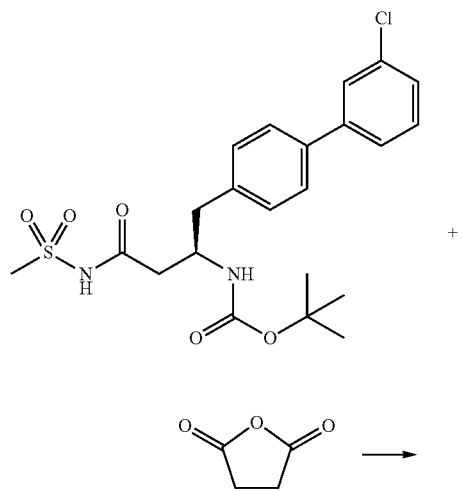

+

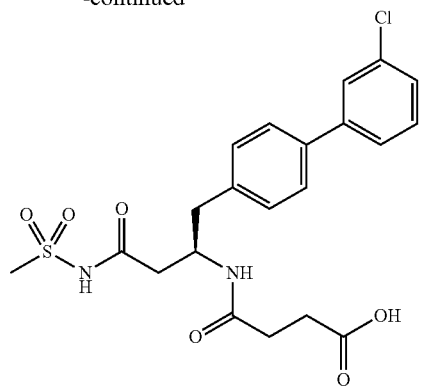

[(R)-1-(3'-Chloro-biphenyl-4-ylmethyl)-3-methanesulfonylamino-3-oxo-propyl]-carbamic acid tert-butyl ester (150 mg, 0.321 mmol) is treated with 4M HCl in dioxane. After being stirred at room temperature for 1 h, the reaction mixture is concentrated in vacuo. To this residue in DCM (2 mL) are added succinic anhydride (48.2 mg, 0.482 mmol) and triethylamine (0.112 mL, 0.803 mmol). After being stirred at room temperature for 2 h, the reaction mixture is diluted with EtOAc and washed with 1M HCl and brine. The organic layer is dried over $Na_2SO_4$ and cocentrated. The residue is purified by reverse phase HPLC (SunFire C18, 0.1% TFA in $H_2O$/$CH_3CN$) to give N—[(R)-1-(3'-chloro-biphenyl-4-ylmethyl)-3-methanesulfonylamino-3-oxo-propyl]-succinamic acid (63 mg). HPLC retentions time=1.32 minutes (condition A); MS (m+1)=467; 1H NMR (400 Mz, DMSO-$d_6$) δ ppm 2.22-2.29 (m, 2 H), 2.32-2.54 (m, 4 H), 2.77 (d, 2 H, J=6.82 Hz), 3.17 (s, 3 H), 4.31 (dt, 1 H, J=7.33, 13.9 Hz), 7.28 (d, 2 H, J=8.08 Hz), 7.38-7.43 (m, 1 H), 7.48 (t, 1 H, J=7.83 Hz), 7.62 (d, 3 H, J=8.34 Hz), 7.70 (t, 1 H, J=2.02 Hz), 7.89 (d, 1 H, J=8.34 Hz), 11.70 (s, 1 H), 12.04 (s, 1 H).

Following compounds are prepared using similar procedure as described in example 16-1:

| Example # | Product | Starting material | HPLC-RT (condition) | MS (M + 1) |
|---|---|---|---|---|
| Example 16-2 | N-[(R)-1-(3'-Chloro-biphenyl-4-ylmethyl)-3-oxo-3-(propane-1-sulfonylamino)-propyl]-succinamic acid | | 1.26 min. (condition A) | 495 |

| Example # | Product | Starting material | HPLC-RT (condition) | MS (M + 1) |
|---|---|---|---|---|
| Example 16-3 | N-[(R)-1-(3'-Chloro-biphenyl-4-ylmethyl)-3-oxo-3-phenylmethanesulfonylamino-propyl]-succinamic acid | | 1.34 min. (condition A) | 543 |
| Example 16-4 | N-[(R)-2-Carbamoyl-1-(3'-chloro-biphenyl-4-ylmethyl)-ethyl]-succinamic acid | | 1.33 min. (condition A) | 389 |

Example 16-2: 1H NMR (400 MHz, DMSO-d₆) δ ppm 0.96 (t, 3 H, J=7.33 Hz), 1.66 (dd, 2 H, J=7.33, 15.2 Hz), 2.25 (t, 2 H, J=7.07 Hz), 2.31-2.45 (m, 4 H), 2.76 (d, 2 H, J=6.82 Hz), 3.25-3.32 (m, 2 H), 4.30 (dd, 1 H, J=7.83, 14.7 Hz), 7.28 (d, 2 H, J=8.34 Hz), 7.38-7.43 (m, 1 H), 7.48 (t, 1 H, J=7.83 Hz), 7.63 (d, 3 H, J=8.08 Hz), 7.70 (t, 1 H, J=1.77 Hz), 7.89 (d, 1 H, J=8.34 Hz), 11.61 (s, 1 H), 12.04 (s, 1 H).

Example 16-3: 1H NMR (400 MHz, DMSO-d₆) δ ppm 2.24-2.31 (m, 2 H), 2.34-2.40 (m, 2 H), 2.44 (d, 2 H, J=6.82 Hz), 2.78 (d, 2 H, J=6.82 Hz), 4.26-4.36 (m, 1 H), 4.67 (s, 2 H), 7.25-7.33 (m, 4 H), 7.34-7.43 (m, 4 H), 7.48 (t, 1 H, J=7.58 Hz), 7.63 (d, 3 H, J=8.34 Hz), 7.70 (t, 1 H, J=1.77 Hz), 7.92 (d, 1 H, J=8.34 Hz), 11.60 (s, 1 H), 12.05 (s, 1 H).

Example 16-4: 1H NMR (400 MHz, DMSO-d₆) δ ppm 2.19-2.29 (m, 4H), 2.36 (dd, 2H, J=6.57, 6.57 Hz), 2.72 (dd, 1H, J=7.83, 13.6 Hz), 2.81 (dd, 1H, J=5.31, 13.6 Hz), 4.17-4.27 (m, 1H), 6.83 (s, 1H), 7.28 (d, 3H, J=8.34 Hz), 7.38-7.43 (m, 1H), 7.47 (t, 1H, J=7.83 Hz), 7.58-7.65 (m, 3H), 7.69 (t, 1H, J=1.77 Hz), 7.78 (d, 1H, J=8.34 Hz), 12.05 (s, 1H).

Example 16-5

Synthesis of N-[(R)-1-(3'-chloro-biphenyl-4-ylmethyl)-3-methanesulfonylamino-3-oxo-propyl]-succinamic acid butyl ester

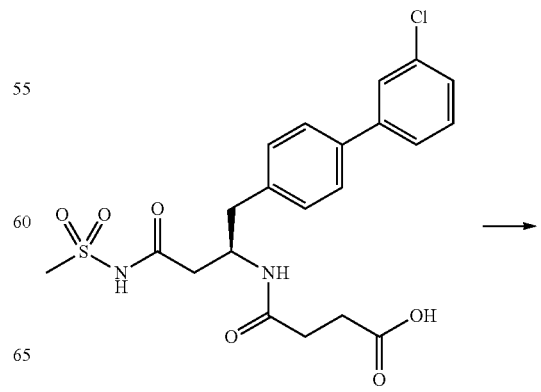

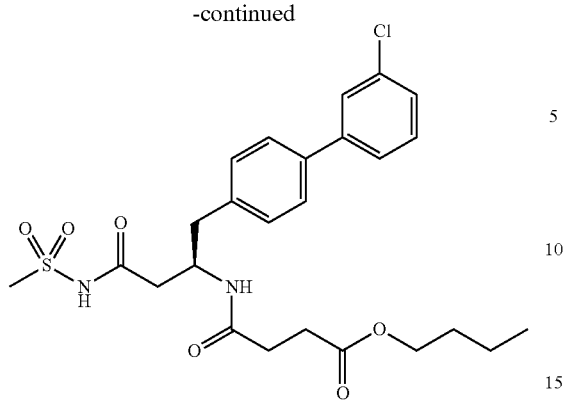

To a solution of N-[(R)-1-(3'-chloro-biphenyl-4-ylmethyl)-3-methanesulfonylamino-3-oxo-propyl]-succinamic acid (50 mg, 0.107 mmol) in n-butanol (2 mL) is added thionyl chloride (9.38 µL, 0.128 mmol). The reaction mixture is warmed to 50° C. and stirred for 1 h. After cooling to room temperature, the reaction mixture is concentrated and purified by reverse phase HPLC (SunFire C18, 0.1% TFA in H$_2$O/CH$_3$CN) to give N-[(R)-1-(3'-chloro-biphenyl-4-ylmethyl)-3-methanesulfonylamino-3-oxo-propyl]-succinamic acid butyl ester (32 mg). HPLC retentions time=1.56 minutes (condition A); MS (m+1)=523; 1H NMR (400 Mz, DMSO-d$_6$) δ ppm 0.86 (t, 3H, J=7.33 Hz), 1.22-1.34 (m, 2H), 1.45-1.55 (m, 2H), 2.23-2.33 (m, 2H), 2.35-2.44 (m, 3H), 2.45-2.55 (m, 3H), 2.71-2.83 (m, 1H), 3.18 (s, 3H), 3.96 (t, 2H, J=6.57 Hz), 4.27-4.38 (m, 1H), 7.28 (d, 2H, J=8.08 Hz), 7.37-7.43 (m, 1H), 7.48 (t, 1H J=7.83 Hz), 7.62 (d, 3H, J=8.34 Hz), 7.70 (s, 1H), 7.91 (d, 1H, J=8.34 Hz), 11.71 (s, 1H).

Example 17

(R)-3-(2-acetyloxazole-5-carboxamido)-4-(3'-chloro-biphenyl-4-yl)butanoic acid

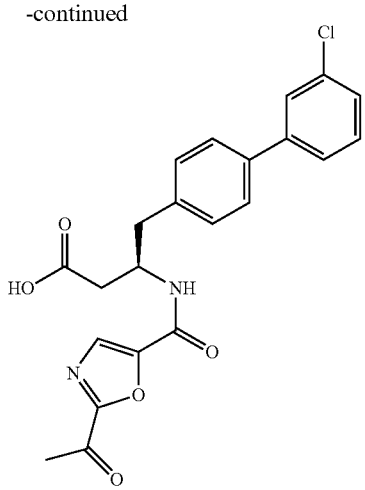

To a solution of (R)-4-(3'-chlorobiphenyl-4-yl)-3-(2-(prop-1-en-2-yl)oxazole-5-carboxamido)butanoic acid (60 mg, 0.14 mmol) in DCM (2 mL) and MeOH (2 mL) at −78° C. is bubbled ozone for 30 seconds. After 30 seconds ozone is removed and oxygen is bubbled for 10 minutes. After bubbling oxygen for 10 minutes the −78° C. bath is removed and the reaction is quenched with polymer supported triphenylphosphine and the reaction is stirred at room temperature for 2 hours. After 2 hours the reaction is filtered to remove triphenylphosphineoxide on supported polymer and the filtrate is collected and concentrated under reduced pressure. The obtained residue is purified by RP-HPLC (SunFire C18, H$_2$O (0.1% TFA)/CH$_3$CN), and then lyophilized to give (R)-3-(2-acetyloxazole-5-carboxamido)-4-(3'-chlorobiphenyl-4-yl)butanoic acid (13 mg). HPLC retention time=1.67 minutes (condition D); MS (m+1)=427.0; 1H NMR (400 MHz, DMSO-d$_6$) δ ppm 2.53-2.59 (m, 2 H) 2.60 (s, 3 H) 2.87 (dd, J=10.9, 3.3 Hz, 1 H) 2.94 (dd, J=10.9, 5.1 Hz, 1 H) 4.46-4.60 (m, 1 H) 7.31 (d, J=8.1 Hz, 2 H) 7.36-7.43 (m, 1 H) 7.47 (t, J=7.8 Hz, 1 H) 7.62 (d, J=8.3 Hz, 3 H) 7.69 (t, J=1.9 Hz, 1 H) 7.94 (s, 1 H) 8.86 (d, J=8.6 Hz, 1 H) 12.31 (br. s., 1 H).

Starting materials or intermediates are prepared in following manner:

Intermediate 1

(R)-ethyl 4-(4-bromophenyl)-3-(4-methoxy-4-oxobutanamido)butanoate

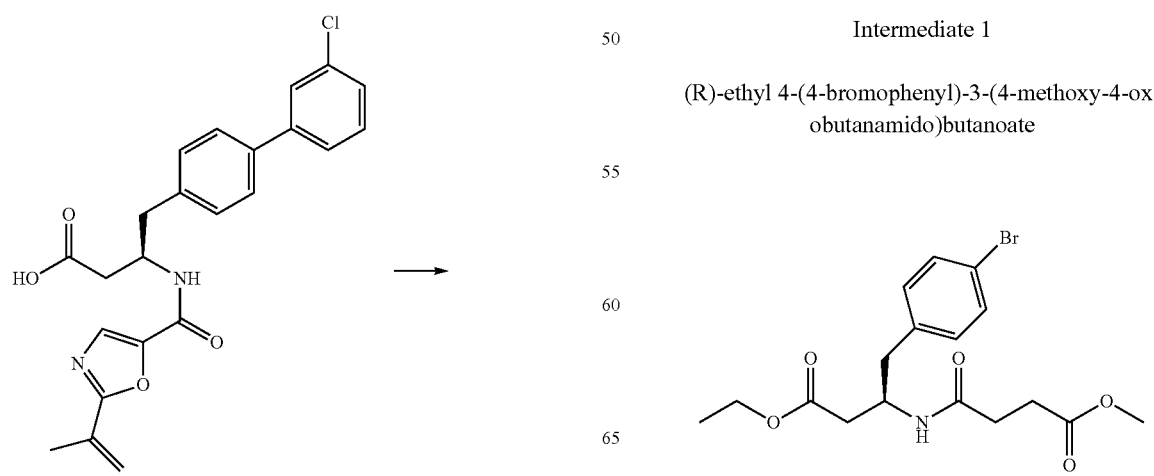

To (R)-ethyl-4-(4-bromophenyl-4-yl)-3-(tert-butoxycarbonylamino)butanoate (2.02 g, 5.23 mmol) is added a solution of 4M HCl in 1,4-dioxane (13.1 mL, 52.3 mmol) at room temperature. After stirring for 1 hour, the reaction mixture is concentrated under reduced pressure to give (R)-3-amino-4-bromophenyl-4-yl-butyric acid ethyl ester hydrochloride. To a solution of (R)-3-amino-4-bromophenyl-4-yl-butyric acid ethyl ester hydrochloride is added succinic anhydride (0.707 g, 7.06 mmol) and DIPEA (2.06 mL, 11.8 mmol) in dichloromethane (20 mL) and allowed to stir for 4 hours. The reaction is quenched with 0.1 M aqueous HCl. The products are extracted with ethyl acetate and washed with brine. The organic layer is dried over $Na_2SO_4$, filtered, and concentrated under reduced pressure to give (R)-4-(1-(4-bromophenyl)-4-ethoxy-4-oxobutan-2-ylamino)-4-oxobutanoic acid (2.26 g). To a solution of the obtained residue (2.26 g) in toluene (25 mL) and MeOH (25 mL), $TMSCHN_2$ in hexanes (5.85 ml, 11.70 mmol) is added portionwise at room temperature under nitrogen. The reaction mixture is allowed to stir for 1.5 hour, then quenched with AcOH (0.5 mL; 8.78 mmol), and the solution is stirred for 10 minutes. The solution is concentrated, and the obtained residue is purified by flash column chromatography on 40 g silica gel (eluent: heptane/EtOAc=100:0 to 0:100) to give (R)-ethyl-4-(4-bromophenyl)-3-(4-methoxy-4-oxobutanamido)butanoate (1.92 g). HPLC retention time=1.04 minutes (condition B); MS (ES+)=400 (m+1), 402.0 (m+3; 100%); 1H NMR (400 MHz, CHLOROFORM-d) δ ppm 1.28 (t, J=7.2 Hz, 3 H) 2.40-2.53 (m, 4 H) 2.60-2.64 (m, 2 H) 2.79 (A of ABX, $J_{ab}$=13.7 Hz, $J_{ax}$=7.85 Hz, 1 H) 2.90 (B of ABX, $J_{ab}$=13.7 Hz, $J_{bx}$=6.65 Hz, 1 H) 3.68 (s, 3 H) 4.10-4.22 (m, 2 H) 4.39-4.47 (m, 1 H) 6.29 (br d, J=8.6 Hz, 1 H) 7.06 (d, J=8.4 Hz, 2 H) 7.40-7.42 (m, 2 H).

Intermediate 2

(R)-ethyl 4-(biphenyl-4-yl)-3-(tert-butoxycarbonylamino)butanoate

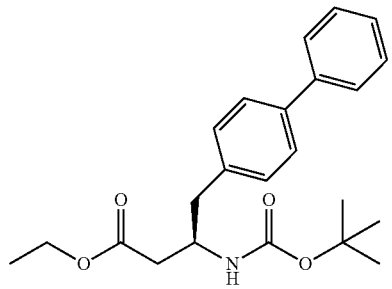 [SMILES: CCOC(=O)C[C@@H](Cc1ccc(-c2ccccc2)cc1)NC(=O)OC(C)(C)C]

A mixture of (R)-ethyl 4-(4-bromophenyl)-3-(tert-butoxycarbonylamino)butanoate (1.5 g, 3.88 mmol), phenylboronic acid (0.710 g, 5.82 mmol), $Pd(Ph_3P)_4$ (0.449 g, 0.388 mmol) and aqueous $Na_2CO_3$ (3.88 mL, 7.77 mmol) in toluene (25 mL) is allowed to stir at 95° C. under nitrogen for 14 hours. The reaction mixture is cooled to room temperature and quenched with brine. The mixture is extracted twice with ethylacetate, and the combined organic layer is washed with brine, dried over $Na_2SO_4$, filtered, and concentrated under reduced pressure. The obtained residue is purified by silica gel flash column chromatography (heptane/EtOAc=100:0 to 50:50) to give (R)-ethyl-4-(biphenyl-4-yl)-3-(tert-butoxycarbonylamino)butanoate (1.30 g); HPLC retention time=1.61 minutes (condition B); MS (ES+)=328.0 (m-tBu+2); 284.1 (m-Boc+2; 100%); 1H NMR (400 MHz, CHLOROFORM-d) δ ppm 1.28 (t, J=7.1 Hz, 3 H) 2.48 (A of ABX, $J_{ab}$=16.1 Hz, $J_{ax}$=5.9 Hz, 1 H) 2.53 (B of ABX, $J_{ab}$=16.0 Hz, $J_{bx}$=5.3 Hz, 1 H) 2.83-3.00 (m, 2 H) 4.14-4.19 (m, 3 H) 5.06 (br s) 7.26-7.27 (m, 2 H) 7.31-7.35 (m, 2 H) 7.43 (t, J=7.6 Hz, 2H) 7.52-7.58 (m, 4 H).

Following intermediates are prepared using similar procedure as described for intermediate 2:

| Intermediate # | Product | Condition | HPLC-RT (condition) | MS (ES+; 100%) |
|---|---|---|---|---|
| Intermediate 2-2 | (R)-ethyl 3-(tert-butoxycarbonylamino)-4-(3'-fluorobiphenyl-4-yl)butanoate | Pd(PPh3)4, 3-fluorobenzeneboronic acid, aq. 2M Na2CO3, toluene, 95° C. | 1.61 min. (B) | 302.1 (m-BOC + 2) |

| Intermediate # | Product | Condition | HPLC-RT (condition) | MS (ES+; 100%) |
|---|---|---|---|---|
| Intermediate 2-3 | 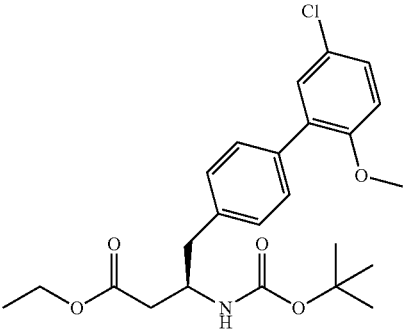 (R)-ethyl 3-(tert-butoxycarbonylamino)-4-(5'-chloro-2'-methoxybiphenyl-4-yl)butanoate | PdCl$_2$(dppf)•CH$_2$Cl$_2$ complex, 5-chloro-2-methoxyphenylboronic acid, aq. 2M Na2CO3, toluene, 95° C. | 1.58 min. (B) | 348.1 (m-BOC + 2) |
| Intermediate 2-4 | 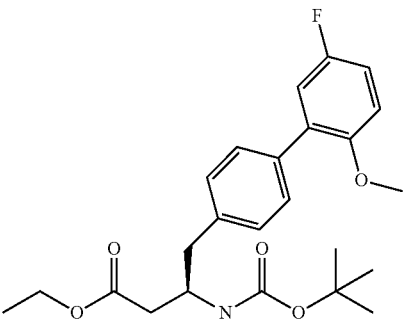 (R)-ethyl 3-(tert-butoxycarbonylamino)-4-(5'-fluoro-2'-methoxybiphenyl-4-yl)butanoate | PdCl$_2$(dppf)•CH$_2$Cl$_2$ complex, 5-fluoro-2-methoxyphenylboronic acid, aq. 2M Na$_2$CO$_3$, toluene, 95° C. | 1.42 min. (B) | 332.2 (m-BOC + 2) |
| Intermediate 2-5 | 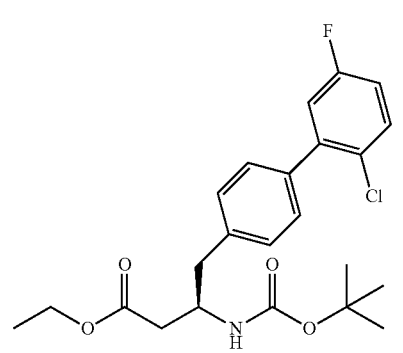 (R)-ethyl 3-(tert-butoxycarbonylamino)-4-(2'-chloro-5'-fluorobiphenyl-4-yl)butanoate | Pd(PPh$_3$)$_4$, 2-chloro-5-fluorophenylboronic acid, aq. 2M Na$_2$CO$_3$, toluene, 95° C. | 1.49 min. (B) | 336.1 (m-BOC + 2) |

-continued

| Intermediate # | Product | Condition | HPLC-RT (condition) | MS (ES+; 100%) |
|---|---|---|---|---|
| Intermediate 2-6 | 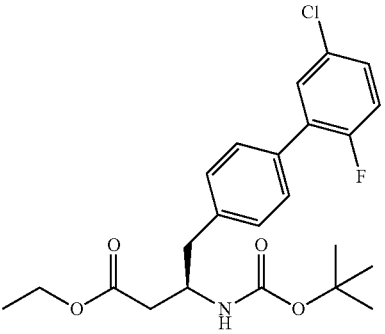<br>(R)-ethyl 3-(tert-butoxycarbonylamino)-4-(5'-chloro-2'-fluorobiphenyl-4-yl)butanoate | Pd(PPh$_3$)$_4$, 5-chloro-2-fluorophenylboronic acid, aq. 2M Na2CO3, DME, 95° C. | 1.47 min. (B) | 336.1 (m-BOC + 2) |

Intermediate 3

(R)-4-(1-(biphenyl-4-yl)-4-tert-butoxy-4-oxobutan-2-ylamino)-4-oxobutanoic acid

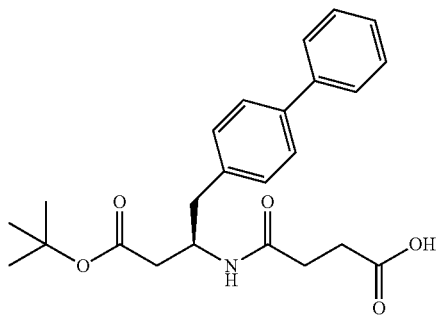 [SMILES: CC(C)(C)OC(=O)C[C@@H](Cc1ccc(-c2ccccc2)cc1)NC(=O)CCC(=O)O]

To (R)-tert-butyl 4-(biphenyl-4-yl)-3-(tert-butoxycarbonylamino)butanoate (26.4 mg, 0.064 mmol) is added 4M HCl in 1,4-dioxane (0.321 ml, 1.283 mmol) at room temperature. The reaction mixture is stirred for 45 minutes and concentrated under reduced pressure. To a solution of the obtained residue in dichloromethane (0.4 mL) is added succinic anhydride (7.70 mg, 0.077 mmol) and DIPEA (0.013 mL, 0.077 mmol). The reaction mixture is allowed to stir at room temperature for 14 hours and concentrated under reduced pressure. The obtained residue is purified by RP-HPLC (SunFire C-18, H$_2$O (0.1% TFA)/CH$_3$CN) to give (R)-4-(1-(biphenyl-4-yl)-4-tert-butoxy-4-oxobutan-2-ylamino)-4-oxobutanoic acid (9.5 mg). HPLC retention time=1.70 minutes (condition A); MS (ES+)=412.1 (m+1); 356.0 (m-tBu+2; 100%); 1H NMR (400 MHz, CHLOROFORM-d) δ ppm 1.48 (s, 9 H) 2.36-2.51 (m, 4 H) 2.64-2.67 (m, 2 H) 2.87 (A of ABX, J$_{ab}$=13.5 Hz, J$_{ax}$=5.7 Hz, 1 H), 2.97 (J$_{ab}$=13.5 Hz, J$_{bx}$=6.2 Hz, 1 H) 7.24-7.26 (m, 2 H) 7.31-7.35 (m, 1 H) 7.43 (t, J=7.75 Hz, 2 H) 7.53(d, J=8.0 Hz, 2 H) 7.57 (d, J=7.6 HZ, 2 H).

Following intermediates are prepared using similar procedure as described in intermediate 3:

| Intermediate # | Product | Starting material | HPLC-RT (condition) | MS (M + 1) |
|---|---|---|---|---|
| Intermediate 3-2 | 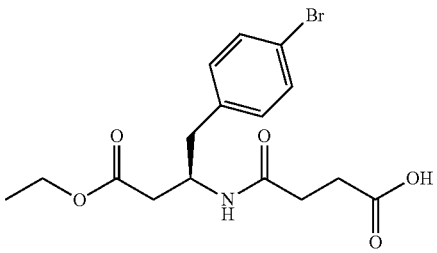<br>(R)-4-(4-Bromo-phenyl)-3-(3-carboxy-propionylamino)-butyric acid ethyl ester | 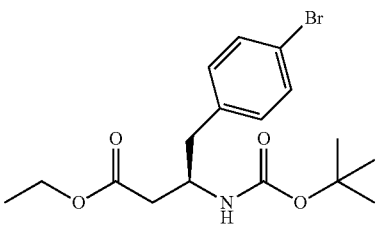 [SMILES: CCOC(=O)C[C@@H](Cc1ccc(Br)cc1)NC(=O)OC(C)(C)C] | 0.90 min. (B) | 385.9 |

Intermediate 4

(R)-tert-butyl 4-(biphenyl-4-yl)-3-(tert-butoxycarbonylamino)butanoate

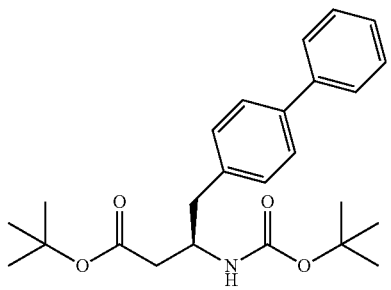 [SMILES: CC(C)(C)OC(=O)C[C@@H](Cc1ccc(-c2ccccc2)cc1)NC(=O)OC(C)(C)C]

A solution of (R)-2-(biphenyl-4-ylmethyl)-4-tert-butoxy-4-oxobutanoic acid (100 mg, 0.294 mmol), DPPA (0.076 mL, 0.353 mmol) and Et₃N (0.049 mL, 0.353 mmol) in Toluene (1.5 mL) is allowed to stir at 100° C. under nitrogen for 2 hours. tBuOH (0.281 ml, 2.94 mmol) is added and the mixture is refluxed for 5 hours at the same temperature. The reaction is cooled to room temperature, and the solvent is removed. Ethyl acetate is added to the obtained residue, and the organic layer is washed with 5% aqueous citric acid, H₂O, saturated aqueous NaHCO₃, and brine. The organic layer is dried over Na₂SO₄, filtered, and concentrated under reduced pressure. The obtained residue is purified by flash column chromatography on 40 g of silica gel (heptane/EtOAc=100:0 to 50:50) to give the corresponding isocyanate (35.7 mg). The obtained isocyanate is dissolved in tBuOH (0.3 mL) and the solution is allowed to stir at 80° C. for 20 hours. The reaction mixture is concentrated, and the residue is purified by flash column chromatography on 12 g of silica gel (heptane/EtOAc=100:0 to 70:30) to give (R)-tert-butyl 4-(biphenyl-4-yl)-3-(tert-butoxycarbonylamino)butanoate (26.4 mg, 22%). HPLC retention time=1.74 minutes (condition B); MS (ES+)=356.0 (m-tBu+2) 300.0 (m-tBux2+3; 100%); 1H NMR (400 MHz, CHLOROFORM-d) δ ppm 1.41 (s, 9 H) 1.47 (s, 9 H) 2.36 (A of ABX, $J_{ab}$=15.6 Hz, $J_{ax}$=6.2 Hz, 1 H) 2.44 (B of ABX, $J_{ab}$=15.5 Hz, $J_{bx}$=5.45 Hz) 2.82-2.97 (m, 2 H) 4.15 (br s) 5.09 (br d) 7.6-7.35 (m, 3H) 7.41-7.45 (m, 2 H) 7.51-7.56 (m, 4 H).

Intermediate 5

(R)-ethyl 4-(4-bromophenyl)-3-(tert-butoxycarbonylamino)butanoate

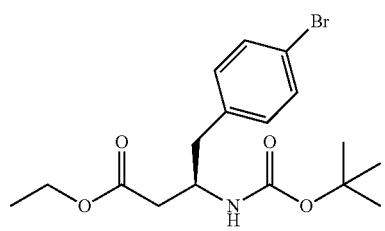 [SMILES: CCOC(=O)C[C@@H](Cc1ccc(Br)cc1)NC(=O)OC(C)(C)C]

To a suspension of (R)-4-(4-bromophenyl)-3-(tert-butoxycarbonylamino)butanoic acid (9.98 g, 27.9 mmol) and NaHCO₃ (4.68 g, 55.7 mmol) in DMF (45 mL) is added Ethyl iodide (6.75 mL, 84 mmol) at room temperature under nitrogen. After stirring for 71 hours, the reaction is quenched with H₂O (300 mL), and then precipitated solid is collected and washed with H₂O (500 mL) to give (R)-ethyl 4-(4-bromophenyl)-3-(tert-butoxycarbonylamino)butanoate (10.25 g, 94%). HPLC retention time=1.48 minutes (condition B); MS (ES+)=329.9 (m-tBu+2); 286.0 (m-Boc+2; 100%); 1H NMR (400 MHz, CHLOROFORM-d) δ ppm 1.27 (t, J=7.2 Hz, 3 H) 1.40 (s, 9 H), 2.43 (A of ABX, $J_{ab}$=15.8 Hz, $J_{ax}$=5.7 Hz, 1 H) 2.50 (B of ABX, $J_{ab}$=15.8 Hz, $J_{bx}$=5.4 Hz, 1 H) 2.74-2.90 (m, 2 H) 4.11 (br s) 4.15 (q, J=7.1 Hz, 2 H) 5.04 (br d) 7.07 (d, J=8.3 Hz, 2 H) 7.40-7.43 (m, 2 H).

Following intermediates are prepared using similar procedure as described for intermediate 5:

| Intermediate # | Product | Condition | HPLC-RT (condition) | MS (ES+; 100%) |
|---|---|---|---|---|
| Intermediate 5-2 | (R)-benzyl 4-(4-bromophenyl)-3-(tert-butoxycarbonylamino)butanoate | BnBr, NaHCO₃, DMF, RT | 1.56 min. (B) | 348 (m-BOC + 2) |

| Intermediate # | Product | Condition | HPLC-RT (condition) | MS (ES+; 100%) |
|---|---|---|---|---|
| Intermediate 5-3 | 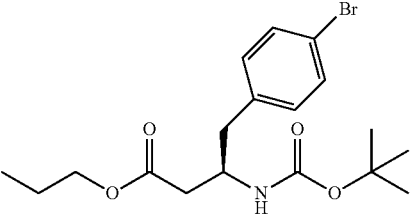<br>(R)-4-(4-Bromo-phenyl)-3-tert-butoxycarbonylamino-butyric acid propyl ester | n-propyl iodide, NaHCO₃, DMF, RT | 1.47 min. (B) | 400 (m + 1) |
| Intermediate 5-4 | 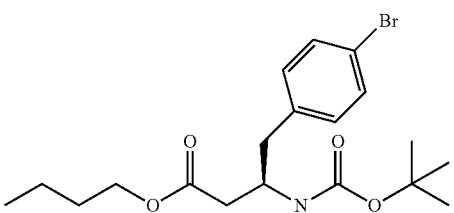<br>(R)-4-(4-Bromo-phenyl)-3-tert-butoxycarbonylamino-butyric acid butyl ester | n-butyl iodide, NaHCO₃, DMF, RT | 1.55 min. (B) | 414 (m + 1) |
| Intermediate 5-5 | 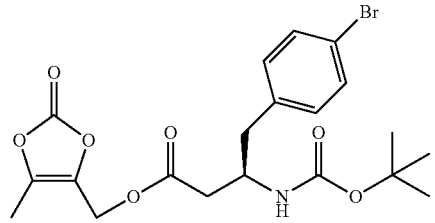<br>(R)-4-(4-Bromo-phenyl)-3-tert-butoxycarbonylamino-butyric acid 5-methyl-2-oxo-[1,3]dioxol-4-ylmethyl ester | 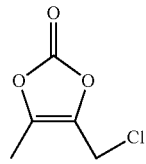<br>K₂CO₃, DMF, RT | 1.28 min. (B) | 470 (m + 1) |
| Intermediate 5-6 | 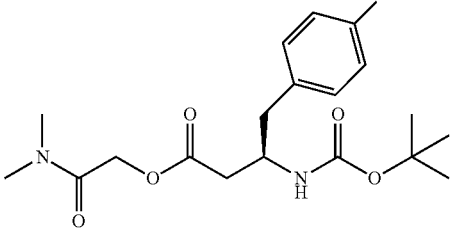<br>(R)-4-(4-Bromo-phenyl)-3-tert-butoxycarbonylamino-butyric acid dimethylcarbamoyl methyl ester | 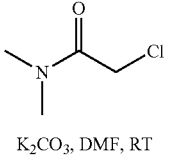<br>K₂CO₃, DMF, RT | 1.65 min. (B) | 444 (m + 1) |
| Intermediate 5-7 | 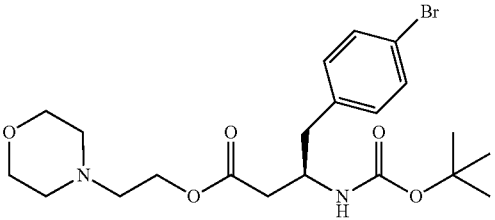<br>(R)-4-(4-Bromo-phenyl)-3-tert-butoxycarbonylamino-butyric acid 2-morpholin-4-yl-ethyl ester | 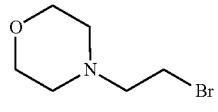<br>K₂CO₃, DMF, RT | 1.19 min. (B) | 471 (m + 1) |

Intermediate 5-2

(R)-benzyl 4-(4-bromophenyl)-3-(tert-butoxycarbonylamino)butanoate

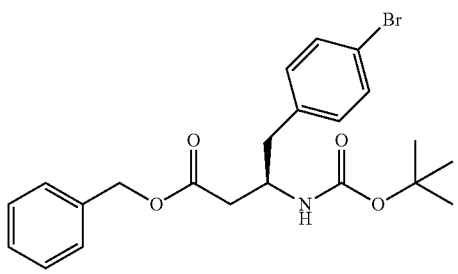 [SMILES: CC(C)(C)OC(=O)N[C@@H](CC(=O)OCc1ccccc1)Cc1ccc(Br)cc1]

To a suspension of (R)-4-(4-bromophenyl)-3-(tert-butoxycarbonylamino)butanoic acid (5.02 g, 14.01 mmol) and NaHCO$_3$ (3.53 g, 42.0 mmol) in DMF (20 mL) is added Benzyl bromide (5.10 mL, 42 mmol) at room temperature under nitrogen. After stirring for 46 hours, the reaction is diluted with H$_2$O (200 mL), and then precipitated solid is collected and washed with H$_2$O (500 mL) and then with heptane (200 ml) to give (R)-benzyl 4-(4-bromophenyl)-3-(tert-butoxycarbonylamino)butanoate (5.61 g, 89%). HPLC retention time=1.56 minutes (condition B); MS (ES+)=392.1 (m-tBu+2); 348.1 (m-Boc+2; 100%); 1H NMR (400 MHz, CHLOROFORM-d) δ ppm 1.39 (s, 9 H) 2.48 (A of ABX, J$_{ab}$=15.9 Hz, J$_{ax}$=5.6 Hz, 1 H) 2.54 (B of ABX, J$_{ab}$=15.9 Hz, J$_{bx}$=5.3 Hz, 1 H) 2.72-2.88 (m, 2 H) 4.11 (br s, 1 H) 5.02 (br s, 1 H) 5.10 (A of AB, J=12.1 Hz, 1 H) 5.16 (A of AB, J=12.1 Hz, 1 H) 7.00 (d, J=8.1 Hz, 2 H) 7.34-7.39 (m, 7 H).

Intermediate 6

(R)-3-(biphenyl-4-ylmethyl)-4-(3-methoxy-3-oxopropylamino)-4-oxobutanoic acid

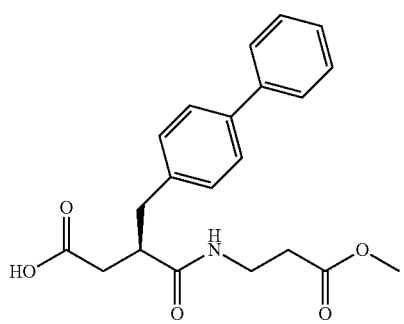 [SMILES: COC(=O)CCNC(=O)[C@@H](CC(=O)O)Cc1ccc(-c2ccccc2)cc1]

To a solution of (R)-tert-butyl 3-(biphenyl-4-ylmethyl)-4-(3-methoxy-3-oxopropylamino)-4-oxobutanoate (40 mg, 0.094 mmol) in DCM (0.5 mL), TFA (0.15 mL) is added at room temperature. The mixture is allowed to stir for 2 hours, and then concentrated under reduced pressure to give (R)-3-(biphenyl-4-ylmethyl)-4-(3-methoxy-3-oxopropylamino)-4-oxobutanoic acid (33.5 mg, 96%). HPLC retention time=1.20 minutes (condition A); MS (m+1)=370.1; 1H NMR (400 MHz, CHLOROFORM-d) δ ppm 2.21-2.29 (m, 1 H) 2.38-2.45 (m, 1 H) 2.62-2.66 (m, 1 H) 2.75-3.00 (m, 4 H) 3.29-3.37 (m, 1 H) 3.45-3.53 (m, 4 H) 6.12 (br s, 1 H) 7.23 (d, J=8 Hz, 2 H) 7.32-7.35 (m, 1 H) 7.41-7.45 (m, 2 H) 7.53 (d, J=8.1 Hz, 2 H) 7.56-7.59 (m, 2 H).

Intermediate 7

(R)-tert-butyl 3-(biphenyl-4-ylmethyl)-4-(3-methoxy-3-oxopropylamino)-4-oxobutanoate

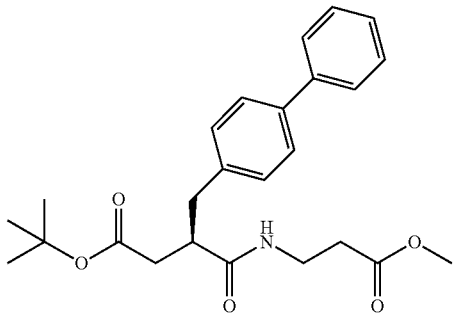 [SMILES: COC(=O)CCNC(=O)[C@@H](CC(=O)OC(C)(C)C)Cc1ccc(-c2ccccc2)cc1]

A solution of (R)-2-(biphenyl-4-ylmethyl)-4-tert-butoxy-4-oxobutanoic acid (142 mg, 0.417 mmol), 3-amino-propionic acid methyl ester hydrochloride (76 mg, 0.542 mmol), WSC hydrochloride (120 mg, 0.626 mmol), 1-hydroxy-7-azabenzotriazole (85 mg, 0.626 mmol) and DIPEA (0.219 ml, 1.251 mmol) in DMF (4 mL) is allowed to stir at room temperature under nitrogen for 13 hours. The reaction is quenched with H$_2$O. The products are extracted with ethyl acetate, washed with aqueous 1M HCl and then with brine, dried over Na$_2$SO$_4$, filtered, and concentrated under reduced pressure. The obtained residue is purified by flash column chromatography on 12 g of silica gel (heptane/EtOAc=70:30 to 0:100) to give (R)-tert-butyl 3-(biphenyl-4-ylmethyl)-4-(3-methoxy-3-oxopropylamino)-4-oxobutanoate (164 mg, 91%). HPLC retention time=1.59 minutes (condition A); MS (ES+)=425.4 (m); 369.4 (m-tBu+1; 100%); 1H NMR (400 MHz, CHLOROFORM-d) δ ppm 2.24-2.44 (m, 2 H) 2.67-2.79 (m, 3 H) 2.89-2.96 (m, 1 H) 3.28-3.36 (m, 1 H) 3.45-3.53 (m, 1 H) 7.23 (d, J=5.8 Hz, 2 H) 7.33 (t, J=7.35 Hz, 1 H) 7.41-7.44 (m, 2 H) 7.51 (d, J=8.1 Hz, 2 H) 7.58 (d, J=7.4 Hz, 2 H).

Following intermediates are prepared using similar procedure as described in intermediate 7:

| Intermediate # | Product | Starting material | Condition | HPLC-RT (condition) | MS (M + 1) |
|---|---|---|---|---|---|
| Intermediate 7-2 | (R)-3-Biphenyl-4-ylmethyl-N-tert-butoxycarbonylmethyl-succinamic acid tert-butyl ester | H₃N⁺–CH₂–C(O)O-tBu Cl⁻; WSC·HCl, HOAt, DIPEA, DMF, rt | | 1.64 min. (B) | 454.1 |
| Intermediate 7-3 | (R)-3-Biphenyl-4-ylmethyl-N-(3-carboxy-propyl)-succinamic acid tert-butyl ester | H₂N–(CH₂)₃–COOH; WSC·HCl, HOAt, DIPEA, DMF, rt | | 1.71 min. (A) | 426.1 |

Intermediate 8

(R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester

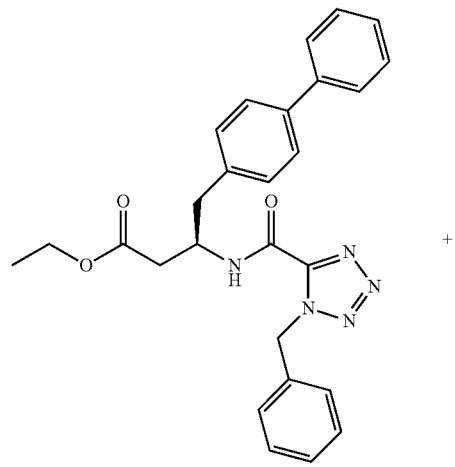

+

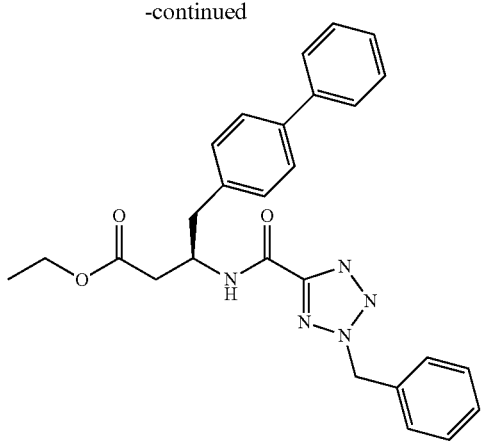

(R)-ethyl 4-(biphenyl-4-yl)-3-(tert-butoxycarbonylamino)butanoate (117 mg, 0.305 mmol) is treated with 4M HCl dioxane solution (2 mL). After stirring for 0.5 hour, the reaction mixture is concentrated under reduced pressure. To a solution of the obtained residue and Et₃N (0.106 mL, 0.763 mmol) in DCM (3 mL) is added benzyl-H-tetrazole-5-carbonyl chloride (mixture of 1 and 2-benzyl isomers, 82 mg, 0.366 mmol, prepared according to *J. Med. Chem.* 1986, 29, 538-549). After stirring for 10 minutes, Et₃N (0.106 mL, 0.763 mmol) and the acid chloride (82 mg, 0.366 mmol) are added. After stirring for 0.5 hour, the reaction mixture is diluted with ethyl acetate, washed with H₂O and brine, dried over Na₂SO₄, and concentrated under reduced pressure. The residue is purified by silica gel column chromatography to give (R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester. HPLC retention time=1.51 minutes (condition D); MS=470.0 (m+1); 1H NMR (400 MHz, CDCl$_3$) δ ppm 1.27 (t, J=7.07, 7.07 Hz, 3H), 2.57-2.70 (m, 2H), 3.00 (dd, J=7.58, 13.77 Hz, 1H), 3.12 (dd, J=6.57, 13.77 Hz, 1H), 4.12-4.23 (m, 2H), 4.71-4.80 (m, 1H), 5.80 (s, 2H), 7.27-7.45 (m, 9H), 7.52 (d, J=8.34 Hz, 2H), 7.56 (d, J=8.46 Hz, 2H), 7.75 (d, J=7.33 Hz, 1H).

Intermediate 9

(R)-4-biphenyl-4-yl-3-{3-[1-(2-cyano-ethyl)-1H-tetrazol-5-yl]-propionylamino}-butyric acid ethyl ester

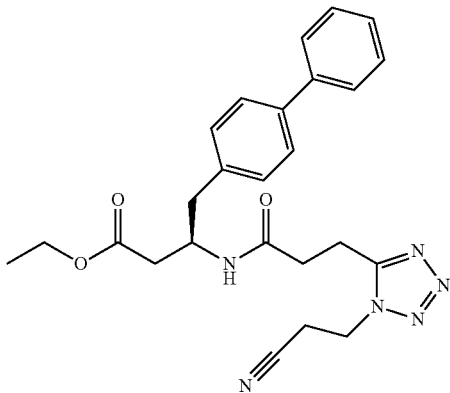 [SMILES: CCOC(=O)C[C@@H](Cc1ccc(-c2ccccc2)cc1)NC(=O)CCc1nnnn1CCC#N]

To a solution of (R)-4-biphenyl-4-yl-3-tert-butoxycarbonylamino-butyric acid ethyl ester (400 mg, 1.04 mmol) in DCM (10 mL) at room temperature is added TFA (2.009 mL, 26.1 mmol) and the mixture is stirred at room temperature for 1 hour. The mixture is concentrated under reduced pressure. To the obtained TFA salt in DCM (10 mL) at ice bath temperature is added succinic anhydride (125 mg, 1.25 mmol) and followed by TEA (0.363 mL, 2.61 mmol). The reaction is stirred at room temperature for 16 hours. The mixture is concentrated under reduced pressure. The obtained residue is purified by flash chromatography (silica gel, 2% to 5% EtOH/DCM) give (R)-4-biphenyl-4-yl-3-(3-carboxy-propionylamino)-butyric acid ethyl ester (200 mg). HPLC retention time=1.53 minutes (condition C); MS=384 (m+1).

Next, to a solution of (R)-4-biphenyl-4-yl-3-(3-carboxy-propionylamino)-butyric acid ethyl ester (200 mg, 0.522 mmol) in THF (10 mL) at room temperature is added EDC HCl (120 mg, 0.626 mmol) and HOBT (96 mg, 0.626 mmol). The reaction is stirred at room temperature for 10 minutes then added 3-aminopropionitrile (0.046 ml, 0.626 mmol) and TEA (0.087 ml, 0.626 mmol). After 1 hour, 0.5 equivalent of EDC HCl, HOBT, and 3-aminopropionitrile are added and stirred for 16 hours. The reaction mixture is quenched by brine and is extracted with ethylacetate. The combined organic layer is washed with brine and dried over anhydrous sodium sulfate, filtered and concentrated under reduced pressure. The obtained residue is purified by flash chromatography (silica gel, 2% to 5% EtOH/DCM) to give (R)-4-biphenyl-4-yl-3-[3-(2-cyano-ethylcarbamoyl)-propionylamino]-butyric acid ethyl ester (218 mg, 96% yield). HPLC retention time=0.77 minutes (condition E); MS=436 (m+1).

Next, to a solution of (R)-4-biphenyl-4-yl-3-[3-(2-cyano-ethylcarbamoyl)-propionylamino]-butyric acid ethyl ester (204 mg, 0.468 mmol) in THF (10 mL) at room temperature is added Ph$_3$P (307 mg, 1.17 mmol) and the mixture is stirred at room temperature for 10 minutes. Then to the mixture at ice bath temperature is added DIAD (0.228 ml, 1.171 mmol) and trimethylsilyl azide (0.155 ml, 1.171 mmol). The resulting mixture is slowly warmed up to room temperature and stirred for 16 hours. The reaction mixture is concentrated under reduced pressure. The obtained residue is purified by flash chromatography (silica gel, 1% to 3% EtOH/DCM) to give (R)-4-biphenyl-4-yl-3-{3-[1-(2-cyano-ethyl)-1H-tetrazol-5-yl]-propionylamino}-butyric acid ethyl ester (137 mg, 64% yield). HPLC retention time=1.61 minutes (condition C); MS=461 (m+1).

Intermediate 10

(R)-2-(biphenyl-4-ylmethyl)-4-tert-butoxy-4-oxobutanoic acid

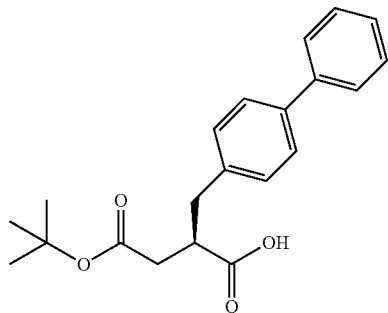 [SMILES: CC(C)(C)OC(=O)C[C@@H](Cc1ccc(-c2ccccc2)cc1)C(=O)O]

To a stirred solution of (R)-tert-butyl 4-((S)-4-benzyl-2-oxooxazolidin-3-yl)-3-(biphenyl-4-ylmethyl)-4-oxobutanoate (1.20 g, 2.402 mmol) in a mixed solvent of THF (20 mL) and water (5 mL), a solution of aqueous H$_2$O$_2$ (0.960 mL, 9.61 mmol) and aqueous LiOH (4.80 ml, 4.80 mmol) is added at 0° C. during 5 minutes. After stirring for 1.5 hour, the reaction is quenched with saturated aqueous Na$_2$SO$_3$ (10 mL) at 0° C., and allowed to stir for 10 minutes at the same temperature. The reaction mixture is warmed up to ambient temperature while stirring for 0.5 hour. Then, saturated aqueous NaHCO$_3$ and brine are added to the mixture. The product is extracted with ethyl acetate, washed with aqueous 1M HCl, dried over MgSO$_4$, filtered, and concentrated under reduced pressure. The obtained residue is purified by flash column chromatography on 120 g of silica gel (heptane/EtOAc=75:25 to 0:100) to give (R)-2-(biphenyl-4-ylmethyl)-4-tert-butoxy-4-oxobutanoic acid (765 mg, 93%). HPLC retention time=1.63 minutes (condition D); MS=338.6 (m−1); 1H NMR (400 MHz, CHLOROFORM-d) δ ppm 1.43 (s, 9 H) 2.41 (A of ABX, J$_{ab}$=16.67 Hz, J$_{ax}$=4.55 Hz, 1 H) 2.52-2.67 (B of ABX, J$_{ab}$=16.75 Hz, J$_{bx}$=8.45 Hz, 1 H) 2.74-2.89 (m, 1 H) 3.06-3.22 (m, 2 H) 7.22-7.29 (m, 2 H) 7.30-7.37 (m, 1 H) 7.43 (t, J=7.58 Hz, 2 H) 7.53 (d, J=8.1 Hz, 2 H) 7.57 (d, J=7.8 Hz, 2 H).

Intermediate 11

Synthesis of (R)-tert-butyl 4-((S)-4-benzyl-2-oxooxazolidin-3-yl)-3-(biphenyl-4-ylmethyl)-4-oxobutanoate

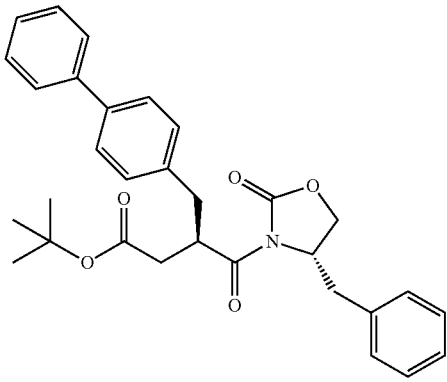 [SMILES: CC(C)(C)OC(=O)C[C@@H](Cc1ccc(-c2ccccc2)cc1)C(=O)N1C(=O)OC[C@@H]1Cc1ccccc1]

A stirred solution of (S)-4-benzyl-3-(3-(biphenyl-4-yl)propanoyl)oxazolidin-2-one (intermediate 12: 5.01 g, 13.00 mmol) in THF (180 mL) is cooled to −73.8° C., and 1M THF solution of sodium hexamethyldisilylamide (14.30 mL, 14.30 mmol) is added during 5 minutes. After 30 minutes, a solution of tert-butyl bromoacetate (2.495 mL, 16.90 mmol) in THF (20 mL) is added dropwise during 5 minutes. The solution is stirred at −74° C. for 1 hour, and the reaction is quenched with saturated aqueous NH$_4$Cl (100 mL), and warmed up to ambient temperature. The precipitated solid is filtered off and washed with ethyl acetate (50 mL). The organic phase is separated, washed with brine, dried over MgSO$_4$, and concentrated under reduced pressure. The obtained residue is suspended in MeOH (70 mL) and then filtered to collect the solid (5.9 g) as a mixture of the desired product and the starting material. The mixture is purified by flash column chromatography on 120 g of silica gel (heptane/EtOAc=90:10 to 50:50) to give (R)-tert-butyl 4-((S)-4-benzyl-2-oxooxazolidin-3-yl)-3-(biphenyl-4-ylmethyl)-4-oxobutanoate (2.40 g, 37%). HPLC retention time=1.74 minutes (condition B); MS=499.4 (m+); 443.4 (m-tBu+1; 100%); 1H NMR (400 MHz, CHLOROFORM-d) δ ppm 1.41 (s, 9 H) 2.42 (dd, J=16.67, 4.04 Hz, 1 H) 2.71 (ddd, J=16.55, 13.26, 9.60 Hz, 2 H) 2.87 (dd, J=16.93, 10.86 Hz, 1 H) 3.04 (dd, J=13.14, 6.32 Hz, 1 H) 3.32 (dd, J=13.39, 3.03 Hz, 1 H) 3.92 (t, J=8.34 Hz, 1 H) 4.07 (dd, J=8.97, 2.15 Hz, 1 H) 4.48-4.58 (m, 2 H) 7.20-7.30 (m, 3 H) 7.30-7.36 (m, 5 H) 7.42 (t, J=7.58 Hz, 2 H) 7.52 (d, J=8.1 Hz, 2 H) 7.56 (d, J=7.8 Hz, 2 H).

Intermediate 12

(S)-4-benzyl-3-(3-(biphenyl-4-yl)propanoyl)oxazolidin-2-one

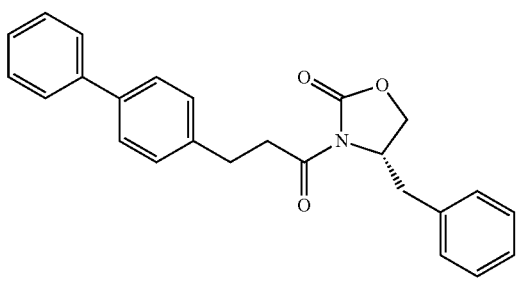 [SMILES: O=C(CCc1ccc(-c2ccccc2)cc1)N1C(=O)OC[C@@H]1Cc1ccccc1]

To a 1.6 M solution of n-BuLi in hexane (12.1 mL, 19.3 mmol) is added dropwise a solution of (S)-(−)-4-benzyl-2-oxazolidinone (3.26 g, 18.4 mmol) in dry THF (80 mL) at −71.6° C. under nitrogen over 10 minutes. The solution is warmed up to −60.5° C. while the addition, and allowed to stir for 1 hour in dry ice/MeOH bath. 3-(Biphenyl-4-yl)propanoyl chloride (intermediate 13: 5.46 g, 22.31 mmol) in dry THF (20 mL) is added dropwise at −72° C. over 5 minutes. The solution is warmed up to −56.5° C. while the addition. After stirring 10 minutes at the same temperature, the reaction mixture is allowed to warm to room temperature and stirring is continued for 3 hours. The reaction mixture is filtered, and the collected precipitate is washed with 20 mL (10 mL×2) of MeOH and then with 150 mL of H$_2$O to give the desired product (4.26 g). The products in the mother liquor is extracted with ethyl acetate, washed with brine, dried over MgSO$_4$, filtered, and concentrated under reduced pressure. The obtained residue is suspended in 80 mL of MeOH, and the suspension is filtered and washed with 20 mL of MeOH (1.79 g). The two fractions are mixed to give (S)-4-benzyl-3-(3-(biphenyl-4-yl)propanoyl)oxazolidin-2-one (6.05 g, 85% in 2 steps). Retention time=1.77 minutes (condition A); MS (m+1)=387.3; 1H NMR (400 MHz, CHLOROFORM-d) δ ppm 2.77 (dd, J=13.39, 9.35 Hz, 1 H) 2.99-3.15 (m, 2 H) 3.20-3.43 (m, 3 H) 4.09-4.24 (m, 2 H), 4.68 (dddd, J=9.76, 6.73, 3.47, 3.28 Hz, 1 H) 7.18 (d, J=7.07 Hz, 2 H) 7.23-7.37 (m, 6 H) 7.42 (t, J=7.58 Hz, 2 H) 7.53 (d, J=8.1 Hz, 2 H), 7.57 (d, J=7.8 Hz, 2 H).

Intermediate 13

3-(biphenyl-4-yl)propanoyl chloride

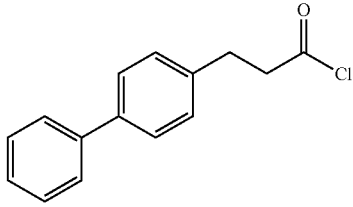 [SMILES: O=C(Cl)CCc1ccc(-c2ccccc2)cc1]

A mixture of 3-(4-biphenylyl)propionic acid (5 g, 22.10 mmol) and SOCl$_2$ (4.03 ml, 55.2 mmol) is refluxed under nitrogen at 85° C. for 1.5 hour. The reaction mixture is concentrated under reduced pressure to give 3-(biphenyl-4-yl)propanoyl chloride (5.46 g). The material is used in the next step without further purification.

Intermediate 14

(2R,4R)-4-Amino-2-methyl-pentanoic acid ethyl ester trifluoroacetate

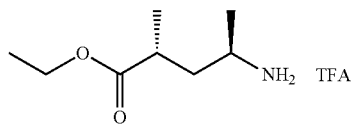

To a stirred solution of 2-(triphenylphosphanylidene)-propionic acid ethyl ester (3.11 g, 8.57 mmol) in methylene chloride (20 mL) is added a solution of 3,3-dimethyl-N-((R)-1-methyl-2-oxo-ethyl)-butyramide (J. Med. Chem. 41, 6 (1998) (1.35 g, 7.79 mmol) in methylene chloride (20 mL) and the mixture is stirred at room temperature for 2 hours. The solvent is removed under reduced pressure and the residue is purified by column chromatography using a gradient of 10-50% heptane/EtOAc to give (E)-(R)-4-tert-butoxycarbonylamino-2-methyl-pent-2-enoic acid ethyl ester. $^1$H-NMR (400 MHz, CDCl$_3$); δ ppm 1.22 (d, J=6.44 Hz, 3H), 1.30 (t, 3H), 1.43 (s, 9H), 1.91 (s, 3H), 4.19 (q, 2H), 6.51 (d, broad, J=7.45 Hz, 1H).

Next, a solution of (E)-(R)-4-tert-butoxycarbonylamino-2-methyl-pent-2-enoic acid ethyl ester (1.83 g, 7.11 mmol) in ethyl acetate (75 mL) is hydrogenated over 10% Pt/C (183 mg) at 1 atm for 18 hours. The catalyst is filtered through Celite and the solvent is removed under reduced pressure. The residue is purified by chiral HPLC to afford (2R,4R)-4-tert-butoxycarbonylamino-2-methyl-pentanoic acid ethyl ester, $^1$H-NMR (400 MHz, CDCl$_3$); δ ppm 1.13 (t, 3H), 1.18 (m, 3H), 1.26 (t, 3H), 1.43 (s, 9H), 1.81 (s, 1H), 2.50 (m, 1H), 3.72 (m broad, 1H), 4.14 (m, 2H), 4.33 (m broad, 1H).

Next, (2R,4R)-4-tert-butoxycarbonylamino-2-methyl-pentanoic acid ethyl ester (142 mg, 0.548 mmol) is added to trifluoroacetic acid (5 mL). After 10 minutes, the solvent is removed under reduced pressure. Methylene chloride is added and the solvent is removed under reduced pressure to give (2R,4R)-4-amino-2-methyl-pentanoic acid ethyl ester trifluoroacetate. This material is used directly in the subsequent coupling reaction.

Intermediate 15

2-Biphenyl-4-ylmethyl-succinic acid 1-methyl ester

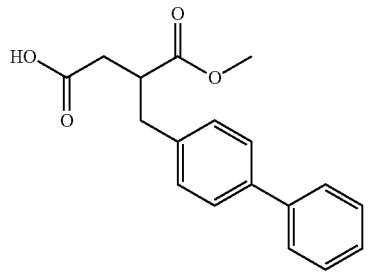 [SMILES: COC(=O)C(CC(=O)O)Cc1ccc(-c2ccccc2)cc1]

To a solution of (triphenylphosphanylidene)-acetic acid methyl ester (2.26 g, 6.77 mmol) in methylene chloride (25 mL) is added t-butyl bromoacetate (1.32 g, 6.77 mmol) and the mixture is stirred at room temperature for 48 hours. The solvent is removed under reduced pressure and the residue is purified by column chromatography using a gradient of 80-100% heptane/EtOAc to afford 2-(triphenylphosphanylidene)-succinic acid 4-tert-butyl ester 1-methyl ester. MS 449.3 (M+1).

Next, a mixture of 2-(triphenylphosphanylidene)-succinic acid 4-tert-butyl ester 1-methyl ester (700 mg, 1.561 mmol) and biphenyl-4-carboxaldehyde (278 mg, 1.419 mmol) in toluene (20 mL) is refluxed for 4 days. The solvent is removed under reduced pressure and the residue is purified by column chromatography using a gradient of 0-30% heptane/EtOAc to give 2-[1-biphenyl-4-yl-meth-(Z)-ylidene]-succinic acid 4-tert-butyl ester 1-methyl ester as an oil, $^1$H-NMR (400 MHz, CDCl$_3$); δ ppm 1.47 (s, 9H), 3.52 (s, 2H), 3.84 (s, 3H), 7.37 (t, 1H), 7.46 (t, 4H), 7.62 (t, 4H), 7.89 (s, 1H).

A solution of 2-[1-biphenyl-4-yl-meth-(Z)-ylidene]-succinic acid 4-tert-butyl ester 1-methyl ester (410 mg, 1.163 mmol) in ethyl acetate (20 mL) is hydrogenated over Pt/C (40 mg) at 1 atm for 18 hours. The catalyst is filtered through Celite and the solvent is removed under reduced pressure to give 2-biphenyl-4-ylmethyl-succinic acid 4-tert-butyl ester 1-methyl ester. The enantiomers are separated by chiral HPLC.

Next, 2-biphenyl-4-ylmethyl-succinic acid 4-tert-butyl ester 1-methyl ester (160 mg, 0.451 mmol) is added to trifluoroacetic acid (5 mL). After 10 minutes, the solvent is removed under reduced pressure. Methylene chloride is added and the solvent is removed under reduced pressure to give 2-biphenyl-4-ylmethyl-succinic acid 1-methyl ester. This material is used directly in the subsequent coupling reaction.

Intermediate 16-1

Synthesis of (R)-ethyl 3-amino-4-(3'-chlorobiphenyl-4-yl)butanoate hydrochloride

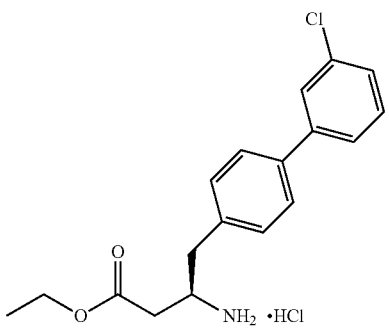 [SMILES: CCOC(=O)C[C@H](N)Cc1ccc(-c2cccc(Cl)c2)cc1 ; Cl]

To (R)-ethyl 3-(tert-butoxycarbonylamino)-4-(3'-chlorobiphenyl-4-yl)butanoate (3.33 g, 7.97 mmol) is added a solution of 4 M HCl in 1,4-dioxane (19.9 mL, 18.0 mmol) at room temperature. After stirring for 0.5 hours, the reaction mixture is concentrated under reduced pressure to give (R)-ethyl 3-amino-4-(3'-chlorobiphenyl-4-yl)butanoate hydrochloride (2.90 g). HPLC retention time=0.70 minutes (condition B); MS (m+1)=318.26; 1H NMR (400 MHz, CHLOROFORM-d) δ ppm 1.19-1.24 (m, 3 H) 2.73-2.78 (m, 1 H) 2.84-2.91 (m, 1 H) 3.05-3.11 (m, 1 H) 3.50-3.54 (m, 1 H) 3.92 (br s, 1 H) 4.14-4.17 (m, 2 H) 7.29-7.53 (m, 8 H) 8.73 (br. s., 3 H).

Following intermediates are prepared using similar procedure as described for intermediate 16-1:

| Intermediate # | Product | Starting Material | Condition | HPLC-RT (condition) | MS (M + 1) |
|---|---|---|---|---|---|
| Intermediate 16-2 | (R)-ethyl 3-amino-4-(biphenyl-4-yl)butanoate hydrochloride | Intermediate 2 | 4M HCl/ 1,4-dioxane | 0.89 min. (B) | 284.1 |

| Intermediate # | Product | Starting Material | Condition | HPLC-RT (condition) | MS (M + 1) |
|---|---|---|---|---|---|
| Intermediate 16-3 | 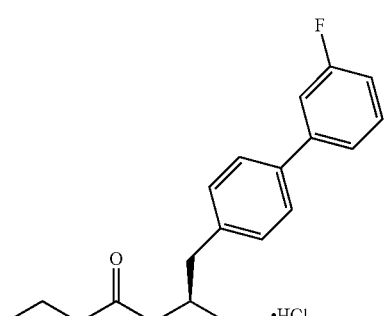<br>(R)-ethyl 3-amino-4-(3'-fluorobiphenyl-4-yl)butanoate hydrochloride | 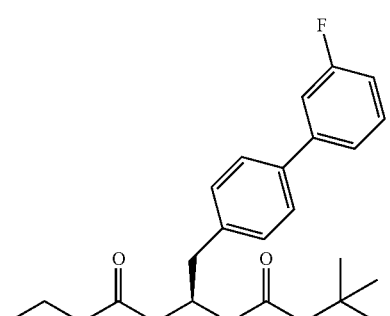<br>Intermediate 2-2 | 4M HCl/ 1,4-dioxane | 0.94 min. (B) | 302.1 |
| Intermediate 16-4 | 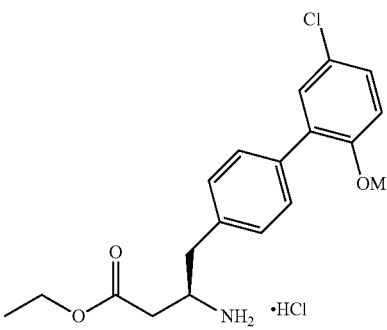<br>(R)-ethyl 3-amino-4-(5'-chloro-2'-methoxybiphenyl-4-yl)butanoate hydrochloride | 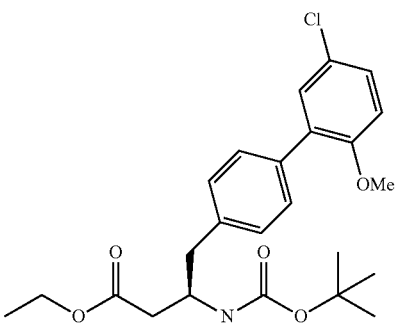<br>Intermediate 2-3 | 4M HCl/ 1,4-dioxane | 0.94 min. (B) | 348.2 |
| Intermediate 16-5 | 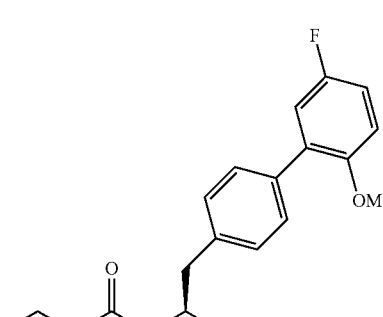<br>(R)-ethyl 3-amino-4-(5'-fluoro-2'-methoxybiphenyl-4-yl)butanoate hydrochloride | 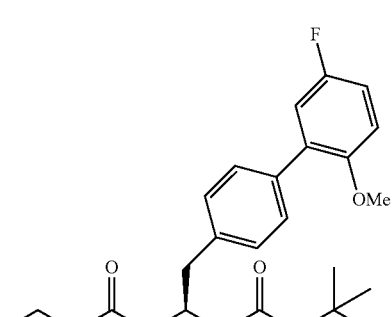<br>Intermediate 2-4 | 4M HCl/ 1,4-dioxane | 1.38 min. (A) | 332.2 |

-continued

| Intermediate # | Product | Starting Material | Condition | HPLC-RT (condition) | MS (M + 1) |
|---|---|---|---|---|---|
| Intermediate 16-6 | 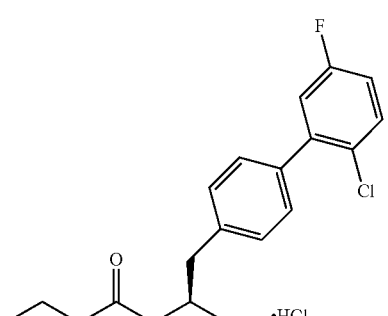<br>(R)-ethyl 3-amino-4-(2'-chloro-5'-fluorobiphenyl-4-yl)butanoate hydrochloride | 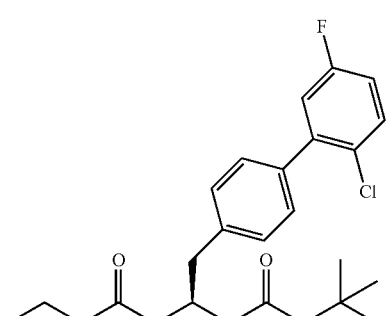<br>Intermediate 2-5 | 4M HCl/ 1,4-dioxane | 0.93 min. (B) | 336.1 |
| Intermediate 16-7 | 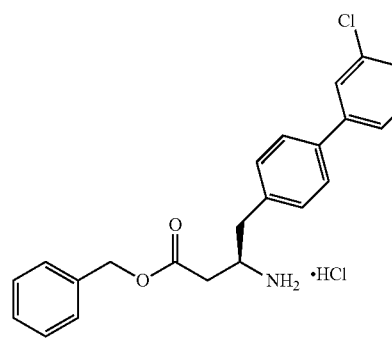<br>(R)-benzyl 3-amino-4-(3'-chlorobiphenyl-4-yl)butanoate | 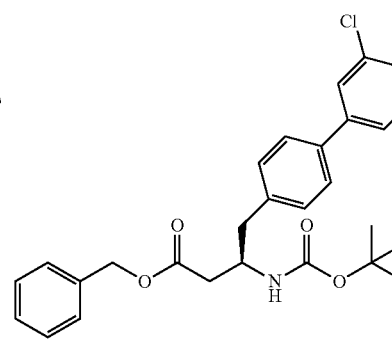<br>Intermediate 17-2 | 4M HCl/ 1,4-dioxane | 1.20 min. (B) | 380.2 |
| Intermediate 16-8 | 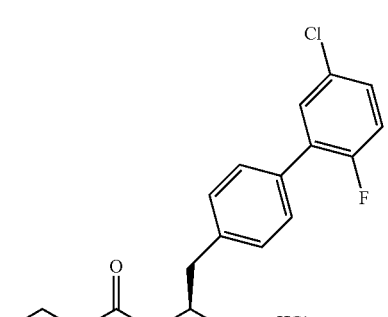<br>(R)-ethyl 3-amino-4-(5'-chloro-2'-fluorobiphenyl-4-yl)butanoate | 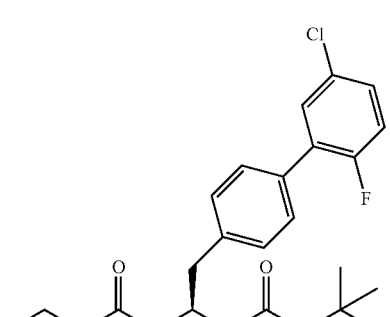<br>Intermediate 2-6 | 4M HCl/ 1,4-dioxane | 0.88 min. (B) | 336.1 |

Intermediate 16-7

(R)-benzyl 3-amino-4-(3'-chlorobiphenyl-4-yl)butanoate hydrochloride

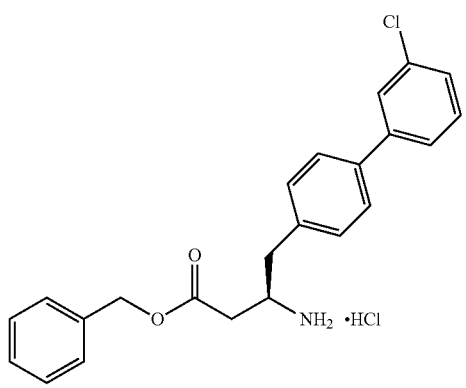 [SMILES: N[C@@H](CC(=O)OCc1ccccc1)Cc1ccc(-c2cccc(Cl)c2)cc1 ; Cl]

To (R)-benzyl 3-(tert-butoxycarbonylamino)-4-(3'-chlorobiphenyl-4-yl)butanoate (3.561 g, 7.42 mmol) is added a solution of 4 M HCl in 1,4-dioxane (18.55 mL, 74.2 mmol) at room temperature. After stirring for 4 hours, the reaction mixture is concentrated under reduced pressure to give (R)-benzyl 3-amino-4-(3'-chlorobiphenyl-4-yl)butanoate hydrochloride (3.11 g). HPLC retention time=1.07 minutes (condition B); MS (m+1)=380.1; 1H NMR (400 MHz, CHLOROFORM-d) δ ppm 2.81 (A of ABX, $J_{ab}$=17.4 Hz, $J_{ax}$=4.5 Hz, 1 H) 2.93 (B of ABX, $J_{ab}$=17.4 Hz, $J_{bx}$=7.6 Hz, 1 H) 3.03-3.09 (m, 1 H) 3.50 (dd, J=4.9 and 13.5 Hz, 1 H) 3.98 (br s, 1 H) 5.09 (s, 2 H) 7.24-7.22 (m, 9 H) 7.35-7.38 (m, 1 H) 7.42 (d, J=8.1 Hz, 2 H) 7.48-7.49 (m, 1 H) 8.78 (br s, 3 H).

Intermediate 17-1

Synthesis of (R)-ethyl 3-(tert-butoxycarbonylamino)-4-(3'-chlorobiphenyl-4-yl)butanoate

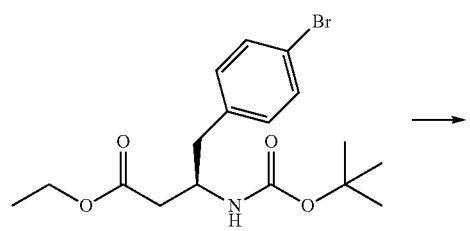

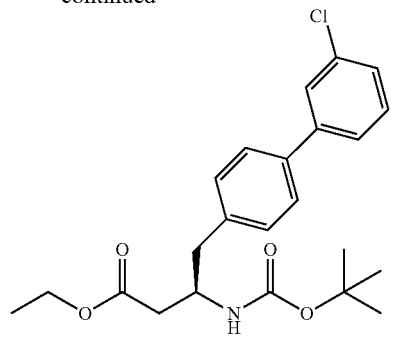

A mixture of (R)-ethyl 4-(4-bromophenyl)-3-(tert-butoxycarbonylamino)butanoate (4.89 g, 12.66 mmol), 3-chlorophenylboronic acid (2.97 g, 18.99 mmol), Pd(PPh$_3$)$_4$ (1.463 g, 1.266 mmol) and 2 M aqueous Na$_2$CO$_3$ (12.66 ml, 25.3 mmol) in 1,2-dimethoxyethane (100 ml) is allowed to stir at 95° C. under nitrogen for 3 hours. The reaction mixture is cooled to room temperature and quenched with brine. The two phases are separated. The mixture is extracted twice with ethyl acetate from the aqueous layer. The combined organic layer is washed with brine, dried over MgSO$_4$, filtered, and concentrated under reduced pressure. The obtained residue is purified by silica gel flash column chromatography (heptane/EtOAc=100:0 to 70:30) to give (R)-ethyl 3-(tert-butoxycarbonylamino)-4-(3'-chlorobiphenyl-4-yl)butanoate (3.33 g); HPLC retention time=1.44 minutes (condition B); MS (ES+)=318.26 (m-BOC+2; 100%); 1H NMR (400 MHz, CHLOROFORM-d) δ ppm 1.28 (t, J=7.2 Hz, 3 H) 1.41 (s, 9 H) 2.47 (A of ABX, $J_{ab}$=15.8 Hz, $J_{ax}$=5.9 Hz, 1 H) 2.52 (B of ABX, $J_{ab}$=15.8 Hz, $J_{bx}$=5.4 Hz, 1 H) 2.83-2.89 (m, 1 H) 2.95-3.00 (m, 1 H) 4.17 (q, J=7.2 Hz, 2 H) 4.18 (br s, 1 H) 5.07 (br s, 1 H) 7.26-7.37 (m, 4 H) 7.43-7.51 (m, 3 H) 7.55 (br t, J=1.8 Hz, 1 H).

Following intermediates are prepared using similar procedure as described for intermediate 17-1:

| Intermediate # | Product | Condition | HPLC-RT (condition) | MS (ES+; 100%) |
|---|---|---|---|---|
| Intermediate 17-2 | 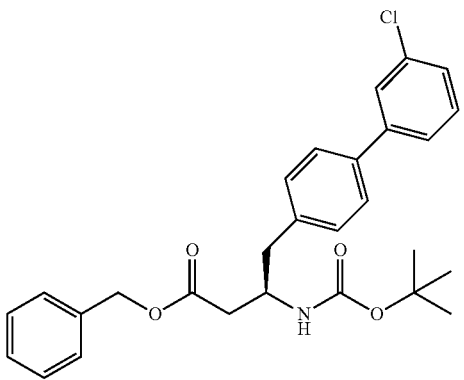<br>(R)-benzyl 3-(tert-butoxycarbonylamino)-4-(3'-chlorobiphenyl-4-yl)butanoate | Pd(PPh$_3$)$_4$, 3-chlorophenylboronic acid, aq. 2M Na2CO3, toluene, 95° C. | 1.74 min. (B) | 380.2 (m-BOC + 2) |
| Intermediate 17-3 | 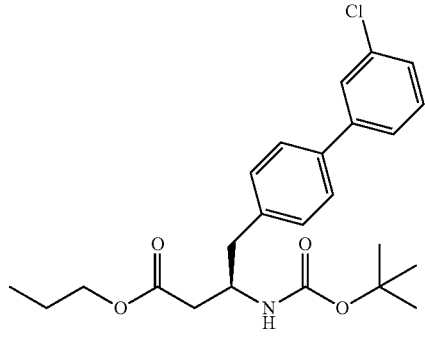<br>(R)-3-tert-Butoxycarbonylamino-4-(3'-chloro-biphenyl-4-yl)-butyric acid propyl ester | Pd(PPh$_3$)$_4$, 3-chlorophenylboronic acid, aq. 2M Na2CO3, toluene, 95° C. | 1.66 min. (B) | 432 (m + 1) |
| Intermediate 17-4 | 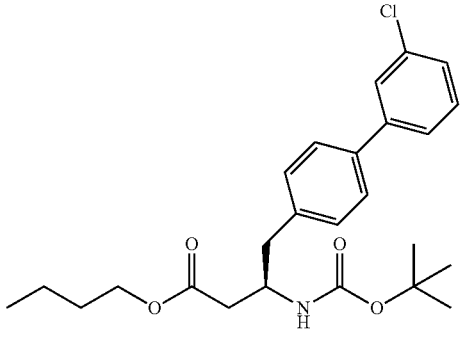<br>(R)-3-tert-Butoxycarbonylamino-4-(3'-chloro-biphenyl-4-yl)-butyric acid butyl ester | Pd(PPh$_3$)$_4$, 3-chlorophenylboronic acid, aq. 2M Na2CO3, toluene, 95° C. | 1.73 min. (B) | 446 (m + 1) |

| Intermediate # | Product | Condition | HPLC-RT (condition) | MS (ES+; 100%) |
|---|---|---|---|---|
| Intermediate 17-5 | 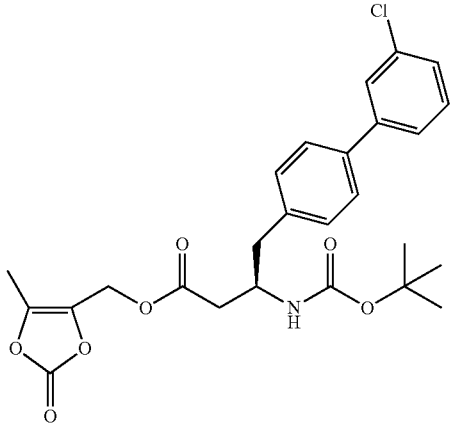<br>(R)-3-tert-Butoxycarbonylamino-4-(3'-chloro-biphenyl-4-yl)-butyric acid 5-methyl-2-oxo-[1,3]dioxol-4-ylmethyl ester | Pd(OAc)$_2$, dicyclohexyl-(2',6'-dimethoxy-biphenyl-2-yl)-phosphane, 3-chlorophenylboronic acid, K$_3$PO$_4$, toluene, 95° C. | 1.53 min. (B) | 502 (m + 1) |
| Intermediate 17-6 | 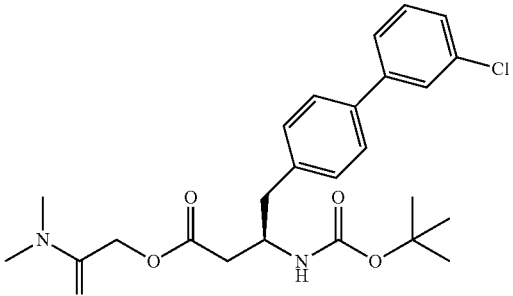<br>(R)-3-tert-Butoxycarbonylamino-4-(3'-chloro-biphenyl-4-yl)-butyric acid dimethylcarbamoyl methyl ester | Pd(PPh$_3$)$_4$, 3-chlorophenylboronic acid, K$_3$PO$_4$, DMF, 95° C. | 1.51 min. (B) | 475 (m + 1) |
| Intermediate 17-7 | 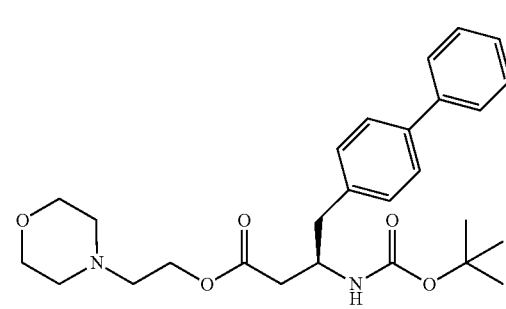<br>(R)-3-tert-Butoxycarbonylamino-4-(3'-chloro-biphenyl-4-yl)-butyric acid 2-morpholin-4-yl-ethyl ester | Pd(PPh$_3$)$_4$, 3-chlorophenylboronic acid, K$_3$PO$_4$, DMF, 95° C. | 1.51 min. (B) | 503 (m + 1) |

Intermediate 17-2

(R)-benzyl 3-(tert-butoxycarbonylamino)-4-(3'-chlorobiphenyl-4-yl)butanoate

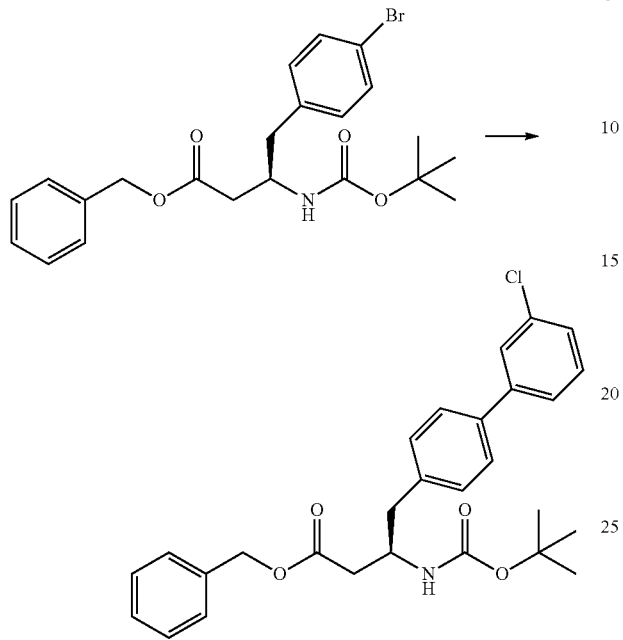

A suspension of give (R)-benzyl 4-(4-bromophenyl)-3-(tert-butoxycarbonylamino)butanoate (2.00 g, 4.46 mmol), 3-chlorophenylboronic acid (1.046 g, 6.69 mmol), Pd(PPh$_3$)$_4$ (0.515 g, 0.446 mmol) and Na$_2$CO$_3$aq (4.46 ml, 8.92 mmol) in Toluene (30 ml) is allowed to stir under nitrogen at 95° C. for 19 hr. The reaction mixture is cooled to ambient temperature, and diluted with brine and EtOAc. The products are extracted twice with EtOAc, washed with brine, dried over MgSO$_4$, filtered, and concentrated. The residue is purified by flash column chromatography on 90 g silica gel (eluent: heptane/EtOAc=100:0 to 65:35) to give (R)-benzyl 3-(tert-butoxycarbonylamino)-4-(3'-chlorobiphenyl-4-yl)butanoate (1.03 g); HPLC retention time=1.74 minutes (condition B); MS (ES+)=380.2 (m-BOC+2; 100%); 1H NMR (400 MHz, CHLOROFORM-d) δ ppm 1.40 (s, 9 H) 2.52 (A of ABX, J$_{ab}$=15.9 Hz, J$_{ax}$=5.8 Hz, 1 H) 2.58 (B of ABX, J$_{ab}$=15.9 Hz, J$_{bx}$=5.6 Hz, 1 H) 2.81-2.98 (m, 2 H) 4.19 (br s, 1 H) 5.07 (br d, 1 H) 5.12 (A of AB, J=12.3 Hz, 1 H) 5.17 (A of AB, J=12.3 Hz, 1 H) 7.20-7.22 (m, 2 H) 7.28-7.39 (m, 7 H) 7.42-7.47 (m, 3 H) 7.53-7.54 (m, 1 H).

Intermediate 18

Synthesis of (S)-benzyl 1-(2-tert-butoxy-2-oxoethyl)pyrrolidine-2-carboxylate

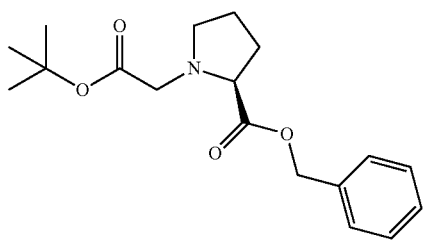 [SMILES: CC(C)(C)OC(=O)CN1CCC[C@H]1C(=O)OCc1ccccc1]

To a suspension of (S)-benzyl pyrrolidine-2-carboxylate hydrochloride (700 mg, 2.90 mmol) and K$_2$CO$_3$ (1201 mg, 8.69 mmol) in DMF (7 ml), t-butyl bromoacetate (0.535 ml, 3.62 mmol) is added. After stirring for 71 hours, aqueous K$_2$CO$_3$ (1.5 g of K$_2$CO$_3$/40 ml of H$_2$O) is added to the reaction mixture. The products are extracted with EtOAc. The organic layer is washed twice with water and once with brine, dried over K$_2$CO$_3$, filtered, and concentrated to give (S)-benzyl 1-(2-tert-butoxy-2-oxoethyl)pyrrolidine-2-carboxylate (458 mg); HPLC retention time=1.38 minutes (condition D); MS (m+1)=320.2; 1H NMR (400 MHz, CHLOROFORM-d) δ ppm 1.44 (s, 9 H) 1.81-2.03 (m, 3 H) 2.13-2.14 (m, 1 H) 2.82-2.88 (m, 1 H) 3.13-3.17 (m, 1 H) 3.46 (A of AB, J=17.3 Hz, 1 H) 3.49 (B of AB, J=17.3 Hz, 1 H) 3.73 (dd, J=8.8 and 4.8 Hz, 1 H) 5.15 (A of AB, J=12.4 Hz, 1 H) 5.17 (B of AB, J=12.4 Hz, 1 H) 7.29-7.38 (m, 5 H).

Intermediate 19

Synthesis of (R)-ethyl 3-(tert-butoxycarbonylamino)-4-(2',5'-dichlorobiphenyl-4-yl)butanoate

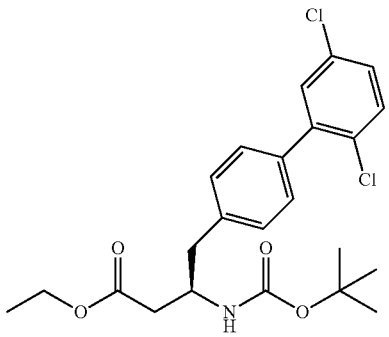 [SMILES: CCOC(=O)C[C@@H](Cc1ccc(-c2cc(Cl)ccc2Cl)cc1)NC(=O)OC(C)(C)C]

A mixture of (R)-ethyl 4-(4-bromophenyl)-3-(tert-butoxycarbonylamino)butanoate (1.005 g, 2.60 mmol), 2,5-dichlorophenylboronic acid (0.745 g, 3.90 mmol), Pd(PPh$_3$)$_4$ (0.301 g, 0.260 mmol) and 2 M aqueous Na$_2$CO$_3$ (2.60 ml, 5.20 mmol) in 1,2-dimethoxyethane (20 ml) is allowed to stir at 95° C. under nitrogen for 3 hours. The reaction mixture is cooled to room temperature and diluted with brine. The two phases are separated. The products are extracted twice with ethyl acetate (2×100 ml) from the aqueous layer. The combined organic layer is washed with brine, dried over MgSO$_4$, filtered, and concentrated under reduced pressure. The obtained residue is purified by silica gel flash column chromatography (heptane/EtOAc=100:0 to 70:30) to give (R)-ethyl 3-(tert-butoxycarbonylamino)-4-(2',5'-dichlorobiphenyl-4-yl)butanoate (1.09 g); HPLC retention time=1.50 minutes (condition B); MS (ES+)=352.00 (m-BOC+2; 100%); 1H NMR (400 MHz, CHLOROFORM-d) δ ppm 1.28 (t, J=7.1 Hz, 3 H) 1.41 (s, 9 H) 2.45-2.58 (m, 2 H) 2.85-3.00 (m, 2 H) 4.17 (t, J=7.1 Hz, 2 H) 4.20 (br s, 1 H) 5.06-5.08 (m, 1 H) 7.23-7.28 (m, 3 H) 7.31-7.40 (m, 4 H).

Intermediate 20

Synthesis of (R)-3-amino-4-(3'-chlorobiphenyl-4-yl)butanoic acid hydrochloride

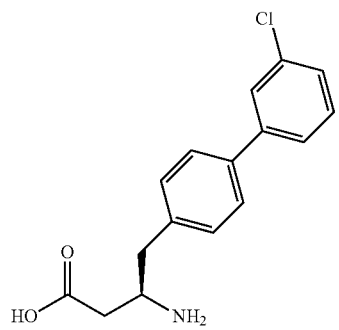 [SMILES: N[C@@H](CC(=O)O)Cc1ccc(-c2cccc(Cl)c2)cc1]

A solution of (R)-benzyl 3-(tert-butoxycarbonylamino)-4-(3'-chlorobiphenyl-4-yl)butanoate (152 mg, 0.317 mmol) and 1 M aqueous NaOH (1.583 ml, 1.583 mmol) in a mixed solvent of MeOH (0.3 ml) and THF (3 ml) is allowed to stir for 2 hours. The reaction is quenched with 1M aqueous HCl (2.5 ml). The products are extracted with EtOAc. The organic layer is dried over Na$_2$SO$_4$, filtered, and concentrated to give crude.

To the crude, a solution of 4 M HCl in 1,4-dioxane (1.583 ml, 6.33 mmol) is added. After stirring for 1 h, the precipitated solid is collected, and dried under reduced pressure to give (R)-3-amino-4-(3'-chlorobiphenyl-4-yl)butanoic acid hydrochloride (60.2 mg) as a white solid; HPLC retention time=0.52 minutes (condition B); MS (m+1)=290.22; 1H NMR (400 MHz, CD$_3$OD) δ ppm 2.58-2.74 (m, 2 H) 2.99-3.11 (m, 2 H) 3.80-3.85 (m, 1 H) 7.34-7.45 (m, 4 H) 7.54-7.57 (m, 1 H) 7.62-7.65 (m, 3 H).

Intermediate 21

Synthesis of a mixture of 1-(2-(benzyloxy)-2-oxoethyl)cyclopentanecarboxylic acid and 2-(1-(benzyloxycarbonyl)cyclopentyl)acetic acid

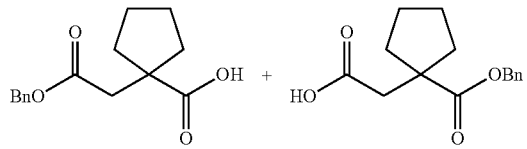 [SMILES: O=C(CC1(C(=O)O)CCCC1)OCc1ccccc1 ; O=C(O)CC1(C(=O)OCc2ccccc2)CCCC1]

A solution of 2-oxaspiro[4.4]nonane-1,3-dione (3 g, 19.46 mmol) and benzyl alcohol (2.023 ml, 19.46 mmol) in toluene (2 ml) is allowed to stir at 100° C. for 19 hours. The reaction mixture is cooled to ambient temperature and concentrated to give 6:1 mixture of 1-(2-(benzyloxy)-2-oxoethyl)cyclopentanecarboxylic acid and 2-(1-(benzyloxycarbonyl)cyclopentyl)acetic acid (4.89 g); 1H NMR (400 MHz, CHLOROFORM-d) δ ppm 1.60-1.78 (m, 6 H) 2.19-2.24 (m, 2 H) 2.75 (s, 2 H) 5.11 (s, 2 H, major isomer) 5.13 (s, 2 H, minor isomer) 7.30-7.37 (m, 5 H).

Intermediate 22

Synthesis of tert-butyl 4-(biphenyl-4-yl)-3-(tert-butoxycarbonylamino)butanoate

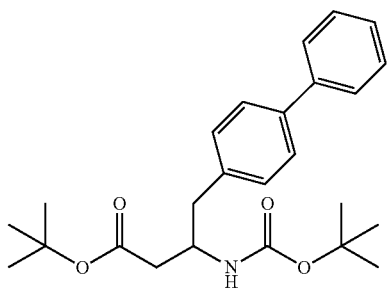 [SMILES: CC(C)(C)OC(=O)CC(Cc1ccc(-c2ccccc2)cc1)NC(=O)OC(C)(C)C]

A solution of 4-(biphenyl-4-yl)-3-(tert-butoxycarbonylamino)butanoic acid (250 mg, 0.703 mmol), tBuOH (0.135 ml, 1.407 mmol), EDCI (270 mg, 1.407 mmol) and 4-dimethylaminopyridine (86.0 mg, 0.704 mmol) in DCM (7 ml) is allowed to stir at room temperature under nitrogen for 62 hours. The reaction is quenched with water, and the organic layer is separated and concentrated. The residue is purified by flash column chromatography on silica gel to give tert-butyl 4-(biphenyl-4-yl)-3-(tert-butoxycarbonylamino)butanoate (110 mg); HPLC retention time=1.77 minutes (condition B); MS (ES+)=412.1 (m+1) 300.0 (m-tBux2+3; 100%); 1H NMR (400 MHz, CHLOROFORM-d) δ ppm 1.41 (s, 9 H) 1.47 (s, 9 H) 2.36 (A of ABX, J$_{ab}$=15.5 Hz, J$_{ax}$=6.2 Hz, 1 H) 2.44 (B of ABX, J$_{ab}$=15.5 Hz, J$_{bx}$=5.6 Hz) 2.82-2.94 (m, 2 H) 4.11-4.17 (m, 1 H) 5.08-5.10 (m, 1 H) 7.25-7.34 (m, 3H) 7.41-7.44 (m, 2 H) 7.51-7.58 (m, 4 H).

Intermediate 23

Synthesis of ethyl 3-amino-4-(3'-chloro-3-fluorobiphenyl-4-yl)butanoate

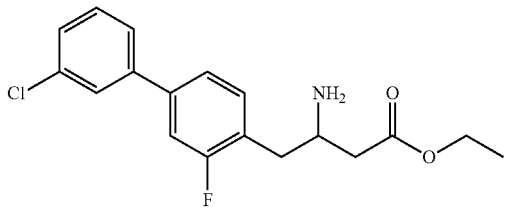 [SMILES: CCOC(=O)CC(N)Cc1ccc(-c2cccc(Cl)c2)cc1F]

A suspension of zinc (479 mg, 7.33 mmol) and 1,2-dibromoethane (0.032 ml, 0.366 mmol) in THF (8 ml) is heated at 70° C. under nitrogen then a few drops of ethyl bromoacetate is added. After stirring for 20 min, a solution of 2-(3'-chloro-3-fluorobiphenyl-4-yl)acetonitrile (300 mg, 1.221 mmol) in THF (2 ml) is added in one portion. The remaining bromoacetate is added dropwise over 50 min (total amount of ethyl bromoacetate: 4.88 mmol). After stirring for 15 min at the same temperature, the reaction mixture is cooled to ambient temperature. To the reaction mixture, sodium triacetoxyborohydride (2588 mg, 12.22 mmol) and AcOH (8 ml) are added. The reaction mixture is allowed to stir for 13 hours, and concentrated to give crude. The crude is diluted with EtOAc, and 2M aqueous Na$_2$CO$_3$ is added to be pH of 10. The products are extracted with EtOAc. The organic layer is dried over K$_2$CO$_3$, filtered, and concentrated to give crude. The resulting residue is purified by preparative HPLC using a gradient of 20% MeCN/water (0.1% NH$_4$OH) to 100% MeCN to give ethyl 3-amino-4-(3'-chloro-3-fluorobiphenyl-4-yl)butanoate (148 mg) as orange oil; HPLC retention time=0.85 minutes (condition B); MS (m+1)=336.13; 1H NMR (400 MHz, CHLOROFORM-d) δ ppm 1.27 (t, J=7.1 Hz, 3 H) 2.36 (A of ABX, J$_{ab}$=15.9 Hz, J$_{ax}$=8.8 Hz, 1 H) 2.52 (B of ABX, J$_{ab}$=15.9 Hz, J$_{bx}$=4.0 Hz, 1 H) 2.71-2.76 (m, 1 H) 2.82-2.87 (m, 1 H) 3.51-3.57 (m, 1 H) 4.15 (d, J=7.1 Hz, 2 H) 7.24-7.39 (m, 5 H) 7.42-7.44 (m, 1 H) 7.54-7.55 (m, 1 H).

Intermediate 24

Synthesis of 2-(3'-chloro-3-fluorobiphenyl-4-yl)acetonitrile

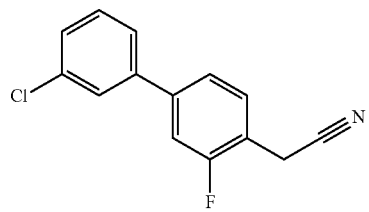 [SMILES: N#CCc1ccc(-c2cccc(Cl)c2)cc1F]

A suspension of 4-bromo-2-fluorobenzyl cyanide (3.50 g, 16.35 mmol), 3-chlorobenzeneboronic acid (2.68 g, 17.17 mmol), Pd(OAc)₂ (0.110 g, 0.491 mmol), K₂CO₃ (5.65 g, 40.9 mmol) and tetrabutylammonium bromide (5.80 g, 17.99 mmol) in water (14 ml) is allowed to stir under nitrogen at 70° C. for 1 hour. The reaction mixture is cooled to room temperature, and diluted with EtOAc. The two phases are separated. The organic layer is washed with brine, dried over MgSO₄, filtered and concentrated. The obtained residue is purified by silica gel flash column chromatography (heptane/EtOAc=100:0 to 70:30) to give 2-(3'-chloro-3-fluorobiphenyl-4-yl)acetonitrile (3.52 g); HPLC retention time=1.17 minutes (condition B); 1H NMR (400 MHz, CHLOROFORM-d) δ ppm 3.81 (s, 2 H) 7.29-7.45 (m, 5 H) 7.50-7.55 (m, 2 H).

Intermediate 25

(R)-tert-butyl 4-(1-(4-bromophenyl)-4-ethoxy-4-oxobutan-2-ylamino)-4-oxobutanoate

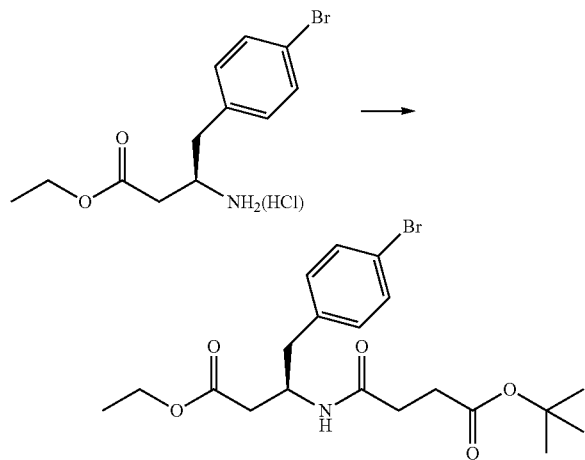

To a solution of 4-tert-butoxy-4-oxobutanoic acid (2.38 g, 13.64 mmol) in DMF (30 mL) and DCM (30 mL) is added (R)-ethyl 3-amino-4-(4-bromophenyl)butanoate hydrochloride (4 g, 12.4 mmol), HATU (5.19 g, 13.64 mmol), and TEA (6.91 mL, 49.6 mmol). After stirring at room temperature for 2 hours, the reaction is quenched with H₂O, and the crude is diluted with EtOAc, the organic layer is washed with brine, dried over Na₂SO₄, filtered, and concentrated under reduced pressure to give (R)-tert-butyl 4-(1-(4-bromophenyl)-4-ethoxy-4-oxobutan-2-ylamino)-4-oxobutanoate (4.0 g). HPLC retention time=1.70 minutes (condition A); MS (m+1)=444.1.

Intermediate 26

(R)-3-amino-4-(5'-fluoro-2'-methoxy-biphenyl-4-yl)-butyric acid ethyl ester hydrochloride salt

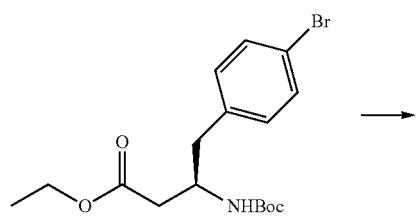

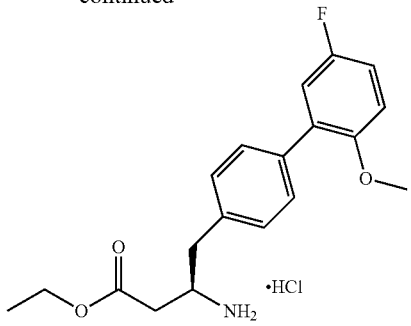

To a solution of (R)-ethyl 4-(4-bromophenyl)-3-(tert-butoxycarbonylamino)butanoate, (3.12 g, 8.08 mmol), and 5-fluoro-2-methoxyphenylboronic acid (2.2 g, 12.93 mmol) in toluene (52 mL) and is added PdCl₂(dppf)CH₂Cl₂ adduct (0.66 g, 0.81 mmol) and 2M aq. Na₂CO₃ (8.1 mL, 16.16 mmol). After stirring at 95° C. under nitrogen for 4 hours, the solution is cooled to ambient temperature and then quenched with ice water. The crude is diluted with ethyl acetate. The organic layer is washed with brine, dried over Na₂SO₄, filtered, and concentrated under reduced pressure. The obtained residue is purified by flash column chromatography on silica gel (eluent: heptane/EtOAc=100:0 to 50:50) to give (R)-ethyl 3-(tert-butoxycarbonylamino)-4-(5'-fluoro-2'-methoxybiphenyl-4-yl)butanoate (2.86 g). HPLC retention time=1.80 minutes (condition A); MS (m+1)=432.2; 1H NMR (400 MHz, CHLOROFORM-d) δ ppm 1.31 (t, J=7.1 Hz, 3 H) 1.45 (s, 9 H) 2.45-2.65 (m, 2 H) 2.83-2.94 (m, 1 H) 2.94-3.09 (m, 1 H) 3.80 (s, 3 H) 4.20 (q, J=7.2 Hz, 2 H) 4.24-4.33 (m, 1 H) 5.11 (br. s., 1 H) 6.90-6.96 (m, 1 H) 7.00 (dd, J=7.8, 3.3 Hz, 1 H) 7.06 (dd, J=9.2, 3.2 Hz, 1 H) 7.27 (d, J=7.8 Hz, 2 H) 7.49 (d, J=7.8 Hz, 2 H)

A solution of (R)-ethyl 3-(tert-butoxycarbonylamino)-4-(5'-fluoro-2'-methoxybiphenyl-4-yl)butanoate, (2.86 g, 6.62 mmol) in 4M HCl in 1,4-dioxane (33.1 ml, 132 mmol) is stirred at room temperature. After stirring for 1 hour, the reaction mixture is concentrated under reduced pressure to give (R)-ethyl 3-amino-4-(5'-fluoro-2'-methoxybiphenyl-4-yl)butanoate hydrochloride salt (2.44 g). HPLC retention time=1.46 minutes (condition A); MS (m+1)=332.3; 1H NMR (400 MHz, CHLOROFORM-d) δ ppm 1.15 (t, J=6.4 Hz, 3 H) 2.66-2.77 (m, 1 H) 2.78-2.91 (m, 1 H) 2.94-3.10 (m, 1 H) 3.42-3.53 (m, 1 H) 3.67 (s, 3 H) 3.83-3.96 (m, 1 H) 4.07 (q, J=6.8 Hz, 2 H) 6.77-6.84 (m, 1 H) 6.87-6.96 (m, 2 H) 7.23 (d, J=7.1 Hz, 2 H) 7.38 (d, J=7.1 Hz, 2 H) 8.64 (br. s., 2 H)

Intermediate 27

(R)-ethyl 4-(3'-chlorobiphenyl-4-yl)-3-(2-ethoxy-2-oxoacetamido)butanoate

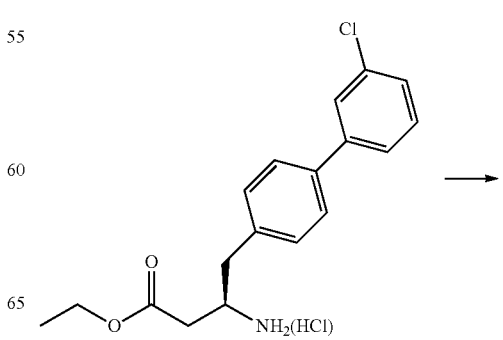

-continued

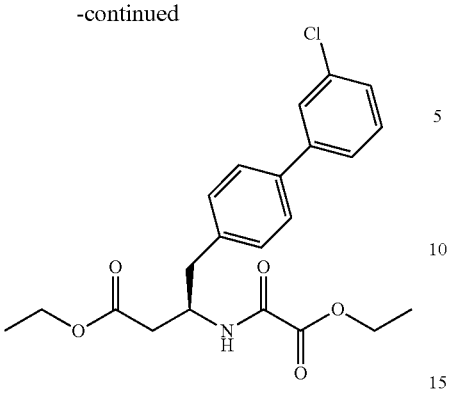

To a solution of (R)-ethyl 3-amino-4-(3'-chlorobiphenyl-4-yl)butanoate hydrochloride (500 mg, 1.57 mmol) in DMF (11 mL) is added TEA (0.23 mL, 1.65 mmol) and ethyl 2-chloro-2-oxoacetate (0.18 mL, 1.57 mmol) at room temperature. After stirring for 1 hour at room temperature, the reaction is quenched with $H_2O$, and the crude is diluted with EtOAc. The organic layer is washed with brine, dried over $Na_2SO_4$, filtered, and concentrated under reduced pressure. The obtained residue is purified by flash column chromatography on silica gel (eluent: heptane/EtOAc=70:30 to 50:50) to give (R)-ethyl 4-(3'-chlorobiphenyl-4-yl)-3-(2-ethoxy-2-oxoacetamido)butanoate (550 mg). HPLC retention time=1.88 minutes (condition A); MS (m+1)=418.3

Intermediate 28

(R)-ethyl 4-(3'-chlorobiphenyl-4-yl)-3-(2-hydrazinyl-2-oxoacetamido)butanoate

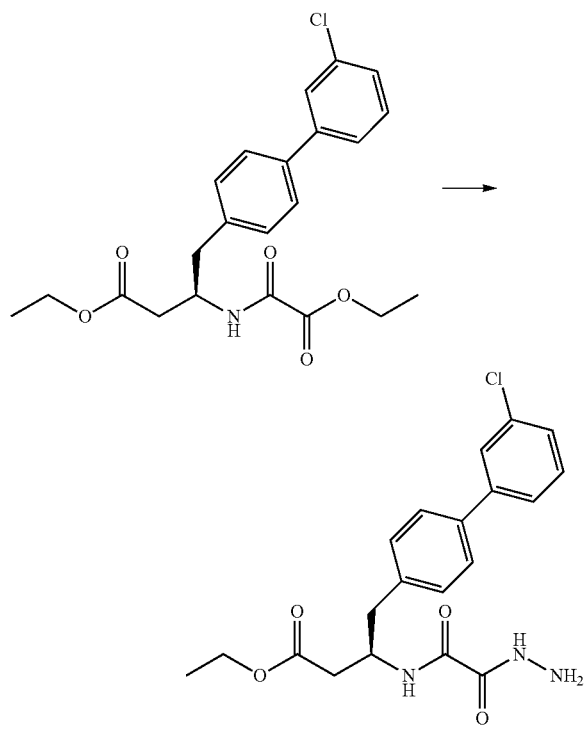

To a solution of (R)-ethyl 4-(3'-chlorobiphenyl-4-yl)-3-(2-ethoxy-2-oxoacetamido)butanoate (450 mg, 1.08 mmol) in MeOH (24 mL) is added a solution of 50% wt hydrazine (0.068 ml, 1.08 mmol) in MeOH (10 mL) at −20° C. After stirring for 18 hours at room temperature, the reaction mixture is concentrated under reduced pressure to give (R)-ethyl 4-(3'-chlorobiphenyl-4-yl)-3-(2-hydrazinyl-2-oxoacetamido)butanoate (412 mg). HPLC retention time=1.76 minutes (condition A); MS (m+1)=404.1

Intermediate 29

(R)-ethyl 4-(3'-chlorobiphenyl-4-yl)-3-(2-methoxythiazole-5-carboxamido)butanoate

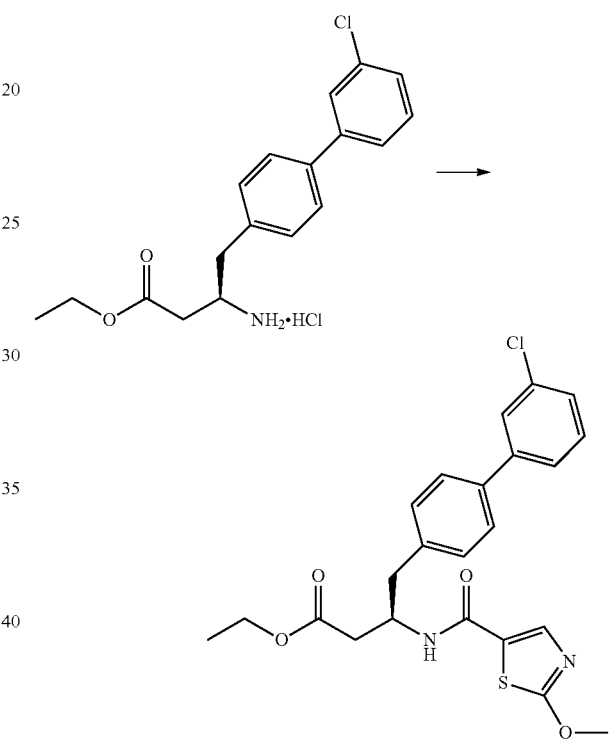

To a solution of 2-methoxythiazole-5-carboxylic acid (80 mg, 0.50 mmol) and (R)-ethyl 3-amino-4-(3'-chlorobiphenyl-4-yl)butanoate hydrochloride (160 mg, 0.45 mmol) in DMF (5 mL) is added HATU (207 mg, 0.55 mmol) and TEA (276 mg, 2.73 mmol). The crude is stirred at room temperature for 2 hrs. The crude is neutralized with 1 N HCl and diluted in water and EtOAc. The organic layer is washed with brine, dried over $MgSO_4$, filtered, and concentrated. The crude is purified via flash chromatography using 30% EtOAc/heptane to 70% EtOAc/heptane to give (R)-ethyl 4-(3'-chlorobiphenyl-4-yl)-3-(2-methoxythiazole-5-carboxamido)butanoate (170 mg). HPLC retention time=1.97 minutes (condition D); MS (m+1)=459.1. 1H NMR (400 MHz, CHLOROFORM-d) δ ppm 1.29 (t, J=7.1 Hz, 3 H) 2.49-2.69 (m, 2 H) 2.93 (dd, J=13.6, 8.1 Hz, 1 H) 3.10 (dd, J=13.5, 6.2 Hz, 1 H) 4.09 (s, 3 H) 4.00-4.15 (m, 2 H) 4.53-4.69 (m, 1 H) 6.78 (d, J=8.6 Hz, 1 H) 7.25-7.32 (m, 3 H) 7.35 (t, J=7.71 Hz, 1 H) 7.44 (dt, J=7.6, 1.5 Hz, 1 H) 7.48-7.54 (m, 3 H) 7.55 (t, J=1.8 Hz, 1 H).

Intermediate 30

(R)-ethyl 4-(3'-chlorobiphenyl-4-yl)-3-(2-methoxy-oxazole-5-carboxamido)butanoate

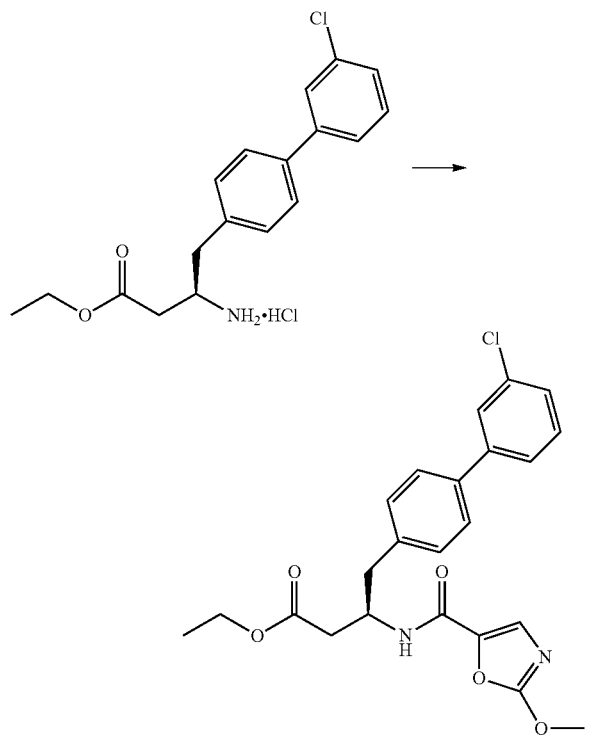

To a solution of 2-methoxyoxazole-5-carboxylic acid, intermediate 16, (98 mg, 0.69 mmol) and (R)-ethyl 3-amino-4-(3'-chlorobiphenyl-4-yl)butanoate hydrochloride (210 mg, 0.57 mmol) in DMF (10 mL) and $CH_2Cl_2$ (4 mL) is added HATU (272 mg, 0.72 mmol) and TEA (0.50 mL, 3.58 mmol). The crude is stirred at room temperature for 2 hrs. The crude is quenched with water and diluted in EtOAc. The organic layer is washed with water 3×, brine, dried over $MgSO_4$, filtered, and concentrated. The crude is purified via flash chromatography using 30% EtOAc/heptane to 70% EtOAc/heptane to give (R)-ethyl 4-(3'-chlorobiphenyl-4-yl)-3-(2-methoxyoxazole-5-carboxamido)butanoate (122 mg). HPLC retention time=1.89 minutes (condition A); MS (m+1)=443.2; 1H NMR (400 MHz, CHLOROFORM-d) δ ppm 1.28 (t, J=7.1 Hz, 3 H), 2.52-2.66 (m, 2 H), 2.94 (dd, 1 H), 3.08 (dd, J=13.6, 6.3 Hz, 1 H), 4.12 (s, 3 H), 4.14-4.23 (m, 2 H), 4.60-4.71 (m, 1 H), 6.81 (d, J=8.8 Hz, 1 H), 7.25-7.32 (m, 3 H), 7.35 (t, J=7.7 Hz, 1 H), 7.42 (s, 1 H), 7.43-7.47 (m, 1 H), 7.48-7.54 (m, 2 H), 7.55 (t, J=1.6 Hz, 1 H).

Intermediate 31

6-(methylsulfonamido)nicotinic acid

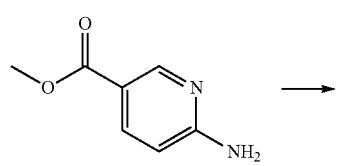

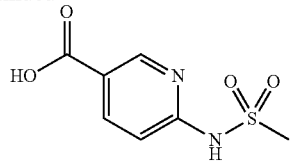

To a solution of methyl 6-aminonicotinate (1.0 g, 6.57 mmol) in $CH_2Cl_2$ (50 mL) with TEA (0.96 mL, 6.90 mmol) cooled in an ice bath is added MsCl (0.54 mL, 6.90 mmol) slowly. The crude is allowed to stir at room temperature for 2 hrs. The crude is then concentrated. The crude is dissolved in MeOH (20 mL) and to the crude is added 1 N NaOH (30 mL, 30 mmol). The crude is stirred at room temperature for 18 hrs. The crude is quenched with 1N HCl (32 mL, 32 mmol). The crude is concentrated to remove MeOH and some water is removed as well. The crude is diluted in $CH_2Cl_2$ and basified with 1 N NaOH (30 mL). The aq. layer is extracted with $CH_2Cl_2$. The aq. layer is acidified with concentrated HCl to bring the PH to 1 via PH paper indicator. The crude is diluted in EtOAc and the aq. layer is extracted with EtOAc. The combined organic layer is washed with brine, dried over MgSO4, filtered, and concentrated to give 6-(methylsulfonamido)nicotinic acid (421 mg) as a yellow solid. HPLC retention time=0.40 minutes (condition D); MS (m+1)=217.2.

Intermediate 32

2-methoxyoxazole-5-carboxylic acid

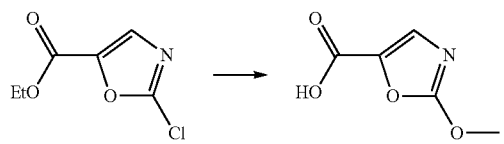

To a solution of ethyl 2-chlorooxazole-5-carboxylate (510 mg, 2.90 mmol) in anhdryous MeCN (10 mL) and anhydrous MeOH (10 mL) is added NaOMe (628 mg, 11.62 mmol). The crude is stirred at reflux for 2 hrs. To this crude is added additional MeOH. The crude is refluxed for another 4 hrs. The crude is concentrated and is redissolved in MeOH (10 mL). To this crude is added 1 N NaOH (10 ml). The crude is stirred at room temperature for 3 hrs. The crude is quenched with concentrated HCl, PH adjusted to 7 via PH paper indicator. The crude is concentrated and diluted in water. The aq. layer is acidified with concentrated HCl and diluted in EtOAc. The organic layer is washed with water, brine, dried over $MgSO_4$, filtered, and concentrated to give 2-methoxyoxazole-5-carboxylic acid (290 mg). HPLC retention time=0.58 minutes (condition D); MS (m+1)=144.0.

Intermediate 33 ethyl 5-oxo-4,5-dihydro-1,2,4-oxadiazole-3-carboxylate

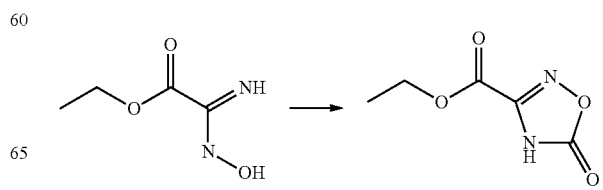

To a solution of ethyl 2-(hydroxyamino)-2-iminoacetate (2 g, 15.14 mmol) in dioxane (15.00 mL) is added CDI (2.7 g, 16.65 mmol) and DBU (2.5 ml, 16.65 mmol) at room temperature. After stirring for 1 hour at 80° C., the reaction is quenched with 1N HCl, and the crude is diluted with EtOAc. The organic layer is washed with brine, dried over Na$_2$SO$_4$, filtered and concentrated under reduced pressure to give ethyl 5-oxo-4,5-dihydro-1,2,4-oxadiazole-3-carboxylate (2.4 g). HPLC retention time=0.72 minutes (condition D); MS 159.1 (M+1).

Intermediate 34

5-oxo-4,5-dihydro-1,2,4-oxadiazole-3-carboxylic acid

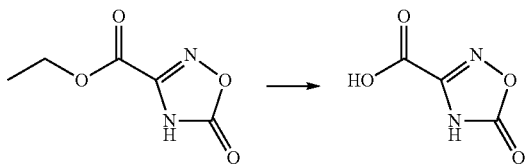

To a solution of crude ethyl 5-oxo-4,5-dihydro-1,2,4-oxadiazole-3-carboxylate (2.4 g, 15.14 mmol) in MeOH (2 mL) is added aqueous 1N NaOH (4 mL, 4 mmol) at room temperature. After stirring for 5 hours at room temperature the reaction is quenched with 1N HCl (5 mL, 5 mmol), the crude is concentrated under reduced pressure to remove MeOH. The crude is diluted with EtOAc, the organic layer is washed with brine, dried over Na$_2$SO$_4$, filtered and concentrated under reduced pressure to give 5-oxo-4,5-dihydro-1,2,4-oxadiazole-3-carboxylic acid (1.9 g).

Intermediate 35

2-oxo-2,3-dihydrooxazole-4-carboxylic acid

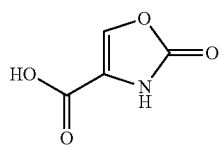

This intermediate is prepared according to: Okonya, J. F.; Hoffman, R. V.; Johnson, M. C.; *J. Org. Chem.* 2002, 67, 1102-1108.

Intermediate 36

3-hydroxyisothiazole-5-carboxylic acid

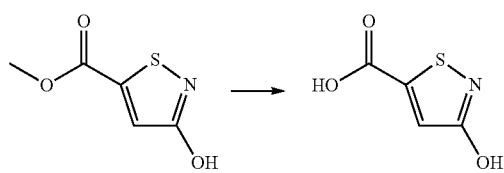

To a solution of methyl 3-hydroxyisothiazole-5-carboxylate (300 mg, 1.73 mmol) in MeOH (2 mL) is added 1N NaOH (6 mL, 6 mmol). After stirring at room temperature for 2 hours, the crude is concentrated under reduced pressure to remove MeOH and is diluted with EtOAc. The organic layer is washed with brine, dried over Na$_2$SO$_4$, filtered and concentrated under reduced pressure to give 3-hydroxyisothiazole-5-carboxylic acid (250 mg).

Intermediate 37 ethyl 2-vinyloxazole-5-carboxylate

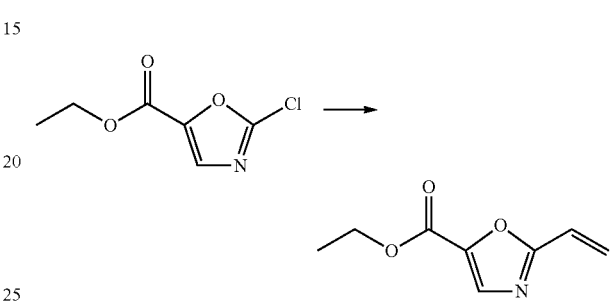

To a solution of tributyl(vinyl)stannane (1.1 mL, 3.83 mmol) and ethyl 2-chlorooxazole-5-carboxylate (546 mg, 3.11 mmol) in dioxane (37 mL) is added Pd(PPh$_3$)$_2$Cl$_2$ (222 mg, 0.32 mmol) at room temperature. After stirring at 100° C. under nitrogen for 4 hours, the solution is cooled to ambient temperature and then quenched with H$_2$O. The crude is diluted with EtOAc, the organic layer is washed with brine, dried over Na$_2$SO$_4$, filtered and concentrated under reduced pressure. The obtained residue is purified by flash column chromatography (eluent: heptane/EtOAc=90:10 to 80:20) to give ethyl 2-vinyloxazole-5-carboxylate (470 mg). HPLC retention time=0.39 minutes (condition B); MS (m+1)= 168.2; 1H NMR (400 MHz, CD$_3$OD) δ ppm 1.38 (t, J=7.1 Hz, 3 H) 4.38 (q, J=7.2 Hz, 2 H) 5.88 (d, J=11.4 Hz, 1 H) 6.39 (d, J=17.7 Hz, 1 H) 6.69 (dd, J=17.6, 11.2 Hz, 1 H) 7.83 (s, 1 H)

Intermediate 38 ethyl 2-ethyloxazole-5-carboxylate

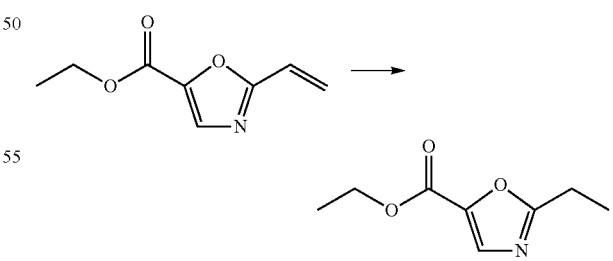

To a solution of ethyl 2-vinyloxazole-5-carboxylate (470 mg, 2.81 mmol) in MeOH (7 mL) is added 10% wt. Pd/C (100 mg, 0.094 mmol) at room temperature. After stirring at room temperature under a balloon of hydrogen for 1 hour, the crude is filtered to remove Pd/C. The filtrate is collected and concentrated to give ethyl 2-ethyloxazole-5-carboxylate (470 mg). HPLC retention time=1.09 minutes (condition A); MS (m+1)=170.3; 1H NMR (400 MHz, CD$_3$OD) δ ppm 1.35 (t, J=7.6 Hz, 3 H) 1.36 (t, J=7.2 Hz, 3 H) 2.87 (q, J=7.7 Hz, 2 H) 4.35 (q, J=7.2 Hz, 2 H) 7.71 (s, 1 H)

Intermediate 39

2-ethyloxazole-5-carboxylic acid

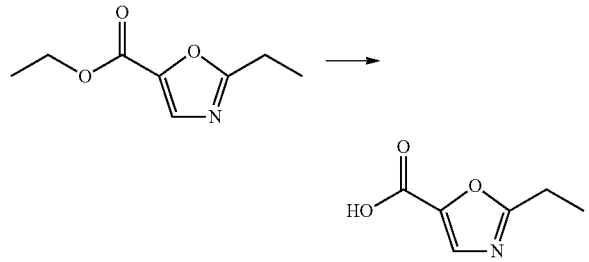

To a solution of 2-ethyloxazole-5-carboxylate (470 mg, 2.81 mmol) in MeOH (10 mL) is added 1N NaOH (6 mL, 6 mmol). After stirring at room temperature for 18 hours, the crude is concentrated under reduced pressure to remove MeOH and is diluted with EtOAc. The organic layer is washed with brine, dried over Na$_2$SO$_4$, filtered and concentrated under reduced pressure to give 2-ethyloxazole-5-carboxylic acid (244 mg). 1H NMR (400 MHz, CD$_3$OD) δ ppm 1.36 (t, J=7.7 Hz, 3 H) 2.89 (q, J=7.6 Hz, 2 H) 5.15 (br. s., 1 H) 7.69 (s, 1 H)

Intermediate 40 ethyl 2-vinylthiazole-5-carboxylate

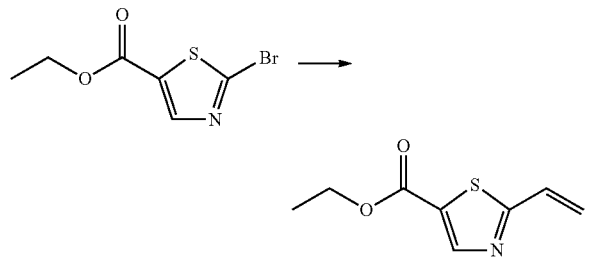

To a solution of tributyl(vinyl)stannane (0.92 mL, 3.14 mmol) and ethyl 2-bromothiazole-5-carboxylate (0.38 mL, 2.54 mmol) in dioxane (33 mL) is added Pd(PPh$_3$)$_2$Cl$_2$ (182 mg, 0.26 mmol) at room temperature. After stirring at 100° C. under nitrogen for 4 hours, the solution is cooled to ambient temperature and then quenched with H$_2$O. The crude is diluted with EtOAc, the organic layer is washed with brine, dried over Na$_2$SO$_4$, filtered and concentrated under reduced pressure. The obtained residue is purified by flash column chromatography on silica gel (eluent: heptane/EtOAc=90:10 to 80:20) to give ethyl 2-vinylthiazole-5-carboxylate (418 mg). HPLC retention time=0.45 minutes (condition B); MS (m+1)=184.1; 1H NMR (400 MHz, CD$_3$OD) δ ppm 1.37 (t, J=7.2 Hz, 3 H) 4.35 (q, J=7.1 Hz, 2 H) 5.71 (d, J=10.9 Hz, 1 H) 6.24 (d, J=17.4 Hz, 1 H) 6.93 (dd, J=17.4, 10.9 Hz, 1 H) 8.29 (s, 1 H)

Intermediate 41 ethyl 2-ethylthiazole-5-carboxylate

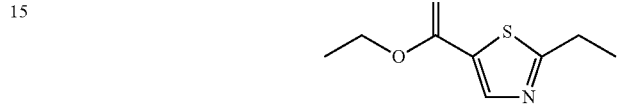

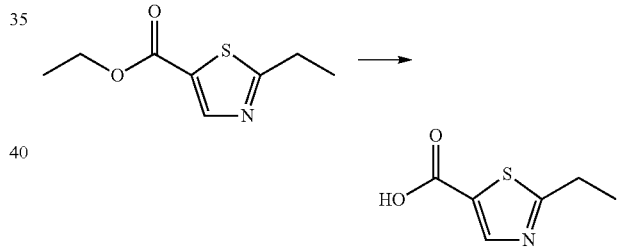

To a solution of ethyl 2-vinylthiazole-5-carboxylate (400 mg, 2.18 mmol) in MeOH (7 mL) is added 10% wt. Pd/C (267 mg, 0.25 mmol) at room temperature. After stirring at room temperature under a balloon of hydrogen for 1 hour, the crude is filtered to remove Pd/C. The filtrate is concentrated to give ethyl 2-ethylthiazole-5-carboxylate (404 mg). HPLC retention time=0.60 minutes (condition B); MS (m+1)=186.3; 1H NMR (400 MHz, CD$_3$OD) δ ppm 1.35 (t, J=7.3 Hz, 2 H) 1.39 (t, J=7.20 Hz, 2 H) 3.07 (q, J=7.58 Hz, 2 H) 4.35 (q, J=7.16 Hz, 2 H) 8.22 (s, 1 H)

Intermediate 42

2-ethylthiazole-5-carboxylic acid

To a solution of ethyl 2-ethylthiazole-5-carboxylate (400 mg, 2.159 mmol) in MeOH (10 mL) is added 1N NaOH (6 mL, 6 mmol) After stirring at room temperature for 18 hours, the crude is concentrated under reduced pressure to remove MeOH. The crude is diluted with EtOAc, the organic layer is washed with brine, dried over Na$_2$SO$_4$, filtered and concentrated under reduced pressure to give 2-ethylthiazole-5-carboxylic acid (282.4 mg). HPLC retention time=0.78 minutes (condition D); MS (m+3)=160.4; 1H NMR (400 MHz, CD$_3$OD) δ ppm 1.40 (t, J=7.6 Hz, 3 H) 3.07 (q, J=7.6 Hz, 2 H) 5.08 (br. s., 1 H) 8.20 (s, 1 H).

Intermediate 43

3-Hydroxy-isoxazole-5-carboxylic acid

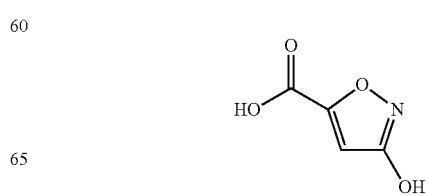

To a solution of 3-hydroxy-isoxazole-5-carboxylic acid methyl ester (286 mg, 2.0 mmol) in methanol (7 mL) is added 1N NaOH (4.0 mL, 4.0 mmol) and the mixture is stirred at room temperature for 18 hrs. The solvent is removed under reduced pressure and 4.0 mL of 1N HCl is added to the residue. The resulting solution is lyophilized to give the product which is used as is in subsequent reactions.

Intermediate 44

5-Methoxycarbonylmethyl-furan-2-carboxylic acid

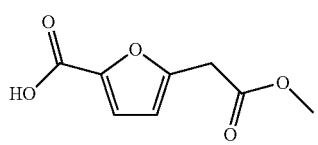

To a solution of 5-methoxycarbonylmethyl-furan-2-carboxylic acid methyl ester (250 mg, 1.26 mmol) in methanol (5 mL) is added 1N NaOH (2.78 mL, 2.78 mmol) and the mixture is stirred at room temperature for 18 hours. The solvent is removed under reduced pressure and 2.78 mL of 1N HCl is added to the residue. The resulting solution is lyophilized to give 5-carboxymethyl-furan-2-carboxylic acid.

Next, to a solution of the above diacid (220 mg, 1.29 mmol) in methanol (8 mL) is added Amberlyst-15 resin (50 mg) and the mixture is stirred at room temperature for 18 hours. The resin is filtered and the solvent is removed under reduced pressure to give the product which is used as is in subsequent reactions. 1H NMR (400 MHz, CHLOROFORM-d) δ ppm 3.75 (s, 3H), 3.82 (s, 2H), 6.45 (d, J=3.54 Hz, 1H), 7.29 (d, J=3.54 Hz, 1H), 10.17 (s, broad, 1H).

Intermediate 45

(R)-4-(3'-Chloro-biphenyl-4-yl)-3-isocyanato-butyric acid ethyl ester

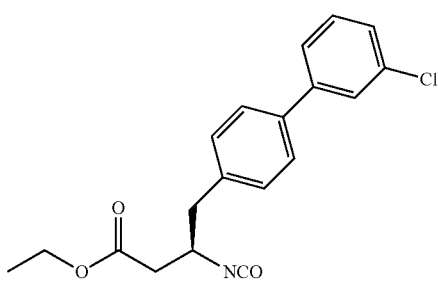

To a vigorously stirred mixture of 8% aqueous sodium bicarbonate (3 mL) and methylene chloride (3 mL) at 0° C. is added triphosgene (28.1 mg, 0.095 mmol) and the mixture is stirred at 0° C. for 5 minutes then Intermediate 17-1 (100 mg, 0.284 mmol) is added and stirring is continued for an additional 15 minutes. The organic layer is separated and dried over sodium sulfate. The solvent is removed under reduced pressure to give the title compound. This is used as is in subsequent reactions.

Intermediate 46

2-(4-Methoxy-benzyl)-2H-tetrazole-5-carbonyl chloride

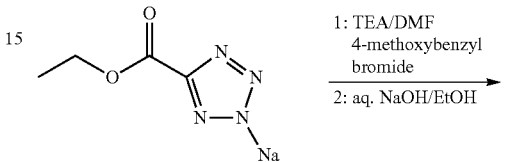

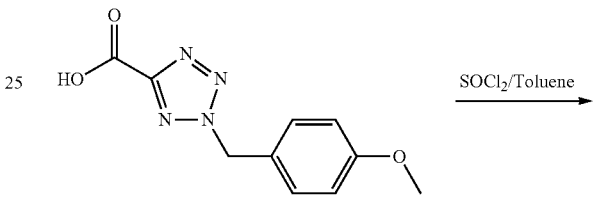

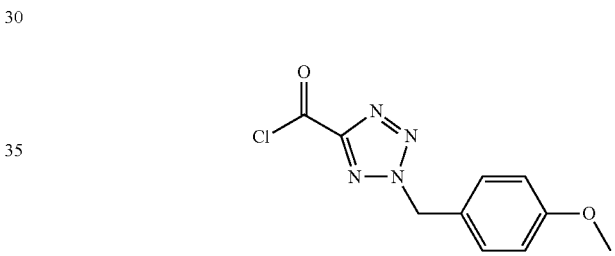

To a solution of 1H-tetrazole-5-carboxylic acid ethyl ester sodium salt (500 mg, 3.05 mmol) in DMF (5 ml) at room temperature is added 4-methoxybenzyl chloride (747 μl, 5.48 mmol) and TEA (1500 μl, 10.76 mmol). The reaction mixture is stirred at room temperature overnight. The reaction is added water and extracted with EtOAc. The combined organic layer is washed with brine and dried over anhydrous sodium sulfate, filtered and concentrated under reduced pressure. The residue is purified by column chromatography (10% to 30% EtOAc/Heptane). To a solution of the purified residue in EtOH (2 ml) at room temperature is added NaOH (2 ml, 2.000 mmol) and the mixture is stirred at room temperature. After stirring for 1 hour, the mixture is concentrated under reduced pressure to remove EtOH and extracted with EtOAC after being acidified to pH<5. The combined organic layer is washed with brine and dried over anhydrous sodium sulfate, filtered and concentrated under reduced pressure to give 2-(4-methoxy-benzyl)-2H-tetrazole-5-carboxylic acid.

Next, to a mixture of 2-(4-methoxy-benzyl)-2H-tetrazole-5-carboxylic acid in Toluene (15 ml) at room temperature is added SOCl₂ (1 ml, 13.70 mmol) and the mixture is heated at 80° C. for 3 hr. The reaction mixture is concentrated under reduced pressure to give the crude product, which is used without further purification.

Intermediate 47

(R)-3-Amino-4-(3'-chloro-biphenyl-4-yl)-butyric acid indan-5-yl ester

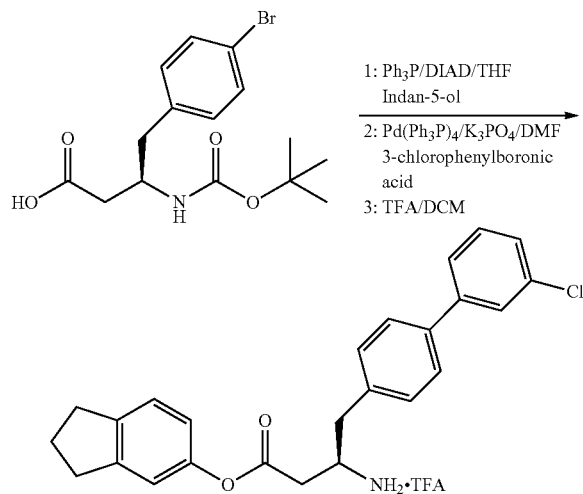

1: Ph₃P/DIAD/THF
   Indan-5-ol
2: Pd(Ph₃P)₄/K₃PO₄/DMF
   3-chlorophenylboronic acid
3: TFA/DCM To a suspension of boc-(R)-3-amino-4-(4-bromo-phenyl)-butanoic acid (500 mg, 1.396 mmol) in THF (12 ml) at room temperature is added 5-indanol (187 mg, 1.396 mmol) and Ph₃P (403 mg, 1.535 mmol). To the mixture at ice bath is added DIAD (0.326 ml, 1.675 mmol) and the mixture is stirred from ice bath to room temperature overnight. The reaction is concentrated under reduced pressure and purified by column chromatography (5% to 20% EtOAc/Heptane) to give 450 mg of solid. To a solution of the obtained solid (200 mg, 0.422 mmol) in DMF (5 ml) at room temperature is added 3-chlorophenylboronic acid (79 mg, 0.506 mmol), tripotassium phosphate (134 mg, 0.632 mmol) and Pd(PPh₃)₄ (48.7 mg, 0.042 mmol). The reaction is stirred at 100° C. overnight. The reaction is quenched by brine and is extracted with EtOAc. The combined organic layer is washed with brine and dried over anhydrous sodium sulfate, filtered and concentrated under reduced pressure. The residue is purified by column chromatography (5% to 30% EtOAc/Heptane). To the obtained residue (143 mg, 0.283 mmol) in DCM (1 ml) at room temperature is added TFA (1 mL, 12.98 mmol) and the mixture is stirred at room temperature for 2 hours. The mixture is concentrated to give the crude salt which is used directly without further purification. HPLC retention time=1.27 minutes (condition B); MS (m+1)=406.

Intermediate 48

(R)-4-Biphenyl-4-yl-3-ureido-butyric acid ethyl ester

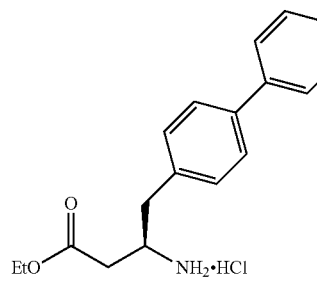

+

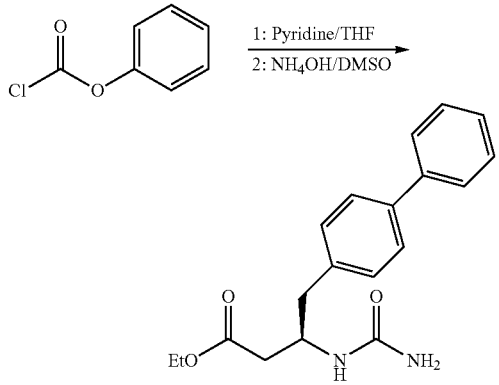

1: Pyridine/THF
2: NH₄OH/DMSO

To a suspension of (R)-3-amino-4-biphenyl-4-yl-butyric acid ethyl ester (200 mg, 0.625 mmol) in THF (10 ml) at 0° C. was added phenyl chloroformate (0.087 ml, 0.688 mmol) and pyridine (0.126 ml, 1.563 mmol). The mixture is stirred at 0° C. for 5 min then is warmed up to room temperature. LCMS monitored the reaction until it is complete. The reaction is extracted with EtOAc. The combined organic layer is washed with 1N HCl, H₂O, sat. aq. NaHCO₃ and brine and dried over anhydrous sodium sulfate, filtered and concentrated to give the crude residue.

Next, to a solution of the obtained residue (0.252 g, 0.625 mmol) in DMSO (1.5 ml) at room temperature is added ammonium hydroxide (0.027 ml, 0.688 mmol). The reaction is stirred at room temperature. 30 min LCMS showed small desired product with big starting material so more ammonium hydroxide is added and the reaction is stirred at room temperature overnight until the reaction is complete. The reaction is extracted with EtOAc. The combined organic layer is washed with H₂O, 1N HCl, H₂O, 1 N NaOH and brine and dried over anhydrous sodium sulfate, filtered and concentrated under reduced pressure. The residue is purified by column chromatography (2% to 6% EtOH/DCM) to give (R)-4-biphenyl-4-yl-3-ureido-butyric acid ethyl ester (169 mg). HPLC retention time=1.04 minutes (condition B); MS (m+1)=327.

Intermediate 49

(R)-3-amino-4-(3'-chloro-biphenyl-4-yl)-2-hydroxy-butyric acid methyl ester hydrochloride

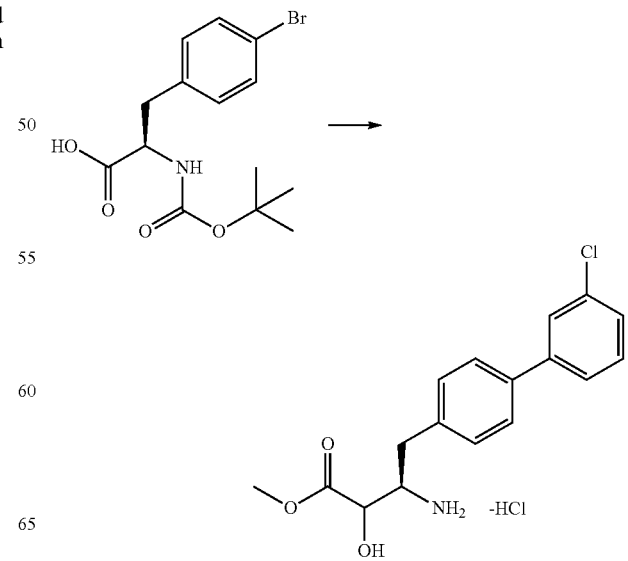

(R)-3-(4-Bromo-phenyl)-2-tert-butoxycarbonylamino-propionic acid (4.0 g, 11.6 mmol), 3-chlorophenylboronic acid (2.36 g, 15.11 mmol), Pd(PPh$_3$)$_4$ (0.067 g, 0.058 mmol) and 2M Na$_2$CO$_3$ aqueous solution (8.0 mL) are refluxed in 1,2-dimethoxyethane (70 mL) for 2.5 h under N$_2$ atmosphere. After cooling to room temperature, the reaction mixture is diluted with EtOAc and washed with 1M HCl and brine. The organic layer is dried over Na$_2$SO$_4$ and concentrated. The residue is purified by flash column chromatography (silica gel, DCM/10% MeOH in DCM=100:0 to 0:100). to give (R)-2-tert-butoxycarbonylamino-3-(3'-chloro-biphenyl-4-yl)-propionic acid (containing impurities). HPLC retention time=1.56 minutes (condition A): MS (m+1)=376.

This is dissolved in 1,2-dimethoxyethane (40 mL) and Et$_3$N (1.46 mL, 10.5 mmol) and ethyl chloroformate (1.00 mL, 10.5 mmol) are added. After being stirred at room temperature for 0.5 h, the resultant precipitate is removed by filtration. To the filtrate is slowly added NaBH$_4$ (0.44 g, 11.6 mmol) in H$_2$O (5 mL). After being stirred for 2 h, the reaction mixture is diluted with EtOAc and washed with H$_2$O and brine. The organic layer is dried over Na$_2$SO$_4$, concentrated and purified by flash column chromatography (silica gel, eluent; heptane/EtOAc=100:0 to 0:100) to give [(R)-2-(3'-chloro-biphenyl-4-yl)-1-hydroxymethyl-ethyl]-carbamic acid tert-butyl ester (2.8 g). HPLC retention time=1.26 minutes (condition A): MS (m+1-Boc)=262. 1 H-NMR (400 MHz, DMSO-d$_6$) δ ppm 1.43 (s, 9 H), 2.90 (d, 2 H, J=7.33 Hz), 3.60 (dd, 1 H, J=5.05, 10.86 Hz), 3.72 (dd, 1 H, J=3.79, 11.12 Hz), 3.91 (bs, 1 H), 4.75 (bs, 1 H), 7.29-7.34 (m, 3 H), 7.37 (t, 1 H, J=7.83 Hz), 7.44-7.48 (m, 1 H), 7.51 (d, 2 H, J=8.08 Hz), 7.57 (t, 1 H, J=1.77 Hz).

Next, to a solution of [(R)-2-(3'-chloro-biphenyl-4-yl)-1-hydroxymethyl-ethyl]-carbamic acid tert-butyl ester (2.0 g, 5.53 mmol) in DCM (30 mL) is added Dess-Martin periodinane (2.81 g, 6.63 mmol). After being stirred at room temperature for 2 h, the reaction mixture is diluted with EtOAc and washed with saturated NaHCO$_3$ aqueous solution and brine. The organic layer is dried over Na$_2$SO$_4$ and concentrated. The residue is purified by flash column chromatography (silica gel, eluent; heptane/EtOAc=100:0 to 0:100) to give [(R)-2-(3'-chloro-biphenyl-4-yl)-1-formyl-ethyl]-carbamic acid tert-butyl ester (1.05 g). HPLC retention time=1.27 minutes (condition A): MS (m+1)=360.

This is dissolved in MeOH (20 mL) and AcOH (0.199 mL, 3.47 mmol). To this solution KCN (0.226 g, 3.47 mmol) in H$_2$O (4 mL) is slowly added. After being stirred at room temperature overnight, the reaction mixture is diluted with EtOAc and washed with saturated NaHCO$_3$ aqueous solution, H$_2$O and brine. The organic layer is dried over Na$_2$SO$_4$ and concentrated. This is treated with 4M HCl in dioxane (20 mL) and MeOH (10 mL) at room temperature. After being stirred overnight, the reaction mixture is concentrated. The residue is dissolved in MeOH and treated with SOCl$_2$ (0.211 mL, 2.89 mmol). After being stirred at 50° C. for 5 h, the reaction mixture is concentrated to dryness. The residue is dissolved in THF (10 mL) and treated with saturated NaHCO$_3$ aqueous solution (5 mL) and Boc$_2$O (0.631 g, 2.89 mmol). After being stirred at room temperature for 2 h, the reaction mixture is diluted with EtOAc and washed with brine. The organic layer is dried over MgSO$_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-hydroxy-butyric acid methyl ester (0.61 g). HPLC retention time=1.01, 1.06 minutes (condition B): MS (m+1-Boc)=320. 1H-NMR (400 MHz, CDCl$_3$) δ ppm 1.40 (s, 9 H), 2.77-3.05 (m, 2 H), 3.63 (s, 0.7 H), 3.77 (s, 2.3 H), 4.11 (s, 0.8 H), 4.25-4.40 (m, 1.2 H), 4.78-4.95 (m, 1 H), 7.27-7.40 (m, 4 H), 7.42-7.58 (m, 4 H).

(R)-3-tert-butoxycarbonylamino-4-(3'-chloro-biphenyl-4-yl)-2-hydroxy-butyric acid methyl ester (113 mg, 0.269 mmol) is treated with 4M HCl in dioxane (2 mL). After being stirred at room temperature for 1 h, the reaction mixture is concentrated. The residue is used for a next step without further purification. HPLC retention time=1.22, 1.29 minutes (condition A): MS (m+1)=320.

Intermediate 50

(R)-3-amino-4-(3'-chloro-biphenyl-4-yl)-2-methoxy-butyric acid methyl ester hydrochloride

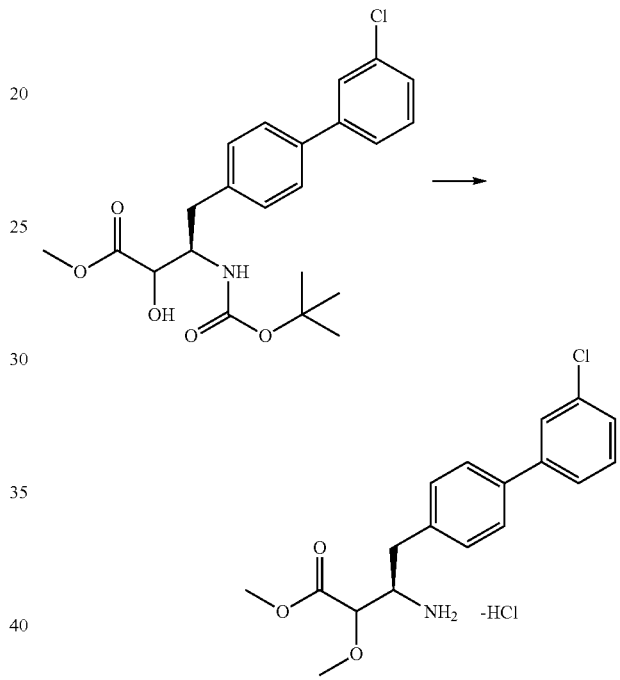

To a solution of (R)-3-tert-butoxycarbonylamino-4-(3'-chloro-biphenyl-4-yl)-2-hydroxy-butyric acid methyl ester (610 mg, 1.45 mmol) in CH$_3$CN (20 mL) are added iodomethane (0.545 mL, 8.72 mmol) and silver oxide (1.35 g, 5.81 mmol). After being stirred at room temperature for 16 h, additional iodomethane (0.545 mL, 8.72 mmol) and silver oxide (1.35 g, 5.81 mmol) are added and stirred for 3 days. The reaction mixture is filtered through celite pad and the filtrate is washed with brine. The organic layer is dried over MgSO$_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-methoxy-butyric acid methyl ester (500 mg). HPLC retention time=1.20, 1.25 minutes (condition B): MS (m+1-Boc)=334. 1H-NMR (400 MHz, CDCl$_3$) δ ppm 1.37, 1.41 (s, 9 H), 2.72-3.03 (m, 2 H), 3.43, 3.71 (s, 3H), 3.63-3.82 (m, 1 H), 4.27-4.41 (m, 1 H), 4.68-5.04 (m, 1 H), 7.28-7.40 (m, 4 H), 7.41-7.61 (m, 4 H).

(R)-3-tert-butoxycarbonylamino-4-(3'-chloro-biphenyl-4-yl)-2-methoxy-butyric acid methyl ester (200 mg, 0.461 mmol) is treated with 4M HCl in dioxane (3 mL). After being stirred at room temperature for 1 h, the reaction mixture is concentrated. The residue is used for a next step without further purification. HPLC retention time=1.26, 1.33 minutes (condition A): MS (m+1)=334.

Intermediate 51

(R)-3-amino-4-(3'-chloro-biphenyl-4-yl)-2-methoxy-butyric acid ethyl ester hydrochloride

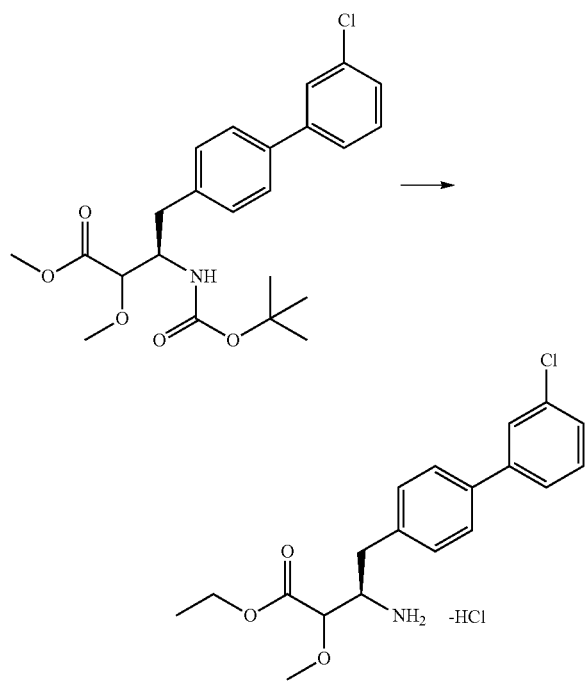

To a solution of (R)-3-amino-4-(3'-chloro-biphenyl-4-yl)-2-methoxy-butyric acid methyl ester (500 mg, 1.15 mmol) in MeOH (5 mL) is added 2M NaOH aqueous solution (5 mL). After being stirred at room temperature for 2 h, the reaction mixture is acidified with 2M HCl and extracted with EtOAc. The organic layer is dried over $Na_2SO_4$ and concentrated. The residue is dissolved in EtOH (5 mL) and treated with $SOCl_2$ (0.252 mL, 3.26 mmol). After being stirred at 55° C., the reaction mixture was cocentrated. The residue is used for a next step without further purification. HPLC retention time=1.49 minutes (condition A): MS (m+1)=348.2

Intermediate 52

(R)-3-Amino-4-(3'-chloro-biphenyl-4-yl)-2-fluoro-butyric acid methyl ester hydrochloride

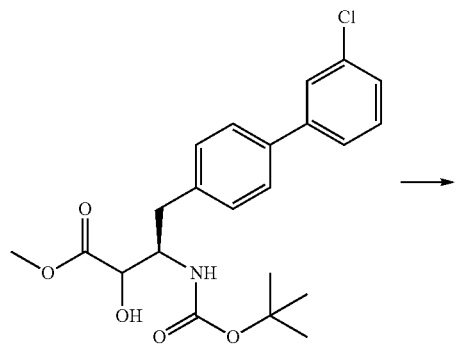

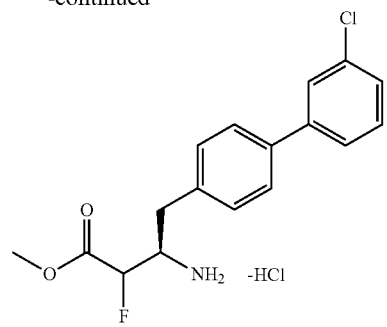

To a solution of (R)-3-tert-butoxycarbonylamino-4-(3'-chloro-biphenyl-4-yl)-2-hydroxy-butyric acid methyl ester (220 mg, 0.524 mmol) is added DAST (0.083 mL, 0.629 mmol) at 0° C. The reaction mixture is gradually warmed to room temperature and stirred for 1 h. Additional DAST (0.083 mL, 0.629 mmol) is added and stirred at room temperature for 2 h. The reaction mixture is diluted with EtOAc and washed with saturated $NaHCO_3$ aqueous solution and brine. The organic layer is dried over $Na_2SO_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-fluoro-butyric acid methyl ester (63 mg). HPLC retention time=1.36 minutes (condition B): MS (m+1-Boc)=322. 1H-NMR (400 MHz, $CDCl_3$) δ ppm 1.39 (s, 9 H), 2.84-2.95 (m, 2 H), 3.06 (bs, 0.5 H), 3.69 (s, 3 H), 4.43-4.61 (m, 1 H), 4.72-4.80 (m, 0.5 H), 5.00 (s, 0.5 H), 5.12 (s, 0.5 H), 7.28-7.34 (m, 3 H), 7.37 (t, 1 H, J=7.58 Hz), 7.42-7.47 (m, 1 H), 7.48-7.53 (m, 1 H), 7.55 (t, 1 H, J=2.02 Hz). 19F-NMR (377 MHz, $CDCl_3$) δ ppm −204.18.

(R)-3-tert-butoxycarbonylamino-4-(3'-chloro-biphenyl-4-yl)-2-fluoro-butyric acid methyl ester (60 mg, 0.142 mmol) is treated with 4M HCl in dioxane (1.5 mL). After being stirred at room temperature for 1 h, the reaction mixture is concentrated. The residue is used for a next step without further purification. HPLC retention time=0.88 minutes (condition B): MS (m+1)=322.

Intermediate 53-1

[(R)-1-(3'-chloro-biphenyl-4-ylmethyl)-3-methanesulfonylamino-3-oxo-propyl]-carbamic acid tert-butyl ester

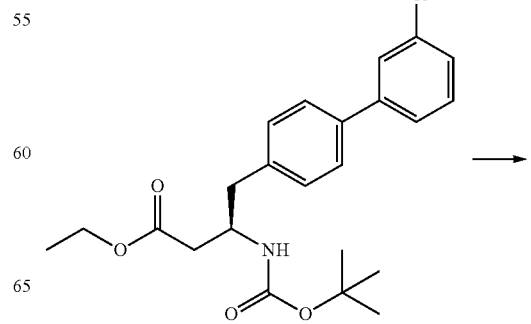

-continued

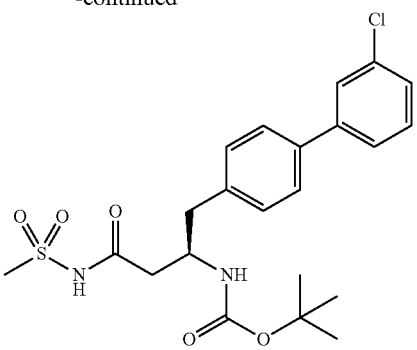

(R)-3-tert-butoxycarbonylamino-4-(3'-chloro-biphenyl-4-yl)-butyric acid ethyl ester (250 mg, 0.598 mmol) is treated with 2M NaOH aqueous solution (1 mL) in THF (1 mL) and EtOH (2 mL). After being stirred for 1 h, the reaction mixture is acidified with 1M HCl and extracted with EtOAc. The organic layer is washed with brine, dried over $Na_2SO_4$ and concentrated in vacuo. To a solution of this residue in DMF (2 mL) are added methylsulfonamide (85 mg, 0.897 mmol), EDC (172 mg, 0.897 mmol), HOAt (98 mg, 0.718 mmol), and $Et_3N$ (0.125 mL, 0.897 mmol). After being stirred at room temperature overnight, the reaction mixture is diluted with EtOAc, washed with 1M HCl and brine. The organic layer is dried over $Na_2SO_4$ and cocentrated. The residue is purified by flash column chromatography (silica gel, eluent: DCM/10% MeOH in DCM=100:0 to 0:100) to give [(R)-1-(3'-chloro-biphenyl-4-ylmethyl)-3-methanesulfonylamino-3-oxo-propyl]-carbamic acid tert-butyl ester (244 mg). HPLC retentions time=1.30 minutes (condition B); MS (m+1)=467; 1H NMR (400 Mz, DMSO-$d_6$) δ ppm 1.30 (s, 9 H), 2.41-2.48 (m, 2 H), 2.70-2.78 (m, 2 H), 3.18 (s, 3 H), 3.99-4.11 (m, 1 H), 7.28 (d, 2 H, J=8.34 Hz), 7.38-7.44 (m, 1 H), 7.48 (t, 1 H, J=7.83 Hz), 7.59-7.66 (m, 3 H), 7.69 (s, 1 H).

Following compounds are prepared using similar procedure as described in example 53-1:

| Example | Product | Reagent | HPLC-RT (condition) | MS (M + 1) |
|---|---|---|---|---|
| Example 53-2 | | | 1.22 min. (condition B) | 496 |
| Example 53-3 | | | 1.33 min. (condition B) | 544 |
| Example 53-4 | | $NH_4Cl$ | 1.17 min. (condition B) | 389 |

Intermediate 54-1

(R)-3-[2-(tert-butoxycarbonyl-ethoxycarbonylmethyl-amino)-propionylamino]-4-(3'-chloro-biphenyl-4-yl)-butyric acid ethyl ester

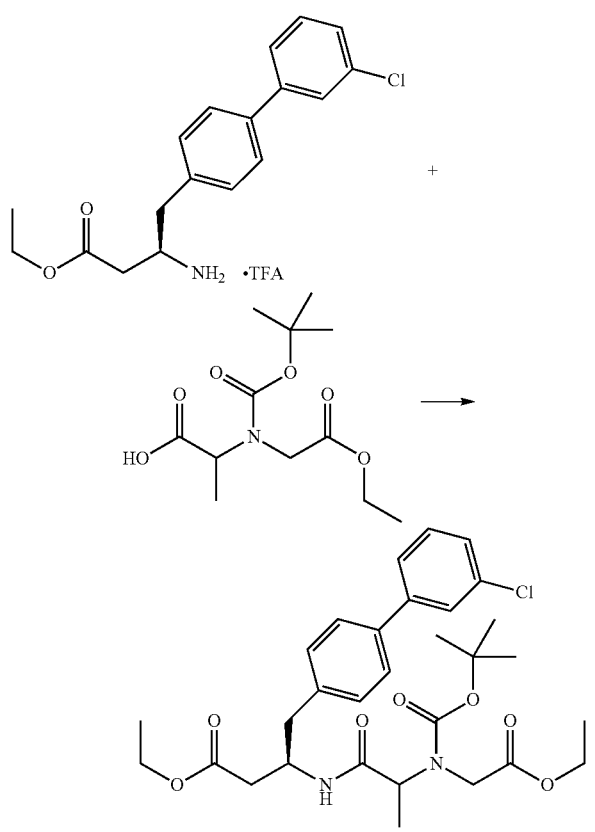

To a suspension of 2-(tert-butoxycarbonyl-ethoxycarbonylmethyl-amino)-propionic acid TFA salt (197 mg, 0.714 mmol) in THF (10 ml) at room temperature is added EDCI (219 mg, 1.142 mmol) and HOBT (164 mg, 1.071 mmol). The mixture is stirred at room temperature for 10 mins and then was added a solution of (R)-3-amino-4-(3'-chloro-biphenyl-4-yl)-butyric acid ethyl ester (202 mg, 0.571 mmol) in THF and TEA (0.199 ml, 1.428 mmol). The mixture is stirred at room temperature. Reverse phase HPLC [30 to 90% ACN—H₂O (0.1% TFA) over 10 min by X-Bridge phenyl column] give the title compound (290 mg, 71% yield). LCMS (condition B): 575 (M+1); retention time=1.52 min.

Intermediate 54-2

2-(tert-Butoxycarbonyl-ethoxycarbonylmethyl-amino)-propionic acid

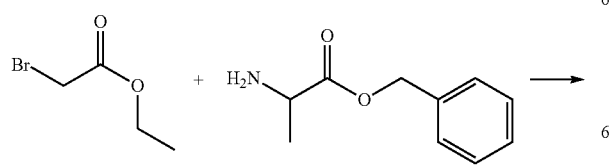

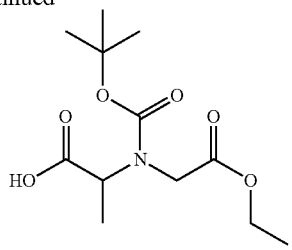

To a solution of H-DL-Ala-OBzl.p-tosylate (2.88 g, 8.20 mmol) in THF (80 ml) at room temperature was added TEA (3.43 ml, 24.60 mmol) and followed by ethyl bromoacetate (1.096 ml, 9.84 mmol). The reaction was stirred at room temperature over night. There were some white solid in the reaction. The reaction mixture was filtered off the white solid and concentrated for purification. Flash chromatography (silica gel, 2 to 4% EtOH/DCM) gave the title compound as an oil (1.7 g, 78% yield). LCMS (condition B): 266 (M+1); retention time=0.70 min.

Next, to a solution of 2-(ethoxycarbonylmethyl-amino)-propionic acid benzyl ester (1.7 g, 6.41 mmol) in DCM (80 ml) at 0° C. was added BOC-anhydride (2.232 ml, 9.61 mmol) and followed by TEA (2.68 ml, 19.22 mmol). The reaction mixture was slowly warmed up to room temperature and stirred over night. The reaction was quenched by brine and was extracted with DCM. The combined organic layer was washed with brine and dried over anhydrous sodium sulfate, filtered and concentrated to give the crude. Flash chromatography (silica gel, 5 to 10% acetone/heptane) gave the title compound as an oil (1.66 g, 71% yield). LCMS (condition B): 366 (M+1); retention time=1.13 min.

Next, a solution of 2-(tert-butoxycarbonyl-ethoxycarbonylmethyl-amino)-propionic acid benzyl ester in EtOAc was hydrogenated under H₂ balloon by catalyst 10% Pd/C wet for 1 hr. The reaction was filtered off the catalyst and concentrated to give the crude for the next reaction.

Intermediate 55

(R)-3-Amino-4-(3'-chloro-biphenyl-4-yl)-2-methyl-butyric acid ethyl ester trifluoroacetate

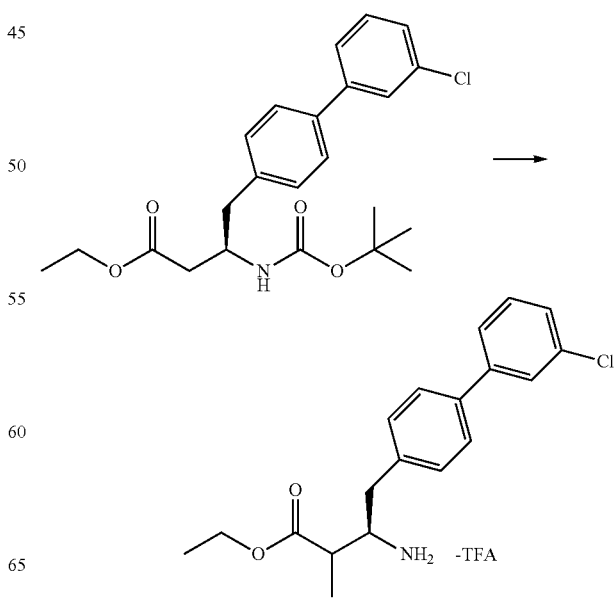

To a solution of (R)-3-tert-butoxycarbonylamino-4-(3'-chloro-biphenyl-4-yl)-butyric acid ethyl ester (300 mg, 0.718 mmol) in THF (10 ml) at −78° C. is added LiHMDS/THF (1M) (1.579 ml, 1.579 mmol). The reaction mixture is stirred at −78° C. for 50 min and then to this mixture is added methyl iodine (0.054 ml, 0.861 mmol) and the reaction is slowly warmed up to room temperature and stirred over night. The reaction is quenched by sat. NH$_4$Cl and is extracted with EtOAc. The combined organic layer is washed with brine and dried over anhydrous sodium sulfate, filtered and concentrated to give the crude. Reverse phase HPLC [20 to 90% ACN—H$_2$O (0.1% TFA) over 10 min by Sunfire C18] give (R)-3-tert-butoxycarbonylamino-4-(3'-chloro-biphenyl-4-yl)-2-methyl-butyric acid ethyl ester. LCMS (condition B): 432 (M+1); retention time=1.55 min. To a solution of (R)-3-tert-butoxycarbonylamino-4-(3'-chloro-biphenyl-4-yl)-2-methyl-butyric acid ethyl ester (240 mg, 0.556 mmol) in DCM (2 ml) at room temperature was added TFA (1.070 ml, 13.89 mmol) and the mixture is stirred at room temperature. 1 hr the reaction is done so the mixture is concentrated to give (R)-3-amino-4-(3'-chloro-biphenyl-4-yl)-2-methyl-butyric acid ethyl ester trifluoroacetate. LCMS (condition B): 332 (M+1); retention time=1.00 min.

It can be seen that the compounds of the invention are useful as inhibitors of Neutral endopeptidase (EC 3.4.24.11) activity and therefore useful in the treatment of diseases and conditions associated with Neutral endopeptidase (EC 3.4.24.11) activity such as the diseases disclosed herein.

It will be understood that the invention has been described by way of example only and modifications may be made whilst remaining within the scope and spirit of the invention.

What is claimed is:
1. A compound selected from:
(R)-4-(1-(3'-chlorobiphenyl-4-yl)-4-ethoxy-4-oxobutan-2-ylamino)-4-oxobutanoic acid;
(R)-5-(1-(3'-chlorobiphenyl-4-yl)-4-ethoxy-4-oxobutan-2-ylamino)-5-oxopentanoic acid;
(R)-5-(4-ethoxy-1-(5'-fluoro-2'-methoxybiphenyl-4-yl)-4-oxobutan-2-ylamino)-5-oxopentanoic acid;
(R)-5-(1-(5'-chloro-2'-methoxybiphenyl-4-yl)-4-ethoxy-4-oxobutan-2-ylamino)-5-oxopentanoic acid;
(R)-4-(4-(benzyloxy)-1-(3'-chlorobiphenyl-4-yl)-4-oxobutan-2-ylamino)-4-oxobutanoic acid;
(R)-4-((1-(3'-chloro-[1,1'-biphenyl]-4-yl)-4-ethoxy-4-oxobutan-2-yl)amino)-2,2,3,3-tetrafluoro-4-oxobutanoic acid;
(R)-4-((1-(3'-chloro-[1,1'-biphenyl]-4-yl)-4-((2,3-dihydro-1H-inden-5-yl)oxy)-4-oxobutan-2-yl)amino)-4-oxobutanoic acid;
(R)-4-(1-(2',5'-dichlorobiphenyl-4-yl)-4-ethoxy-4-oxobutan-2-ylamino)-4-oxobutanoic acid;
(R)-3-(3-Carboxy-propionylamino)-4-(3'-chloro-biphenyl-4-yl)-butyric acid propyl ester;
(R)-3-(3-Carboxy-propionylamino)-4-(3'-chloro-biphenyl-4-yl)-butyric acid butyl ester;
(R)-3-(3-Carboxy-propionylamino)-4-(3'-chloro-biphenyl-4-yl)-butyric acid 5-methyl-2-oxo-[1,3]dioxol-4-yl methyl ester;
(R)-3-(3-Carboxy-propionylamino)-4-(3'-chloro-biphenyl-4-yl)-butyric acid dimethylcarbamoylmethyl ester;
(R)-3-(3-Carboxy-propionylamino)-4-(3'-chloro-biphenyl-4-yl)-butyric acid dimethylcarbamoylmethyl ester;
(R)-3-(3-Carboxy-propionylamino)-4-(3'-chloro-biphenyl-4-yl)-butyric acid 2-morpholin-4-ylmethyl ester;
N-[(R)-2-Carboxy-1-(3'-chloro-biphenyl-4-ylmethyl)-ethyl]-2,2,3,3-tetrafluoro-succinamic acid;
(R)-4-(1-(5'-chloro-2'-fluorobiphenyl-4-yl)-4-ethoxy-4-oxobutan-2-ylamino)-4-oxobutanoic acid;
(R)-4-(4-ethoxy-1-(5'-fluoro-2'-methoxybiphenyl-4-yl)-4-oxobutan-2-ylamino)-4-oxobutanoic acid;
(R)-4-(1-(5'-chloro-2'-methoxybiphenyl-4-yl)-4-ethoxy-4-oxobutan-2-ylamino)-4-oxobutanoic acid;
(R)-4-(4-ethoxy-1-(5'-fluoro-2'-hydroxybiphenyl-4-yl)-4-oxobutan-2-ylamino)-4-oxobutanoic acid;
(R)-4-(4-ethoxy-1-(2'-hydroxybiphenyl-4-yl)-4-oxobutan-2-ylamino)-4-oxobutanoic acid;
(R)-benzyl 4-(3'-chlorobiphenyl-4-yl)-3-(4-ethoxy-4-oxobutanamido)butanoate;
(R)-ethyl 5-(4-(benzyloxy)-1-(3'-chlorobiphenyl-4-yl)-4-oxobutan-2-ylamino)-5-oxopentanoate;
(2S,3R)-3-(3-Carboxy-propionylamino)-4-(3'-chloro-biphenyl-4-yl)-2-hydroxy-butyric acid methyl ester;
(2R,3R)-3-(3-Carboxy-propionylamino)-4-(3'-chloro-biphenyl-4-yl)-2-hydroxy-butyric acid methyl ester;
(R)-4-(3'-chlorobiphenyl-4-yl)-3-(5-ethoxy-5-oxopentanamido)butanoic acid;
(2S,3R)-3-(3-Carboxy-propionylamino)-4-(3'-chloro-biphenyl-4-yl)-2-methoxy-butyric acid methyl ester;
(2R,3R)-3-(3-Carboxy-propionylamino)-4-(3'-chloro-biphenyl-4-yl)-2-methoxy-butyric acid methyl ester;
(R)-ethyl 4-(3'-fluoro-[1,1'-biphenyl]-4-yl)-3-(4-methoxy-4-oxobutanamido)butanoate;
(R)-ethyl 4-(2'-chloro-5'-fluoro-[1,1'-biphenyl]-4-yl)-3-(4-methoxy-4-oxobutanamido)butanoate;
R)-benzyl 3-(4-butoxy-4-oxobutanamido)-4-(3'-chlorobiphenyl-4-yl)butanoate;
(R)-benzyl 4-(3'-chlorobiphenyl-4-yl)-3-(4-(2,3-dihydro-1H-inden-5-yloxy)-4-oxobutanamido)butanoate;
(R)-3-(4-butoxy-4-oxobutanamido)-4-(3'-chlorobiphenyl-4-yl)butanoic acid;
(R)-4-(3'-chlorobiphenyl-4-yl)-3-(4-(2,3-dihydro-1H-inden-5-yloxy)-4-oxobutanamido)butanoic acid;
(R)-4-(3'-chlorobiphenyl-4-yl)-3-(4-ethoxy-4-oxobutanamido)butanoic acid;
(R)-3-(4-(benzyloxy)-4-oxobutanamido)-4-(3'-chlorobiphenyl-4-yl)butanoic acid;
4-(biphenyl-4-yl)-3-(1-(carboxymethyl)cyclopentanecarboxamido)butanoic acid;
(R)-ethyl 3-(4-amino-4-oxobutanamido)-4-(3'-chlorobiphenyl-4-yl)butanoate;
(R)-4-(1-carboxy-3-(5'-fluoro-2'-methoxybiphenyl-4-yl)propan-2-ylamino)-4-oxobutanoic acid;
R-4-(1-carboxy-3-(5'-chloro-2'-methoxybiphenyl-4-yl)propan-2-ylamino)-4-oxobutanoic acid;
R-4-(1-carboxy-3-(5'-fluoro-2'-hydroxybiphenyl-4-yl)propan-2-ylamino)-4-oxobutanoic acid;
(R)-3-(4-amino-4-oxobutanamido)-4-(3'-chlorobiphenyl-4-yl)butanoic acid;
(R)-5-(1-carboxy-3-(5'-chloro-2'-methoxybiphenyl-4-yl)propan-2-ylamino)-5-oxopentanoic acid;
(R)-4-(1-carboxy-3-(2'-chloro-5'-fluorobiphenyl-4-yl)propan-2-ylamino)-4-oxobutanoic acid;
(R)-5-(1-carboxy-3-(3'-chlorobiphenyl-4-yl)propan-2-ylamino)-5-oxopentanoic acid;
(R)-3-(3-Carboxy-propionylamino)-4-(5'-chloro-2'-fluoro-biphenyl-4-yl)-butyric acid;
(R)-3-(3-Carboxy-propionylamino)-4-(3'-chloro-biphenyl-4-yl)-2-hydroxy-butyric acid;
(R)-3-(3-Carboxy-propionylamino)-4-(3'-chloro-biphenyl-4-yl)-2-methoxy-butyric acid;
(R)-4-(1-carboxy-3-(3'-chlorobiphenyl-4-yl)propan-2-ylamino)-4-oxobutanoic acid;

(R)-5-(1-carboxy-3-(5'-fluoro-2'-methoxybiphenyl-4-yl) propan-2-ylamino)-5-oxopentanoic acid;

N-[(R)-1-(3'-chloro-biphenyl-4-ylmethyl)-3-methanesulfonylamino-3-oxo-propyl]-succinamic acid;

N-[(R)-1-(3'-Chloro-biphenyl-4-ylmethyl)-3-oxo-3-(propane-1-sulfonylamino)-propyl]-succinamic acid;

N-[(R)-1-(3'-Chloro-biphenyl-4-ylmethyl)-3-oxo-3-phenylmethanesulfonylamino-propyl]-succinamic acid;

N-[(R)-2-Carbamoyl-1-(3'-chloro-biphenyl-4-ylmethyl)-ethyl]-succinamic acid; and N-[(R)-1-(3'-chloro-biphenyl-4-ylmethyl)-3-methanesulfonylamino-3-oxo-propyl]succinamic acid butyl ester;

or a pharmaceutically acceptable salt thereof.

2. A pharmaceutical composition comprising a compound according to claim 1, or a pharmaceutically acceptable salt thereof, and one or more pharmaceutically acceptable carriers.

* * * * *